US011447553B2

(12) United States Patent
Pierce et al.

(10) Patent No.: US 11,447,553 B2
(45) Date of Patent: Sep. 20, 2022

(54) FGFR2 INHIBITORS ALONE OR IN COMBINATION WITH IMMUNE STIMULATING AGENTS IN CANCER TREATMENT

(71) Applicant: Five Prime Therapeutics, Inc., South San Francisco, CA (US)

(72) Inventors: Kristen Pierce, Burlingame, CA (US); Janine Powers, Alameda, CA (US); Servando Palencia, San Francisco, CA (US); Robert Sikorski, Woodside, CA (US); Majid Ghoddusi, South San Francisco, CA (US); Kartik Krishnan, South San Francisco, CA (US)

( * ) Notice: Subject to any disclaimer, the term of this patent is extended or adjusted under 35 U.S.C. 154(b) by 0 days.

(21) Appl. No.: 15/358,756

(22) Filed: Nov. 22, 2016

(65) Prior Publication Data
US 2017/0145102 A1 May 25, 2017

Related U.S. Application Data

(60) Provisional application No. 62/258,731, filed on Nov. 23, 2015, provisional application No. 62/314,174, filed on Mar. 28, 2016, provisional application No. 62/379,094, filed on Aug. 24, 2016.

(51) Int. Cl.
| C07K 16/28 | (2006.01) |
| C07K 16/30 | (2006.01) |
| A61K 39/00 | (2006.01) |
| G01N 33/50 | (2006.01) |
| G01N 33/574 | (2006.01) |

(52) U.S. Cl.
CPC ...... *C07K 16/2863* (2013.01); *C07K 16/2818* (2013.01); *C07K 16/2896* (2013.01); *C07K 16/303* (2013.01); *C07K 16/3015* (2013.01); *C07K 16/3023* (2013.01); *C07K 16/3038* (2013.01); *C07K 16/3046* (2013.01); *C07K 16/3069* (2013.01); *C07K 16/3084* (2013.01); *G01N 33/5091* (2013.01); *G01N 33/57407* (2013.01); *G01N 33/57446* (2013.01); *G01N 33/57492* (2013.01); *A61K 2039/505* (2013.01); *A61K 2039/507* (2013.01); *A61K 2039/55* (2013.01); *C07K 2317/34* (2013.01); *C07K 2317/41* (2013.01); *G01N 2333/71* (2013.01); *G01N 2800/52* (2013.01)

(58) Field of Classification Search
CPC ............................................. C07K 16/00–468
See application file for complete search history.

(56) References Cited

U.S. PATENT DOCUMENTS

| 5,591,639 A | 1/1997 | Bebbington et al. |
| 5,707,632 A | 1/1998 | Williams et al. |
| 5,863,888 A | 1/1999 | Dionne et al. |
| 5,981,216 A | 11/1999 | Kenten et al. |
| 6,342,221 B1 | 1/2002 | Thorpe et al. |
| 6,946,292 B2 | 9/2005 | Kanda et al. |
| 7,214,775 B2 | 5/2007 | Hanai et al. |
| 7,297,493 B2 | 11/2007 | Lorenzi et al. |
| 7,425,446 B2 | 9/2008 | Kanda et al. |
| 7,708,992 B2 | 5/2010 | Hanai et al. |
| 7,737,325 B2 | 6/2010 | Kanda et al. |
| 7,872,016 B2 | 1/2011 | Eswarakumar et al. |
| 8,067,232 B2 | 11/2011 | Kanda et al. |
| 8,101,721 B2 * | 1/2012 | Yayon ............... C07K 16/2863 |
| | | 530/387.3 |
| 8,101,723 B2 | 1/2012 | Kim et al. |
| 8,263,074 B2 | 9/2012 | Sun et al. |
| 8,481,688 B2 | 7/2013 | Weng et al. |
| 8,603,987 B2 | 12/2013 | Kim et al. |
| 8,664,365 B2 | 3/2014 | Luehrsen et al. |
| 8,679,491 B2 | 3/2014 | Hanai et al. |
| 8,945,572 B2 | 2/2015 | Chant et al. |
| 9,140,689 B2 | 9/2015 | Byron et al. |
| 9,254,288 B2 | 2/2016 | Pollock |
| 9,260,525 B2 | 2/2016 | Chang et al. |
| 9,382,324 B2 | 7/2016 | Kim et al. |
| 9,415,118 B2 | 8/2016 | Batt et al. |
| 9,481,733 B2 | 11/2016 | Ohtsaka et al. |
| 9,498,532 B2 | 11/2016 | Batt et al. |
| 9,714,298 B2 | 7/2017 | Ohtsuka et al. |

(Continued)

FOREIGN PATENT DOCUMENTS

| CN | 103096915 B | 8/2016 |
| EP | 2018442 A2 | 1/2009 |

(Continued)

OTHER PUBLICATIONS

Gemo et al., AACR Abstract No. 5446, Apr. 2014 (Year: 2014).*
Bendell et al., ASCO Gastrointestinal Cancers Symposium, Jan. 2016, poster #140 (Year: 2016).*
Powles et al., Nature 515:558-563 (Year: 2014).*
Lote et al., Cancer Treatment Rev. 41:893-903 (Year: 2015).*
Chaffer et al., Cancer Res. 66:11271-8 (Year: 2006).*
Ahmad, Imran, et al. "Mechanisms of FGFR-mediated carcinogenesis" Biochimica et Biophysica Acta, 1823(4):850-860 (2012).

(Continued)

*Primary Examiner* — Jessica H Roark
(74) *Attorney, Agent, or Firm* — Melissa E. Karabinis

(57) ABSTRACT

Provided herein are uses of fibroblast growth factor receptor 2 (FGFR2) inhibitors in cancer treatment, in some cases in combination with immune stimulating agents, such as inhibitors of PD-1 or PD-L1. In some embodiments, FGFR2 inhibitors may comprise FGFR2 antibodies or FGFR2 extracellular domain (ECD) polypeptides, or FGFR2 ECD fusion molecules comprising an FGFR2 ECD and a fusion partner. In some embodiments, PD-1/PD-L1 inhibitors may comprise anti-PD-1 antibodies such as antibodies that bind to PD-1 or to PD-L1 and inhibit interactions between these proteins, as well as PD-1 fusion proteins or polypeptides.

10 Claims, 21 Drawing Sheets

Specification includes a Sequence Listing.

(56) References Cited

U.S. PATENT DOCUMENTS

| | | |
|---|---|---|
| 9,834,609 B2 | 12/2017 | Kim et al. |
| 10,172,937 B2* | 1/2019 | Harding ............ A61K 39/3955 |
| 11,091,555 B2* | 8/2021 | Collins ............ C07K 16/2863 |
| 2005/0147612 A1 | 7/2005 | Yayon et al. |
| 2007/0248605 A1 | 10/2007 | Hestir et al. |
| 2009/0068110 A1 | 3/2009 | Shang et al. |
| 2009/0170715 A1 | 7/2009 | Glinsky |
| 2009/0311250 A1 | 12/2009 | Chant et al. |
| 2010/0047251 A1 | 2/2010 | Yayon et al. |
| 2010/0111944 A1 | 5/2010 | Pollock et al. |
| 2010/0173323 A1 | 7/2010 | Strome et al. |
| 2010/0196364 A1 | 8/2010 | Kim et al. |
| 2011/0059091 A1 | 3/2011 | Chang et al. |
| 2011/0009147 A1 | 4/2011 | Golab et al. |
| 2011/0160216 A1 | 6/2011 | Lenz |
| 2011/0305687 A1 | 12/2011 | Weng et al. |
| 2011/0318373 A1 | 12/2011 | Sasikumar et al. |
| 2012/0258496 A1 | 10/2012 | Ellwanger et al. |
| 2013/0142802 A1 | 6/2013 | Chang et al. |
| 2013/0183288 A1 | 7/2013 | Reff et al. |
| 2013/0288305 A1 | 10/2013 | Weng et al. |
| 2013/0309250 A1 | 11/2013 | Cogswell et al. |
| 2014/0322220 A1 | 10/2014 | Harrenga et al. |
| 2015/0050273 A1 | 2/2015 | Harding et al. |
| 2015/0125454 A1 | 5/2015 | Ohtsuka et al. |
| 2015/0167101 A1 | 6/2015 | Chant et al. |
| 2015/0210769 A1 | 7/2015 | Freeman et al. |
| 2015/0366866 A1 | 12/2015 | Mahamed et al. |
| 2016/0009820 A1 | 1/2016 | Ohtsuka et al. |
| 2016/0130661 A1 | 5/2016 | Brooks et al. |
| 2016/0244525 A1* | 8/2016 | Yin .................... C07K 16/3069 |
| 2016/0287699 A1* | 10/2016 | Karkera ............ C07K 16/2818 |
| 2016/0339100 A1 | 11/2016 | Harding et al. |
| 2017/0008964 A1 | 1/2017 | Batt et al. |
| 2017/0145102 A1 | 5/2017 | Pierce et al. |
| 2018/0094063 A1 | 4/2018 | Kim et al. |
| 2019/0175730 A1* | 6/2019 | Harding ............ C07K 16/2863 |

FOREIGN PATENT DOCUMENTS

| | | |
|---|---|---|
| EP | 1423428 A2 | 8/2009 |
| EP | 2046384 A2 | 12/2009 |
| EP | 2569012 A2 | 10/2013 |
| EP | 2603521 A2 | 10/2014 |
| EP | 2782934 A1 | 10/2014 |
| EP | 2837685 A1 | 2/2015 |
| EP | 2871236 A1 | 5/2015 |
| EP | 3008210 A1 | 4/2016 |
| JP | 2013534922 A | 9/2013 |
| KR | 1020040020107 A1 | 3/2004 |
| TW | 201345924 A | 11/2013 |
| TW | 201536804 A | 10/2015 |
| TW | 201536808 A | 10/2015 |
| WO | 00/61739 | 10/2000 |
| WO | 01/079266 A1 | 10/2001 |
| WO | 02/31140 | 4/2002 |
| WO | 2002102972 A2 | 12/2002 |
| WO | 2003063893 A2 | 8/2003 |
| WO | 2005/066211 A2 | 7/2005 |
| WO | 2007134210 A2 | 11/2007 |
| WO | 07/144893 A2 | 12/2007 |
| WO | 2008017963 A2 | 2/2008 |
| WO | 2008042236 A2 | 4/2008 |
| WO | 2008052796 A1 | 5/2008 |
| WO | 2008065543 A2 | 6/2008 |
| WO | 2009052830 A1 | 4/2009 |
| WO | 09/100105 A2 | 8/2009 |
| WO | 2010040571 A2 | 4/2010 |
| WO | 2010/054265 A2 | 5/2010 |
| WO | 2010/054265 A3 | 5/2010 |
| WO | 2010054265 | 5/2010 |
| WO | 11/025814 A1 | 3/2011 |
| WO | 2011088196 A2 | 7/2011 |
| WO | 2011/143318 A2 | 11/2011 |
| WO | 2011161699 A2 | 12/2011 |
| WO | 2012021841 A2 | 2/2012 |
| WO | 2012045085 A1 | 4/2012 |
| WO | 2012162561 A2 | 11/2012 |
| WO | 2013/076186 | 5/2013 |
| WO | 2012162561 A3 | 5/2013 |
| WO | 2013076186 A1 | 5/2013 |
| WO | 2013087716 A3 | 6/2013 |
| WO | 2013148263 A1 | 10/2013 |
| WO | 2013154206 A1 | 10/2013 |
| WO | 2014089193 A1 | 6/2014 |
| WO | 2014160160 A2 | 10/2014 |
| WO | WO-2014160160 A2 * | 10/2014 ............ A61K 45/06 |
| WO | 2014179448 A2 | 11/2014 |
| WO | 2014197937 A1 | 12/2014 |
| WO | 2015017600 A1 | 2/2015 |
| WO | 2015112900 A1 | 7/2015 |
| WO | 2015116868 A2 | 8/2015 |
| WO | 2016100882 A1 | 6/2016 |

OTHER PUBLICATIONS

International Search Report and Written Opinion issued in PCT/US2016/06332 dated Feb. 27, 2017.

International Search Report and Written Opinion issued in PCT/US2016/063340 dated Feb. 24, 2017.

Ricol, David et al. "Tumour suppressive properties of fibroblast growth factor receptor 2-IIIB in human bladder cancer" Oncogene 18:7234-7243 (1999).

Tiong, Kai Hung et al. "Functional roles of fibroblast growth factor receptors (FGFRs) signaling in human cancers" Apoptosis 18:1447-1468 (2013).

Bai et al., "GP369, an FGFR2-IIIb-specific antibody, exhibits potent antitumor activity against human cancers driven by activated FGFR2 signaling," Cancer Res., 70:7630-7639, (2010).

Campbell, "General properties and applications of monoclonal antibodies," Monoclonal Antibody Technology, pp. 1-32, (1984).

De Moerlooze et al., "An important role for the IIIb isoform of fibroblast growth factor receptor 2 (FGFR2) in mesenchymal-epithelial signalling during mouse organogenesis," Development, 127:483-492, (2000).

De Pascalis et al., "Grafting of abbreviated complementarity determining regions containing specificity determining residues essential for ligand contact to engineer a less immunogenic humanized monoclonal antibody," Journal of Immunology, 169: 3076-3084, (2002).

Dutt et al., "Drug-sensitive FGFR2 mutations in endometrial carcinoma," Proc Natl Acad Sci USA, 105:8713-7, (2008).

Hattori et al., "Immunohistochemical detection of K-sam protein in stomach cancer," Clin Cancer Res, 2:1373-81, (1996).

Katoh "Cancer genomics and genetics of FGFR2 (Review)," Int J Oncology, 33:233-237, (2008).

Kunii et al., "FGFR2-amplified gastric cancer cell lines require FGFR2 and Erbb3 signaling for growth and survival," Cancer Res, 68:2340-2348, (2008).

Nakamura et al., "A novel molecular targeting compound as K-samII/FGF-R2 phosphorylation inhibitor, Ki23057, for scirrhous gastric cancer," Gastroenterology, 131:1530-1541, (2006).

Ornitz et al., "Fibroblast growth factors," Genome Biol, 2:REVIEWS3005, (2001).

Ornitz et al., "Receptor specificity of the fibroblast growth factor family," J Biol Chem, 271:15292-15297, (1996).

PCT/US2009/063647 International Preliminary Report on Patentability and Written Opinion dated May 10, 2011.

PCT/US2009/063647 International Search Report dated Jun. 23, 2010.

Pollock et al., "Frequent activating FGFR2 mutations in endometrial carcinomas parallel germline mutations associated with craniosynostosis and skeletal dysplasia syndromes," Oncogene, 26:7158-7162, (2007).

Rudikoff et al., "Single amino acid substitution altering antigen-binding specificity," Proceedings of the National Academy of Sciences, 79:1979-1983, (1982).

(56) References Cited

OTHER PUBLICATIONS

Steele et al., "Induction of FGF receptor 2-IIIb expression and response to its ligands in epithelial ovarian cancer," Oncogene, 20:5878-5887, (2001).
Supplementary European Search Report and European Search Opinion for application EP09825523 dated May 7, 2012.
Trudel et al., "The inhibitory anti-FGFR3 antibody, PRO-001, is cytotoxic to t(4;14) multiple myeloma cells," Blood, 107:4039-4046, (2006).
U.S. Appl. No. 12/614,282, Non-Final Rejection dated Apr. 7, 2011.
U.S. Appl. No. 12/614,282, Notice of Allowance dated Sep. 29, 2011.
U.S. Appl. No. 12/614,282, Requirement for Restriction/Election dated Dec. 27, 2010.
Yashiro et al., "Establishment of two new scirrhous gastric cancer cell lines: analysis of factors associated with disseminated metastasis," Br J Cancer, 72:1200-1210 (1995).
Zhang et al., "Receptor specificity of the fibroblast growth factor family. The complete mammalian FGF family," J Biol Chem, 281:15694-156700, (2006).
Zhao et al., "Monoclonal antibodies to fibroblast growth factor receptor 2 effectively inhibit growth of gastric tumor xenografts," Clin Cancer Res, 16:5750-5758, (2010).
International Search Report and Written Opinion of the International Searching Authority for International Application No. PCT/US2014/049008, dated Nov. 11, 2014.
Yamane-Ohnuki N, et al., "Production of therapeutic antibodies with controlled fucosylation," MABS, Jun. 2009, 1(3):230-236.
Niwa R. "IgG subclass-independent improvement of antibody-dependent cellular cytotoxicity by fucose removal from Asn297-linked oligosaccharides," Journal of Immunological Methods, Sep. 22, 2005, 306:151-160.
Kurban, et al., "Expression of keratinocyte growth factor receptor (KGFR/FGFR2 nib) in human uterine cervical cancer," Oncology Reports, 11:987-991, (2004).
"Potelligent® CHOK1SV." LONZA. Web, Product Information available from Lonza. com (2009).
Miki, et al., "Determination of ligand-binding specificity by alternative splicing: Two distinct growth factor receptors encoded by a single gene," Proc. Natl. Acad. Sci. USA, Biochemistry, 89:246-250, (1992).
Otte, et al., "Expression of keratinocyte growth factor and its receptor in colorectal cancer," European Journal of Clinical Investigation, 30:222-229, (2000).
Watanabe, et al., "Overexpression of keratinocyte growth factor in cancer cells and enterochromaffin cells in human colorectal cancer," Pathology International, 50:363-372, (2000).
Yoshino, et al., "Keratinocyte growth factor receptor expression in normal colorectal epithelial cells and differentiated type of colorectal cancer," Oncology Reports, 13:247-252, (2005).
"Monoclonal Anti-human FGF R2 Antibody," R&D Systems Product Description, Catalog No. MAB665, Clone 98707, Lot No. DWH02, printed Mar. 1, 2005, 2 pages.
W. Zhao et al., "Monoclonal Antibodies to Fibroblast Growth Factor Receptor 2 Effectively Inhibit Growth of Gastric Tumor Xenografts," Clin. Cancer Res., 16(23): 5750-5758 (2010).
Genbank Accession No. ABI81225, "Fibroblast growth factor receptor 1 IIIc [Ovis aries]," Mar. 5, 2008 (1 page).
Genbank Accession No. AAF26719, "Fibroblast growth factor receptor 2 IIIb [Ovis aries]," Nov. 17, 2000 (1 page).
G. Gratz, "Final Report: Single Dose Intravenous Pharmacokinetic Study of FPA144-A and FPA144-F in Cynomolgus Monkeys, Study No. 0787-12156," Test Facility: BASi, Mt. Vernon, IN, report completed Jun. 26, 2014 (133 pages).
G. Gratz, "Final Report: A Twenty-eight Day Intravenous Toxicity Study of FPA144-A and FPA144-F in Cynomolgus Monkeys, Study No. 0787-12157," Test Facility: BASi, Mt. Vernon, IN, report completed Jun. 27, 2014 (295 pages).
G. Gratz, "Final Report: A Twenty-eight Day Intravenous Toxicity Study of FPA144-A and FPA144-F in Rats, Study No. 0787-12212," Test Facility: BASi, Mt. Vernon, IN, report completed Jun. 27, 2014 (483 pages).
M. Brown et al., "Tolerance to Single, but Not Multiple, Amino Acid Replacements in Antibody VH CDR2," J. Immunol., 156: 3285-3291, 1996.
F. Casset et al., "A Peptide Mimetic of an Anti-CD4 Monoclonal Antibody by Rational Design," Biochem. Biophys. Res. Comm., 307: 198-205 (2003).
Y. Chen et al., "Selection and Analysis of an Optimized Anti-VEGF Antibody: Crystal Structure of an Affinity-matured Fab in Complex with Antigen," J. Mol. Biol., 293: 865-881 (1999).
J. Davies et al., "Affinity Improvement of Single Antibody VH Domains: residues in all three hypervariable regions affect antigen binding," Immunotech., 2: 169-179 (1996).
D. Fortin et al., "Distinct Fibroblast Growth Factor (FGF)/FGF Receptor Signaling Pairs Initiate Diverse Cellular Responses in the Oligodendrocyte Lineage," J Neurosci., 25(32): 7470-7479 (2005).
R. Grose et al., "Fibroblast Growth Factor Signaling in Tumorigenesis," Cytokine & Growth Factor Reviews, 16: 179-186 (2005).
L. Holt et al., "Domain Antibodies: proteins for therapy," Trends in Biotech., 21(11): 484-490 (2003).
T. Junttila et al., "Superior In vivo Efficacy of Afucosylated Trastuzumab in the Treatment of HER2-Amplified Breast Cancer," Cancer Res., 70(11): 4481-1489 (2010).
R. Maccallum et al., "Antibody-antigen Interactions: Contact analysis and binding site topography," J. Mol. Biol., 262: 732-745 (1996).
M. Mohammadi et al., "Structural Basis for Fibroblast Growth Factor Receptor Activation," Cytokine & Growth Factor Reviews, 16: 107-137 (2005).
R. Ogle et al., "Regulation of Cranial Suture Morphogenesis," Cells Tissues Organs, 176: 54-66 (2004).
M. Presta et al., "Fibroblast Growth Factor/Fibroblast Growth Factor Receptor System in Angiogenesis," Cytokine & Growth Factor Reviews, 16: 159-178 (2005).
D. Reusch et al., "Fc Glycans of Therapeutic Antibodies as Critical Quality Attributes," Glycobiol., advance access published Sep. 12, 2015, pp. 1-10 (2015).
M. Takeda et al., "AZD2171Shows Potent Antitumor Activity Against Gastric Cancer Over-Expressing Fibroblast Growth Factor Receptor 2/Keratinocyte Growth Factor Receptor," Clin. Cancer Res., 13(10): 3051-3057 (2007).
L. Wang et al., "Abstract #1236: Blocking antibody to fibroblast growth factor-2 as a potential cancer therapeutic agent," 100th AACR Annual Meeting, Apr. 18-22, 2009, Denver, CO, Cancer Res., 69: 1236 (2009).
P. Wei et al., "Generation and Characterization of Monoclonal Antibodies to Human Keratinocyte Growth Factor Receptor," Hybridoma, 25(3): 115-124 (2006).
H. Wu et al., "Humanization of a Murine Monoclonal Antibody by Simultaneous Optimization of Framework and CDR Residues," J. Mol. Biol., 294:151-162 (1999).
USPTO Prosecution History of U.S. Appl. No. 14/447,751.
Lazar, G. et al. "Engineered antibody Fc variants with enhaced effector funtion" PNAS USA 103(11): 4005-4010.
Office Action issued in Japanese Patent Application No. 2016-531878 dated Aug. 7, 2018.
Beer et al., "Expression and Function of Keratinocyte Growth Factor and Activin in Skin Morphogenesis and Cutaneous Wound Repair," Journal of Investigative Dermatology Symposium Proceedings, 5:34-39 (2000).
Beer et al., "Fibroblast Growth Factor (FGF) Receptor 1-IIIb Is a Naturally Occurring Functional Receptor for FGFs That is Preferentially Expressed in the Skin and the Brain," J Biol Chem, 275:16091-16097 (2000).
Byron et al., "Inhibition of Activated Fibroblast Growth Factor Receptor 2 in Endometrial Cancer Cells Induces Cell Death Despite PTEN Abrogation," Cancer Res., 68:6902-6907, 2008).
Carter et al., "Identification and validation of cell surface antigens for antibody targeting in oncology," Endocrine-Related Cancer, 11:659-687, (2004).

(56) References Cited

OTHER PUBLICATIONS

Cho et al., "Enhanced Expression of Keratinocyte Growth Factor and Its Receptor Correlates with Venous Invasion in Pancreatic Cancer," Am. J. Pathol., 170(6):1964-1974, doi: http://dx.doi.org/10.2353/ajpath.2007.060935, (2007).
Davies et al., Cancer Res., Immunotechnol 2: 169-179 (1996).
Easton et al., "Genome-wide Association Study Identifies Novel Breast Cancer Susceptibility Locus," Nature, 447:1087-1093, (2007).
Finch and Rubin, "Keratinocyte Growth Factor Expression and Activity in Cancer Implications For Use in Patients with Solid Tumors,"Journal of the National Cancer Institute, 98:812-824 (2006).
Grose et al., "The Role of Fibroblast Growth Factor Receptor 2b in Skin Homeostasis and Cancer Development," The Embo Journal, 26:1268-1278 (2007).
Hughes, "Differential Expression of the Fibroblast Growth Factor Receptor (FGFR) Multigene Family in Normal Human Adult Tissues," J Histochem cytochem, 45:1005-1019 (1997).
Hunter et al., "A Genome-Wide Association Study Identifies Alleles in FGFR2 Associated With Risk of Sporadic Postmenopausal Breast Cancer," Nature Genetics, 39:870-874, (2007).
Ibrahimi et al., "Biochemical Analysis of Pathogenic Ligand-Dependent FGFR2 Mutations Suggests Distinct Pathophysiological Mechanisms for Craniofacial and Limb Abnormalities," Human Molecular Genetics, 13:2313-2324, (2004).
Itoh et al., "Preferential Alternative Splicing in Cancer Generates a K-sam Messenger RNA with Higher Transforming Activity," Cancer Res., 54:3237-3241, (1994).
Jang et al., "Mutations in Fibroblast Growth Factor Receptor 2 and Fibroblast Growth Factor Receptor 3 Genes Associated with Human Gastric and Colorectal Cancers," Cancer Res., 61 :3541-3543, (2001 ).
Kono et al., "Impaired Antibody-Dependent Cellular Cytotoxicity Mediated by Herceptin in Patients with Gastric Cancer," Cancer Res 62:5813-5817, (2002).
Liang et al., "Genetic Variants in Fibroblast Growth Factor Receptor 2 (FGFR2) Contribute to Susceptibility of Breast Cancer in Chinese Women," Cardnoaenesis, 29: 2341-2346, (2008).
Luqmani et al., "Expression of Basic Fibroblast Growth Factor, FGFR1 and FGFR2 in Normal and Malignant Human Breast, and Comparison with Other Normal Tissues," Br. J. Cancer, 66:273-280, (1992).
Takeda et al. "AZD2171 Shows Potent Antitumor Activity Against Gastric Cancer Over-Expressing Fibroblast Growth Factor Receptor 2/Keratinocyte Growth Factor Receptor," Clinical Cancer Research, 13(10):3051-3057, (2007).
Matsunobu et al., "Expression of Keratinocyte Growth Factor Receptor Correlates with Expansive Growth and Early Stage of Gastric Cancer," International Journal of Oncology, 28:307-314, (2006).
Brown et al. "Tolerance to single, but not multiple, amino acid replacements in antibody V-HCDR2: A means of minimizing B cell wastage from somatic hypermutation?," Journal Of Immunology, 156(9):3285-3291, (1996).
Moloney et al., "Exclusive Paternal Origin of New Mutations in Apert Syndrome," Nature Genetics, 13:48-53, (1996).
Mor et al., "DNA Amplification in Human Gastric Carcinomas," Cancer Genet Cytogenet, 65:111-114, (1993).
Mor et al., "Novel DNA Sequences at Chromosome 1 0Q26 Are Amplified in Human Gastric Carcinoma Cell Lines: Molecular Cloning by Competitive DNA Reassociation," Nucleic Acids Research, 19:117-123, (1991).
Nakatani et al., "Isolation of an Amplified DNA Sequence in Stomach Cancer," Jpn J. Cancer Res., 81 :707-710, (1990).
Yamane-Ohnuki et al. Production of therapeutic antibodies with controlled fucosylation, MAbs, 2009; V.1, pp. 230-236.
Pascal et al., "Correlation of mRNA and protein levels: Cell type-specific gene expression of duster desianation antiaens in the prostate," BMC Genomics, 9:246, 13 pages, (2008).
R&D Systems online catalog page for MAB665 dated Mar. 1, 2005.

Tamaru et al., "Estrogen receptor-associated expression of keratinocyte growth factor and its possible role in the inhibition of apoptosis in human breast cancer," Lab. Invest, 84(11 ):1460-1471, (2004).
Tannheimer et al. "Characterization of Fibroblast Growth Factor Receptor 2 Overexpression in the Human Breast Cancer Cell Line SUM-52 PE," Breast Cancer Res, 2:311-320 (2000).
Tsujimoto et al., "Amplification of Growth Factor Receptor Genes and DNA Ploidy Pattern in the Progression of Gastric Cancer," Virchows Arch 431 :383-389, (1997).
Ueda et al., "Deletion of the Carboxyl-Terminal Exons of K-sam/FGFR2 by Short Homology-Mediated Recombination, Generating Preferential Expression of Specific Messenger RNAs," Cancer Res., 59:6080-6086, (1999).
Vajdos et al., "Comprehensive functional maps of the antigen-binding site of an anti-ErbB2 antibody obtained with shotgun scanning mutagenesis," J. Mol. Biol., 320:415-428, (2002)—Ordered Jun. 2011 from Reprints desk.
Visco et al., "Expression of keratinocyte growth factor receptor compared with that of epidermal growth factor receptor and erbB-2 in endometrial adenocarcinoma," Int. J. Oncol., 15(3):431-435, doi: https://doi.org/10.3892/ijo.15.3.431, (1999).
Werner, "Molecular and Cellular Mechanisms of Tissue Repair", Experimental Dermatology, 14(10):786-787, (2005).
Winter, et al., "Humanized antibodies," Immunology Today, 14(6):243-246, (1993)—Ordered Jun. 2011 from Reprints desk.
Lo et al., Effector-attenuating substitutions that maintain antibody stability and reduce toxicity in mice, J. Biol. Chem, 292(9): 3900-08 (2017).
Gong et al., "Increased in vivo effector function of human IgG4 isotype antibodies through afucosylation," Monoclonal Antibodies 8(6): 1098-1106 (2016).
Clarivate Analytics, Cortellis search results for search query: (afucosyl* OR non-fucosyl* OR non fucosylation) AND monocolonal AND antibody, four pages, Jul. 20, 2018.
Actip, monoclonal antibodies approved by the EMA and FDA for therapeutic use, available at: http://www.ACTIP.org/products/monodonal-antibodies-approved-by-the-ema-and-fda-for-therapeutic-use/, 10 pages, last viewed May 18, 2018.
Eswarakumar, V.P. et al. "Cellular signaling by fibroblast growth factor receptors" Cytokine & Growth Factor Reviews 16: 139-149 (2005).
Catenacci, D.V.T. et al. "Updated antitumor activity and safety of FPA144, an ADCC-enhanced, FGFR2b isoform-specific monoclonal antibody, in patients with FGFR2b+ gastric cancer" 2017 ASCO Annual Meeting, Abstract No. 4067, J. Clin. Oncol. 35(Suppl): Abst. 4067 (May 17, 2017).
Declaration of Dr. Kristen Pierce, Sep. 15, 2017.
Dr. Kristen Pierce 2017 CV.
Keam et al., Modified FOLFOX-6 chemotherapy in advanced gastric cancer: Results of phase II study and comprehensive analysis of polymorphisms as a predictive and prognostic marker. BMC Cancer, 8, 1-48, 2008.
Kanda et al. "Comparison of Cell Lines for Stable Production of Fucose-Negative Antibodies With Enhanced ADCC" Biotechnology and Bioengineering, 94(4): 680-688 (2006).
Office Action issued in Russian Patent application No. 2016106101, dated Oct. 9, 2018.
Von Horsten et.al. "Production of non-fucosylated antibodies by co-expression of heterologous GDP-6-deoxy-D-lyxo-4-hexulose reductase" 2010, Glycobiology, v.20 n.12 pp. 1607-1618.
Wong et.al., "Enhancement of DNA Uptake in FUT8-Deleted CHO Cells for Transient Production of Afucosylated Antibodies" 2010, Biotechnology and Bioengineering, V.106, N.5, pp. 751-763.
Adelaide et al., "Integrated Profiling of Basal and Luminal Breast Cancers," Cancer Res., 67:11565-11575, (2007).
Clarivate Analytics, Cortellis internet portal printed pages (://www.cortellis.com/intelligence/advsearch/view.do), two pages, Jul. 20, 2018.
Davies et al., "Somatic Mutations of the Protein Kinase Gene Family in Human Lung Cancer," Cancer Res., 65:7591-7595, (2005).
Machine translation of KR1020040020107 to Chong et al.; application published Mar. 9, 2004.

(56) References Cited

OTHER PUBLICATIONS

Shields, R. L. et al. "Lack of fucose on human IgG1 N-linked oligosaccharide improves binding to human Fcgamma RIII and antibody-dependent cellular toxicity" J Biol Chem., vol. 277, No. 30, 2002, pp. 26733-26740.
Suzuki, E. et al. "A nonfucosylated anti-HER2 antibody augments antibody-dependent cellular cytotoxicity in breast cancer patients" Clin. Cancer Res., vol. 13, No. 6, 2007, pp. 1875-1882.
Fedyanin M. Yu. et al., Prospects of therapeutic action on FGFR signaling pathway. Advances of molecular oncology. 2015, No. 1, pp. 27-38 entire text.
Keam, B. et al. "Modified FOLFOX-6 chemotherapy in advanced gastric cancer: Results of phase II study and comprehensice analysis of polymorphisms as a predictive and prognostic marker" BMC Cancer 2008, 8:148.
NCT02318329, Sponsor Five Prime Therapeutics, Inc., "Open-label, dose-finding study evaluating safety and PK of FPA144 in patients with advanced solid tumors," available at clinicaltrials (dot) gov, Jan. 2017 (last viewed May 25, 2017).
Pellegrinet, L. et al. "Dll1- and Dll4-mediated Notch signaling are required for homeostasis of intestinal stem cells" Gastroenterology 140: 1230-1240 (2011).
Schuster, M. et al. "Improved effector functions of a therapeutic monoclonal Lewis Y-specific antibody by glycoform engineering" Cancer Res. 65(17): 7934-41 (2005).
Amgen Press Release, "Amgen to Acquire Five Prime Therapeutics for $1.9 Billion in Cash," Mar. 4, 2021 (8 pages).
Amgen Press Release, "Amgen's Investigational Targeted Treatment Bemarituzumab Granted Breakthrough Therapy Designation," Apr. 19, 2021 (7 pages).
Anonymous, "Five Prime announces bemarituzumab plus chemotherapy demonstrates significant progression-free and overall survival benefit compared to placebo plus chemotherapy in front-line advanced gastric and gastrointestinal junction cancer," press release Nov. 10, 2020, available at www(dot)fiveprime(dot)com. (3 pages).
Anonymous: "Five Prime Therapeutics Initiates Phase Patient Dosing in Phase 1 Lead-In to Phase 3, Global Registrational Trial of FPA144 in Front-Line Advanced Gastric Cancer" Five Prime, Jan. 2, 2018, p. 1-2, retrieved from the internet: Retrieved from the URL:http://investor.fiveprime.com/news-releases/news-release-details/five-prime-therapeutics-initiates-patient-dosing-phase-1-lead.
Catenacci et al., "Phase 1 Escalation and Expansion Study of Bemarituzumab (FPA144) in Patients with Advanced Solid Tumors and FGFR2b-Selected Gastroesophageal Adenocarcinoma," J Clin Oncol, 2020, 1-10.
Chao, J., "Adding bemarituzumab to chemotherapy improves outcomes in certain gastric cancers," available at: www.healio.com/news/hematology-oncology/20210120/, Jan. 20, 2021, 3 pages.
File History of U.S. Appl. No. 16/181,784, filed Nov. 6, 2018.
File History of U.S. Appl. No. 16/613,579, filed Nov. 14, 2019.
Five Prime Corporate Overview, "Rewriting cancer, together," Jan. 2021, 36 pages.
Gemo, et al. "Abstract 5446: FPA144L A therapeutic antibondy for treating patients with gastric cancers bearing FGFR2 gene amplifications" Cancer Research, 74(19):1-4 (2014).
Grothey, A., "Bemarituzumab plus modified FOLFOX6 for advanced gastric/GE junction adenocarcinoma," Oncology (/explore/channel/oncology/sp1), Expert Opinion, Interview, Feb. 10, 2021, 4 pages.
Hacibekiroglu et al., "Comparative analysis of the efficacy and safety of modified FOLFOX-6 and DCF regimens as first-line treatment in advanced gastric cancer," Mol Clin Oncol, 2015, 3:1160-1164.
International Search Report and Written Opinion for PCT/US2018/032757 dated Aug. 10, 2018.
J.P. Morgan, Analyst Report on Five Prime Therapeutics, Inc., Nov. 11, 2020 (10 pages).
Jefferies, Analyst Report on Five Prime Therapeutics, Inc., Nov. 10, 2020 (10 pages).
Jefferis, "Antibody Therapeutics: Isotype and Glycoform Selection," Expert. Opin. Biol. Ther., 2007, 7(9):1401-1413.
Kim et al., "Oxaliplatin, 5-fluorouracil and leucovorin (modified FOLFOX-6) as first-line chemotherapy for advanced gastric cancer patients with poor performance status," Oncology Letters, 2012, 3:425-428.
Pectasides, D. et al. "Randomized phase III clinical trial comparing the combination of pacecitabine and oxaliplatin (CAPOX) with the combination of 5-fluorouracil, leucovorin and oxaliplatin (modified FOLFOX6) as adjuvant therapy in patients with operated high-risk stage II or stage III colorectal cancer" BMC Cancer, 15(1):384 (2015).
Sibertin-Blanc, C. et al. "Monoclonal antibodies for treating gastric cancer: promises and pitfalls", Expert Opinion on Biological Therapy. 16(6): 759-769 (2016).
Van Cutsem et al., "A randomized, open-label study of the efficacy and safety of AZD4547 monotherapy versus paclitaxel for the treatment of advanced gastric adenocarcinoma with FGFR2 polysomy or gene amplification," Anals of Oncology, 28: 1316-24 (2017).
Wainberg et al., "Randomized Double-blind Placebo-Controlled Phase 2 Study of Bemarituzumab Combined with Modified FOLFOX6 (mFOLFOX6) in 1st Line (1L) Treatment of Advanced Gastric/Gastroesophageal Junction Adenocarcinoma (FIGHT)," Abstract, ASCO-GI, Jan. 15, 2021, 2 pages.
Wainberg et al., "A double-blind randomized study of bemarituzumab (bema) plus mFOLFOX6 versus placebo plus mFOLFOX6 as first-line treatment for advanced gastric/gastroesophageal junction cancer (FIGHT)," Late Breaking Abstract (LBA160), ASCO Gastrointestinal Cancer Symposium 2021, 15 pages.
Wang et al.,"A phase II study of a modified FOLFOX6 regimen as neoadjuvant chemotherapy for locally advanced gastric cancer," British J Cancer, 2016, 114:1326-1333.
Xiang et al., "Population pharmacokinetic analysis of phase 1 bemarituzumab data to support phase 2 gastroesophageal adenocarcinoma FIGHT trial," Cancer Chemotherapy and Pharmacology, 2020, 86:595-606.
Yashiro, M. et al. "Synergistic antitumor effects of FGFR2 inhibitor with 5-fluorouracil on scirrhous gastric carcinoma", International Journal of Cancer, 126(4): 1004-1015 (2010).
Zak et al., "Structure of the Complex of Human Programmed Death 1, PD-1, and its Ligand PD-L1," Structure, 2015, 23(12): 2341-2348.
Zitvogel et al., Targeting PD-1/PD-L1 Interactions for Cancer Immunotherapy, OncoImmunology, 2012, 1(8):1223-1225.
Pardoll, et al., "The blockade of immune checkpoints in cancer immunotherapy", Nat Rev Cancer; 12 (4): 252-264 (May 4, 2016).

* cited by examiner

SEQUENCE LISTING

<160> NUMBER OF SEQ ID NOS: 46

<210> SEQ ID NO 1
<211> LENGTH: 801
<212> TYPE: PRT
<213> ORGANISM: Homo sapiens
<220> FEATURE:
<221> NAME/KEY: MISC_FEATURE
<223> OTHER INFORMATION: Mature human FGFR2-IIIb

<400> SEQUENCE: 1

```
Arg Pro Ser Phe Ser Leu Val Glu Asp Thr Thr Leu Glu Pro Glu Glu
1               5                   10                  15

Pro Pro Thr Lys Tyr Gln Ile Ser Gln Pro Glu Val Tyr Val Ala Ala
            20                  25                  30

Pro Gly Glu Ser Leu Glu Val Arg Cys Leu Leu Lys Asp Ala Ala Val
        35                  40                  45

Ile Ser Trp Thr Lys Asp Gly Val His Leu Gly Pro Asn Asn Arg Thr
    50                  55                  60

Val Leu Ile Gly Glu Tyr Leu Gln Ile Lys Gly Ala Thr Pro Arg Asp
65                  70                  75                  80

Ser Gly Leu Tyr Ala Cys Thr Ala Ser Arg Thr Val Asp Ser Glu Thr
                85                  90                  95

Trp Tyr Phe Met Val Asn Val Thr Asp Ala Ile Ser Ser Gly Asp Asp
            100                 105                 110

Glu Asp Asp Thr Asp Gly Ala Glu Asp Phe Val Ser Glu Asn Ser Asn
        115                 120                 125

Asn Lys Arg Ala Pro Tyr Trp Thr Asn Thr Glu Lys Met Glu Lys Arg
    130                 135                 140

Leu His Ala Val Pro Ala Ala Asn Thr Val Lys Phe Arg Cys Pro Ala
145                 150                 155                 160

Gly Gly Asn Pro Met Pro Thr Met Arg Trp Leu Lys Asn Gly Lys Glu
                165                 170                 175

Phe Lys Gln Glu His Arg Ile Gly Gly Tyr Lys Val Arg Asn Gln His
            180                 185                 190

Trp Ser Leu Ile Met Glu Ser Val Val Pro Ser Asp Lys Gly Asn Tyr
        195                 200                 205

Thr Cys Val Val Glu Asn Glu Tyr Gly Ser Ile Asn His Thr Tyr His
    210                 215                 220
```

```
Leu Asp Val Val Glu Arg Ser Pro His Arg Pro Ile Leu Gln Ala Gly
225                 230                 235                 240

Leu Pro Ala Asn Ala Ser Thr Val Val Gly Gly Asp Val Glu Phe Val
            245                 250                 255

Cys Lys Val Tyr Ser Asp Ala Gln Pro His Ile Gln Trp Ile Lys His
            260                 265                 270

Val Glu Lys Asn Gly Ser Lys Tyr Gly Pro Asp Gly Leu Pro Tyr Leu
        275                 280                 285

Lys Val Leu Lys His Ser Gly Ile Asn Ser Ser Asn Ala Glu Val Leu
        290                 295                 300

Ala Leu Phe Asn Val Thr Glu Ala Asp Ala Gly Glu Tyr Ile Cys Lys
305                 310                 315                 320

Val Ser Asn Tyr Ile Gly Gln Ala Asn Gln Ser Ala Trp Leu Thr Val
            325                 330                 335

Leu Pro Lys Gln Gln Ala Pro Gly Arg Glu Lys Glu Ile Thr Ala Ser
            340                 345                 350

Pro Asp Tyr Leu Glu Ile Ala Ile Tyr Cys Ile Gly Val Phe Leu Ile
        355                 360                 365

Ala Cys Met Val Val Thr Val Ile Leu Cys Arg Met Lys Asn Thr Thr
370                 375                 380

Lys Lys Pro Asp Phe Ser Ser Gln Pro Ala Val His Lys Leu Thr Lys
385                 390                 395                 400

Arg Ile Pro Leu Arg Arg Gln Val Thr Val Ser Ala Glu Ser Ser Ser
            405                 410                 415

Ser Met Asn Ser Asn Thr Pro Leu Val Arg Ile Thr Thr Arg Leu Ser
            420                 425                 430

Ser Thr Ala Asp Thr Pro Met Leu Ala Gly Val Ser Glu Tyr Glu Leu
            435                 440                 445

Pro Glu Asp Pro Lys Trp Glu Phe Pro Arg Asp Lys Leu Thr Leu Gly
450                 455                 460

Lys Pro Leu Gly Glu Gly Cys Phe Gly Gln Val Val Met Ala Glu Ala
465                 470                 475                 480

Val Gly Ile Asp Lys Asp Lys Pro Lys Glu Ala Val Thr Val Ala Val
            485                 490                 495

Lys Met Leu Lys Asp Asp Ala Thr Glu Lys Asp Leu Ser Asp Leu Val
            500                 505                 510

Ser Glu Met Glu Met Met Lys Met Ile Gly Lys His Lys Asn Ile Ile
            515                 520                 525

Asn Leu Leu Gly Ala Cys Thr Gln Asp Gly Pro Leu Tyr Val Ile Val
530                 535                 540

Glu Tyr Ala Ser Lys Gly Asn Leu Arg Glu Tyr Leu Arg Ala Arg Arg
545                 550                 555                 560

Pro Pro Gly Met Glu Tyr Ser Tyr Asp Ile Asn Arg Val Pro Glu Glu
            565                 570                 575

Gln Met Thr Phe Lys Asp Leu Val Ser Cys Thr Tyr Gln Leu Ala Arg
            580                 585                 590

Gly Met Glu Tyr Leu Ala Ser Gln Lys Cys Ile His Arg Asp Leu Ala
            595                 600                 605

Ala Arg Asn Val Leu Val Thr Glu Asn Asn Val Met Lys Ile Ala Asp
        610                 615                 620

Phe Gly Leu Ala Arg Asp Ile Asn Asn Ile Asp Tyr Tyr Lys Lys Thr
625                 630                 635                 640

Thr Asn Gly Arg Leu Pro Val Lys Trp Met Ala Pro Glu Ala Leu Phe
```

```
                645                 650                 655
Asp Arg Val Tyr Thr His Gln Ser Asp Val Trp Ser Phe Gly Val Leu
            660                 665                 670

Met Trp Glu Ile Phe Thr Leu Gly Gly Ser Pro Tyr Pro Gly Ile Pro
        675                 680                 685

Val Glu Glu Leu Phe Lys Leu Leu Lys Glu Gly His Arg Met Asp Lys
    690                 695                 700

Pro Ala Asn Cys Thr Asn Glu Leu Tyr Met Met Met Arg Asp Cys Trp
705                 710                 715                 720

His Ala Val Pro Ser Gln Arg Pro Thr Phe Lys Gln Leu Val Glu Asp
            725                 730                 735

Leu Asp Arg Ile Leu Thr Leu Thr Thr Asn Glu Glu Tyr Leu Asp Leu
        740                 745                 750

Ser Gln Pro Leu Glu Gln Tyr Ser Pro Ser Tyr Pro Asp Thr Arg Ser
    755                 760                 765

Ser Cys Ser Ser Gly Asp Asp Ser Val Phe Ser Pro Asp Pro Met Pro
770                 775                 780

Tyr Glu Pro Cys Leu Pro Gln Tyr Pro His Ile Asn Gly Ser Val Lys
785                 790                 795                 800

Thr

<210> SEQ ID NO 2
<211> LENGTH: 444
<212> TYPE: PRT
<213> ORGANISM: Artificial Sequence
<220> FEATURE:
<223> OTHER INFORMATION: anti-FGFR2b heavy chain
<220> FEATURE:
<221> NAME/KEY: MISC_FEATURE
<222> LOCATION: (294)..(294)
<223> OTHER INFORMATION: Asn297

<400> SEQUENCE: 2

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Thr Thr Tyr
            20                  25                  30

Asn Val His Trp Val Arg Gln Ala Pro Gly Gln Gly Leu Glu Trp Ile
        35                  40                  45

Gly Ser Ile Tyr Pro Asp Asn Gly Asp Thr Ser Tyr Asn Gln Asn Phe
    50                  55                  60

Lys Gly Arg Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Gly Asp Phe Ala Tyr Trp Gly Gln Gly Thr Leu Val Thr Val
        100                 105                 110

Ser Ser Ala Ser Thr Lys Gly Pro Ser Val Phe Pro Leu Ala Pro Ser
    115                 120                 125

Ser Lys Ser Thr Ser Gly Gly Thr Ala Ala Leu Gly Cys Leu Val Lys
130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
            165                 170                 175

Tyr Ser Leu Ser Ser Val Val Thr Val Pro Ser Ser Ser Leu Gly Thr
```

```
                180             185                 190
Gln Thr Tyr Ile Cys Asn Val Asn His Lys Pro Ser Asn Thr Lys Val
            195                 200             205

Asp Lys Arg Val Glu Pro Lys Ser Cys Asp Lys Thr His Thr Cys Pro
            210                 215             220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250             255

Thr Cys Val Val Val Asp Val Ser His Glu Asp Pro Glu Val Lys Phe
            260                 265             270

Asn Trp Tyr Val Asp Gly Val Glu Val His Asn Ala Lys Thr Lys Pro
            275                 280             285

Arg Glu Glu Gln Tyr Asn Ser Thr Tyr Arg Val Val Ser Val Leu Thr
            290                 295             300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
            325                 330             335

Lys Gly Gln Pro Arg Glu Pro Gln Val Tyr Thr Leu Pro Pro Ser Arg
            340                 345             350

Glu Glu Met Thr Lys Asn Gln Val Ser Leu Thr Cys Leu Val Lys Gly
            355                 360             365

Phe Tyr Pro Ser Asp Ile Ala Val Glu Trp Glu Ser Asn Gly Gln Pro
            370                 375             380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
            405                 410             415

Gly Asn Val Phe Ser Cys Ser Val Met His Glu Ala Leu His Asn His
            420                 425             430

Tyr Thr Gln Lys Ser Leu Ser Leu Ser Pro Gly Lys
            435                 440

<210> SEQ ID NO 3
<211> LENGTH: 214
<212> TYPE: PRT
<213> ORGANISM: Artificial Sequence
<220> FEATURE:
<223> OTHER INFORMATION: anti-FGFR2b light chain

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Gly Val Ser Asn Asp
            20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
            50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Ser Thr Thr Pro Tyr
            85                  90                  95

Thr Phe Gly Gln Gly Thr Lys Leu Glu Ile Lys Arg Thr Val Ala Ala
```

```
                100                 105                 110
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 4
<211> LENGTH: 114
<212> TYPE: PRT
<213> ORGANISM: Artificial Sequence
<220> FEATURE:
<223> OTHER INFORMATION: anti-FGFR2b heavy chain variable region

<400> SEQUENCE: 4

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Thr Thr Tyr
            20                  25                  30

Asn Val His Trp Val Arg Gln Ala Pro Gly Gln Gly Leu Glu Trp Ile
        35                  40                  45

Gly Ser Ile Tyr Pro Asp Asn Gly Asp Thr Ser Tyr Asn Gln Asn Phe
    50                  55                  60

Lys Gly Arg Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Phe Ala Tyr Trp Gly Gln Gly Thr Leu Val Thr Val
            100                 105                 110

Ser Ser

<210> SEQ ID NO 5
<211> LENGTH: 107
<212> TYPE: PRT
<213> ORGANISM: Artificial Sequence
<220> FEATURE:
<223> OTHER INFORMATION: anti-FGFR2b light chain variable region

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Gly Val Ser Asn Asp
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
```

```
                65                  70                  75                  80
Glu Asp Ile Ala Thr Tyr Tyr Cys Gln Gln His Ser Thr Thr Pro Tyr
                    85                  90                  95

Thr Phe Gly Gln Gly Thr Lys Leu Glu Ile Lys
            100                 105

<210> SEQ ID NO 6
<211> LENGTH: 5
<212> TYPE: PRT
<213> ORGANISM: Artificial Sequence
<220> FEATURE:
<223> OTHER INFORMATION: anti-FGFR2b heavy chain (HC) HVR1

<400> SEQUENCE: 6

Thr Tyr Asn Val His
1               5

<210> SEQ ID NO 7
<211> LENGTH: 17
<212> TYPE: PRT
<213> ORGANISM: Artificial Sequence
<220> FEATURE:
<223> OTHER INFORMATION: anti-FGFR2b HC HVR2

<400> SEQUENCE: 7

Ser Ile Tyr Pro Asp Asn Gly Asp Thr Ser Tyr Asn Gln Asn Phe Lys
1               5                   10                  15

Gly

<210> SEQ ID NO 8
<211> LENGTH: 5
<212> TYPE: PRT
<213> ORGANISM: Artificial Sequence
<220> FEATURE:
<223> OTHER INFORMATION: anti-FGFR2b HC HVR3

<400> SEQUENCE: 8

Gly Asp Phe Ala Tyr
1               5

<210> SEQ ID NO 9
<211> LENGTH: 11
<212> TYPE: PRT
<213> ORGANISM: Artificial Sequence
<220> FEATURE:
<223> OTHER INFORMATION: anti-FGFR2b light chain (LC) HVR1

<400> SEQUENCE: 9

Lys Ala Ser Gln Gly Val Ser Asn Asp Val Ala
1               5                   10

<210> SEQ ID NO 10
<211> LENGTH: 7
<212> TYPE: PRT
<213> ORGANISM: Artificial Sequence
<220> FEATURE:
<223> OTHER INFORMATION: anti-FGFR2b LC HVR2

<400> SEQUENCE: 10

Ser Ala Ser Tyr Arg Tyr Thr
1               5

<210> SEQ ID NO 11
<211> LENGTH: 9
<212> TYPE: PRT
```

<213> ORGANISM: Artificial Sequence
<220> FEATURE:
<223> OTHER INFORMATION: anti-FGFR2b LC HVR3

<400> SEQUENCE: 11

Gln Gln His Ser Thr Thr Pro Tyr Thr
1               5

<210> SEQ ID NO 12
<211> LENGTH: 444
<212> TYPE: PRT
<213> ORGANISM: Artificial Sequence
<220> FEATURE:
<223> OTHER INFORMATION: anti-FGFR2b N297Q heavy chain
<220> FEATURE:
<221> NAME/KEY: MISC_FEATURE
<222> LOCATION: (294)..(294)
<223> OTHER INFORMATION: N297Q

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Thr Thr Tyr
            20                  25                  30

Asn Val His Trp Val Arg Gln Ala Pro Gly Gln Gly Leu Glu Trp Ile
        35                  40                  45

Gly Ser Ile Tyr Pro Asp Asn Gly Asp Thr Ser Tyr Asn Gln Asn Phe
    50                  55                  60

Lys Gly Arg Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Phe Ala Tyr Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Arg Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Gln Ser Thr Tyr Arg Val Val Ser Val Leu Thr
    290                 295                 300

```
Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
            435                 440
```

<210> SEQ ID NO 13
<211> LENGTH: 800
<212> TYPE: PRT
<213> ORGANISM: Homo sapiens
<220> FEATURE:
<221> NAME/KEY: MISC_FEATURE
<223> OTHER INFORMATION: Mature human FGFR2-IIIc

<400> SEQUENCE: 13

```
Arg Pro Ser Phe Ser Leu Val Glu Asp Thr Thr Leu Glu Pro Glu Glu
1               5                   10                  15

Pro Pro Thr Lys Tyr Gln Ile Ser Gln Pro Glu Val Tyr Val Ala Ala
                20                  25                  30

Pro Gly Glu Ser Leu Glu Val Arg Cys Leu Leu Lys Asp Ala Ala Val
            35                  40                  45

Ile Ser Trp Thr Lys Asp Gly Val His Leu Gly Pro Asn Asn Arg Thr
50                  55                  60

Val Leu Ile Gly Glu Tyr Leu Gln Ile Lys Gly Ala Thr Pro Arg Asp
65                  70                  75                  80

Ser Gly Leu Tyr Ala Cys Thr Ala Ser Arg Thr Val Asp Ser Glu Thr
                85                  90                  95

Trp Tyr Phe Met Val Asn Val Thr Asp Ala Ile Ser Ser Gly Asp Asp
            100                 105                 110

Glu Asp Asp Thr Asp Gly Ala Glu Asp Phe Val Ser Glu Asn Ser Asn
        115                 120                 125

Asn Lys Arg Ala Pro Tyr Trp Thr Asn Thr Glu Lys Met Glu Lys Arg
    130                 135                 140

Leu His Ala Val Pro Ala Ala Asn Thr Val Lys Phe Arg Cys Pro Ala
145                 150                 155                 160

Gly Gly Asn Pro Met Pro Thr Met Arg Trp Leu Lys Asn Gly Lys Glu
                165                 170                 175

Phe Lys Gln Glu His Arg Ile Gly Gly Tyr Lys Val Arg Asn Gln His
            180                 185                 190

Trp Ser Leu Ile Met Glu Ser Val Val Pro Ser Asp Lys Gly Asn Tyr
        195                 200                 205

Thr Cys Val Val Glu Asn Glu Tyr Gly Ser Ile Asn His Thr Tyr His
```

-continued

```
            210                 215                 220
Leu Asp Val Val Glu Arg Ser Pro His Arg Pro Ile Leu Gln Ala Gly
225                 230                 235                 240

Leu Pro Ala Asn Ala Ser Thr Val Val Gly Gly Asp Val Glu Phe Val
                245                 250                 255

Cys Lys Val Tyr Ser Asp Ala Gln Pro His Ile Gln Trp Ile Lys His
                260                 265                 270

Val Glu Lys Asn Gly Ser Lys Tyr Gly Pro Asp Gly Leu Pro Tyr Leu
                275                 280                 285

Lys Val Leu Lys Ala Ala Gly Val Asn Thr Thr Asp Lys Glu Ile Glu
                290                 295                 300

Val Leu Tyr Ile Arg Asn Val Thr Phe Glu Asp Ala Gly Glu Tyr Thr
305                 310                 315                 320

Cys Leu Ala Gly Asn Ser Ile Gly Ile Ser Phe His Ser Ala Trp Leu
                325                 330                 335

Thr Val Leu Pro Ala Pro Gly Arg Glu Lys Glu Ile Thr Ala Ser Pro
                340                 345                 350

Asp Tyr Leu Glu Ile Ala Ile Tyr Cys Ile Gly Val Phe Leu Ile Ala
                355                 360                 365

Cys Met Val Val Thr Val Ile Leu Cys Arg Met Lys Asn Thr Thr Lys
                370                 375                 380

Lys Pro Asp Phe Ser Ser Gln Pro Ala Val His Lys Leu Thr Lys Arg
385                 390                 395                 400

Ile Pro Leu Arg Arg Gln Val Thr Val Ser Ala Glu Ser Ser Ser Ser
                405                 410                 415

Met Asn Ser Asn Thr Pro Leu Val Arg Ile Thr Thr Arg Leu Ser Ser
                420                 425                 430

Thr Ala Asp Thr Pro Met Leu Ala Gly Val Ser Glu Tyr Glu Leu Pro
                435                 440                 445

Glu Asp Pro Lys Trp Glu Phe Pro Arg Asp Lys Leu Thr Leu Gly Lys
450                 455                 460

Pro Leu Gly Glu Gly Cys Phe Gly Gln Val Val Met Ala Glu Ala Val
465                 470                 475                 480

Gly Ile Asp Lys Asp Lys Pro Lys Glu Ala Val Thr Val Ala Val Lys
                485                 490                 495

Met Leu Lys Asp Asp Ala Thr Glu Lys Asp Leu Ser Asp Leu Val Ser
                500                 505                 510

Glu Met Glu Met Met Lys Met Ile Gly Lys His Lys Asn Ile Ile Asn
                515                 520                 525

Leu Leu Gly Ala Cys Thr Gln Asp Gly Pro Leu Tyr Val Ile Val Glu
                530                 535                 540

Tyr Ala Ser Lys Gly Asn Leu Arg Glu Tyr Leu Arg Ala Arg Arg Pro
545                 550                 555                 560

Pro Gly Met Glu Tyr Ser Tyr Asp Ile Asn Arg Val Pro Glu Glu Gln
                565                 570                 575

Met Thr Phe Lys Asp Leu Val Ser Cys Thr Tyr Gln Leu Ala Arg Gly
                580                 585                 590

Met Glu Tyr Leu Ala Ser Gln Lys Cys Ile His Arg Asp Leu Ala Ala
                595                 600                 605

Arg Asn Val Leu Val Thr Glu Asn Asn Val Met Lys Ile Ala Asp Phe
                610                 615                 620

Gly Leu Ala Arg Asp Ile Asn Asn Ile Asp Tyr Tyr Lys Lys Thr Thr
625                 630                 635                 640
```

```
Asn Gly Arg Leu Pro Val Lys Trp Met Ala Pro Glu Ala Leu Phe Asp
                645                 650                 655

Arg Val Tyr Thr His Gln Ser Asp Val Trp Ser Phe Gly Val Leu Met
            660                 665                 670

Trp Glu Ile Phe Thr Leu Gly Gly Ser Pro Tyr Pro Gly Ile Pro Val
        675                 680                 685

Glu Glu Leu Phe Lys Leu Leu Lys Glu Gly His Arg Met Asp Lys Pro
690                 695                 700

Ala Asn Cys Thr Asn Glu Leu Tyr Met Met Met Arg Asp Cys Trp His
705                 710                 715                 720

Ala Val Pro Ser Gln Arg Pro Thr Phe Lys Gln Leu Val Glu Asp Leu
                725                 730                 735

Asp Arg Ile Leu Thr Leu Thr Thr Asn Glu Glu Tyr Leu Asp Leu Ser
            740                 745                 750

Gln Pro Leu Glu Gln Tyr Ser Pro Ser Tyr Pro Asp Thr Arg Ser Ser
        755                 760                 765

Cys Ser Ser Gly Asp Asp Ser Val Phe Ser Pro Asp Pro Met Pro Tyr
770                 775                 780

Glu Pro Cys Leu Pro Gln Tyr Pro His Ile Asn Gly Ser Val Lys Thr
785                 790                 795                 800

<210> SEQ ID NO 14
<211> LENGTH: 356
<212> TYPE: PRT
<213> ORGANISM: Homo sapiens
<220> FEATURE:
<221> NAME/KEY: MISC_FEATURE
<223> OTHER INFORMATION: FGFR2 ECD

<400> SEQUENCE: 14

Arg Pro Ser Phe Ser Leu Val Glu Asp Thr Thr Leu Glu Pro Glu Glu
1               5                   10                  15

Pro Pro Thr Lys Tyr Gln Ile Ser Gln Pro Glu Val Tyr Val Ala Ala
            20                  25                  30

Pro Gly Glu Ser Leu Glu Val Arg Cys Leu Leu Lys Asp Ala Ala Val
        35                  40                  45

Ile Ser Trp Thr Lys Asp Gly Val His Leu Gly Pro Asn Asn Arg Thr
50                  55                  60

Val Leu Ile Gly Glu Tyr Leu Gln Ile Lys Gly Ala Thr Pro Arg Asp
65                  70                  75                  80

Ser Gly Leu Tyr Ala Cys Thr Ala Ser Arg Thr Val Asp Ser Glu Thr
                85                  90                  95

Trp Tyr Phe Met Val Asn Val Thr Asp Ala Ile Ser Ser Gly Asp Asp
            100                 105                 110

Glu Asp Asp Thr Asp Gly Ala Glu Asp Phe Val Ser Glu Asn Ser Asn
        115                 120                 125

Asn Lys Arg Ala Pro Tyr Trp Thr Asn Thr Glu Lys Met Glu Lys Arg
130                 135                 140

Leu His Ala Val Pro Ala Ala Asn Thr Val Lys Phe Arg Cys Pro Ala
145                 150                 155                 160

Gly Gly Asn Pro Met Pro Thr Met Arg Trp Leu Lys Asn Gly Lys Glu
                165                 170                 175

Phe Lys Gln Glu His Arg Ile Gly Gly Tyr Lys Val Arg Asn Gln His
            180                 185                 190

Trp Ser Leu Ile Met Glu Ser Val Val Pro Ser Asp Lys Gly Asn Tyr
```

```
                195                 200                 205
Thr Cys Val Val Glu Asn Glu Tyr Gly Ser Ile Asn His Thr Tyr His
    210                 215                 220

Leu Asp Val Val Glu Arg Ser Pro His Arg Pro Ile Leu Gln Ala Gly
225                 230                 235                 240

Leu Pro Ala Asn Ala Ser Thr Val Val Gly Asp Val Glu Phe Val
                245                 250                 255

Cys Lys Val Tyr Ser Asp Ala Gln Pro His Ile Gln Trp Ile Lys His
                260                 265                 270

Val Glu Lys Asn Gly Ser Lys Tyr Gly Pro Asp Gly Leu Pro Tyr Leu
                275                 280                 285

Lys Val Leu Lys Ala Ala Gly Val Asn Thr Thr Asp Lys Glu Ile Glu
                290                 295                 300

Val Leu Tyr Ile Arg Asn Val Thr Phe Glu Asp Ala Gly Glu Tyr Thr
305                 310                 315                 320

Cys Leu Ala Gly Asn Ser Ile Gly Ile Ser Phe His Ser Ala Trp Leu
                325                 330                 335

Thr Val Leu Pro Ala Pro Gly Arg Glu Lys Glu Ile Thr Ala Ser Pro
                340                 345                 350

Asp Tyr Leu Glu
        355

<210> SEQ ID NO 15
<211> LENGTH: 353
<212> TYPE: PRT
<213> ORGANISM: Homo sapiens
<220> FEATURE:
<221> NAME/KEY: MISC_FEATURE
<223> OTHER INFORMATION: FGFR2 ECD delta-3

<400> SEQUENCE: 15

Arg Pro Ser Phe Ser Leu Val Glu Asp Thr Thr Leu Glu Pro Glu Glu
1               5                   10                  15

Pro Pro Thr Lys Tyr Gln Ile Ser Gln Pro Glu Val Tyr Val Ala Ala
                20                  25                  30

Pro Gly Glu Ser Leu Glu Val Arg Cys Leu Leu Lys Asp Ala Ala Val
                35                  40                  45

Ile Ser Trp Thr Lys Asp Gly Val His Leu Gly Pro Asn Asn Arg Thr
    50                  55                  60

Val Leu Ile Gly Glu Tyr Leu Gln Ile Lys Gly Ala Thr Pro Arg Asp
65                  70                  75                  80

Ser Gly Leu Tyr Ala Cys Thr Ala Ser Arg Thr Val Asp Ser Glu Thr
                85                  90                  95

Trp Tyr Phe Met Val Asn Val Thr Asp Ala Ile Ser Ser Gly Asp Asp
                100                 105                 110

Glu Asp Asp Thr Asp Gly Ala Glu Asp Phe Val Ser Glu Asn Ser Asn
            115                 120                 125

Asn Lys Arg Ala Pro Tyr Trp Thr Asn Thr Glu Lys Met Glu Lys Arg
            130                 135                 140

Leu His Ala Val Pro Ala Ala Asn Thr Val Lys Phe Arg Cys Pro Ala
145                 150                 155                 160

Gly Gly Asn Pro Met Pro Thr Met Arg Trp Leu Lys Asn Gly Lys Glu
                165                 170                 175

Phe Lys Gln Glu His Arg Ile Gly Gly Tyr Lys Val Arg Asn Gln His
                180                 185                 190
```

Trp Ser Leu Ile Met Glu Ser Val Pro Ser Asp Lys Gly Asn Tyr
            195                 200                 205

Thr Cys Val Val Glu Asn Glu Tyr Gly Ser Ile Asn His Thr Tyr His
        210                 215                 220

Leu Asp Val Val Glu Arg Ser Pro His Arg Pro Ile Leu Gln Ala Gly
225                 230                 235                 240

Leu Pro Ala Asn Ala Ser Thr Val Val Gly Asp Val Glu Phe Val
                245                 250                 255

Cys Lys Val Tyr Ser Asp Ala Gln Pro His Ile Gln Trp Ile Lys His
            260                 265                 270

Val Glu Lys Asn Gly Ser Lys Tyr Gly Pro Asp Gly Leu Pro Tyr Leu
            275                 280                 285

Lys Val Leu Lys Ala Ala Gly Val Asn Thr Thr Asp Lys Glu Ile Glu
290                 295                 300

Val Leu Tyr Ile Arg Asn Val Thr Phe Glu Asp Ala Gly Glu Tyr Thr
305                 310                 315                 320

Cys Leu Ala Gly Asn Ser Ile Gly Ile Ser Phe His Ser Ala Trp Leu
                325                 330                 335

Thr Val Leu Pro Ala Pro Gly Arg Glu Lys Glu Ile Thr Ala Ser Pro
                340                 345                 350

Asp

<210> SEQ ID NO 16
<211> LENGTH: 352
<212> TYPE: PRT
<213> ORGANISM: Homo sapiens
<220> FEATURE:
<221> NAME/KEY: MISC_FEATURE
<223> OTHER INFORMATION: FGFR2 ECD delta-4

<400> SEQUENCE: 16

Arg Pro Ser Phe Ser Leu Val Glu Asp Thr Thr Leu Glu Pro Glu Glu
1               5                   10                  15

Pro Pro Thr Lys Tyr Gln Ile Ser Gln Pro Glu Val Tyr Val Ala Ala
                20                  25                  30

Pro Gly Glu Ser Leu Glu Val Arg Cys Leu Leu Lys Asp Ala Ala Val
            35                  40                  45

Ile Ser Trp Thr Lys Asp Gly Val His Leu Gly Pro Asn Asn Arg Thr
50                  55                  60

Val Leu Ile Gly Glu Tyr Leu Gln Ile Lys Gly Ala Thr Pro Arg Asp
65                  70                  75                  80

Ser Gly Leu Tyr Ala Cys Thr Ala Ser Arg Thr Val Asp Ser Glu Thr
                85                  90                  95

Trp Tyr Phe Met Val Asn Val Thr Asp Ala Ile Ser Ser Gly Asp Asp
            100                 105                 110

Glu Asp Asp Thr Asp Gly Ala Glu Asp Phe Val Ser Glu Asn Ser Asn
        115                 120                 125

Asn Lys Arg Ala Pro Tyr Trp Thr Asn Thr Glu Lys Met Glu Lys Arg
130                 135                 140

Leu His Ala Val Pro Ala Ala Asn Thr Val Lys Phe Arg Cys Pro Ala
145                 150                 155                 160

Gly Gly Asn Pro Met Pro Thr Met Arg Trp Leu Lys Asn Gly Lys Glu
                165                 170                 175

Phe Lys Gln Glu His Arg Ile Gly Gly Tyr Lys Val Arg Asn Gln His
            180                 185                 190

```
Trp Ser Leu Ile Met Glu Ser Val Val Pro Ser Asp Lys Gly Asn Tyr
            195                 200                 205

Thr Cys Val Val Glu Asn Glu Tyr Gly Ser Ile Asn His Thr Tyr His
    210                 215                 220

Leu Asp Val Val Glu Arg Ser Pro His Arg Pro Ile Leu Gln Ala Gly
225                 230                 235                 240

Leu Pro Ala Asn Ala Ser Thr Val Val Gly Gly Asp Val Glu Phe Val
            245                 250                 255

Cys Lys Val Tyr Ser Asp Ala Gln Pro His Ile Gln Trp Ile Lys His
            260                 265                 270

Val Glu Lys Asn Gly Ser Lys Tyr Gly Pro Asp Gly Leu Pro Tyr Leu
            275                 280                 285

Lys Val Leu Lys Ala Ala Gly Val Asn Thr Thr Asp Lys Glu Ile Glu
            290                 295                 300

Val Leu Tyr Ile Arg Asn Val Thr Phe Glu Asp Ala Gly Glu Tyr Thr
305                 310                 315                 320

Cys Leu Ala Gly Asn Ser Ile Gly Ile Ser Phe His Ser Ala Trp Leu
            325                 330                 335

Thr Val Leu Pro Ala Pro Gly Arg Glu Lys Glu Ile Thr Ala Ser Pro
            340                 345                 350

<210> SEQ ID NO 17
<211> LENGTH: 351
<212> TYPE: PRT
<213> ORGANISM: Homo sapiens
<220> FEATURE:
<221> NAME/KEY: MISC_FEATURE
<223> OTHER INFORMATION: FGFR2 ECD delta-5

<400> SEQUENCE: 17

Arg Pro Ser Phe Ser Leu Val Glu Asp Thr Thr Leu Glu Pro Glu Glu
1               5                   10                  15

Pro Pro Thr Lys Tyr Gln Ile Ser Gln Pro Glu Val Tyr Val Ala Ala
            20                  25                  30

Pro Gly Glu Ser Leu Glu Val Arg Cys Leu Leu Lys Asp Ala Ala Val
            35                  40                  45

Ile Ser Trp Thr Lys Asp Gly Val His Leu Gly Pro Asn Asn Arg Thr
    50                  55                  60

Val Leu Ile Gly Glu Tyr Leu Gln Ile Lys Gly Ala Thr Pro Arg Asp
65                  70                  75                  80

Ser Gly Leu Tyr Ala Cys Thr Ala Ser Arg Thr Val Asp Ser Glu Thr
            85                  90                  95

Trp Tyr Phe Met Val Asn Val Thr Asp Ala Ile Ser Ser Gly Asp Asp
            100                 105                 110

Glu Asp Asp Thr Asp Gly Ala Glu Asp Phe Val Ser Glu Asn Ser Asn
            115                 120                 125

Asn Lys Arg Ala Pro Tyr Trp Thr Asn Thr Glu Lys Met Glu Lys Arg
            130                 135                 140

Leu His Ala Val Pro Ala Ala Asn Thr Val Lys Phe Arg Cys Pro Ala
145                 150                 155                 160

Gly Gly Asn Pro Met Pro Thr Met Arg Trp Leu Lys Asn Gly Lys Glu
            165                 170                 175

Phe Lys Gln Glu His Arg Ile Gly Gly Tyr Lys Val Arg Asn Gln His
            180                 185                 190

Trp Ser Leu Ile Met Glu Ser Val Val Pro Ser Asp Lys Gly Asn Tyr
            195                 200                 205
```

```
Thr Cys Val Val Glu Asn Glu Tyr Gly Ser Ile Asn His Thr Tyr His
    210                 215                 220

Leu Asp Val Val Glu Arg Ser Pro His Arg Pro Ile Leu Gln Ala Gly
225                 230                 235                 240

Leu Pro Ala Asn Ala Ser Thr Val Val Gly Gly Asp Val Glu Phe Val
                245                 250                 255

Cys Lys Val Tyr Ser Asp Ala Gln Pro His Ile Gln Trp Ile Lys His
                260                 265                 270

Val Glu Lys Asn Gly Ser Lys Tyr Gly Pro Asp Gly Leu Pro Tyr Leu
            275                 280                 285

Lys Val Leu Lys Ala Ala Gly Val Asn Thr Thr Asp Lys Glu Ile Glu
290                 295                 300

Val Leu Tyr Ile Arg Asn Val Thr Phe Glu Asp Ala Gly Glu Tyr Thr
305                 310                 315                 320

Cys Leu Ala Gly Asn Ser Ile Gly Ile Ser Phe His Ser Ala Trp Leu
                325                 330                 335

Thr Val Leu Pro Ala Pro Gly Arg Glu Lys Glu Ile Thr Ala Ser
                340                 345                 350

<210> SEQ ID NO 18
<211> LENGTH: 348
<212> TYPE: PRT
<213> ORGANISM: Homo sapiens
<220> FEATURE:
<221> NAME/KEY: MISC_FEATURE
<223> OTHER INFORMATION: FGFR2 ECD delta-8

<400> SEQUENCE: 18

Arg Pro Ser Phe Ser Leu Val Glu Asp Thr Thr Leu Glu Pro Glu Glu
1               5                   10                  15

Pro Pro Thr Lys Tyr Gln Ile Ser Gln Pro Glu Val Tyr Val Ala Ala
                20                  25                  30

Pro Gly Glu Ser Leu Glu Val Arg Cys Leu Leu Lys Asp Ala Ala Val
            35                  40                  45

Ile Ser Trp Thr Lys Asp Gly Val His Leu Gly Pro Asn Asn Arg Thr
50                  55                  60

Val Leu Ile Gly Glu Tyr Leu Gln Ile Lys Gly Ala Thr Pro Arg Asp
65                  70                  75                  80

Ser Gly Leu Tyr Ala Cys Thr Ala Ser Arg Thr Val Asp Ser Glu Thr
                85                  90                  95

Trp Tyr Phe Met Val Asn Val Thr Asp Ala Ile Ser Ser Gly Asp Asp
                100                 105                 110

Glu Asp Asp Thr Asp Gly Ala Glu Asp Phe Val Ser Glu Asn Ser Asn
            115                 120                 125

Asn Lys Arg Ala Pro Tyr Trp Thr Asn Thr Glu Lys Met Glu Lys Arg
130                 135                 140

Leu His Ala Val Pro Ala Ala Asn Thr Val Lys Phe Arg Cys Pro Ala
145                 150                 155                 160

Gly Gly Asn Pro Met Pro Thr Met Arg Trp Leu Lys Asn Gly Lys Glu
                165                 170                 175

Phe Lys Gln Glu His Arg Ile Gly Gly Tyr Lys Val Arg Asn Gln His
            180                 185                 190

Trp Ser Leu Ile Met Glu Ser Val Val Pro Ser Asp Lys Gly Asn Tyr
        195                 200                 205

Thr Cys Val Val Glu Asn Glu Tyr Gly Ser Ile Asn His Thr Tyr His
```

```
                 210                 215                 220
Leu Asp Val Val Glu Arg Ser Pro His Arg Pro Ile Leu Gln Ala Gly
225                 230                 235                 240

Leu Pro Ala Asn Ala Ser Thr Val Val Gly Gly Asp Val Glu Phe Val
                245                 250                 255

Cys Lys Val Tyr Ser Asp Ala Gln Pro His Ile Gln Trp Ile Lys His
                260                 265                 270

Val Glu Lys Asn Gly Ser Lys Tyr Gly Pro Asp Gly Leu Pro Tyr Leu
                275                 280                 285

Lys Val Leu Lys Ala Ala Gly Val Asn Thr Thr Asp Lys Glu Ile Glu
                290                 295                 300

Val Leu Tyr Ile Arg Asn Val Thr Phe Glu Asp Ala Gly Glu Tyr Thr
305                 310                 315                 320

Cys Leu Ala Gly Asn Ser Ile Gly Ile Ser Phe His Ser Ala Trp Leu
                325                 330                 335

Thr Val Leu Pro Ala Pro Gly Arg Glu Lys Glu Ile
                340                 345

<210> SEQ ID NO 19
<211> LENGTH: 347
<212> TYPE: PRT
<213> ORGANISM: Homo sapiens
<220> FEATURE:
<221> NAME/KEY: MISC_FEATURE
<223> OTHER INFORMATION: FGFR2 ECD delta-9

<400> SEQUENCE: 19

Arg Pro Ser Phe Ser Leu Val Glu Asp Thr Thr Leu Glu Pro Glu Glu
1               5                   10                  15

Pro Pro Thr Lys Tyr Gln Ile Ser Gln Pro Glu Val Tyr Val Ala Ala
                20                  25                  30

Pro Gly Glu Ser Leu Glu Val Arg Cys Leu Leu Lys Asp Ala Ala Val
                35                  40                  45

Ile Ser Trp Thr Lys Asp Gly Val His Leu Gly Pro Asn Asn Arg Thr
50                  55                  60

Val Leu Ile Gly Glu Tyr Leu Gln Ile Lys Gly Ala Thr Pro Arg Asp
65                  70                  75                  80

Ser Gly Leu Tyr Ala Cys Thr Ala Ser Arg Thr Val Asp Ser Glu Thr
                85                  90                  95

Trp Tyr Phe Met Val Asn Val Thr Asp Ala Ile Ser Ser Gly Asp Asp
                100                 105                 110

Glu Asp Asp Thr Asp Gly Ala Glu Asp Phe Val Ser Glu Asn Ser Asn
                115                 120                 125

Asn Lys Arg Ala Pro Tyr Trp Thr Asn Thr Glu Lys Met Glu Lys Arg
130                 135                 140

Leu His Ala Val Pro Ala Ala Asn Thr Val Lys Phe Arg Cys Pro Ala
145                 150                 155                 160

Gly Gly Asn Pro Met Pro Thr Met Arg Trp Leu Lys Asn Gly Lys Glu
                165                 170                 175

Phe Lys Gln Glu His Arg Ile Gly Gly Tyr Lys Val Arg Asn Gln His
                180                 185                 190

Trp Ser Leu Ile Met Glu Ser Val Val Pro Ser Asp Lys Gly Asn Tyr
                195                 200                 205

Thr Cys Val Val Glu Asn Glu Tyr Gly Ser Ile Asn His Thr Tyr His
                210                 215                 220
```

```
Leu Asp Val Val Glu Arg Ser Pro His Arg Pro Ile Leu Gln Ala Gly
225                 230                 235                 240

Leu Pro Ala Asn Ala Ser Thr Val Val Gly Gly Asp Val Glu Phe Val
                245                 250                 255

Cys Lys Val Tyr Ser Asp Ala Gln Pro His Ile Gln Trp Ile Lys His
            260                 265                 270

Val Glu Lys Asn Gly Ser Lys Tyr Gly Pro Asp Gly Leu Pro Tyr Leu
        275                 280                 285

Lys Val Leu Lys Ala Ala Gly Val Asn Thr Thr Asp Lys Glu Ile Glu
    290                 295                 300

Val Leu Tyr Ile Arg Asn Val Thr Phe Glu Asp Ala Gly Glu Tyr Thr
305                 310                 315                 320

Cys Leu Ala Gly Asn Ser Ile Gly Ile Ser Phe His Ser Ala Trp Leu
                325                 330                 335

Thr Val Leu Pro Ala Pro Gly Arg Glu Lys Glu
                340                 345
```

<210> SEQ ID NO 20
<211> LENGTH: 346
<212> TYPE: PRT
<213> ORGANISM: Homo sapiens
<220> FEATURE:
<221> NAME/KEY: MISC_FEATURE
<223> OTHER INFORMATION: FGFR2 ECD delta-10

<400> SEQUENCE: 20

```
Arg Pro Ser Phe Ser Leu Val Glu Asp Thr Thr Leu Glu Pro Glu Glu
1               5                   10                  15

Pro Pro Thr Lys Tyr Gln Ile Ser Gln Pro Glu Val Tyr Val Ala Ala
                20                  25                  30

Pro Gly Glu Ser Leu Glu Val Arg Cys Leu Leu Lys Asp Ala Ala Val
            35                  40                  45

Ile Ser Trp Thr Lys Asp Gly Val His Leu Gly Pro Asn Asn Arg Thr
    50                  55                  60

Val Leu Ile Gly Glu Tyr Leu Gln Ile Lys Gly Ala Thr Pro Arg Asp
65                  70                  75                  80

Ser Gly Leu Tyr Ala Cys Thr Ala Ser Arg Thr Val Asp Ser Glu Thr
                85                  90                  95

Trp Tyr Phe Met Val Asn Val Thr Asp Ala Ile Ser Ser Gly Asp Asp
                100                 105                 110

Glu Asp Asp Thr Asp Gly Ala Glu Asp Phe Val Ser Glu Asn Ser Asn
            115                 120                 125

Asn Lys Arg Ala Pro Tyr Trp Thr Asn Thr Glu Lys Met Glu Lys Arg
    130                 135                 140

Leu His Ala Val Pro Ala Ala Asn Thr Val Lys Phe Arg Cys Pro Ala
145                 150                 155                 160

Gly Gly Asn Pro Met Pro Thr Met Arg Trp Leu Lys Asn Gly Lys Glu
                165                 170                 175

Phe Lys Gln Glu His Arg Ile Gly Gly Tyr Lys Val Arg Asn Gln His
            180                 185                 190

Trp Ser Leu Ile Met Glu Ser Val Val Pro Ser Asp Lys Gly Asn Tyr
    195                 200                 205

Thr Cys Val Val Glu Asn Glu Tyr Gly Ser Ile Asn His Thr Tyr His
    210                 215                 220

Leu Asp Val Val Glu Arg Ser Pro His Arg Pro Ile Leu Gln Ala Gly
225                 230                 235                 240
```

```
Leu Pro Ala Asn Ala Ser Thr Val Val Gly Gly Asp Val Glu Phe Val
                245                 250                 255

Cys Lys Val Tyr Ser Asp Ala Gln Pro His Ile Gln Trp Ile Lys His
            260                 265                 270

Val Glu Lys Asn Gly Ser Lys Tyr Gly Pro Asp Gly Leu Pro Tyr Leu
        275                 280                 285

Lys Val Leu Lys Ala Ala Gly Val Asn Thr Thr Asp Lys Glu Ile Glu
    290                 295                 300

Val Leu Tyr Ile Arg Asn Val Thr Phe Glu Asp Ala Gly Glu Tyr Thr
305                 310                 315                 320

Cys Leu Ala Gly Asn Ser Ile Gly Ile Ser Phe His Ser Ala Trp Leu
                325                 330                 335

Thr Val Leu Pro Ala Pro Gly Arg Glu Lys
            340                 345
```

<210> SEQ ID NO 21
<211> LENGTH: 342
<212> TYPE: PRT
<213> ORGANISM: Homo sapiens
<220> FEATURE:
<221> NAME/KEY: MISC_FEATURE
<223> OTHER INFORMATION: FGFR2 ECD delta-14

<400> SEQUENCE: 21

```
Arg Pro Ser Phe Ser Leu Val Glu Asp Thr Thr Leu Glu Pro Glu Glu
1               5                   10                  15

Pro Pro Thr Lys Tyr Gln Ile Ser Gln Pro Glu Val Tyr Val Ala Ala
            20                  25                  30

Pro Gly Glu Ser Leu Glu Val Arg Cys Leu Leu Lys Asp Ala Ala Val
        35                  40                  45

Ile Ser Trp Thr Lys Asp Gly Val His Leu Gly Pro Asn Asn Arg Thr
    50                  55                  60

Val Leu Ile Gly Glu Tyr Leu Gln Ile Lys Gly Ala Thr Pro Arg Asp
65                  70                  75                  80

Ser Gly Leu Tyr Ala Cys Thr Ala Ser Arg Thr Val Asp Ser Glu Thr
                85                  90                  95

Trp Tyr Phe Met Val Asn Val Thr Asp Ala Ile Ser Ser Gly Asp Asp
            100                 105                 110

Glu Asp Asp Thr Asp Gly Ala Glu Asp Phe Val Ser Glu Asn Ser Asn
        115                 120                 125

Asn Lys Arg Ala Pro Tyr Trp Thr Asn Thr Glu Lys Met Glu Lys Arg
    130                 135                 140

Leu His Ala Val Pro Ala Ala Asn Thr Val Lys Phe Arg Cys Pro Ala
145                 150                 155                 160

Gly Gly Asn Pro Met Pro Thr Met Arg Trp Leu Lys Asn Gly Lys Glu
                165                 170                 175

Phe Lys Gln Glu His Arg Ile Gly Gly Tyr Lys Val Arg Asn Gln His
            180                 185                 190

Trp Ser Leu Ile Met Glu Ser Val Val Pro Ser Asp Lys Gly Asn Tyr
        195                 200                 205

Thr Cys Val Val Glu Asn Glu Tyr Gly Ser Ile Asn His Thr Tyr His
    210                 215                 220

Leu Asp Val Val Glu Arg Ser Pro His Arg Pro Ile Leu Gln Ala Gly
225                 230                 235                 240

Leu Pro Ala Asn Ala Ser Thr Val Val Gly Gly Asp Val Glu Phe Val
```

```
            245                 250                 255
Cys Lys Val Tyr Ser Asp Ala Gln Pro His Ile Gln Trp Ile Lys His
            260                 265                 270

Val Glu Lys Asn Gly Ser Lys Tyr Gly Pro Asp Gly Leu Pro Tyr Leu
            275                 280                 285

Lys Val Leu Lys Ala Ala Gly Val Asn Thr Thr Asp Lys Glu Ile Glu
            290                 295                 300

Val Leu Tyr Ile Arg Asn Val Thr Phe Glu Asp Ala Gly Glu Tyr Thr
305                 310                 315                 320

Cys Leu Ala Gly Asn Ser Ile Gly Ile Ser Phe His Ser Ala Trp Leu
            325                 330                 335

Thr Val Leu Pro Ala Pro
            340

<210> SEQ ID NO 22
<211> LENGTH: 341
<212> TYPE: PRT
<213> ORGANISM: Homo sapiens
<220> FEATURE:
<221> NAME/KEY: MISC_FEATURE
<223> OTHER INFORMATION: FGFR2 ECD delta-15

<400> SEQUENCE: 22

Arg Pro Ser Phe Ser Leu Val Glu Asp Thr Thr Leu Glu Pro Glu Glu
1               5                   10                  15

Pro Pro Thr Lys Tyr Gln Ile Ser Gln Pro Glu Val Tyr Val Ala Ala
            20                  25                  30

Pro Gly Glu Ser Leu Glu Val Arg Cys Leu Leu Lys Asp Ala Ala Val
            35                  40                  45

Ile Ser Trp Thr Lys Asp Gly Val His Leu Gly Pro Asn Asn Arg Thr
50                  55                  60

Val Leu Ile Gly Glu Tyr Leu Gln Ile Lys Gly Ala Thr Pro Arg Asp
65                  70                  75                  80

Ser Gly Leu Tyr Ala Cys Thr Ala Ser Arg Thr Val Asp Ser Glu Thr
            85                  90                  95

Trp Tyr Phe Met Val Asn Val Thr Asp Ala Ile Ser Ser Gly Asp Asp
            100                 105                 110

Glu Asp Asp Thr Asp Gly Ala Glu Asp Phe Val Ser Glu Asn Ser Asn
            115                 120                 125

Asn Lys Arg Ala Pro Tyr Trp Thr Asn Thr Glu Lys Met Glu Lys Arg
130                 135                 140

Leu His Ala Val Pro Ala Ala Asn Thr Val Lys Phe Arg Cys Pro Ala
145                 150                 155                 160

Gly Gly Asn Pro Met Pro Thr Met Arg Trp Leu Lys Asn Gly Lys Glu
            165                 170                 175

Phe Lys Gln Glu His Arg Ile Gly Gly Tyr Lys Val Arg Asn Gln His
            180                 185                 190

Trp Ser Leu Ile Met Glu Ser Val Val Pro Ser Asp Lys Gly Asn Tyr
            195                 200                 205

Thr Cys Val Val Glu Asn Glu Tyr Gly Ser Ile Asn His Thr Tyr His
            210                 215                 220

Leu Asp Val Val Glu Arg Ser Pro His Arg Pro Ile Leu Gln Ala Gly
225                 230                 235                 240

Leu Pro Ala Asn Ala Ser Thr Val Val Gly Gly Asp Val Glu Phe Val
            245                 250                 255
```

```
Cys Lys Val Tyr Ser Asp Ala Gln Pro His Ile Gln Trp Ile Lys His
            260                 265                 270

Val Glu Lys Asn Gly Ser Lys Tyr Gly Pro Asp Gly Leu Pro Tyr Leu
        275                 280                 285

Lys Val Leu Lys Ala Ala Gly Val Asn Thr Thr Asp Lys Glu Ile Glu
    290                 295                 300

Val Leu Tyr Ile Arg Asn Val Thr Phe Glu Asp Ala Gly Glu Tyr Thr
305                 310                 315                 320

Cys Leu Ala Gly Asn Ser Ile Gly Ile Ser Phe His Ser Ala Trp Leu
                325                 330                 335

Thr Val Leu Pro Ala
            340

<210> SEQ ID NO 23
<211> LENGTH: 340
<212> TYPE: PRT
<213> ORGANISM: Homo sapiens
<220> FEATURE:
<221> NAME/KEY: MISC_FEATURE
<223> OTHER INFORMATION: FGFR2 ECD delta-16

<400> SEQUENCE: 23

Arg Pro Ser Phe Ser Leu Val Glu Asp Thr Thr Leu Glu Pro Glu Glu
1               5                   10                  15

Pro Pro Thr Lys Tyr Gln Ile Ser Gln Pro Glu Val Tyr Val Ala Ala
            20                  25                  30

Pro Gly Glu Ser Leu Glu Val Arg Cys Leu Leu Lys Asp Ala Ala Val
        35                  40                  45

Ile Ser Trp Thr Lys Asp Gly Val His Leu Gly Pro Asn Asn Arg Thr
    50                  55                  60

Val Leu Ile Gly Glu Tyr Leu Gln Ile Lys Gly Ala Thr Pro Arg Asp
65                  70                  75                  80

Ser Gly Leu Tyr Ala Cys Thr Ala Ser Arg Thr Val Asp Ser Glu Thr
                85                  90                  95

Trp Tyr Phe Met Val Asn Val Thr Asp Ala Ile Ser Ser Gly Asp Asp
            100                 105                 110

Glu Asp Asp Thr Asp Gly Ala Glu Asp Phe Val Ser Glu Asn Ser Asn
        115                 120                 125

Asn Lys Arg Ala Pro Tyr Trp Thr Asn Thr Glu Lys Met Glu Lys Arg
    130                 135                 140

Leu His Ala Val Pro Ala Ala Asn Thr Val Lys Phe Arg Cys Pro Ala
145                 150                 155                 160

Gly Gly Asn Pro Met Pro Thr Met Arg Trp Leu Lys Asn Gly Lys Glu
                165                 170                 175

Phe Lys Gln Glu His Arg Ile Gly Gly Tyr Lys Val Arg Asn Gln His
            180                 185                 190

Trp Ser Leu Ile Met Glu Ser Val Val Pro Ser Asp Lys Gly Asn Tyr
        195                 200                 205

Thr Cys Val Val Glu Asn Glu Tyr Gly Ser Ile Asn His Thr Tyr His
    210                 215                 220

Leu Asp Val Val Glu Arg Ser Pro His Arg Pro Ile Leu Gln Ala Gly
225                 230                 235                 240

Leu Pro Ala Asn Ala Ser Thr Val Val Gly Gly Asp Val Glu Phe Val
                245                 250                 255

Cys Lys Val Tyr Ser Asp Ala Gln Pro His Ile Gln Trp Ile Lys His
            260                 265                 270
```

Val Glu Lys Asn Gly Ser Lys Tyr Gly Pro Asp Gly Leu Pro Tyr Leu
            275                 280                 285

Lys Val Leu Lys Ala Ala Gly Val Asn Thr Thr Asp Lys Glu Ile Glu
            290                 295                 300

Val Leu Tyr Ile Arg Asn Val Thr Phe Glu Asp Ala Gly Glu Tyr Thr
305                 310                 315                 320

Cys Leu Ala Gly Asn Ser Ile Gly Ile Ser Phe His Ser Ala Trp Leu
            325                 330                 335

Thr Val Leu Pro
            340

<210> SEQ ID NO 24
<211> LENGTH: 339
<212> TYPE: PRT
<213> ORGANISM: Homo sapiens
<220> FEATURE:
<221> NAME/KEY: MISC_FEATURE
<223> OTHER INFORMATION: FGFR2 ECD delta-17

<400> SEQUENCE: 24

Arg Pro Ser Phe Ser Leu Val Glu Asp Thr Thr Leu Glu Pro Glu Glu
1               5                   10                  15

Pro Pro Thr Lys Tyr Gln Ile Ser Gln Pro Glu Val Tyr Val Ala Ala
            20                  25                  30

Pro Gly Glu Ser Leu Glu Val Arg Cys Leu Leu Lys Asp Ala Ala Val
            35                  40                  45

Ile Ser Trp Thr Lys Asp Gly Val His Leu Gly Pro Asn Asn Arg Thr
50                  55                  60

Val Leu Ile Gly Glu Tyr Leu Gln Ile Lys Gly Ala Thr Pro Arg Asp
65                  70                  75                  80

Ser Gly Leu Tyr Ala Cys Thr Ala Ser Arg Thr Val Asp Ser Glu Thr
            85                  90                  95

Trp Tyr Phe Met Val Asn Val Thr Asp Ala Ile Ser Ser Gly Asp Asp
            100                 105                 110

Glu Asp Asp Thr Asp Gly Ala Glu Asp Phe Val Ser Glu Asn Ser Asn
            115                 120                 125

Asn Lys Arg Ala Pro Tyr Trp Thr Asn Thr Glu Lys Met Glu Lys Arg
130                 135                 140

Leu His Ala Val Pro Ala Ala Asn Thr Val Lys Phe Arg Cys Pro Ala
145                 150                 155                 160

Gly Gly Asn Pro Met Pro Thr Met Arg Trp Leu Lys Asn Gly Lys Glu
            165                 170                 175

Phe Lys Gln Glu His Arg Ile Gly Gly Tyr Lys Val Arg Asn Gln His
            180                 185                 190

Trp Ser Leu Ile Met Glu Ser Val Val Pro Ser Asp Lys Gly Asn Tyr
            195                 200                 205

Thr Cys Val Val Glu Asn Glu Tyr Gly Ser Ile Asn His Thr Tyr His
            210                 215                 220

Leu Asp Val Val Glu Arg Ser Pro His Arg Pro Ile Leu Gln Ala Gly
225                 230                 235                 240

Leu Pro Ala Asn Ala Ser Thr Val Val Gly Gly Asp Val Glu Phe Val
            245                 250                 255

Cys Lys Val Tyr Ser Asp Ala Gln Pro His Ile Gln Trp Ile Lys His
            260                 265                 270

Val Glu Lys Asn Gly Ser Lys Tyr Gly Pro Asp Gly Leu Pro Tyr Leu

```
                    275                 280                 285
Lys Val Leu Lys Ala Ala Gly Val Asn Thr Thr Asp Lys Glu Ile Glu
    290                 295                 300

Val Leu Tyr Ile Arg Asn Val Thr Phe Glu Asp Ala Gly Glu Tyr Thr
305                 310                 315                 320

Cys Leu Ala Gly Asn Ser Ile Gly Ile Ser Phe His Ser Ala Trp Leu
                325                 330                 335

Thr Val Leu

<210> SEQ ID NO 25
<211> LENGTH: 232
<212> TYPE: PRT
<213> ORGANISM: Artificial Sequence
<220> FEATURE:
<223> OTHER INFORMATION: Fc C237S

<400> SEQUENCE: 25

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 26
<211> LENGTH: 228
<212> TYPE: PRT
<213> ORGANISM: Artificial Sequence
<220> FEATURE:
<223> OTHER INFORMATION: Fc

<400> SEQUENCE: 26

Glu Arg Lys Cys Cys Val Glu Cys Pro Pro Cys Pro Ala Pro Pro Val
```

```
            1               5                  10                 15
Ala Gly Pro Ser Val Phe Leu Phe Pro Pro Lys Pro Lys Asp Thr Leu
                20                  25                 30

Met Ile Ser Arg Thr Pro Glu Val Thr Cys Val Val Val Asp Val Ser
                35                  40                 45

His Glu Asp Pro Glu Val Gln Phe Asn Trp Tyr Val Asp Gly Val Glu
                50                  55                 60

Val His Asn Ala Lys Thr Lys Pro Arg Glu Glu Gln Phe Asn Ser Thr
 65                 70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
                100                 105                110

Ile Glu Lys Thr Ile Ser Lys Thr Lys Gly Gln Pro Arg Glu Pro Gln
                115                 120                125

Val Tyr Thr Leu Pro Pro Ser Arg Glu Glu Met Thr Lys Asn Gln Val
                130                 135                140

Ser Leu Thr Cys Leu Val Lys Gly Phe Tyr Pro Ser Asp Ile Ala Val
145                 150                 155                160

Glu Trp Glu Ser Asn Gly Gln Pro Glu Asn Asn Tyr Lys Thr Thr Pro
                165                 170                175

Pro Met Leu Asp Ser Asp Gly Ser Phe Phe Leu Tyr Ser Lys Leu Thr
                180                 185                190

Val Asp Lys Ser Arg Trp Gln Gln Gly Asn Val Phe Ser Cys Ser Val
                195                 200                205

Met His Glu Ala Leu His Asn His Tyr Thr Gln Lys Ser Leu Ser Leu
                210                 215                220

Ser Pro Gly Lys
225
```

```
<210> SEQ ID NO 27
<211> LENGTH: 229
<212> TYPE: PRT
<213> ORGANISM: Artificial Sequence
<220> FEATURE:
<223> OTHER INFORMATION: Fc

<400> SEQUENCE: 27

Glu Ser Lys Tyr Gly Pro Pro Cys Pro Ser Cys Pro Ala Pro Glu Phe
 1               5                  10                 15

Leu Gly Gly Pro Ser Val Phe Leu Phe Pro Pro Lys Pro Lys Asp Thr
                20                  25                 30

Leu Met Ile Ser Arg Thr Pro Glu Val Thr Cys Val Val Val Asp Val
                35                  40                 45

Ser Gln Glu Asp Pro Glu Val Gln Phe Asn Trp Tyr Val Asp Gly Val
                50                  55                 60

Glu Val His Asn Ala Lys Thr Lys Pro Arg Glu Glu Gln Phe Asn Ser
 65                 70                  75                 80

Thr Tyr Arg Val Val Ser Val Leu Thr Val Leu His Gln Asp Trp Leu
                85                  90                 95

Asn Gly Lys Glu Tyr Lys Cys Lys Val Ser Asn Lys Gly Leu Pro Ser
                100                 105                110

Ser Ile Glu Lys Thr Ile Ser Lys Ala Lys Gly Gln Pro Arg Glu Pro
                115                 120                125

Gln Val Tyr Thr Leu Pro Pro Ser Gln Glu Glu Met Thr Lys Asn Gln
```

```
                130                 135                 140
Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
                180                 185                 190

Thr Val Asp Lys Ser Arg Trp Gln Glu Gly Asn Val Phe Ser Cys Ser
                195                 200                 205

Val Met His Glu Ala Leu His Asn His Tyr Thr Gln Lys Ser Leu Ser
                210                 215                 220

Leu Ser Leu Gly Lys
225

<210> SEQ ID NO 28
<211> LENGTH: 8
<212> TYPE: PRT
<213> ORGANISM: Homo sapiens
<220> FEATURE:
<221> NAME/KEY: MISC_FEATURE
<223> OTHER INFORMATION: FGFR2(111-118)

<400> SEQUENCE: 28

Asp Asp Glu Asp Asp Thr Asp Gly
1               5

<210> SEQ ID NO 29
<211> LENGTH: 8
<212> TYPE: PRT
<213> ORGANISM: Homo sapiens
<220> FEATURE:
<221> NAME/KEY: MISC_FEATURE
<223> OTHER INFORMATION: FGFR1(105-112)

<400> SEQUENCE: 29

Glu Asp Asp Asp Asp Asp Asp Asp
1               5

<210> SEQ ID NO 30
<211> LENGTH: 356
<212> TYPE: PRT
<213> ORGANISM: Artificial Sequence
<220> FEATURE:
<223> OTHER INFORMATION: FGFR2 ECD with R2(111-118) replaced by
      R1(105-112)

<400> SEQUENCE: 30

Arg Pro Ser Phe Ser Leu Val Glu Asp Thr Thr Leu Glu Pro Glu Glu
1               5                   10                  15

Pro Pro Thr Lys Tyr Gln Ile Ser Gln Pro Glu Val Tyr Val Ala Ala
                20                  25                  30

Pro Gly Glu Ser Leu Glu Val Arg Cys Leu Leu Lys Asp Ala Ala Val
                35                  40                  45

Ile Ser Trp Thr Lys Asp Gly Val His Leu Gly Pro Asn Asn Arg Thr
50                  55                  60

Val Leu Ile Gly Glu Tyr Leu Gln Ile Lys Gly Ala Thr Pro Arg Asp
65                  70                  75                  80

Ser Gly Leu Tyr Ala Cys Thr Ala Ser Arg Thr Val Asp Ser Glu Thr
                85                  90                  95

Trp Tyr Phe Met Val Asn Val Thr Asp Ala Ile Ser Ser Gly Glu Asp
                100                 105                 110
```

Asp Asp Asp Asp Asp Ala Glu Asp Phe Val Ser Glu Asn Ser Asn
        115                 120                 125

Asn Lys Arg Ala Pro Tyr Trp Thr Asn Thr Glu Lys Met Glu Lys Arg
        130                 135                 140

Leu His Ala Val Pro Ala Ala Asn Thr Val Lys Phe Arg Cys Pro Ala
145                 150                 155                 160

Gly Gly Asn Pro Met Pro Thr Met Arg Trp Leu Lys Asn Gly Lys Glu
                165                 170                 175

Phe Lys Gln Glu His Arg Ile Gly Gly Tyr Lys Val Arg Asn Gln His
            180                 185                 190

Trp Ser Leu Ile Met Glu Ser Val Val Pro Ser Asp Lys Gly Asn Tyr
        195                 200                 205

Thr Cys Val Val Glu Asn Glu Tyr Gly Ser Ile Asn His Thr Tyr His
        210                 215                 220

Leu Asp Val Val Glu Arg Ser Pro His Arg Pro Ile Leu Gln Ala Gly
225                 230                 235                 240

Leu Pro Ala Asn Ala Ser Thr Val Val Gly Gly Asp Val Glu Phe Val
                245                 250                 255

Cys Lys Val Tyr Ser Asp Ala Gln Pro His Ile Gln Trp Ile Lys His
            260                 265                 270

Val Glu Lys Asn Gly Ser Lys Tyr Gly Pro Asp Gly Leu Pro Tyr Leu
        275                 280                 285

Lys Val Leu Lys Ala Ala Gly Val Asn Thr Thr Asp Lys Glu Ile Glu
        290                 295                 300

Val Leu Tyr Ile Arg Asn Val Thr Phe Glu Asp Ala Gly Glu Tyr Thr
305                 310                 315                 320

Cys Leu Ala Gly Asn Ser Ile Gly Ile Ser Phe His Ser Ala Trp Leu
                325                 330                 335

Thr Val Leu Pro Ala Pro Gly Arg Glu Lys Glu Ile Thr Ala Ser Pro
            340                 345                 350

Asp Tyr Leu Glu
        355

<210> SEQ ID NO 31
<211> LENGTH: 588
<212> TYPE: PRT
<213> ORGANISM: Artificial Sequence
<220> FEATURE:
<223> OTHER INFORMATION: FGFR2 ECD with R2(111-118) replaced by
      R1(105-112) + Fc

<400> SEQUENCE: 31

Arg Pro Ser Phe Ser Leu Val Glu Asp Thr Thr Leu Glu Pro Glu Glu
1               5                   10                  15

Pro Pro Thr Lys Tyr Gln Ile Ser Gln Pro Glu Val Tyr Val Ala Ala
            20                  25                  30

Pro Gly Glu Ser Leu Glu Val Arg Cys Leu Leu Lys Asp Ala Ala Val
        35                  40                  45

Ile Ser Trp Thr Lys Asp Gly Val His Leu Gly Pro Asn Asn Arg Thr
    50                  55                  60

Val Leu Ile Gly Glu Tyr Leu Gln Ile Lys Gly Ala Thr Pro Arg Asp
65                  70                  75                  80

Ser Gly Leu Tyr Ala Cys Thr Ala Ser Arg Thr Val Asp Ser Glu Thr
                85                  90                  95

Trp Tyr Phe Met Val Asn Val Thr Asp Ala Ile Ser Ser Gly Glu Asp

```
                100                 105                 110
Asp Asp Asp Asp Asp Ala Glu Asp Phe Val Ser Glu Asn Ser Asn
            115                 120                 125

Asn Lys Arg Ala Pro Tyr Trp Thr Asn Thr Glu Lys Met Glu Lys Arg
        130                 135                 140

Leu His Ala Val Pro Ala Ala Asn Thr Val Lys Phe Arg Cys Pro Ala
145                 150                 155                 160

Gly Gly Asn Pro Met Pro Thr Met Arg Trp Leu Lys Asn Gly Lys Glu
                165                 170                 175

Phe Lys Gln Glu His Arg Ile Gly Gly Tyr Lys Val Arg Asn Gln His
            180                 185                 190

Trp Ser Leu Ile Met Glu Ser Val Val Pro Ser Asp Lys Gly Asn Tyr
        195                 200                 205

Thr Cys Val Val Glu Asn Glu Tyr Gly Ser Ile Asn His Thr Tyr His
    210                 215                 220

Leu Asp Val Val Glu Arg Ser Pro His Arg Pro Ile Leu Gln Ala Gly
225                 230                 235                 240

Leu Pro Ala Asn Ala Ser Thr Val Val Gly Gly Asp Val Glu Phe Val
                245                 250                 255

Cys Lys Val Tyr Ser Asp Ala Gln Pro His Ile Gln Trp Ile Lys His
            260                 265                 270

Val Glu Lys Asn Gly Ser Lys Tyr Gly Pro Asp Gly Leu Pro Tyr Leu
        275                 280                 285

Lys Val Leu Lys Ala Ala Gly Val Asn Thr Thr Asp Lys Glu Ile Glu
    290                 295                 300

Val Leu Tyr Ile Arg Asn Val Thr Phe Glu Asp Ala Gly Glu Tyr Thr
305                 310                 315                 320

Cys Leu Ala Gly Asn Ser Ile Gly Ile Ser Phe His Ser Ala Trp Leu
                325                 330                 335

Thr Val Leu Pro Ala Pro Gly Arg Glu Lys Glu Ile Thr Ala Ser Pro
            340                 345                 350

Asp Tyr Leu Glu Glu Pro Lys Ser Ser Asp Lys Thr His Thr Cys Pro
        355                 360                 365

Pro Cys Pro Ala Pro Glu Leu Leu Gly Gly Pro Ser Val Phe Leu Phe
    370                 375                 380

Pro Pro Lys Pro Lys Asp Thr Leu Met Ile Ser Arg Thr Pro Glu Val
385                 390                 395                 400

Thr Cys Val Val Val Asp Val Ser His Glu Asp Pro Glu Val Lys Phe
                405                 410                 415

Asn Trp Tyr Val Asp Gly Val Glu Val His Asn Ala Lys Thr Lys Pro
            420                 425                 430

Arg Glu Glu Gln Tyr Asn Ser Thr Tyr Arg Val Val Ser Val Leu Thr
        435                 440                 445

Val Leu His Gln Asp Trp Leu Asn Gly Lys Glu Tyr Lys Cys Lys Val
    450                 455                 460

Ser Asn Lys Ala Leu Pro Ala Pro Ile Glu Lys Thr Ile Ser Lys Ala
465                 470                 475                 480

Lys Gly Gln Pro Arg Glu Pro Gln Val Tyr Thr Leu Pro Pro Ser Arg
                485                 490                 495

Asp Glu Leu Thr Lys Asn Gln Val Ser Leu Thr Cys Leu Val Lys Gly
            500                 505                 510

Phe Tyr Pro Ser Asp Ile Ala Val Glu Trp Glu Ser Asn Gly Gln Pro
        515                 520                 525
```

```
Glu Asn Asn Tyr Lys Thr Thr Pro Pro Val Leu Asp Ser Asp Gly Ser
            530                 535                 540

Phe Phe Leu Tyr Ser Lys Leu Thr Val Asp Lys Ser Arg Trp Gln Gln
545                 550                 555                 560

Gly Asn Val Phe Ser Cys Ser Val Met His Glu Ala Leu His Asn His
                565                 570                 575

Tyr Thr Gln Lys Ser Leu Ser Leu Ser Pro Gly Lys
            580                 585

<210> SEQ ID NO 32
<211> LENGTH: 587
<212> TYPE: PRT
<213> ORGANISM: Artificial Sequence
<220> FEATURE:
<223> OTHER INFORMATION: FGFR2 ECD delta-3 + GS linker + Fc

<400> SEQUENCE: 32

Arg Pro Ser Phe Ser Leu Val Glu Asp Thr Thr Leu Glu Pro Glu Glu
1               5                   10                  15

Pro Pro Thr Lys Tyr Gln Ile Ser Gln Pro Glu Val Tyr Val Ala Ala
            20                  25                  30

Pro Gly Glu Ser Leu Glu Val Arg Cys Leu Leu Lys Asp Ala Ala Val
        35                  40                  45

Ile Ser Trp Thr Lys Asp Gly Val His Leu Gly Pro Asn Asn Arg Thr
50                  55                  60

Val Leu Ile Gly Glu Tyr Leu Gln Ile Lys Gly Ala Thr Pro Arg Asp
65                  70                  75                  80

Ser Gly Leu Tyr Ala Cys Thr Ala Ser Arg Thr Val Asp Ser Glu Thr
                85                  90                  95

Trp Tyr Phe Met Val Asn Val Thr Asp Ala Ile Ser Ser Gly Asp Asp
            100                 105                 110

Glu Asp Asp Thr Asp Gly Ala Glu Asp Phe Val Ser Glu Asn Ser Asn
        115                 120                 125

Asn Lys Arg Ala Pro Tyr Trp Thr Asn Thr Glu Lys Met Glu Lys Arg
130                 135                 140

Leu His Ala Val Pro Ala Ala Asn Thr Val Lys Phe Arg Cys Pro Ala
145                 150                 155                 160

Gly Gly Asn Pro Met Pro Thr Met Arg Trp Leu Lys Asn Gly Lys Glu
                165                 170                 175

Phe Lys Gln Glu His Arg Ile Gly Gly Tyr Lys Val Arg Asn Gln His
            180                 185                 190

Trp Ser Leu Ile Met Glu Ser Val Val Pro Ser Asp Lys Gly Asn Tyr
        195                 200                 205

Thr Cys Val Val Glu Asn Glu Tyr Gly Ser Ile Asn His Thr Tyr His
    210                 215                 220

Leu Asp Val Val Glu Arg Ser Pro His Arg Pro Ile Leu Gln Ala Gly
225                 230                 235                 240

Leu Pro Ala Asn Ala Ser Thr Val Val Gly Gly Asp Val Glu Phe Val
                245                 250                 255

Cys Lys Val Tyr Ser Asp Ala Gln Pro His Ile Gln Trp Ile Lys His
            260                 265                 270

Val Glu Lys Asn Gly Ser Lys Tyr Gly Pro Asp Gly Leu Pro Tyr Leu
        275                 280                 285

Lys Val Leu Lys Ala Ala Gly Val Asn Thr Thr Asp Lys Glu Ile Glu
    290                 295                 300
```

```
Val Leu Tyr Ile Arg Asn Val Thr Phe Glu Asp Ala Gly Glu Tyr Thr
305                 310                 315                 320

Cys Leu Ala Gly Asn Ser Ile Gly Ile Ser Phe His Ser Ala Trp Leu
            325                 330                 335

Thr Val Leu Pro Ala Pro Gly Arg Glu Lys Glu Ile Thr Ala Ser Pro
        340                 345                 350

Asp Gly Ser Glu Pro Lys Ser Ser Asp Lys Thr His Thr Cys Pro Pro
    355                 360                 365

Cys Pro Ala Pro Glu Leu Leu Gly Gly Pro Ser Val Phe Leu Phe Pro
370                 375                 380

Pro Lys Pro Lys Asp Thr Leu Met Ile Ser Arg Thr Pro Glu Val Thr
385                 390                 395                 400

Cys Val Val Val Asp Val Ser His Glu Asp Pro Glu Val Lys Phe Asn
                405                 410                 415

Trp Tyr Val Asp Gly Val Glu Val His Asn Ala Lys Thr Lys Pro Arg
            420                 425                 430

Glu Glu Gln Tyr Asn Ser Thr Tyr Arg Val Val Ser Val Leu Thr Val
        435                 440                 445

Leu His Gln Asp Trp Leu Asn Gly Lys Glu Tyr Lys Cys Lys Val Ser
    450                 455                 460

Asn Lys Ala Leu Pro Ala Pro Ile Glu Lys Thr Ile Ser Lys Ala Lys
465                 470                 475                 480

Gly Gln Pro Arg Glu Pro Gln Val Tyr Thr Leu Pro Pro Ser Arg Asp
                485                 490                 495

Glu Leu Thr Lys Asn Gln Val Ser Leu Thr Cys Leu Val Lys Gly Phe
            500                 505                 510

Tyr Pro Ser Asp Ile Ala Val Glu Trp Glu Ser Asn Gly Gln Pro Glu
        515                 520                 525

Asn Asn Tyr Lys Thr Thr Pro Pro Val Leu Asp Ser Asp Gly Ser Phe
    530                 535                 540

Phe Leu Tyr Ser Lys Leu Thr Val Asp Lys Ser Arg Trp Gln Gln Gly
545                 550                 555                 560

Asn Val Phe Ser Cys Ser Val Met His Glu Ala Leu His Asn His Tyr
                565                 570                 575

Thr Gln Lys Ser Leu Ser Leu Ser Pro Gly Lys
            580                 585

<210> SEQ ID NO 33
<211> LENGTH: 353
<212> TYPE: PRT
<213> ORGANISM: Artificial Sequence
<220> FEATURE:
<223> OTHER INFORMATION: FGFR2 ECD delta-3 with R2(111-118) replaced by
      R1(105-112)

<400> SEQUENCE: 33

Arg Pro Ser Phe Ser Leu Val Glu Asp Thr Thr Leu Glu Pro Glu Glu
1               5                   10                  15

Pro Pro Thr Lys Tyr Gln Ile Ser Gln Pro Glu Val Tyr Val Ala Ala
            20                  25                  30

Pro Gly Glu Ser Leu Glu Val Arg Cys Leu Leu Lys Asp Ala Ala Val
        35                  40                  45

Ile Ser Trp Thr Lys Asp Gly Val His Leu Gly Pro Asn Asn Arg Thr
    50                  55                  60

Val Leu Ile Gly Glu Tyr Leu Gln Ile Lys Gly Ala Thr Pro Arg Asp
```

```
                65                  70                  75                  80
Ser Gly Leu Tyr Ala Cys Thr Ala Ser Arg Thr Val Asp Ser Glu Thr
                    85                  90                  95

Trp Tyr Phe Met Val Asn Val Thr Asp Ala Ile Ser Ser Gly Glu Asp
                100                 105                 110

Asp Asp Asp Asp Asp Ala Glu Asp Phe Val Ser Glu Asn Ser Asn
                115                 120                 125

Asn Lys Arg Ala Pro Tyr Trp Thr Asn Thr Glu Lys Met Glu Lys Arg
    130                 135                 140

Leu His Ala Val Pro Ala Ala Asn Thr Val Lys Phe Arg Cys Pro Ala
145                 150                 155                 160

Gly Gly Asn Pro Met Pro Thr Met Arg Trp Leu Lys Asn Gly Lys Glu
                165                 170                 175

Phe Lys Gln Glu His Arg Ile Gly Gly Tyr Lys Val Arg Asn Gln His
                180                 185                 190

Trp Ser Leu Ile Met Glu Ser Val Val Pro Ser Asp Lys Gly Asn Tyr
                195                 200                 205

Thr Cys Val Val Glu Asn Glu Tyr Gly Ser Ile Asn His Thr Tyr His
                210                 215                 220

Leu Asp Val Val Glu Arg Ser Pro His Arg Pro Ile Leu Gln Ala Gly
225                 230                 235                 240

Leu Pro Ala Asn Ala Ser Thr Val Val Gly Gly Asp Val Glu Phe Val
                245                 250                 255

Cys Lys Val Tyr Ser Asp Ala Gln Pro His Ile Gln Trp Ile Lys His
                260                 265                 270

Val Glu Lys Asn Gly Ser Lys Tyr Gly Pro Asp Gly Leu Pro Tyr Leu
                275                 280                 285

Lys Val Leu Lys Ala Ala Gly Val Asn Thr Thr Asp Lys Glu Ile Glu
                290                 295                 300

Val Leu Tyr Ile Arg Asn Val Thr Phe Glu Asp Ala Gly Glu Tyr Thr
305                 310                 315                 320

Cys Leu Ala Gly Asn Ser Ile Gly Ile Ser Phe His Ser Ala Trp Leu
                325                 330                 335

Thr Val Leu Pro Ala Pro Gly Arg Glu Lys Glu Ile Thr Ala Ser Pro
                340                 345                 350

Asp

<210> SEQ ID NO 34
<211> LENGTH: 587
<212> TYPE: PRT
<213> ORGANISM: Artificial Sequence
<220> FEATURE:
<223> OTHER INFORMATION: FGFR2 ECD delta-3 with R2(111-118) replaced by
      R1(105-112) + GS linker + Fc (also called FGFR2ECD(FGFR2(111-118):
      FGFR1(105-112):delta3)-GS linker-Fc and R2(111-118):R1(105-112))

<400> SEQUENCE: 34

Arg Pro Ser Phe Ser Leu Val Glu Asp Thr Thr Leu Glu Pro Glu Glu
1               5                   10                  15

Pro Pro Thr Lys Tyr Gln Ile Ser Gln Pro Glu Val Tyr Val Ala Ala
                20                  25                  30

Pro Gly Glu Ser Leu Glu Val Arg Cys Leu Leu Lys Asp Ala Ala Val
                35                  40                  45

Ile Ser Trp Thr Lys Asp Gly Val His Leu Gly Pro Asn Asn Arg Thr
    50                  55                  60
```

```
Val Leu Ile Gly Glu Tyr Leu Gln Ile Lys Ala Thr Pro Arg Asp
 65                  70                  75                  80

Ser Gly Leu Tyr Ala Cys Thr Ala Ser Arg Thr Val Asp Ser Glu Thr
                 85                  90                  95

Trp Tyr Phe Met Val Asn Val Thr Asp Ala Ile Ser Ser Gly Glu Asp
            100                 105                 110

Asp Asp Asp Asp Asp Ala Glu Asp Phe Val Ser Glu Asn Ser Asn
            115                 120                 125

Asn Lys Arg Ala Pro Tyr Trp Thr Asn Thr Glu Lys Met Glu Lys Arg
    130                 135                 140

Leu His Ala Val Pro Ala Ala Asn Thr Val Lys Phe Arg Cys Pro Ala
145                 150                 155                 160

Gly Gly Asn Pro Met Pro Thr Met Arg Trp Leu Lys Asn Gly Lys Glu
                165                 170                 175

Phe Lys Gln Glu His Arg Ile Gly Gly Tyr Lys Val Arg Asn Gln His
            180                 185                 190

Trp Ser Leu Ile Met Glu Ser Val Val Pro Ser Asp Lys Gly Asn Tyr
            195                 200                 205

Thr Cys Val Val Glu Asn Glu Tyr Gly Ser Ile Asn His Thr Tyr His
    210                 215                 220

Leu Asp Val Val Glu Arg Ser Pro His Arg Pro Ile Leu Gln Ala Gly
225                 230                 235                 240

Leu Pro Ala Asn Ala Ser Thr Val Val Gly Gly Asp Val Glu Phe Val
                245                 250                 255

Cys Lys Val Tyr Ser Asp Ala Gln Pro His Ile Gln Trp Ile Lys His
            260                 265                 270

Val Glu Lys Asn Gly Ser Lys Tyr Gly Pro Asp Gly Leu Pro Tyr Leu
            275                 280                 285

Lys Val Leu Lys Ala Ala Gly Val Asn Thr Thr Asp Lys Glu Ile Glu
    290                 295                 300

Val Leu Tyr Ile Arg Asn Val Thr Phe Glu Asp Ala Gly Glu Tyr Thr
305                 310                 315                 320

Cys Leu Ala Gly Asn Ser Ile Gly Ile Ser Phe His Ser Ala Trp Leu
                325                 330                 335

Thr Val Leu Pro Ala Pro Gly Arg Glu Lys Glu Ile Thr Ala Ser Pro
            340                 345                 350

Asp Gly Ser Glu Pro Lys Ser Ser Asp Lys Thr His Thr Cys Pro Pro
            355                 360                 365

Cys Pro Ala Pro Glu Leu Leu Gly Gly Pro Ser Val Phe Leu Phe Pro
    370                 375                 380

Pro Lys Pro Lys Asp Thr Leu Met Ile Ser Arg Thr Pro Glu Val Thr
385                 390                 395                 400

Cys Val Val Val Asp Val Ser His Glu Asp Pro Glu Val Lys Phe Asn
                405                 410                 415

Trp Tyr Val Asp Gly Val Glu Val His Asn Ala Lys Thr Lys Pro Arg
            420                 425                 430

Glu Glu Gln Tyr Asn Ser Thr Tyr Arg Val Val Ser Val Leu Thr Val
            435                 440                 445

Leu His Gln Asp Trp Leu Asn Gly Lys Glu Tyr Lys Cys Lys Val Ser
    450                 455                 460

Asn Lys Ala Leu Pro Ala Pro Ile Glu Lys Thr Ile Ser Lys Ala Lys
465                 470                 475                 480

Gly Gln Pro Arg Glu Pro Gln Val Tyr Thr Leu Pro Pro Ser Arg Asp
```

```
                            485                 490                 495
Glu Leu Thr Lys Asn Gln Val Ser Leu Thr Cys Leu Val Lys Gly Phe
                500                 505                 510

Tyr Pro Ser Asp Ile Ala Val Glu Trp Glu Ser Asn Gly Gln Pro Glu
                515                 520                 525

Asn Asn Tyr Lys Thr Thr Pro Pro Val Leu Asp Ser Asp Gly Ser Phe
            530                 535                 540

Phe Leu Tyr Ser Lys Leu Thr Val Asp Lys Ser Arg Trp Gln Gln Gly
545                 550                 555                 560

Asn Val Phe Ser Cys Ser Val Met His Glu Ala Leu His Asn His Tyr
                565                 570                 575

Thr Gln Lys Ser Leu Ser Leu Ser Pro Gly Lys
                580                 585

<210> SEQ ID NO 35
<211> LENGTH: 288
<212> TYPE: PRT
<213> ORGANISM: Homo sapiens
<220> FEATURE:
<221> NAME/KEY: MISC_FEATURE
<223> OTHER INFORMATION: human PD-1 precursor (with signal sequence)

<400> SEQUENCE: 35

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
            210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255
```

```
Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285
```

<210> SEQ ID NO 36
<211> LENGTH: 268
<212> TYPE: PRT
<213> ORGANISM: Homo sapiens
<220> FEATURE:
<221> NAME/KEY: MISC_FEATURE
<223> OTHER INFORMATION: human PD-1 (mature, without signal sequence)

<400> SEQUENCE: 36

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Pro Leu Lys Glu Asp
            180                 185                 190

Pro Ser Ala Val Pro Val Phe Ser Val Asp Tyr Gly Glu Leu Asp Phe
        195                 200                 205

Gln Trp Arg Glu Lys Thr Pro Glu Pro Pro Val Pro Cys Val Pro Glu
    210                 215                 220

Gln Thr Glu Tyr Ala Thr Ile Val Phe Pro Ser Gly Met Gly Thr Ser
225                 230                 235                 240

Ser Pro Ala Arg Arg Gly Ser Ala Asp Gly Pro Arg Ser Ala Gln Pro
                245                 250                 255

Leu Arg Pro Glu Asp Gly His Cys Ser Trp Pro Leu
            260                 265
```

<210> SEQ ID NO 37
<211> LENGTH: 290
<212> TYPE: PRT
<213> ORGANISM: Homo sapiens
<220> FEATURE:
<221> NAME/KEY: MISC_FEATURE
<223> OTHER INFORMATION: human PD-L1 precursor (with signal sequence)

<400> SEQUENCE: 37

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Glu Tyr
            20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
            85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
            165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
            195                 200                 205

Cys Thr Phe Arg Arg Leu Asp Pro Glu Glu Asn His Thr Ala Glu Leu
            210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
            245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
            275                 280                 285

Glu Thr
    290

<210> SEQ ID NO 38
<211> LENGTH: 272
<212> TYPE: PRT
<213> ORGANISM: Homo sapiens
<220> FEATURE:
<221> NAME/KEY: MISC_FEATURE
<223> OTHER INFORMATION: human PD-L1 (mature, without signal sequence)

<400> SEQUENCE: 38

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
            35                  40                  45

Phe Val His Gly Glu Glu Asp Leu Lys Val Gln His Ser Ser Tyr Arg
50                  55                  60

Gln Arg Ala Arg Leu Leu Lys Asp Gln Leu Ser Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Asn Glu Ile Phe Tyr Cys Thr
            180                 185                 190

Phe Arg Arg Leu Asp Pro Glu Glu Asn His Thr Ala Glu Leu Val Ile
            195                 200                 205

Pro Glu Leu Pro Leu Ala His Pro Pro Asn Glu Arg Thr His Leu Val
210                 215                 220

Ile Leu Gly Ala Ile Leu Leu Cys Leu Gly Val Ala Leu Thr Phe Ile
225                 230                 235                 240

Phe Arg Leu Arg Lys Gly Arg Met Met Asp Val Lys Lys Cys Gly Ile
                245                 250                 255

Gln Asp Thr Asn Ser Lys Lys Gln Ser Asp Thr His Leu Glu Glu Thr
            260                 265                 270

<210> SEQ ID NO 39
<211> LENGTH: 119
<212> TYPE: PRT
<213> ORGANISM: Artificial Sequence
<220> FEATURE:
<223> OTHER INFORMATION: Anti-FGFR2 Gal-FR22 heavy chain variable region

<400> SEQUENCE: 39

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Phe
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Ala Asp Phe Arg
    50                  55                  60

Ser Arg Leu Ser Ile Ser Lys Asp Asn Ser Lys Ser Gln Ile Phe Phe
65                  70                  75                  80

Lys Met Asn Ser Leu Gln Pro Asp Asp Thr Ile Ala Tyr Cys Ala Asn
                85                  90                  95

Phe Tyr Tyr Gly Tyr Asp Asp Tyr Val Met Asp Tyr Trp Gly Gln Gly
            100                 105                 110

Thr Ser Val Thr Val Ser Ser
        115

<210> SEQ ID NO 40
<211> LENGTH: 5
<212> TYPE: PRT
<213> ORGANISM: Artificial Sequence

```
<220> FEATURE:
<223> OTHER INFORMATION: Anti-FGFR2 Gal-FR22 heavy chain CDR1

<400> SEQUENCE: 40

Ser Phe Gly Val His
1               5

<210> SEQ ID NO 41
<211> LENGTH: 16
<212> TYPE: PRT
<213> ORGANISM: Artificial Sequence
<220> FEATURE:
<223> OTHER INFORMATION: Anti-FGFR2 Gal-FR22 heavy chain CDR2

<400> SEQUENCE: 41

Val Ile Trp Ser Gly Gly Ser Thr Asp Tyr Asn Ala Asp Phe Arg Ser
1               5                   10                  15

<210> SEQ ID NO 42
<211> LENGTH: 12
<212> TYPE: PRT
<213> ORGANISM: Artificial Sequence
<220> FEATURE:
<223> OTHER INFORMATION: Anti-FGFR2 Gal-FR22 heavy chain CDR3

<400> SEQUENCE: 42

Phe Tyr Tyr Gly Tyr Asp Asp Tyr Val Met Asp Tyr
1               5                   10

<210> SEQ ID NO 43
<211> LENGTH: 107
<212> TYPE: PRT
<213> ORGANISM: Artificial Sequence
<220> FEATURE:
<223> OTHER INFORMATION: Anti-FGFR2 Gal-FR22 light chain variable region

<400> SEQUENCE: 43

Asp Ile Gln Met Thr Gln Ser Pro Ser Ser Leu Ser Ala Ser Leu Gly
1               5                   10                  15

Gly Arg Val Thr Ile Thr Cys Lys Ala Ser Gln Asp Ile Lys Asn Tyr
            20                  25                  30

Ile Ala Trp Tyr Gln His Lys Pro Gly Lys Ser Pro Arg Leu Leu Ile
        35                  40                  45

His Tyr Thr Ser Thr Leu Gln Pro Gly Val Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asp Leu Tyr
                85                  90                  95

Met Phe Gly Gly Gly Thr Lys Leu Asp Ile Lys
            100                 105

<210> SEQ ID NO 44
<211> LENGTH: 11
<212> TYPE: PRT
<213> ORGANISM: Artificial Sequence
<220> FEATURE:
<223> OTHER INFORMATION: Anti-FGFR2 Gal-FR22 light chain CDR1

<400> SEQUENCE: 44

Lys Ala Ser Gln Asp Ile Lys Asn Tyr Ile Ala
1               5                   10
```

```
<210> SEQ ID NO 45
<211> LENGTH: 7
<212> TYPE: PRT
<213> ORGANISM: Artificial Sequence
<220> FEATURE:
<223> OTHER INFORMATION: Anti-FGFR2 Gal-FR22 light chain CDR2

<400> SEQUENCE: 45

Tyr Thr Ser Thr Leu Gln Pro
1               5

<210> SEQ ID NO 46
<211> LENGTH: 8
<212> TYPE: PRT
<213> ORGANISM: Artificial Sequence
<220> FEATURE:
<223> OTHER INFORMATION: Anti-FGFR2 Gal-FR22 light chain CDR3

<400> SEQUENCE: 46

Leu Gln Tyr Asp Asp Leu Tyr Met
1               5
```

FGFR2 INHIBITORS ALONE OR IN COMBINATION WITH IMMUNE STIMULATING AGENTS IN CANCER TREATMENT

CROSS REFERENCE TO RELATED APPLICATIONS

This application claims priority to the following three United States provisional patent applications: Nos. 62/258,731, filed Nov. 23, 2015, 62/314,174, filed Mar. 28, 2016, and 62/379,094, filed Aug. 24, 2016, each of which is incorporated by reference in its entirety herein.

SEQUENCE LISTING

The present application is filed with a Sequence Listing in electronic format. The Sequence Listing is provided as a file entitled "2016-11-17_01134-0046-00US_SeqList_ST25.txt" created on Nov. 17, 2016, which is 103,516 bytes in size. The information in the electronic format of the sequence listing is incorporated herein by reference in its entirety.

FIELD

This application relates to uses of fibroblast growth factor receptor 2 (FGFR2) inhibitors in treatment of cancer, in some cases in combinations with immune stimulating agents, such as inhibitors of PD-1 or PD-L1.

BACKGROUND

The fibroblast growth factor (FGF) family members bind to four known tyrosine kinase receptors, fibroblast growth factor receptors 1-4 (FGFR1-4) and their isoforms, with the various FGFs binding the different FGFRs to varying extents (Zhang et al., J. Biol. Chem. 281:15694, 2006). A protein sequence of human FGFR2 is provided in, e.g., GenBank Locus AF487553. Each FGFR consists of an extracellular domain (ECD) comprising three immunoglobulin (Ig)-like domains (D1, D2 and D3), a single transmembrane helix, and an intracellular catalytic kinase domain (Mohammadi et al., Cytokine Growth Factor Revs, 16:107, 2005). FGFs bind to the receptors primarily through regions in D2 and D3 of the receptors. There is a contiguous stretch of acidic amino acids in the linker between D1 and D2 called the "acid box" (AB). The region containing D1 and AB is believed to be involved in autoinhibition of the receptor, which is relieved by binding to ligand.

The FGFRs are characterized by multiple alternative splicing of their mRNAs, leading to a variety of isoforms (Ornitz et al., J. Biol. Chem. 271:15292, 1996; see also Swiss-Prot P21802 and isoforms P21802-1 to -20 for sequences of FGFR2 and its isoforms). Notably, there are forms containing all three Ig domains (α isoform) or only the two Ig domains D2 and D3 domains without D1 (β isoform). In FGFR1, FGFR2, and FGFR3, all forms contain the first half of D3 denoted IIIa, but two alternative exons can be utilized for the second half of D3, leading to IIIb and IIIc forms. For FGFR2, these are respectively denoted FGFR2-IIIb and FGFR2-IIIc (or just FGFR2b and FGFR2c); the corresponding beta forms are denoted FGFR2(beta)IIIb and FGFR2(beta)IIIc. The FGFR2-IIIb form of FGFR2 (also denoted K-sam-II) is a high affinity receptor for both FGF1 and KGF family members (FGF7, FGF10, and FGF22) whereas FGFR2-IIIc (also denoted K-sam-I) binds both FGF1 and FGF2 well but does not bind the KGF family members (Miki et al., Proc. Natl. Acad. Sci. USA 89:246, 1992). Indeed, FGFR2-IIIb is the only receptor for KGF family members (Ornitz et al., 1996, op. cit.) and is therefore also designated KGFR.

The FGFRs and their isoforms are differentially expressed in various tissues. FGFR2-IIIb (and the Mb forms of FGFR1 and FGFR3) is expressed in epithelial tissues, while FGFR2-IIIc is expressed in mesenchymal tissues (Duan et al., J. Biol. Chem. 267:16076, 1992; Ornitz et al., 1996, op. cit.). Certain of the FGF ligands of these receptors have an opposite pattern of expression. Thus, KGF subfamily members, including FGF7 (KGF), FGF10, and FGF22, bind only to FGFR2-IIIb (Zhang et al., op. cit.) and are expressed in mesenchymal tissues so may be paracrine effectors of epithelial cells (Ornitz et al., 1996, op. cit.). In contrast, the FGF4 subfamily members FGF4-6 bind to FGFR2-IIIc and are expressed in both epithelial and mesenchymal lineages so may have either autocrine or paracrine functions. Because of the expression patterns of the isoforms of FGFR2 and their ligands, FGFR2 plays a role in epithelial-mesynchymal interactions (Finch et al., Dev. Dyn. 203:223, 1995), so it is not surprising that knock-out of FGFR2-IIIb in mice leads to severe embryonic defects and lethality (De Moerlooze et al., Development 127:483, 2000).

KGF (FGF7) and KGFR (FGFR2-IIIb) are overexpressed in many pancreatic cancers (Ishiwata et al., Am. J. Pathol. 153: 213, 1998), and their coexpression correlates with poor prognosis (Cho et al., Am. J. Pathol. 170:1964, 2007). Somatic mutations of the FGFR2 gene were found in 12% of a large panel of endometrial (uterine) carcinomas, and in several tested cases were required for tumor cell survival (Dutt et al., Proc. Natl. Acad. Sci. USA 105:8713, 2008). In two tumors the FGFR2 mutation was found to be the same S252W substitution associated with Apert syndrome. Amplification and overexpression of FGFR2 is associated with the undifferentiated, diffuse type of gastric cancer, which has a particularly poor prognosis, and inhibition of the FGFR2 activity by small molecule compounds potently inhibited proliferation of such cancer cells (Kunii et al., Cancer Res. 68:2340, 2008; Nakamura et al., Gastroenterol. 131:1530, 2006).

Inhibitors of FGFR2 may include antibodies and FGFR2 ECD domains or FGFR2 ECD fusion molecules. For example, U.S. Pat. No. 8,101,723 B2 describes, for example, monoclonal antibodies that bind human FGFR2-IIIb but bind less well or do not bind to FGFR2-IIIc and vice versa. U.S. Patent Publication No. 2015-0050273 A1 describes certain afucosylated antibodies that bind to FGFR2-IIIb. U.S. Patent Publication No. US 2013-0324701 A1 describes, for example, particular FGFR2 ECD fusion molecules comprising an extracellular domain of FGFR2-IIIc and a fusion partner. Additional FGFR ECD fusion molecules are described in U.S. Pat. No. 8,338,569 B2.

Genetic alterations in cancer provide a diverse set of antigens that can mediate anti-tumor immunity. Antigen recognition through T-cell receptors (TCRs) initiates T-cell-responses, which are regulated by a balance between activating and inhibitory signals. The inhibitory signals, or "immune checkpoints," play an important role in normal tissues by preventing autoimmunity. Up-regulation of immune checkpoint proteins may allow cancers to evade anti-tumor immunity. Two immune checkpoint proteins have been a focus of clinical cancer immuno therapeutics, cytotoxic T-lymphocyte-associated antigen 4 (CTLA-4) and programmed cell death protein 1 (PD-1). An anti-CTLA-4 antibody and an anti-PD-1 antibody have been approved for treatment of metastatic melanoma and are currently in clinical trials for other cancers. Anti-PD-L1 antibody, directed to the ligand for PD-1, is also currently in clinical development.

Inhibition of FGFR signaling has been reported to improve anti-tumor immunity and impair metastasis in breast cancer. (See, e.g., T. Ye et al., *Breast Cancer Res. Treat.* 143: 435-446 (2014).) Anti-FGFR2 antibodies have also been tested in models of gastric cancer, for example. However, whether co-administering an FGFR2 inhibitor with an immune checkpoint inhibitor such as a PD-1 or PD-L1 inhibitor would further improve treatment in a tumor model was unknown. The inventors herein have demonstrated that a combination of an FGFR2 inhibitory antibody and a PD-1 inhibitory antibody demonstrates at least additive effects in a mouse breast tumor model. The inventors further show that treatment with an FGFR2 inhibitory antibody alone leads to an increase in PD-L1-expressing cells, NK cells, and CD3+, CD8+, and CD4+ T cells in tumor tissue in a mouse breast tumor model, and results in an increased lymphoid to myeloid cell ratio in the tumor tissue. In addition, an FGFR2 inhibitor given alone has also benefitted a human bladder cancer subject. The results herein, taken together, indicate that FGFR2 inhibitors may alter the tumor microenvironment and may therefore enhance tumor-killing immune responses, either alone or in combination with a PD-1/PD-L1 inhibitor.

SUMMARY

In some embodiments, methods of treating cancer in a subject are provided, comprising administering to the subject an FGFR2 inhibitor such as an anti-FGFR2 antibody or FGFR2 ECD or FGFR2 ECD fusion molecule in combination with at least one immune stimulating agent. In some embodiments, the immune stimulating agent is a PD-1/PD-L1 inhibitor such as an anti-PD-1 antibody, anti-PD-L1 antibody, PD-1 fusion molecule, or PD-1 polypeptide. In some embodiments, the immune stimulating agent comprises one or more of the agents described in the section below entitled "combinations with other immune stimulating agents." In some embodiments, the FGFR2 inhibitor is an antibody. In some embodiments, the FGFR2 inhibitor is an antibody that recognizes FGFR2-IIIb. In some embodiments, the FGFR2-IIIb antibody binds with lower affinity to FGFR2-IIIc than to -IIIb or does not detectably bind to FGFR2-IIIc. In some embodiments, the FGFR2 inhibitor is an FGFR2 ECD. In some embodiments, the FGFR2 inhibitor is an FGFR2 ECD fusion molecule comprising an FGFR2 ECD and a fusion partner, such as an Fc domain, albumin, or polyethylene glycol (PEG). In some embodiments, where the at least one immune stimulating agent comprises a PD-1/PD-L1 inhibitor, the PD-1/PD-L1 inhibitor is an antibody. In some embodiments, the PD-1/PD-L1 inhibitor is an anti-PD-1 antibody or an anti-PD-L1 antibody. In some embodiments, the PD-1/PD-L1 inhibitor is a PD-1 polypeptide, while in some embodiments, the PD-1/PD-L1 inhibitor is a PD-1 fusion molecule.

In any of the embodiments of the methods and compositions herein, the PD-1/PD-L1 inhibitor may have the following characteristics. In some embodiments, the inhibitor is an anti-PD-1 antibody comprising the heavy chain and light chain CDRs of an antibody selected from nivolumab, pidilizumab, and pembrolizumab. In some embodiments, the anti-PD-1 antibody comprises the heavy chain and light chain variable regions of an antibody selected from nivolumab, pidilizumab, and pembrolizumab. In some embodiments, the anti-PD-1 antibody is selected from nivolumab, pidilizumab, and pembrolizumab. In some embodiments, the PD-1/PD-L1 inhibitor is an anti-PD-L1 antibody. In some embodiments, the anti-PD-L1 antibody comprises the heavy chain and light chain CDRs of an antibody selected from, BMS-936559, MPDL3280A (atezolizumab), MEDI4736, and MSB0010718C (avelumab). In some embodiments, the anti-PD-L1 antibody comprises the heavy chain and light chain variable regions of an antibody selected from BMS-936559, MPDL3280A, MEDI4736, and MSB0010718C. In some embodiments, the anti-PD-L1 antibody is selected from BMS-936559, MPDL3280A, MEDI4736, and MSB0010718C. In some embodiments, the PD-1/PD-L1 inhibitor is a fusion molecule. In some embodiments, the fusion molecule is AMP-224. In some embodiments, the PD-1/PD-L1 inhibitor is a PD-1 polypeptide, such as AUR-012.

In any of the compositions or methods described herein involving an anti-PD-1 antibody, the anti-PD-1 antibody may be a humanized antibody. In any of the compositions or methods described herein, the anti-PD-1 antibody may be selected from a Fab, an Fv, an scFv, a Fab', and a (Fab')$_2$. In any of the compositions or methods described herein, the anti-PD-1 antibody may be a chimeric antibody. In any of the compositions or methods described herein, the anti-PD-1 antibody may be selected from an IgA, an IgG, and an IgD. In any of the compositions or methods described herein, the anti-PD-1 antibody may be an IgG. In any of the methods described herein, the antibody may be an IgG1 or IgG2.

In any of the compositions or methods described herein, the FGFR2 inhibitor may have the following characteristics. In some embodiments, the inhibitor is an FGFR2 antibody. In some embodiments, the FGFR2 antibody is an FGFR2-IIIb antibody (also denoted αFGFR2b herein). In some embodiments, the FGFR2-IIIb antibody binds to FGFR2-IIIb with higher affinity than to FGFR2-IIIc, or alternatively, does not bind detectably to FGFR2-IIIc. In some embodiments, the antibody inhibits binding of FGF2 and/or FGF7 to FGFR2.

In some embodiments, the FGFR2 antibody has the heavy and light chain hypervariable region (HVR) H1, H2, H3, L1, L2, and L3 amino acid sequences of monoclonal antibodies GAL-FR21, GAL-FR22, or GAL-FR23, described in U.S. Pat. No. 8,101,723 B2. In some embodiments the FGFR2-IIIb antibody heavy chain variable region comprises: (i) HVR-H1 comprising the amino acid sequence of SEQ ID NO: 6; (ii) HVR-H2 comprising the amino acid sequence of SEQ ID NO: 7; and (iii) HVR-H3 comprising the amino acid sequence of SEQ ID NO: 8; and the light chain variable region comprises: (iv) HVR-L1 comprising the amino acid sequence of SEQ ID NO: 9; (v) HVR-L2 comprising the amino acid sequence of SEQ ID NO: 10; and (vi) HVR-L3 comprising the amino acid sequence of SEQ ID NO: 11.

In some embodiments, the FGFR2 antibody comprises an FGFR2-IIIb antibody in which the heavy chain variable domain that is at least 95%, such as at least 97%, at least 98%, or at least 99% identical to the amino acid sequence of SEQ ID NO:4, or that comprises the amino acid sequence of SEQ ID NO: 4. In some embodiments, the FGFR2 antibody comprises an FGFR2-IIIb antibody in which the light chain variable domain is at least 95%, such as at least 97%, at least 98%, or at least 99% identical to the amino acid sequence of SEQ ID NO:5, or that comprises the amino acid sequence of SEQ ID NO: 5. In some embodiments, the heavy chain variable domain is at least 95%, such as at least 97%, at least 98%, or at least 99% identical to the amino acid sequence of SEQ ID NO:4, or that comprises the amino acid sequence of SEQ ID NO: 4 and the light chain variable domain is at least 95%, such as at least 97%, at least 98%, or at least 99% identical to the amino acid sequence of SEQ ID NO:5, or that comprises the amino acid sequence of SEQ ID NO: 5. In some embodiments, the FGFR2 antibody comprises an FGFR2-IIIb antibody in which the heavy chain is at least 95%, such as at least 97%, at least 98%, or at least 99% identical to the amino acid sequence of SEQ ID NO: 2, or that comprises the amino acid sequence of SEQ ID NO: 2. In some embodiments, the FGFR2 antibody comprises an FGFR2-IIIb antibody in which the light chain is at least 95%, such as at least 97%, at least 98%, or at least 99% identical to the amino acid sequence of SEQ ID NO:3, or that comprises the amino acid sequence of SEQ ID NO: 3. In some embodiments, the heavy chain is at least 95%, such as at least 97%, at least 98%, or at least 99% identical to the amino acid sequence of SEQ ID NO:2, or that comprises the amino acid sequence of SEQ ID NO: 2 and the light chain is at least 95%, such as at least 97%, at least 98%, or at least 99% identical to the amino acid sequence of SEQ ID NO:3, or that comprises the amino acid sequence of SEQ ID NO: 3.

In some embodiments the FGFR2-IIIb antibody heavy chain variable region comprises: (i) CDR1 comprising the amino acid sequence of SEQ ID NO: 40; (ii) CDR2 comprising the amino acid sequence of SEQ ID NO: 41; and (iii) CDR3 comprising the amino acid sequence of SEQ ID NO: 42; and the light chain variable region comprises: (iv) CDR1 comprising the amino acid sequence of SEQ ID NO: 44; (v) CDR2 comprising the amino acid sequence of SEQ ID NO: 45; and (vi) CDR3 comprising the amino acid sequence of SEQ ID NO: 46.

In some embodiments, the FGFR2 antibody comprises an FGFR2-IIIb antibody in which the heavy chain variable domain that is at least 95%, such as at least 97%, at least 98%, or at least 99% identical to the amino acid sequence of SEQ ID NO:39, or that comprises the amino acid sequence of SEQ ID NO: 39. In some embodiments, the FGFR2 antibody comprises an FGFR2-IIIb antibody in which the light chain variable domain is at least 95%, such as at least 97%, at least 98%, or at least 99% identical to the amino acid sequence of SEQ ID NO:43, or that comprises the amino acid sequence of SEQ ID NO: 43. In some embodiments, the heavy chain variable domain is at least 95% such as at least 97%, at least 98%, or at least 99% identical to the amino acid sequence of SEQ ID NO:39, or that comprises the amino acid sequence of SEQ ID NO: 39 and the light chain variable domain is at least 95%, such as at least 97%, at least 98%, or at least 99% identical to the amino acid sequence of SEQ ID NO:43, or that comprises the amino acid sequence of SEQ ID NO: 43.

In some embodiments the FGFR2 antibody is afucosylated. In some embodiments, the antibody lacks fucose at Asn297. In some embodiments, the antibody comprises a kappa light chain constant region. In some embodiments, the antibody comprises an IgG1 heavy chain constant region. In some embodiments, an afucosylated antibody has enhanced ADCC (antibody-dependent cell cytotoxic) activity in vitro and/or in vivo compared to an antibody having the same amino acid sequence that is fucosylated at Asn297. In some embodiments, an afucosylated antibody has enhanced affinity for Fc gamma RIIIA compared to an antibody having the same amino acid sequence that is fucosylated at position Asn297. In some embodiments, the afucosylated antibody is capable of increasing the number of one or more of PD-L1 positive cells, NK cells, CD3+ T cells, CD4+ T cells, CD8+ T cells, and macrophages in tumor tissue in a mouse xenograft and/or syngeneic tumor model compared to a control (e.g. as compared to a control antibody that does not target FGFR2).

In some embodiments, the FGFR2 inhibitor is an FGFR2 ECD such as an FGFR2 ECD fusion molecule. FGFR2 ECD fusion molecules may comprise fusion partners such as an Fc domain, albumin, or PEG.

In some embodiments, and FGFR2 inhibitor is capable of binding to FGFR2 as well as to an FGFR2 mutant with an activating mutation, such as the FGFR2-S252W mutation, which is found in some cancer cells.

In any of the compositions or methods described herein involving an FGFR2 antibody, the FGFR2 antibody may be a humanized antibody. In any of the compositions or methods described herein, the FGFR2 antibody may be selected from a Fab, an Fv, an scFv, a Fab', and a (Fab')$_2$. In any of the compositions or methods described herein, the FGFR2 antibody may be a chimeric antibody. In any of the compositions or methods described herein, the FGFR2 antibody may be selected from an IgA, an IgG, and an IgD. In any of the compositions or methods described herein, the FGFR2 antibody may be an IgG. In any of the methods described herein, the antibody may be an IgG1, IgG2, IgG3, or IgG4.

In some embodiments, the FGFR2 inhibitor is administered at a dose of at least 0.1, 0.3, 0.5, 1, 2, 3, 4, 5, 10, 15, 20, 20, or 30 mg/kg, or within a range bounded by any two of those doses. In some embodiments, an PD-1/PD-L1 inhibitor is administered at a dose of at least 0.1, 0.3, 0.5, 1, 2, 3, 4, 5, or 10 mg/kg or at a range bounded by any two of these doses such as at a range of 0.5-10 mg/kg. In some embodiments, the FGFR2 inhibitor and the at least one immune stimulating agent, such as a PD-1/PD-L1 inhibitor, are administered at least once per 1, 2, 3, 4, or 5 weeks.

In some embodiments, the cancer overexpresses FGFR2IIIb either in the presence or in the absence of FGFR2 gene amplification. In some embodiments, the FGFR2IIIb overexpression is determined by immunohistochemistry (IHC). For example, the overexpression may be determined by an IHC signal of 1+, 2+, or 3+ in at least 10% of tumor cells, such as in at least 20%, 30%, 40%, or 50% of tumor cells.

In some embodiments, the cancer is selected from gastric cancer, breast cancer, non-small cell lung cancer, melanoma, squamous cell carcinoma of the head and neck, ovarian cancer, pancreatic cancer, renal cell carcinoma, hepatocellular carcinoma, bladder cancer, cholangiocarcinoma, esophageal cancer (including gastroesophageal junction adenocarcinoma), and endometrial cancer. In some embodiments, the cancer is recurrent or progressive after a therapy selected from surgery, chemotherapy, radiation therapy, or a combination thereof. In some embodiments, the subject is a PD-1/PD-L1 inhibitor inadequate responder. In some embodiments, the subject has previously received PD-1/PD-L1 inhibitor therapy.

In some embodiments, a method of treating cancer further comprises administering at least one additional therapeutic agent selected from a platinum agent, paclitaxel, ABRAXANE®, docetaxel, gemcitabine, capecitabine, irinotecan, epirubicin, FOLFOX, FOLFIRI, leucovorin, fluorouracil, mitomycin C, and doxorubicin hydrochloride. In some embodiments, the platinum agent is selected from cisplatin, oxaliplatin, and carboplatin. In some embodiments, a method of treating cancer further comprises administering paclitaxel. In some embodiments, a method of treating cancer further comprises administering cisplatin and/or 5-FU.

In some embodiments, the FGFR2 inhibitor and the PD-1/PD-L1 inhibitor are administered concurrently or sequentially. In some embodiments, the FGFR2 inhibitor and the immune stimulating agent are administered concurrently. In some embodiments, one or more doses of immune stimulating agent are administered prior to administering an FGFR2 inhibitor. In some embodiments, the subject received a complete course of immune stimulating agent therapy prior to administration of the FGFR2 inhibitor. In some embodiments, the FGFR2 inhibitor is administered during a second course of immune stimulating agent therapy. In some embodiments, the subject received at least one, at least two, at least three, or at least four doses of immune stimulating agent prior to administration of the FGFR2 inhibitor. In some embodiments, at least one dose of immune stimulating agent is administered concurrently with the FGFR2 inhibitor. In some embodiments, one or more doses of the FGFR2 inhibitor are administered prior to administering an immune stimulating agent. In some embodiments, the subject may receive at least two, at least three, at least three, or at least four doses of the FGFR2 inhibitor prior to administration of immune stimulating agent. In some embodiments, at least one dose of the FGFR2 inhibitor is administered concurrently with immune stimulating agent.

In some embodiments, administration of the FGFR2 inhibitor and a PD-1/PD-L1 inhibitor in a mouse xenograft and/or syngeneic tumor model results in either additive or synergistic inhibition of tumor growth. In some embodiments, the model is a breast cancer model. In some embodiments, the model comprises 4T1 cells.

In any of the above method embodiments, the combination of the FGFR2 inhibitor and PD-1/PD-L1 inhibitor may inhibit tumor growth in a mouse xenograft and/or syngeneic tumor model over a period of at least 1 week, 10 days, or 2 weeks, for example, by at least 10% A, at least 20%, at least 30%, at least 40%, at least 50%, at least 60%, at least 70%, at least 80%, at least 90%, or at least 95%. In any of the above method embodiments, administration of the combination of the FGFR2 inhibitor and immune stimulating agent, such as PD-1/PD-L1 inhibitor, to the subject may reduce the volume of at least one tumor in the subject by at least 10%, at least 20%, at least 30%, at least 40%, at least 50%, at least 60%, at least 70%, at least 80%, at least 90%, or at least 95%, for example, over a period of at least one month, two months, three months, six months, or one year.

In any of the above method embodiments, administration of the FGFR2 inhibitor in a xenograft and/or syngeneic tumor model may show an increase in NK cells, such as NKp46+ cells, an increase in PD-L1 expressing cells, an increase in macrophages such as F480+ macrophages, an increase in one or more of CD3+, CD8+, and CD4+ T cells, and/or an increase in the ratio of lymphoid to myeloid cells in tumor tissue compared to a control over a period of at least 1 day, at least 4 days, at least 1 week, at least 10 days, or at least 2 weeks, and for example, by at least 10%, at least 20%, at least 30%, at least 40%, at least 50%, at least 60%, at least 70%, at least 80%, at least 90%, or at least 95%. In some embodiments, the mouse syngeneic tumor model is a 4T1 mammary tumor model. In some embodiments, the control is a vehicle or is an Ig-Fc molecule or another compound that does not inhibit tumor growth in the model.

Also provided herein are methods of increasing the number of NK cells, PD-L1 positive cells, and/or CD3+, CD8+, and/or CD8+ T cells and/or macrophages in a tumor tissue of a subject with cancer, and/or methods of increasing the lymphoid cell to myeloid cell ratio in a tumor tissue of a subject with cancer, comprising administering to said subject an effective amount of an FGFR2 inhibitory antibody, such as any of the FGFR2 antibodies described in the preceding paragraphs. An increase in one or more of CD3+, CD8+, and CD4+ T cells, and/or an increase in the ratio of lymphoid to myeloid cells in tumor tissue compared to a control over a period of at least 1 day, at least 4 days, at least 1 week, at least 10 days, or at least 2 weeks, and for example, by at least 10%, at least 20%, at least 30%, at least 40%, at least 50%, at least 60%, at least 70%, at least 80%, at least 90%, or at least 95%. In some embodiments, the antibody may have one or more of the following properties: (a) lacks a fucose at position Asn297; (b) comprises a κ light chain constant region; (c) comprises an IgG1 heavy chain constant region; (d) has enhanced ADCC activity in vitro compared to an antibody having the same amino acid sequence that is fucosylated at position Asn297; and (e) has enhanced affinity for Fc gamma RIIIA compared to an antibody having the same amino acid sequence that is fucosylated at position Asn297. In some embodiments, the afucosylated antibody is capable of increasing the number of one or more of PD-L1 positive cells, NK cells, CD3+ T cells, CD4+ T cells, CD8+ T cells, and macrophages in tumor tissue in a mouse xenograft and/or syngeneic tumor model compared to a control (e.g. as compared to a control antibody that does not target FGFR2). In some embodiments, the method inhibits tumor growth or reduces volume of at least one tumor in the subject. In some embodiments, the subject suffers from breast cancer, gastric cancer, non-small cell lung cancer, melanoma, squamous cell carcinoma of the head and neck, ovarian cancer, pancreatic cancer, renal cell carcinoma, hepatocellular carcinoma, bladder cancer, cholangiocarcinoma, esophageal cancer (including gatroesophageal junction adenocarcinoma), and endometrial cancer. In some embodiments, the method further comprises, following administration of the FGFR2 antibody, obtaining at least one tumor sample from the subject and determining the number of NK cells, PD-L1 positive cells, and/or CD3+, CD8+, and/or CD4+ T cells in the sample, and, if the number of one or more of those types of cells is increased relative to a sample prior to FGFR2 antibody administration or relative to a non-tumor sample from the subject, administering a PD-1/PD-L1 inhibitor to the subject. In some embodiments, the method further comprises, following administration of the FGFR2 antibody, obtaining at least one tumor sample from the subject and determining the ratio of lymphoid cells to myeloid cells in the sample, and, if the ratio is increased relative to a sample prior to FGFR2 antibody administration or relative to a non-tumor sample from the subject, administering at least one to the subject. The at least one immune stimulating agent, such as at least one PD-1/PD-L1 inhibitor, of these methods may be any of those described in the preceding paragraphs or described in the section below entitled "combinations with other immune stimulating agents." In some embodiments, the patient may be administered a combination of FGFR2 inhibitor, PD-1/PD-L1 inhibitor, and at least one other immune stimulating agent.

Also provided herein are methods of treating cancer in a subject comprising administering to the subject an FGFR2 inhibitor and, if the subject is determined to have an increased number of NK cells, PD-L1 positive cells, macrophages, CD3+ T cells, CD8+ T cells, and/or CD4+ T cells relative to a control, such as a sample prior to FGFR2 antibody administration or relative to a non-tumor sample from the subject, administering at least one immune stimulating agent to the subject, such as a PD-1/PD-L1 inhibitor. Also provided herein are methods of treating cancer in a subject comprising administering to the subject an FGFR2 inhibitor and, if the subject is determined to have an increased ratio of lymphoid cells to myeloid cells relative to a control, such as a sample prior to FGFR2 antibody administration or relative to a non-tumor sample from the subject, administering at least one immune stimulating agent to the subject, such as a PD-1/PD-L1 inhibitor. In such methods, the FGFR2 inhibitor and immune stimulating agent may be any of those described in the preceding paragraphs or in the section below entitled "combinations with other immune stimulating agents." Furthermore, the FGFR2 and immune stimulating agent administration may be according to the previously described methods in which administration of immune stimulating agent does not begin until at least one dose of FGFR2 inhibitor is administered. In such cases, a test to determine the number of NK cells, PD-L1 positive cells, macrophages, CD3+, CD8+, and/or CD4+ T cells, lymphoid, and/or myeloid cells may, for example, be conducted after FGFR2 inhibitor administration has begun but prior to the start of FGFR2 and immune stimulating agent combination administration.

Compositions comprising any of the FGFR2 inhibitors described herein and any of the immune stimulating agents described herein are also provided. In such compositions, the FGFR2 inhibitor and the at least one immune stimulating agent may be located in separate containers or separate compartments of the same container, or alternatively, they may be mixed together into the same container or compartment. Such compositions may be used, for example, for treatment of cancer, such as any of the cancers described above. In some embodiments, instructions for use may also be included, such as instructions for use in treating cancer.

Provided herein are also methods of increasing the number of one or more of PD-L1 positive cells, NK cells, macrophages, CD3+ T cells, CD4+ T cells, and CD8+ T cells in tumor tissue of a cancer subject, comprising administering an FGFR2 inhibitor, wherein the inhibitor is an FGFR2 antibody with enhanced ADCC activity. In some such embodiments, no immune stimulating agent is administered with the FGFR2 antibody. In some such embodiments, administration of the FGFR2 antibody in a mouse xenograft and/or syngeneic tumor model increases the number of one or more of PD-L1 positive cells, NK cells, macrophages, CD3+ T cells, CD8+ T cells, and CD4+ T cells in tumor tissue compared to a control, and/or increases the ratio of lymphoid to myeloid cells in the tumor tissue. In some such embodiments, the subject suffers from breast cancer, gastric cancer, non-small cell lung cancer, melanoma, squamous cell carcinoma of the head and neck, ovarian cancer, pancreatic cancer, renal cell carcinoma, hepatocellular carcinoma, bladder cancer, cholangiocarcinoma, esophageal cancer (including gatroesophageal junction adenocarcinoma), or endometrial cancer, such as from bladder cancer.

In the above methods, the FGFR2 antibody may be an FGFR2-IIIb antibody, which may have one or more of the following properties: (a) binds to FGFR2-IIIb with higher affinity than to FGFR2-IIIc or does not detectably bind to FGFR2-IIIc; (b) inhibits binding of FGF2 and/or FGF7 to human FGFR2; (c) inhibits growth of a human tumor in a mouse xenograft and/or syngeneic tumor model; (d) induces an ADCC activity; (e) possesses enhanced ADCC activity; and (f) is afucosylated.

In some embodiments of the above method, the FGFR2 antibody comprises heavy chain and light chain variable regions, wherein the heavy chain variable region comprises: (i) HVR-H1 comprising the amino acid sequence of SEQ ID NO: 6; HVR-H2 comprising the amino acid sequence of SEQ ID NO: 7; and (iii) HVR-H3 comprising the amino acid sequence of SEQ ID NO: 8;

and the light chain variable region comprises: (iv) HVR-L1 comprising the amino acid sequence of SEQ ID NO: 9; (v) HVR-L2 comprising the amino acid sequence of SEQ ID NO: 10; and (vi) HVR-L3 comprising the amino acid sequence of SEQ ID NO: 11.

In some cases, the heavy chain variable domain of the FGFR2 antibody comprises an amino acid sequence at least 95% identical to the amino acid sequence of SEQ ID NO: 4 and/or the light chain variable domain of the FGFR2 antibody comprises an amino acid sequence at least 95% identical to the amino acid sequence of SEQ ID NO: 5. In some cases, the heavy chain variable domain of the FGFR2 antibody comprises the amino acid sequence of SEQ ID NO: 4 and/or the light chain variable domain of the FGFR2 antibody comprises the amino acid sequence of SEQ ID NO: 5. In some cases, the heavy chain of the FGFR2 antibody comprises an amino acid sequence at least 95% identical to the amino acid sequence of SEQ ID NO: 2 and/or the light chain of the FGFR2 antibody comprises an amino acid sequence at least 95% identical to the amino acid sequence of SEQ ID NO: 3. In some cases, the heavy chain of the FGFR2 antibody comprises the amino acid sequence of SEQ ID NO: 2 and/or the light chain of the FGFR2 antibody comprises the amino acid sequence of SEQ ID NO: 3. In some cases, the FGFR2 antibody is chimeric, humanized, or human. In some embodiments, the FGFR2 antibody is selected from a Fab, an Fv, an scFv, a Fab', and a (Fab')$_2$. In some embodiments, the FGFR2 antibody has one or more of the following properties: (a) lacks a fucose at position Asn297; (b) comprises a κ light chain constant region; (c) comprises an IgG1 heavy chain constant region; (d) has enhanced ADCC activity in vitro compared to an antibody having the same amino acid sequence that is fucosylated at position Asn297; and (e) has enhanced affinity for Fc gamma RIIIA compared to an antibody having the same amino acid sequence that is fucosylated at position Asn297. In some embodiments, the afucosylated antibody is capable of increasing the number of one or more of PD-L1 positive cells, NK cells, CD3+ T cells, CD4+ T cells, CD8+ T cells, and macrophages in tumor tissue in a mouse xenograft and/or syngeneic tumor model compared to a control (e.g. as compared to a control antibody that does not target FGFR2).

In any of the methods or uses described in this summary section, the cancer may have been previously determined to overexpress FGFR2IIIb, either in the presence or absence of amplification of the FGFR2 gene. Alternatively, any of the methods or uses described in this section, the method may further comprise testing the subject's cancer, for example prior to administration of an FGFR2 inhibitor, to determine if the cancer overexpresses FGFR2IIIb and/or to determine if the FGFR2 gene is amplified in tumor cells. In either case, FGFR2IIIb may optionally be determined by immunohistochemistry (IHC) and FGFR2 gene amplification may optionally be determined by fluorescence in situ hybridization (FISH), for example using probes for the FGFR2 gene locus and the centromere of chromosome 10 on which the FGFR2 gene is located. In some embodiments, an IHC signal of 1+, 2+, or 3+ in at least 10% of tumor cells, such as at least 20%, 30%, 40%, or 50% of tumor cells indicates overexpression of FGFR2IIIb. In some embodiments, an FGFR2 to centromere of chromosome 10 (CEN10) ratio of greater than or equal to 2 indicates FGFR2 gene amplification.

In some embodiments in which the patient suffers from gastric or bladder cancer, the subject may have been previously determined to have one of the following profiles or alternatively the method of treatment includes determining whether the patient fits one of the following profiles with respect to FGFR2 expression/gene amplification, and which may indicate the level of expected responsiveness to the treatment: a) in the case of a gastric cancer subject, an IHC signal of 3+ in at least 10% of tumor cells; b) in the case of a gastric cancer subject, an IHC signal of 3+ in at least 10% of tumor cells as well as amplification of the FGFR2 gene; c) in the case of a gastric cancer subject, an IHC signal of 3+ in at least 10% of tumor cells without amplification of the FGFR2 gene; d) in the case of a gastric cancer subject, an IHC signal of 1+ or 2+ in at least 10% of tumor cells; e) in the case of a bladder cancer subject, an IHC signal of 1+ in at least 10% of tumor cells; f) in the case of a bladder cancer subject, an IHC signal of 2+ in at least 10% of tumor cells; g) in the case of a bladder cancer subject, an H score of greater than 20; h) in the case of a bladder cancer subject, an H score of 10-19; i) in the case of a bladder cancer subject, an H score of less than 10.

This disclosure also provides methods of determining responsiveness to any of the FGFR2 inhibitors, treatments, and uses described above. Such methods may comprise testing the subject's cancer to determine if the cancer overexpresses FGFR2IIIb and/or to determine if the FGFR2 gene is amplified in tumor cells. Overexpression of FGFR2IIIb may optionally be determined by immunohistochemistry (IHC) and FGFR2 gene amplification may optionally be determined by fluorescence in situ hybridization (FISH), for example using probes for the FGFR2 gene locus and the centromere of chromosome 10 on which the FGFR2 gene is located. In some embodiments, an IHC signal of 1+, 2+, or 3+ in at least 10% of tumor cells, such as at least 20%, 30%, 40%, or 50% of tumor cells indicates overexpression of FGFR2IIIb. In some embodiments, an FGFR2 to centromere of chromosome 10 (CEN10) ratio of greater than or equal to 2 indicates FGFR2 gene amplification.

In some embodiments in which the patient suffers from gastric or bladder cancer, the method may comprise determining if the patient's cancer falls into one of the following categories, which may indicate responsiveness to the treatment or FGFR2 inhibitor composition: a) in the case of a gastric cancer subject, an IHC signal of 3+ in at least 10% of tumor cells; b) in the case of a gastric cancer subject, an IHC signal of 3+ in at least 10% of tumor cells as well as amplification of the FGFR2 gene; c) in the case of a gastric cancer subject, an IHC signal of 3+ in at least 10% of tumor cells without amplification of the FGFR2 gene; d) in the case of a gastric cancer subject, an IHC signal of 1+ or 2+ in at least 10% of tumor cells; e) in the case of a bladder cancer subject, an IHC signal of 1+ in at least 10% of tumor cells; f) in the case of a bladder cancer subject, an IHC signal of 2+ in at least 10% of tumor cells; g) in the case of a bladder cancer subject, an H score of greater than 20; h) in the case of a bladder cancer subject, an H score of 10-19; i) in the case of a bladder cancer subject, an H score of less than 10.

It is to be understood that both the foregoing general description and the following detailed description are exemplary and explanatory only and are not restrictive of the claims. The section headings used herein are for organizational purposes only and are not to be construed as limiting the subject matter described. All references cited herein, including patent applications and publications, are incorporated herein by reference in their entireties for any purpose.

BRIEF DESCRIPTION OF THE DRAWINGS

As shown in FIG. 4a, the combination of anti-FGFR2 (10 mg/kg BIW) and the anti-PD1 antibody (5 mg/kg BIW) resulted in significant inhibition of the growth of the 4T1 tumors compared to the control and either antibody alone by day 18. As shown in FIG. 4b, at day 18 post-tumor implantation, the combination showed a statistically significant inhibition of growth in the 4T1 tumors compared to the Ig-Fc control or the anti-PD1 antibody. Statistical significance was determined by 1 way ANOVA followed by Tukey multiple comparisons test.

The images show that treatment with anti-FGFR2 led to an increase in the number of all three types of T cells in the tumor tissue by day 4 as compared to the vehicle control and treatment with anti-FGFR2 N297Q.

Figure 7A:
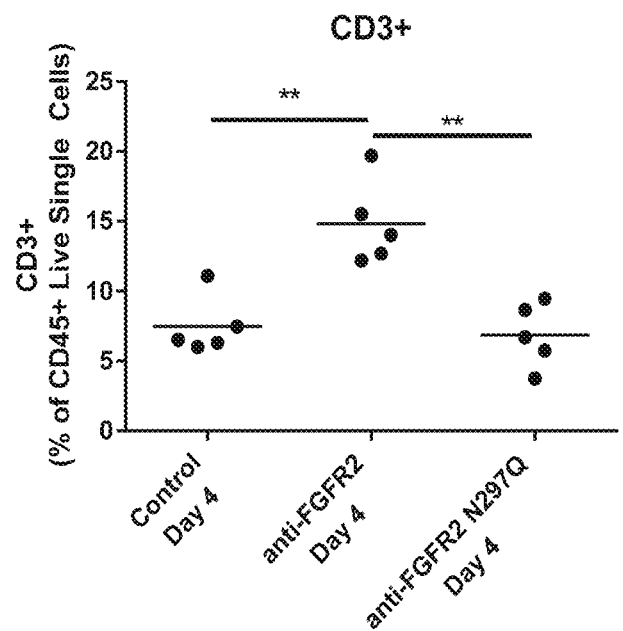
Figure 7B:
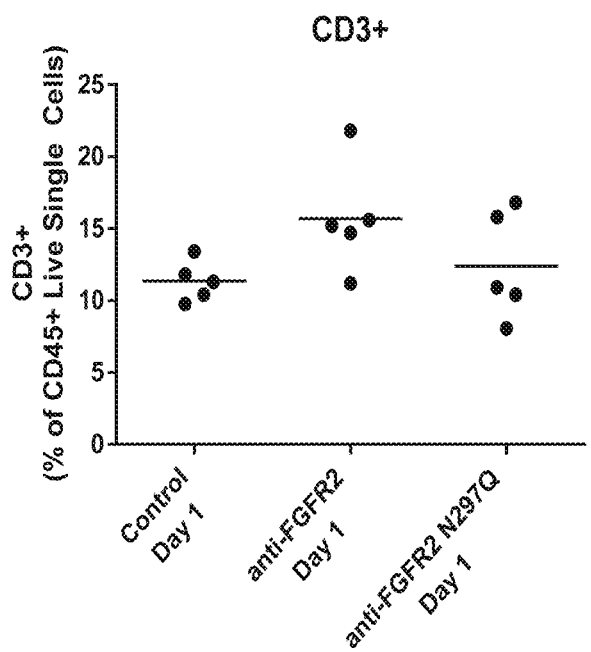

FIGS. 7a-7b show results of a FACS analysis of tumor cells in the 4T1 syngeneic tumor model at day 1 and day 4, respectively. CD3+ T cells are provided for each of the treatment groups as a percentage of CD45+ live single cells. As shown in the figures, the anti-FGFR2 group showed an increase in the percentage of CD3+ T cells compared to both the vehicle control and the anti-FGFR2 N297Q groups by day 4. The increase was also statistically significant according to a student T-test, as noted by the ** symbols, indicating $P \leq 0.01$.

Figure 8A:
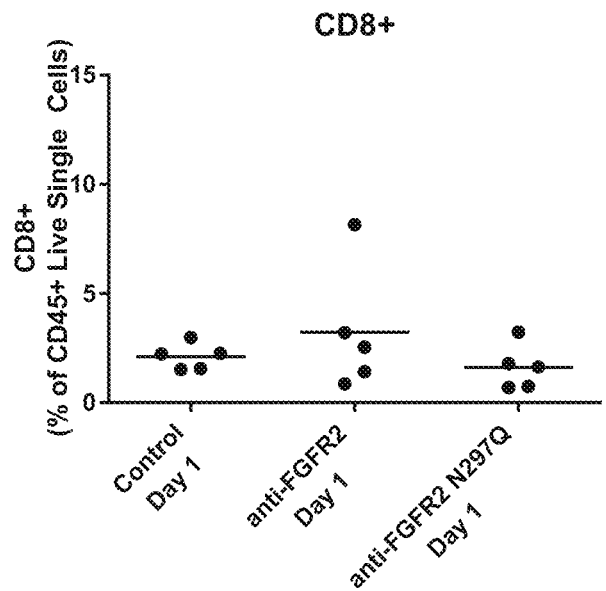
Figure 8B:
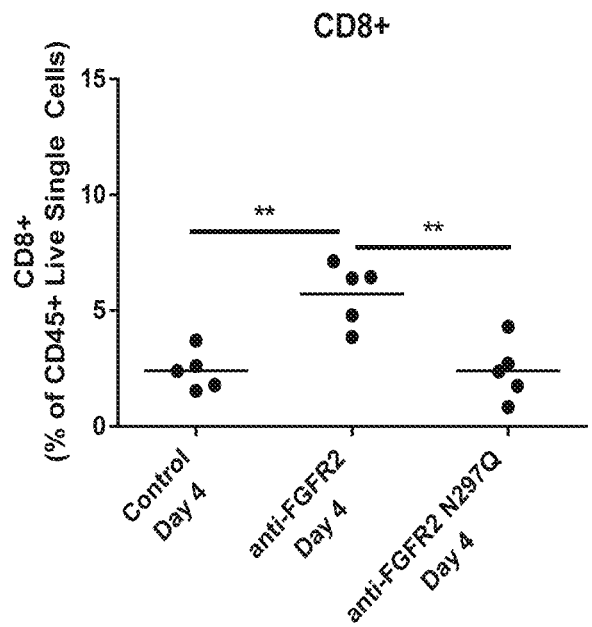

FIGS. 8a-8b show results of a FACS analysis of tumor cells in the 4T1 syngeneic tumor model at day 1 and day 4, respectively. CD8+ T cells are provided for each of the treatment groups as a percentage of CD45+ live single cells. As shown in the figures, the anti-FGFR2 group showed an increase in the percentage of CD8+ T cells compared to both the vehicle control and the anti-FGFR2 N297Q groups by day 4. The increase was also statistically significant according to a student T-test, as noted by the ** symbols, indicating $P \leq 0.01$.

Figure 9A:
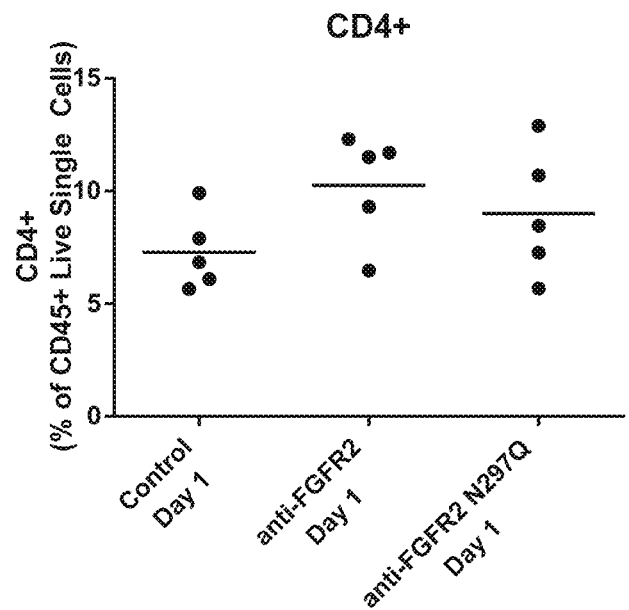
Figure 9B:
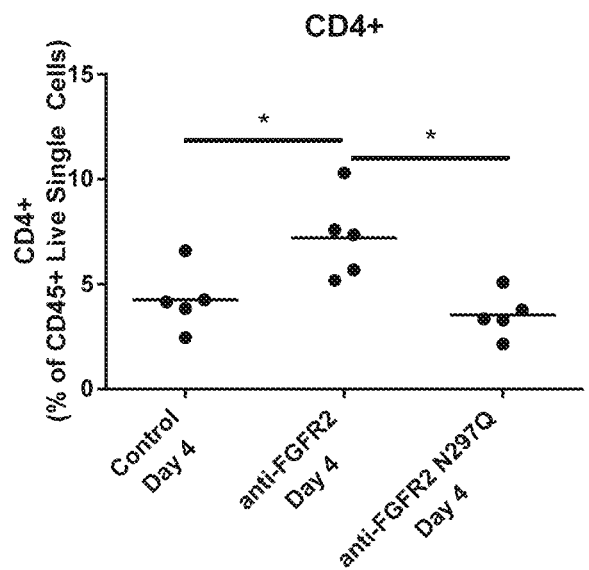

FIGS. 9a-9b show results of a FACS analysis of tumor cells in the 4T1 syngeneic tumor model at day 1 and day 4, respectively. CD4+ T cells are provided for each of the treatment groups as a percentage of CD45+ live single cells. As shown in the figures, the anti-FGFR2 group showed an increase in the percentage of CD4+ T cells compared to both the vehicle control and the anti-FGFR2 N297Q groups by day 4. The increase was also statistically significant according to a student T-test, as noted by the * symbols, indicating $P \leq 0.5$.

Figure 10A:
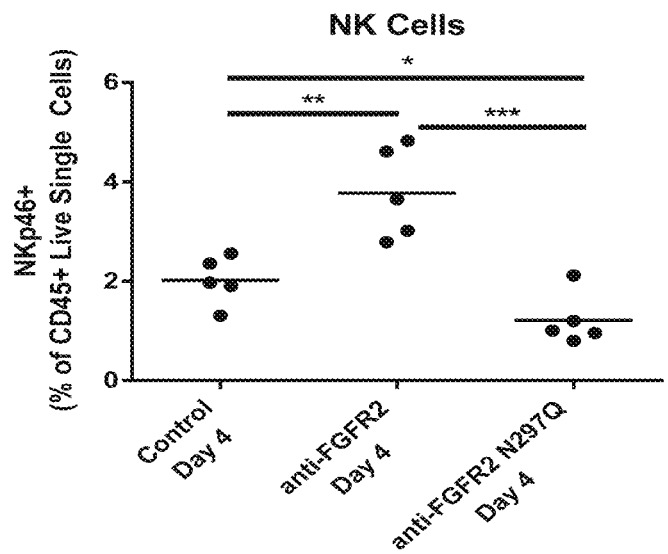
Figure 10B:
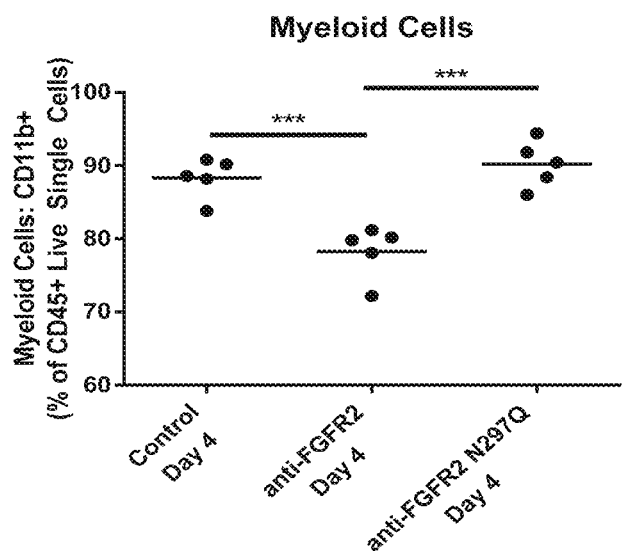
Figure 10C:
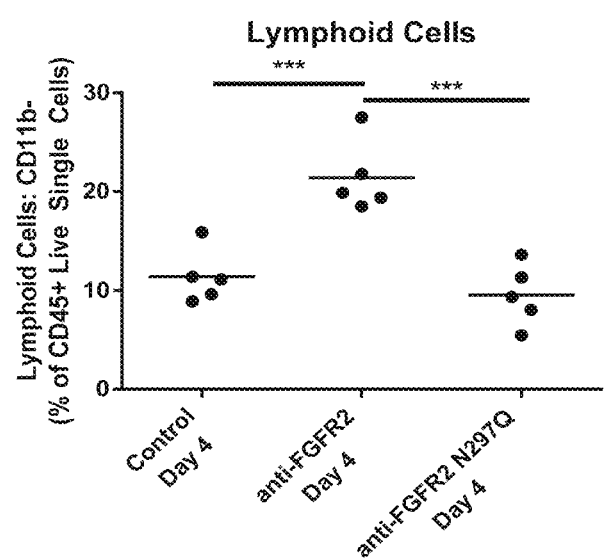

FIGS. 10a-10c show further results of a FACS analysis of tumor cells in the 4T1 syngeneic tumor model at day 4. In FIG. 10a, NKp46+ cells are provided for each of the treatment groups as a percentage of CD45+ live single cells. The figure shows a statistically significant increase in NKp46+ cells in the anti-FGFR2 group compared to the other groups, according to a student T-test, wherein * denotes $P \leq 0.5$,  denotes $P \leq 0.01$, and * denotes $P \leq 0.001$. FIGS. 10b and 10c show that myeloid cells are significantly reduced in the anti-FGFR2 group while lymphoid cells are significantly increased, thus showing that, in comparison to the other groups, the lymphoid to myeloid ratio increases on day 4 after treatment with anti-FGFR2.

Figure 11:
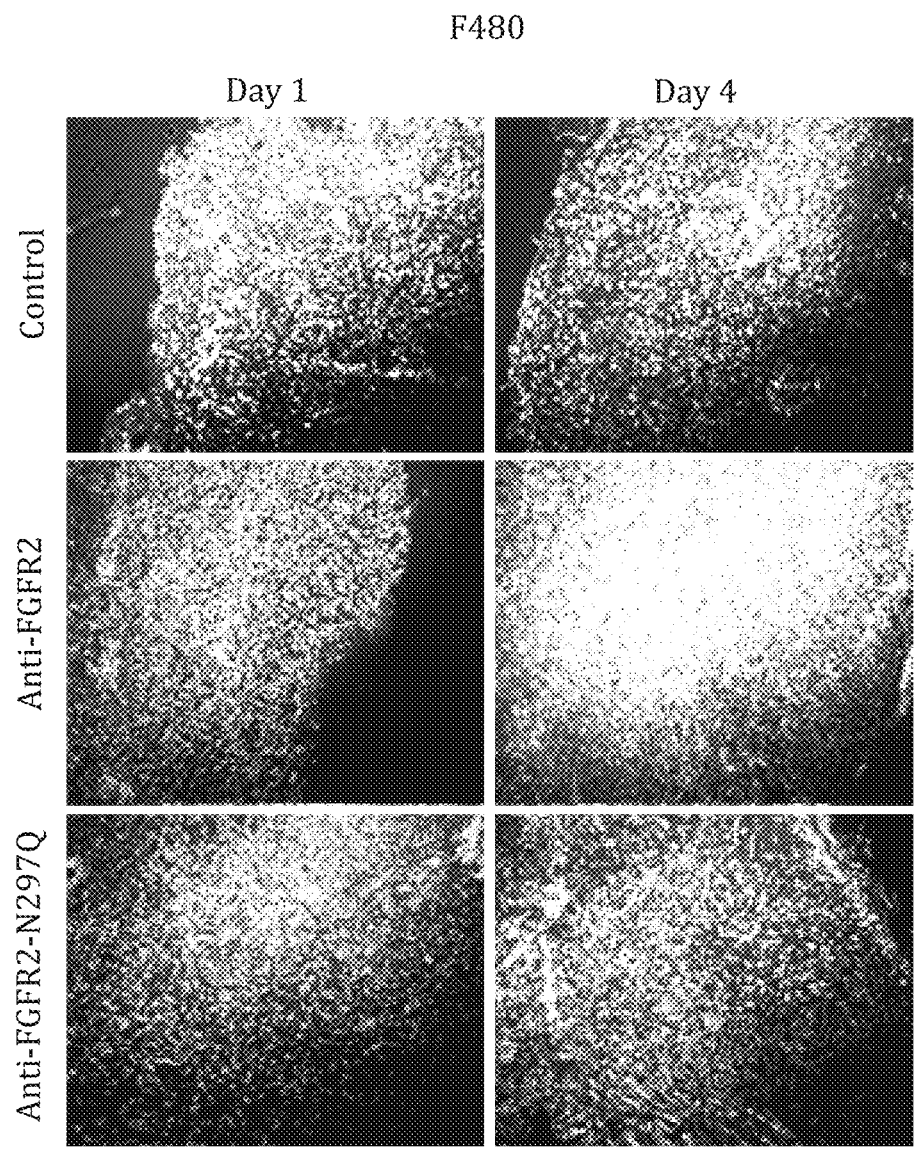

FIG. 11 shows staining of 4T1 tumor tissue in a mouse syngeneic tumor model 1 or 4 days following treatment with a vehicle control (top panels), anti-FGFR2 antibody (middle panels), or anti-FGFR2-N297Q antibody (bottom panels). The images show staining with an anti-F480 antibody to look for infiltration of F480+ macrophages into the tumor tissue and corresponding DAPI staining of cell nuclei. As can be seen from the figure, after anti-FGFR2 treatment, F480+ macrophages are much more numerous compared to the control (compare the top and middle panels at day 4). No differences were observed between the control and anti-FGFR2-N297Q panels (compare the top and bottom panels at day 4). Images were collected using a 10× objective.

Figure 12:
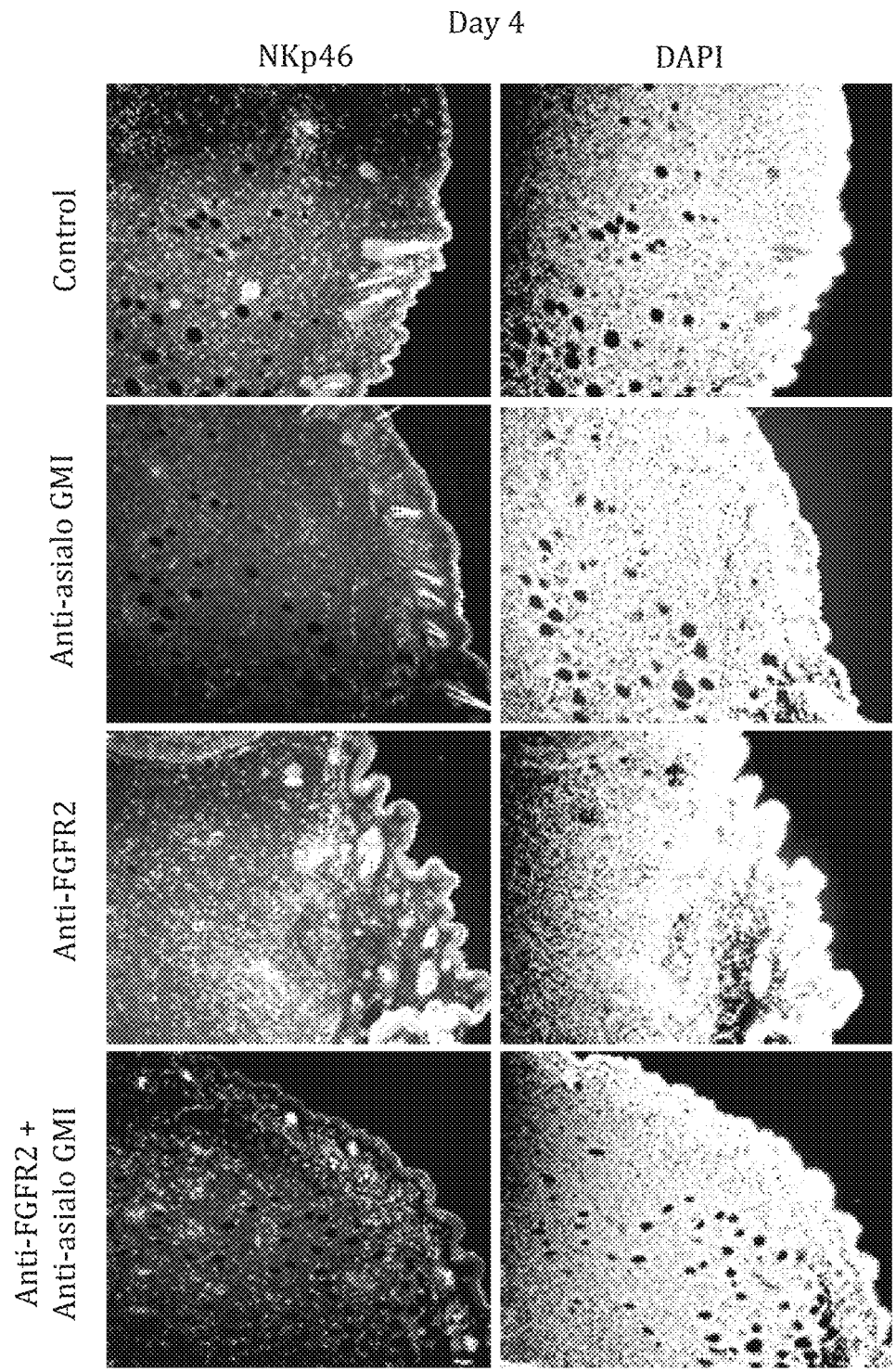

FIG. 12 shows staining of 4T1 tumor tissue in a mouse syngeneic tumor model 4 days after treatment with various antibodies: control antibody (Fc-G1 antibody) (top panels), rabbit anti-asialo GM1 antibody—intended to reduce the number of NKp46 cells (second panels), anti-FGFR2 antibody (third panels), and a combination of anti-FGFR2 antibody plus anti-asialo GM1 antibody (bottom panels). Tissue was stained with reagents for NKp46 or with DAPI to stain cell nuclei (left and right panels, respectively). The anti-asialo GM1 antibody was dosed at 1.25 mg/kg and the anti-FGFR2 antibody was dosed at 10 mg/kg. Images were collected using a 10× objective. As can be seen in the four different NKp46 staining panels, the anti-asialo GM1 antibody depleted NKp46 cells in tumor tissue, while the anti-FGFR2 antibody increased the number of NKp46 cells. (Compare the top and third left panels.) The anti-FGFR2 antibody in combination with the anti-asialo GM1 antibody increased the number of NKp46 cells compared to the anti-asialo GM1 antibody alone (although not compared to the control), indicating that the anti-FGFR2 antibody can increase the number of NKp46 cells in tumor tissue even when those cells are being depleted by presence of a competing antibody. (Compare the top, second, and bottom left panels.)

Figure 13:
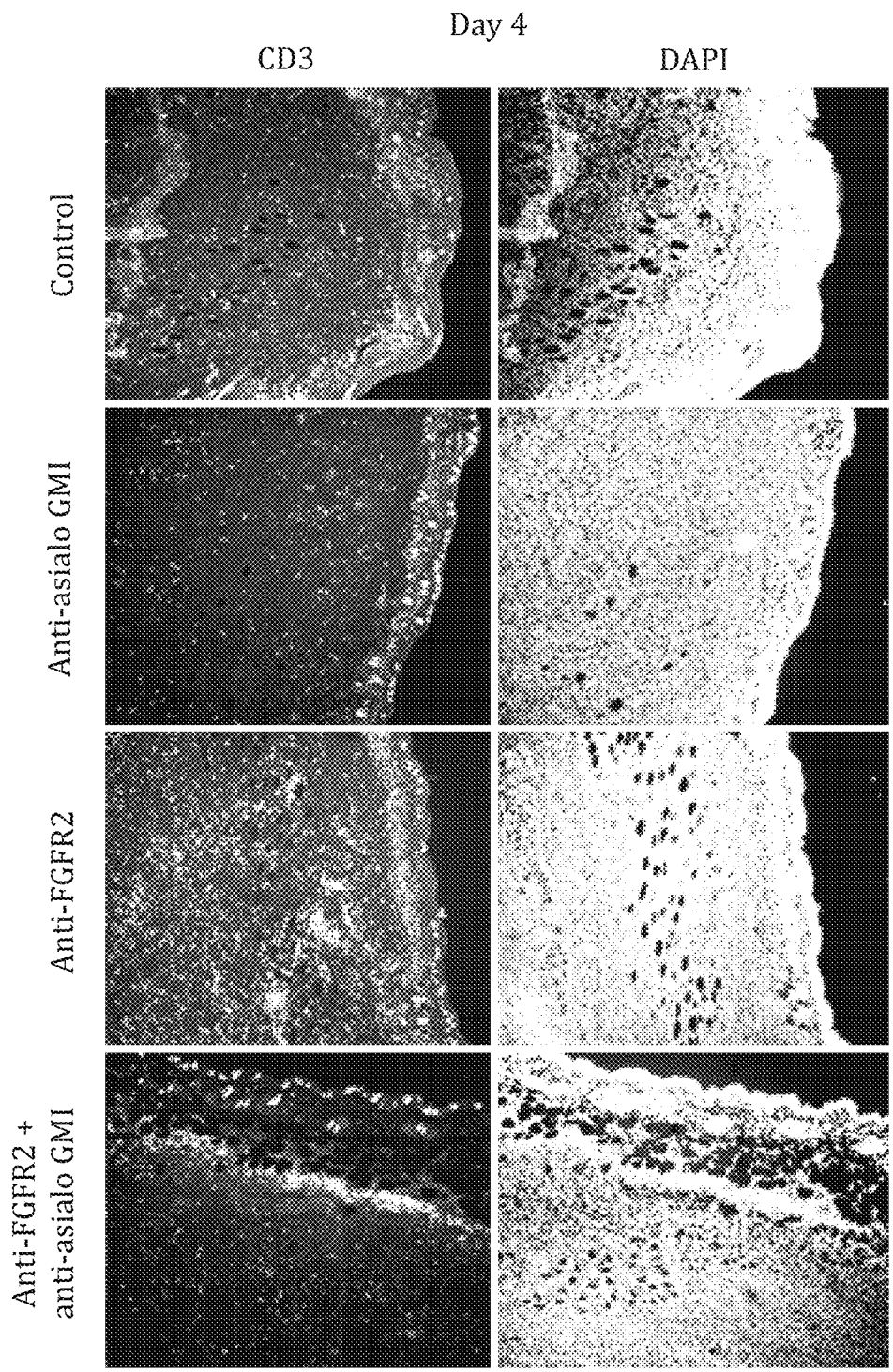

FIG. 13 shows staining for CD3+ T cells and corresponding DAPI staining of cell nuclei of 4T1 tumor tissue in a mouse syngeneic tumor model 4 days after treatment with control antibody (Fc-G1 antibody) (top panels), rabbit anti-asialo GM1 antibody (second panels), anti-FGFR2 antibody (third panels), and a combination of anti-FGFR2 antibody plus anti-asialo GM1 antibody (bottom panels). The anti-asialo GM1 antibody was dosed at 1.25 mg/kg and the anti-FGFR2 antibody was dosed at 10 mg/kg. Images were collected using a 10× objective. As can be seen by comparing the four left panels of the figure, treatment with anti-FGFR2 antibody increased the number of CD3+ T cells in tumor tissue, but not when administered together with the anti-asialo GM1 antibody.

Figure 14:
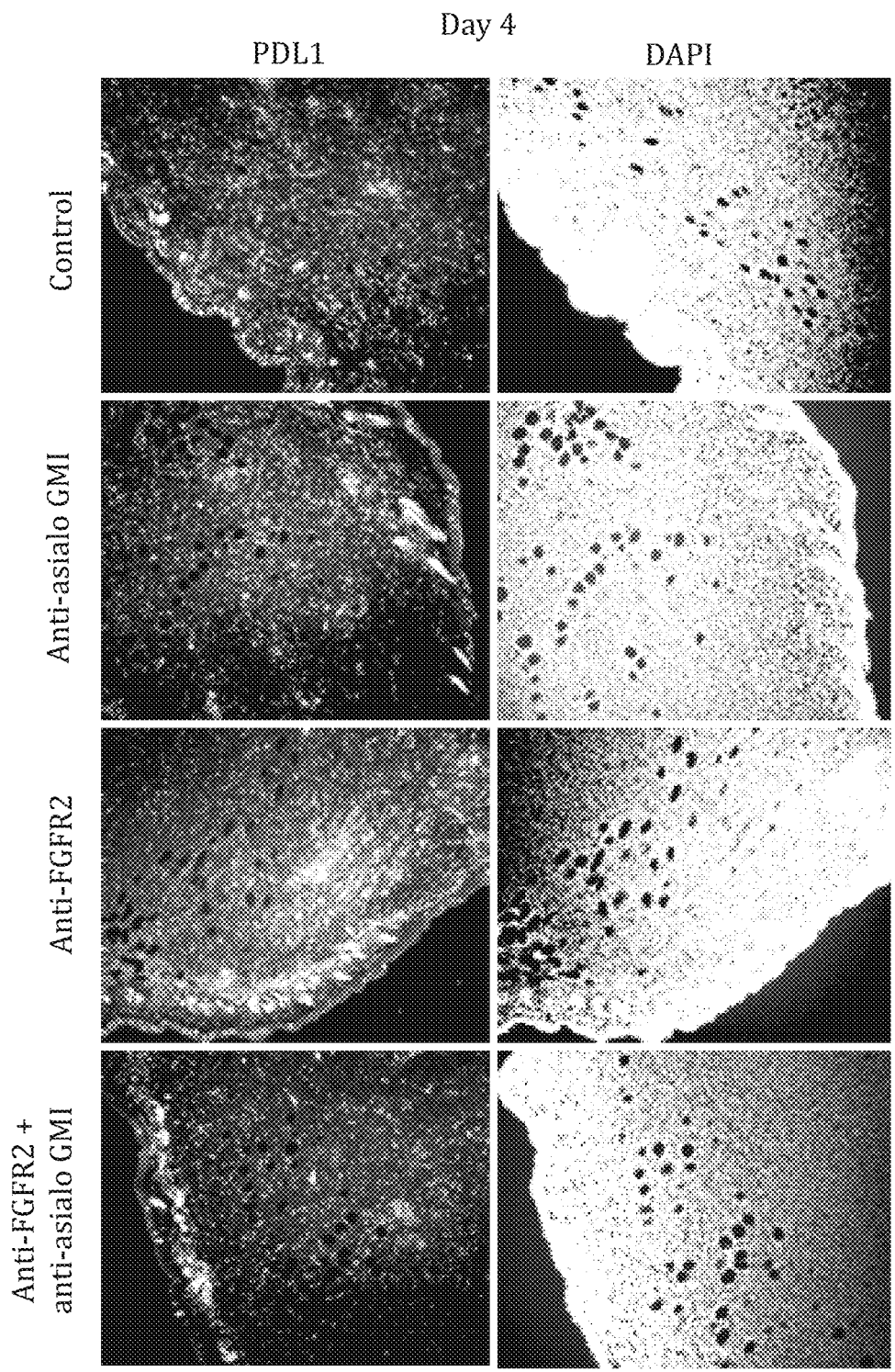

FIG. 14 shows staining for PD-L1 positive cells and corresponding DAPI staining of cell nuclei of 4T1 tumor tissue in a mouse syngeneic tumor model 4 days after treatment with control antibody (Fc-G1 antibody) (top panels), rabbit anti-asialo GM1 antibody (second panels), anti-FGFR2 antibody (third panels), and a combination of anti-FGFR2 antibody plus anti-asialo GM1 antibody (bottom panels). The anti-asialo GM1 antibody was dosed at 1.25 mg/kg and the anti-FGFR2 antibody was dosed at 10 mg/kg. Images were collected using a 10× objective. As can be seen by comparing the four left panels of the figure, treatment with anti-FGFR2 antibody increased the number of PD-L1 positive cells in tumor tissue, but not when administered together with the anti-asialo GM1 antibody.

Figure 15A:
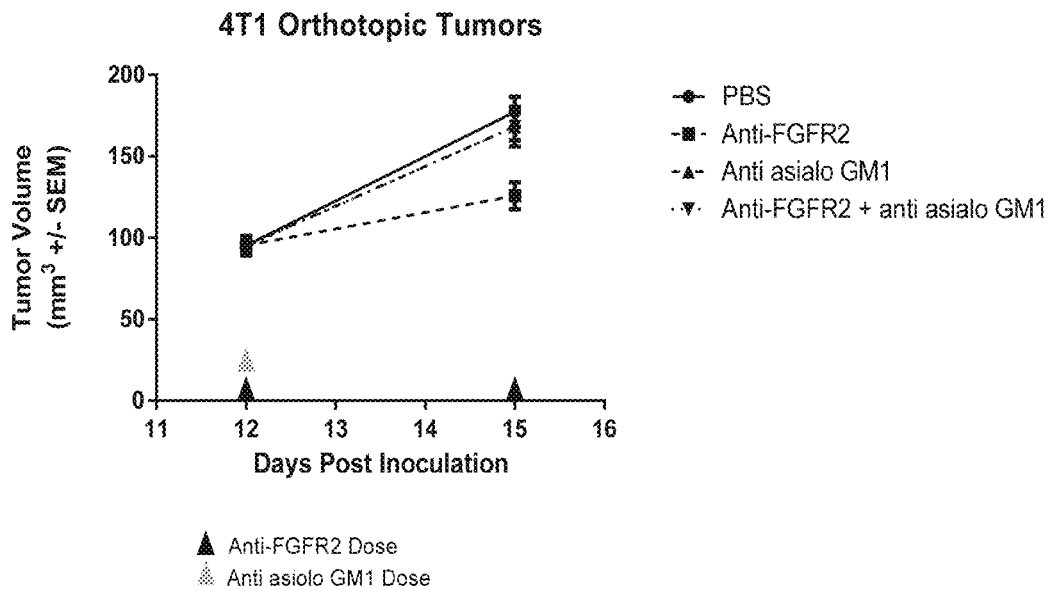
Figure 15B:
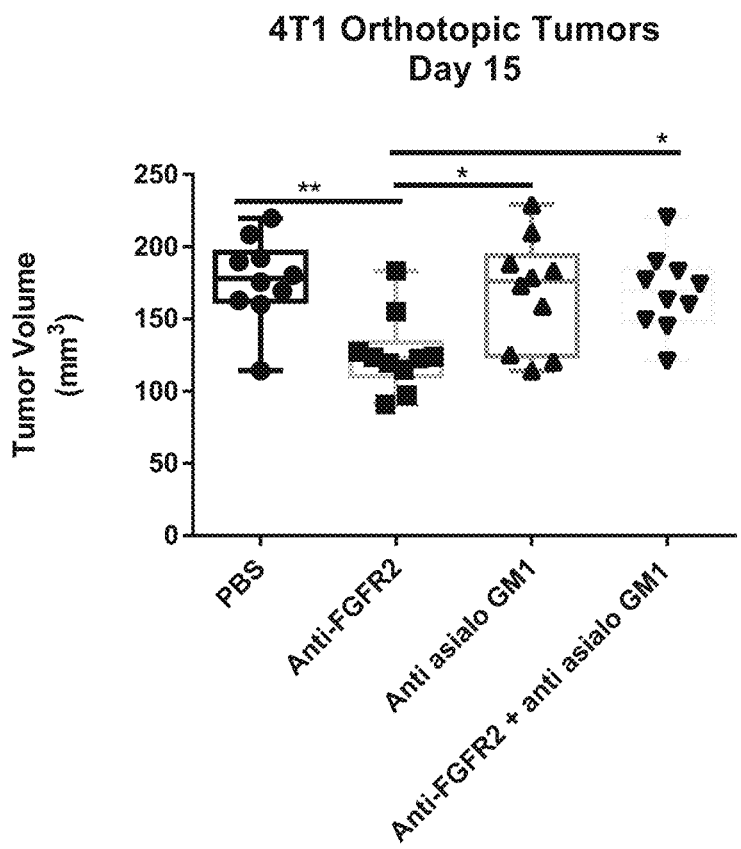

FIGS. 15a and 15b show growth of 4T1 orthotopic tumors in mice after inoculation with phosphate buffered saline (PBS) control, anti-FGFR2 antibody, anti-asialo GM1 antibody, or a combination of anti-FGFR2 and anti-asialo GM1 antibodies. FIG. 15a shows tumor volume at 12 and 15 days post inoculation. FIG. 15b shows a plot of tumor volume in the individual mice in each group 15 days post innoculation. The figure shows a statistically significant decrease in tumor volume in the anti-FGFR2 group compared to the control and the anti-asialo GM1 groups according to a student T-test, wherein * denotes $P \leq 0.5$ and ** denotes $P \leq 0.01$, as well as a statistically significant change in tumor volume between the group receiving anti-FGFR2 antibody alone and the group receiving the combination of anti-FGFR2 and anti-asialo GM1 antibodies.

Figure 16A:
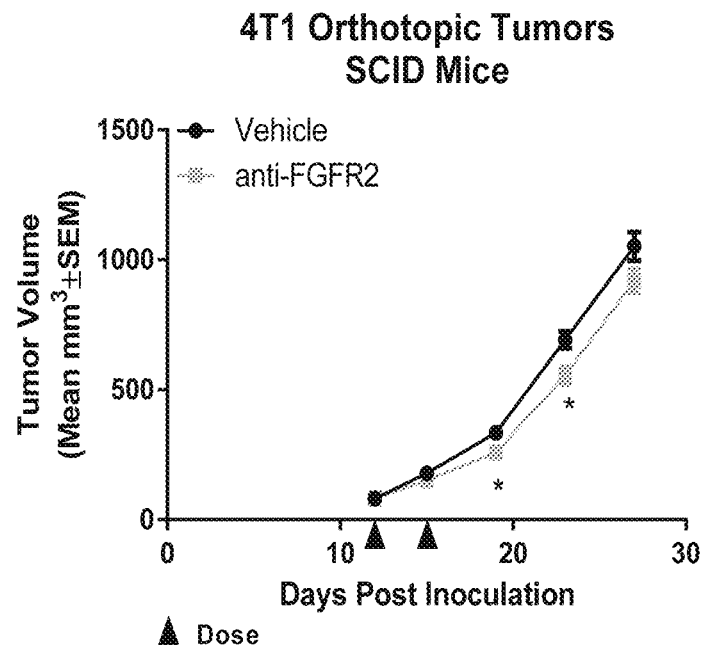
Figure 16B:
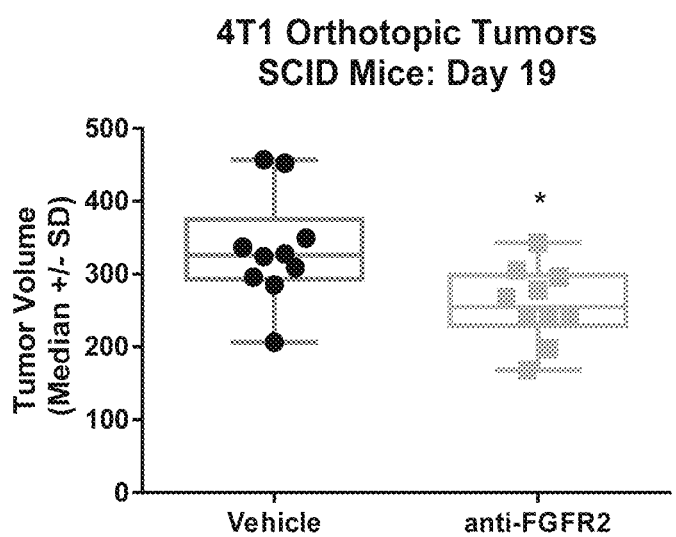
Figure 16C:
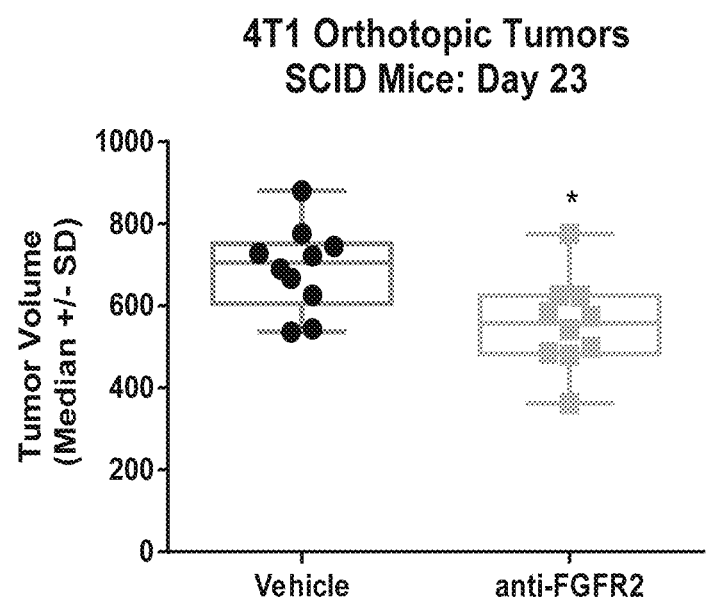
Figure 16D:
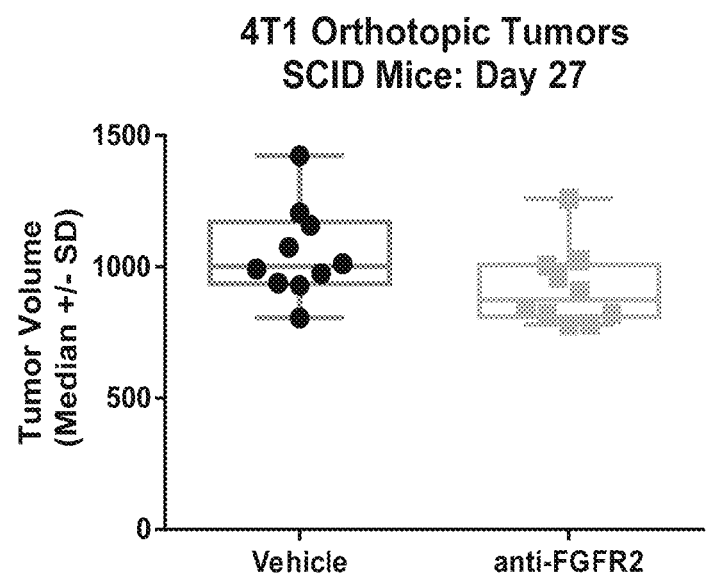

FIGS. 16a, b, c, and d show growth of 4T1 orthotopic tumors in SCID mice after inoculation with a vehicle control or anti-FGFR2 antibody up to 27 days post-innoculation with tumor cells. FIG. 16a shows tumor volume over time. Arrows below the graphs show the dosing with either vehicle or 20 mg/kg anti-FGFR2 antibody at days 12 and 15 post-innoculation. The asterisk (*) denotes statistical significant differences between tumor growth under vehicle or anti-FGFR2 antibody according to a student T-test at P≤0.5 level. FIG. 16b depicts tumor volume in individual mice in each group at day 19 post-innoculation. The asterisk (*) denotes statistical significant differences between tumor growth in the two groups according to a student T-test at P≤0.5 level. FIG. 16c depicts tumor volume in individual mice in each group at day 23 post-innoculation. The asterisk (*) denotes statistical significant differences between tumor growth in the two groups according to a student T-test at P≤0.5 level. FIG. 16d depicts tumor volume in individual mice in each group at day 27 post-innoculation.

DESCRIPTION OF PARTICULAR EMBODIMENTS

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

Exemplary techniques used in connection with recombinant DNA, oligonucleotide synthesis, tissue culture and transformation (e.g., electroporation, lipofection), enzymatic reactions, and purification techniques are known in the art. Many such techniques and procedures are described, e.g., in Sambrook et al. *Molecular Cloning: A Laboratory Manual* (2nd ed., Cold Spring Harbor Laboratory Press, Cold Spring Harbor, N.Y. (1989)), among other places. In addition, exemplary techniques for chemical syntheses, chemical analyses, pharmaceutical preparation, formulation, and delivery, and treatment of patients are also known in the art.

In this application, the use of "or" means "and/or" unless stated otherwise. In the context of a multiple dependent claim, the use of "or" refers back to more than one preceding independent or dependent claim in the alternative only. Also, terms such as "element" or "component" encompass both elements and components comprising one unit and elements and components that comprise more than one subunit unless specifically stated otherwise.

As utilized in accordance with the present disclosure, the following terms, unless otherwise indicated, shall be understood to have the following meanings:

The terms "nucleic acid molecule" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein that includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts that produce the proteins or errors due to PCR amplification.

"FGFR2" refers to fibroblast growth factor receptor 2 including any of its alternatively spliced forms such as the IIIa, IIIb and IIIc splice forms. The term FGFR2 encompasses wild-type FGFR2 and naturally occurring mutant forms such as FGFR2 activating mutant forms such as FGFR2-S252W, which is found in some cancer cells. "FGFR2-IIIb" or "FGFR2b" are used interchangeably to refer to the fibroblast growth factor receptor 2 IIIb splice form. An exemplary human FGFR2-IIIb is shown in GenBank Accession No. NP_075259.4, dated Jul. 7, 2013. A nonlimiting exemplary mature human FGFR2-IIIb amino acid sequence is shown in SEQ ID NO: 1. "FGFR2-IIIc" or "FGFR2c" are used interchangeably to refer to the fibroblast growth factor receptor 2 IIIc splice form. An exemplary human FGFR2-IIIc is shown in GenBank Accession No. NP_000132.3, dated Jul. 7, 2013. A nonlimiting exemplary mature FGFR2-IIIc amino acid sequence is shown in SEQ ID NO: 12.

An "FGFR2 ECD" refers to an extracellular domain of FGFR2, including natural and engineered variants thereof. Nonlimiting examples of FGFR2 ECDs include SEQ ID NOs: 13-23, 29, and 32. An "FGFR2 ECD fusion molecule" refers to a molecule comprising an FGFR2 ECD and a fusion partner such as an Fc domain, albumin, or PEG. The fusion partner may be covalently attached, for example, to the N- or C-terminal of the FGFR2 ECD or at an internal location. Nonlimiting examples of FGFR2 ECD fusion molecules include SEQ ID NOs: 30, 31, and 33.

An "FGFR2 inhibitor" refers to a molecule, such as an antibody that binds FGFR2, or such as an FGFR2 ECD or FGFR2 ECD fusion molecule, that inhibits binding of FGFR2 to one or more of its ligands such as FGF1, FGF7, and/or FGF2. In some embodiments, and FGFR2 inhibitor is capable of binding to FGFR2 as well as to an FGFR2 mutant with an activating mutation, such as FGFR2-S252W.

The term "immune stimulating agent" as used herein refers to a molecule that stimulates the immune system by either acting as an agonist of an immune-stimulatory molecule, including a co-stimulatory molecule, or acting as an antagonist of an immune inhibitory molecule, including a co-inhibitory molecule. An immune stimulating agent may be a biologic, such as an antibody or antibody fragment, other protein, or vaccine, or may be a small molecule drug.

The terms "programmed cell death protein 1" and "PD-1" refer to an immunoinhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. U64863. In some embodiments, the PD-1 is a human PD-1 having the amino acid sequence of SEQ ID NO: 34 (precursor, with signal sequence) or SEQ ID NO: 35 (mature, without signal sequence).

The terms "programmed cell death 1 ligand 1" and "PD-L1" refer to one of two cell surface glycoprotein ligands for PD-1 (the other being PD-L2) that down regulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7. In some embodiments, the PD-L1 is a human PD-L1 having the amino acid sequence of SEQ ID NO: 37 (precursor, with signal sequence) or SEQ ID NO: 38 (mature, without signal sequence).

The term "PD-1/PD-L1 inhibitor" refers to a moiety that disrupts the PD-1/PD-L1 signaling pathway. In some embodiments, the inhibitor inhibits the PD-1/PD-L1 signaling pathway by binding to PD-1 and/or PD-L1. In some embodiments, the inhibitor also binds to PD-L2. In some embodiments, a PD-1/PD-L1 inhibitor inhibits binding of PD-1 to PD-L1 and/or PD-L2. Nonlimiting exemplary PD-1/PD-L1 inhibitors include antibodies that bind to PD-1; antibodies that bind to PD-L1; PD-1 fusion molecules such as AMP-224; and PD-1 polypeptides such as AUR-012.

The term "antibody that inhibits PD-1" refers to an antibody that binds to PD-1 or binds to PD-L1 and thereby inhibits PD-1 and/or PD-L1 signaling. In some embodiments, an antibody that inhibits PD-1 binds to PD-1 and blocks binding of PD-L1 and/or PD-L2 to PD-1. In some embodiments, an antibody that inhibits PD-1 binds to PD-L1 and blocks binding of PD-1 to PD-L1. An antibody that inhibits PD-1 and that binds to PD-L1 may be referred to as an anti-PD-L1 antibody. An antibody that inhibits PD-1 and that binds to PD-1 may be referred to as an anti-PD-1 antibody.

With reference to FGFR2 antibodies, FGFR2 ECDs, and FGFR2 ECD fusion molecules, the terms "blocks binding of" or "inhibits binding of" a ligand refer to the ability to inhibit an interaction between FGFR2 and an FGFR2 ligand, such as FGF1 or FGF2. Such inhibition may occur through any mechanism, including direct interference with ligand binding, e.g., because of overlapping binding sites on FGFR2, and/or conformational changes in FGFR2 induced by an antibody that alter ligand affinity, or, e.g., in the case of an FGFR2 ECD or FGFR2 ECD fusion molecule, by competing for binding to FGFR2 ligands.

With reference to anti-PD-1 antibodies and PD-1 fusion molecules or polypeptides the terms "blocks binding of" or "inhibits binding of" a ligand, such as PD-L1, and grammatical variants thereof, refer to the ability to inhibit the interaction between PD-1 and a PD-1 ligand, such as PD-L1. Such inhibition may occur through any mechanism, including direct interference with ligand binding, e.g., because of overlapping binding sites on PD-1, and/or conformational changes in PD-1 induced by the antibody that alter ligand affinity, etc., or by competing for binding with a PD-1 ligand.

The term "antibody" as used herein refers to a molecule comprising at least hypervariable regions (HVRs) H1, H2, and H3 of a heavy chain and L1, L2, and L3 of a light chain, wherein the molecule is capable of binding to antigen. The term antibody includes, but is not limited to, fragments that are capable of binding antigen, such as Fv, single-chain Fv (scFv), Fab, Fab', and (Fab')$_2$. The term antibody also includes, but is not limited to, chimeric antibodies, humanized antibodies, human antibodies, and antibodies of various species such as mouse, human, cynomolgus monkey, etc. It also includes antibodies conjugated to other molecules such as small molecule drugs, bispecific antibodies and multispecific antibodies.

The term "heavy chain variable region" refers to a region comprising heavy chain HVR1, framework (FR) 2, HVR2, FR3, and HVR3. In some embodiments, a heavy chain variable region also comprises at least a portion of an FR1 and/or at least a portion of an FR4.

The term "heavy chain constant region" refers to a region comprising at least three heavy chain constant domains, $C_H1$, $C_H2$, and $C_H3$. Nonlimiting exemplary heavy chain constant regions include γ, δ, and α. Nonlimiting exemplary heavy chain constant regions also include ε and μ. Each heavy constant region corresponds to an antibody isotype. For example, an antibody comprising a γ constant region is an IgG antibody, an antibody comprising a δ constant region is an IgD antibody, and an antibody comprising an α constant region is an IgA antibody. Further, an antibody comprising a μ constant region is an IgM antibody, and an antibody comprising an ε constant region is an IgE antibody. Certain isotypes can be further subdivided into subclasses. For example, IgG antibodies include, but are not limited to, IgG1 (comprising a $γ_1$ constant region), IgG2 (comprising a $γ_2$ constant region), IgG3 (comprising a $γ_3$ constant region), and IgG4 (comprising a $γ_4$ constant region) antibodies; IgA antibodies include, but are not limited to, IgA1 (comprising an $α_1$ constant region) and IgA2 (comprising an $α_2$ constant region) antibodies; and IgM antibodies include, but are not limited to, IgM1 and IgM2.

The term "heavy chain" refers to a polypeptide comprising at least a heavy chain variable region, with or without a leader sequence. In some embodiments, a heavy chain comprises at least a portion of a heavy chain constant region. The term "full-length heavy chain" refers to a polypeptide comprising a heavy chain variable region and a heavy chain constant region, with or without a leader sequence.

The term "light chain variable region" refers to a region comprising light chain HVR1, framework (FR) 2, HVR2, FR3, and HVR3. In some embodiments, a light chain variable region also comprises an FR1 and/or an FR4.

The term "light chain constant region" refers to a region comprising a light chain constant domain, $C_L$. Nonlimiting exemplary light chain constant regions include λ and κ.

The term "light chain" refers to a polypeptide comprising at least a light chain variable region, with or without a leader sequence. In some embodiments, a light chain comprises at least a portion of a light chain constant region. The term "full-length light chain" refers to a polypeptide comprising a light chain variable region and a light chain constant region, with or without a leader sequence.

The term "hypervariable region" or "HVR" refers to each of the regions of an antibody variable domain that are hypervariable in sequence and/or form structurally defined loops ("hypervariable loops"). Generally, native four-chain antibodies comprise six HVRs; three in the $V_H$ (H1, H2, H3), and three in the $V_L$ (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, J. Mol. Biol. 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., Sequences of Proteins of Immunological Interest, 5th Ed. Public Health Service, National Institutes of Health, Bethesda, Md. (1991)). The terms hypervariable regions (HVRs) and complementarity determining regions (CDRs) both refer to portions of the variable region that form the antigen binding regions.

"Affinity" or "binding affinity" refers to the strength of the sum total of noncovalent interactions between a single binding site of a molecule (e.g., an antibody) and its binding partner (e.g., an antigen). In some embodiments, "binding affinity" refers to intrinsic binding affinity which reflects a 1:1 interaction between members of a binding pair (e.g., antibody and antigen). The affinity of a molecule X for its partner Y can generally be represented by the dissociation constant ($K_d$).

"Antibody-dependent cell-mediated cytotoxicity" or "ADCC" refers to a form of cytotoxicity in which secreted Ig bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 or U.S. Pat. No. 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. *Proc. Natl. Acad. Sci.* (*USA*) 95:652-656 (1998). Additional antibodies with altered Fc region amino acid sequences and increased or decreased ADCC activity are described, e.g., in U.S. Pat. Nos. 7,923,538, and 7,994,290.

An antibody having an "enhanced ADCC activity" refers to an antibody that is more effective at mediating ADCC in vitro or in vivo compared to the parent antibody, wherein the antibody and the parent antibody differ in at least one structural aspect, and when the amounts of such antibody and parent antibody used in the assay are essentially the same. In some embodiments, the antibody and the parent antibody have the same amino acid sequence, but the antibody is afucosylated while the parent antibody is fucosylated. In some embodiments, ADCC activity will be determined using the in vitro ADCC assay such as disclosed in US Publication No. 2015-0050273-A1, but other assays or methods for determining ADCC activity, e.g. in an animal model etc., are contemplated. In some embodiments, an antibody with enhanced ADCC activity also has enhanced affinity for Fc gamma RIIIA. In some embodiments, an antibody with enhanced ADCC activity has enhanced affinity for Fc gamma RIIIA (V158). In some embodiments, an antibody with enhanced ADCC activity has enhanced affinity for Fc gamma RIIIA (F158).

"Enhanced affinity for Fc gamma RIIIA" refers to an antibody that has greater affinity for Fc gamma RIIIA (also referred to, in some instances, as CD16a) than a parent antibody, wherein the antibody and the parent antibody differ in at least one structural aspect. In some embodiments, the antibody and the parent antibody have the same amino acid sequence, but the antibody is afucosylated while the parent antibody is fucosylated. Any suitable method for determining affinity for Fc gamma RIIIA may be used. In some embodiments, affinity for Fc gamma RIIIA is determined by a method described in U.S. Publication No. 2015-0050273-A1. In some embodiments, an antibody with enhanced affinity for Fc gamma RIIIA also has enhanced ADCC activity. In some embodiments, an antibody with enhanced affinity for Fc gamma RIIIA has enhanced affinity for Fc gamma RIIIA (V158). In some embodiments, an antibody with enhanced affinity for Fc gamma RIIIA has enhanced affinity for Fc gamma RIIIA (F158).

A "chimeric antibody" as used herein refers to an antibody comprising at least one variable region from a first species (such as mouse, rat, cynomolgus monkey, etc.) and at least one constant region from a second species (such as human, cynomolgus monkey, etc.). In some embodiments, a chimeric antibody comprises at least one mouse variable region and at least one human constant region. In some embodiments, a chimeric antibody comprises at least one cynomolgus variable region and at least one human constant region. In some embodiments, a chimeric antibody comprises at least one rat variable region and at least one mouse constant region. In some embodiments, all of the variable regions of a chimeric antibody are from a first species and all of the constant regions of the chimeric antibody are from a second species.

A "humanized antibody" as used herein refers to an antibody in which at least one amino acid in a framework region of a non-human variable region has been replaced with the corresponding amino acid from a human variable region. In some embodiments, a humanized antibody comprises at least one human constant region or fragment thereof. In some embodiments, a humanized antibody is a Fab, an scFv, a (Fab')$_2$, etc.

A "human antibody" as used herein refers to antibodies produced in humans, antibodies produced in non-human animals that comprise human immunoglobulin genes, such as XenoMouse®, and antibodies selected using in vitro methods, such as phage display, wherein the antibody repertoire is based on a human immunoglobulin sequences.

An "afucosylated" antibody or an antibody "lacking fucose" refers to an IgG1 or IgG3 isotype antibody that lacks fucose in its constant region glycosylation. Glycosylation of human IgG1 or IgG3 occurs at Asn297 (N297) as core fucosylated biantennary complex oligosaccharide glycosylation terminated with up to 2 Gal residues. In some embodiments, an afucosylated antibody lacks fucose at Asn297. These structures are designated as G0, G1 (α1,6 or α1,3) or G2 glycan residues, depending on the amount of terminal Gal residues. See, e.g., Raju, T. S., *BioProcess Int.* 1: 44-53 (2003). CHO type glycosylation of antibody Fc is described, e.g., in Routier, F. H., *Glycoconjugate J.* 14: 201-207 (1997). Within a population of antibodies, the antibodies are considered to be afucosylated if <5% of the antibodies of the population comprise fucose at Asn297.

"Effector functions" refer to biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 or U.S. Pat. No. 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. *Proc. Natl. Acad. Sci.* (*USA*) 95:652-656 (1998). Additional antibodies with altered Fc region amino acid sequences and increased or decreased ADCC activity are described, e.g., in U.S. Pat. Nos. 7,923,538, and 7,994,290.

An antibody having an "enhanced ADCC activity" refers to an antibody that is more effective at mediating ADCC in an in vitro or in vivo assay compared to a parent antibody with the same sequence apart from at least one structural alteration designed to alter ADCC activity, when the amounts of such antibody and parent antibody used in the assay are essentially the same. In some embodiments, the antibody and the parent antibody have the same amino acid sequence apart from a mutation in the Fc domain, such as an amino acid substitution causing afucosylation where the parent antibody is fucosylated. In some embodiments, ADCC activity will be determined using the in vitro ADCC assay as herein disclosed, but other assays or methods for determining ADCC activity, e.g. in an animal model etc., are contemplated. In some embodiments, an antibody with enhanced ADCC activity has enhanced affinity for Fc gamma RIIIA. In some embodiments, an antibody with enhanced ADCC activity has enhanced affinity for Fc gamma RIIIA (V158). In some embodiments, an antibody with enhanced ADCC activity has enhanced affinity for Fc gamma RIIIA (F158).

"Enhanced affinity for Fc gamma RIIIA" refers to an antibody that has greater affinity for Fc gamma RIIIA (also referred to, in some instances, as CD16a) than a parent antibody, wherein the antibody and the parent antibody differ in at least one structural aspect. In some embodiments, the antibody and the parent antibody have the same amino acid sequence, but the antibody is afucosylated while the parent antibody is fucosylated. Any suitable method for determining affinity for Fc gamma RIIIA may be used. In some embodiments, affinity for Fc gamma RIIIA is determined by a method described herein. In some embodiments, an antibody with enhanced affinity for Fc gamma RIIIA has enhanced ADCC activity. In some embodiments, an antibody with enhanced affinity for Fc gamma RIIIA has enhanced affinity for Fc gamma RIIIA(V158). In some embodiments, an antibody with enhanced affinity for Fc gamma RIIIA has enhanced affinity for Fc gamma RIIIA (F158).

The term "leader sequence" refers to a sequence of amino acid residues located at the N terminus of a polypeptide that facilitates secretion of a polypeptide from a mammalian cell. A leader sequence may be cleaved upon export of the polypeptide from the mammalian cell, forming a mature protein. Leader sequences may be natural or synthetic, and they may be heterologous or homologous to the protein to which they are attached. Nonlimiting exemplary leader sequences also include leader sequences from heterologous proteins. In some embodiments, an antibody lacks a leader sequence. In some embodiments, an antibody comprises at least one leader sequence, which may be selected from native antibody leader sequences and heterologous leader sequences.

The term "vector" is used to describe a polynucleotide that may be engineered to contain a cloned polynucleotide or polynucleotides that may be propagated in a host cell. A vector may include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that may be used in colorimetric assays, e.g., β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NS0 cells, PER.C6® cells (Crucell), and 293 and CHO cells, and their derivatives, such as 293-6E and DG44 cells, respectively.

The term "isolated" as used herein refers to a molecule that has been separated from at least some of the components with which it is typically found in nature. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated" so long as that polynucleotide is not found in that vector in nature.

The term "elevated level" means a higher level of a protein in a particular tissue of a subject relative to the same tissue in a control, such as an individual or individuals who are not suffering from cancer or other condition described herein. The elevated level may be the result of any mechanism, such as increased expression, increased stability, decreased degradation, increased secretion, decreased clearance, etc., of the protein.

The terms "reduce" or "reduces" or "increase" or "increases" with respect to a protein or cell type means to change the level of that protein or cell type in a particular tissue of a subject, such as in a tumor, by at least 10%. In some embodiments, an agent, such as an FGFR2 or a PD-1/PD-L1 inhibitor, increases or reduces the level of a protein or a cell type in a particular tissue of a subject, such as a tumor, by at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90%. In some embodiments, the level of a protein or cell type is reduced or increased relative to the level of the protein prior to contacting with an agent, such as an FGFR2 or PD-1/PD-L1 inhibitor, or relative to the level of a control treatment.

The terms "subject" and "patient" are used interchangeably herein to refer to a human. In some embodiments, methods of treating other mammals, including, but not limited to, rodents, simians, felines, canines, equines, bovines, porcines, ovines, caprines, mammalian laboratory animals, mammalian farm animals, mammalian sport animals, and mammalian pets, are also provided.

The term "sample," as used herein, refers to a composition that is obtained or derived from a subject that contains a cellular and/or other molecular entity that is to be characterized, quantitated, and/or identified, for example based on physical, biochemical, chemical and/or physiological characteristics. An exemplary sample is a tissue sample.

The term "cancer" refers to a malignant proliferative disorder associated with uncontrolled cell proliferation, unrestrained cell growth, and decreased cell death via apoptosis. Examples of cancer include but are not limited to, carcinoma, lymphoma, blastoma, sarcoma, and leukemia. More particular nonlimiting examples of such cancers include squamous cell cancer, small-cell lung cancer, pituitary cancer, esophageal cancer (including gastroesophageal junction adenocarcinoma), astrocytoma, soft tissue sarcoma, non-small cell lung cancer (including squamous cell non-small cell lung cancer), adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, renal cell carcinoma, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer (including squamous cell carcinoma of the head and neck).

In some embodiments, the cancer is gastric cancer (which includes gastroesophageal cancer). In some embodiments, the cancer is bladder cancer. Bladder cancer as defined herein includes forms of the disease such as urinary bladder cancer (UBC) and transitional cell carcinoma (TCC), which is also known as urothelial cancer (UC), as well as non-transitional cell carcinomas that develop in the bladder.

In some embodiments, a cancer comprises an FGFR2 gene amplification, whereas in some embodiments the cancer does not comprise an FGFR2 amplification. In some embodiments, where an amplification occurs, the FGFR2 amplification comprises an FGFR2:CEN10 (chromosome 10 centromere) ratio of >3. In some embodiments, FGFR2 amplification comprises an FGFR2:CEN10 ratio of ≥2. In other embodiments, however, the FGFR2 level comprises an FGFR2:CEN10 ratio of between 1 and 2, indicating that FGFR2 is not amplified. In some embodiments, mutations or translocations may cause an FGFR2 gene amplification. Gene amplification may be determined using a fluorescence in situ hybridization assay (FISH), for example.

In some embodiments, where the cancer comprises an FGFR2 gene amplification, the cancer overexpresses FGFR2-IIIb. In some embodiments, a cancer comprising FGFR2 amplification overexpresses FGFR2-IIIb to a greater extent than FGFR2-IIIc. In some embodiments, a cancer comprising FGFR2 amplification expresses FGFR2-IIIb at a normalized level that is more than 2-fold, 3-fold, 5-fold, or 10-fold greater than the normalized level of FGFR2-IIIc expression. In some embodiments, the expression levels are normalized to GUSB. In some embodiments, a cancer overexpresses FGFR2-IIIb but does not comprise a FGFR2 gene amplification.

In some embodiments, a cancer comprises FGFR2, such as FGFR2-IIIb protein overexpression, while in some other embodiments, a cancer does not comprise FGFR2 or FGFR2-IIIb protein overexpression. FGFR2-IIIb protein overexpression may be determined by any suitable method in the art, including but not limited to, antibody-based methods such as immunohistochemistry (IHC). In some embodiments, the IHC staining is scored according to methods in the art. The terms "FGFR2-IIIb protein overexpression" and "FGFR2IIIb overexpression" and the like mean elevated levels of FGFR2-IIIb protein, regardless of the cause of such elevated levels (i.e., whether the elevated levels are a result of increased translation and/or decreased degradation of protein, other mechanism, or a combination of mechanisms).

The level of FGFR2 or FGFR2IIIb expression by IHC may be determined by giving a tumor sample an IHC score on a scale of 0-3. Herein, a score of "0" is given if no reactivity is observed or if there is membranous reactivity only in <10% of tumor cells; a score of "1+" is given if there is faint or barely perceptible membranous reactivity in at least 10% of tumor cells or if the cells are reactive only in a part of their membranes; a score of "2+" is given if there is weak to moderate complete, basolateral or lateral membranous reactivity in at least 10% of tumor cells; and a score of "3+" is given if there is strong complete basolateral or lateral membranous reactivity in at least 10% of tumor cells. In some embodiments, 1+, 2+, or 3+ staining of tumor cells by IHC indicates FGFR2IIIb overexpression. In some embodiments, 2+ or 3+ staining of tumor cells by IHC indicates FGFR2IIIb overexpression. In some embodiments, 3+ staining of tumor cells by IHC indicates FGFR2IIIb overexpression. In some embodiments, a gastric or bladder cancer comprises an FGFR2 gene amplification. In some embodiments, a gastric or bladder cancer comprising an FGFR2 gene amplification overexpresses FGFR2-IIIb. In some embodiments, a gastric or bladder cancer comprising FGFR2 amplification overexpresses FGFR2-IIIb to a greater extent than FGFR2-IIIc. In some embodiments, a gastric or bladder cancer overexpresses FGFR2-IIIb but does not comprise a FGFR2 gene amplification. In some embodiments, a gastric or bladder cancer comprising an FGFR2 amplification expresses FGFR2-IIIb at a normalized level that is more than 2-fold, 3-fold, 5-fold, or 10-fold greater than the normalized level of FGFR2-IIIc expression. In some embodiments, the expression levels are normalized to GUSB. In some embodiments, overexpression is mRNA overexpression. In some embodiments, overexpression is protein overexpression.

"Treatment," as used herein, refers to both therapeutic treatment and prophylactic or preventative measures, wherein the object is to prevent or slow down (lessen) the targeted pathologic condition or disorder. In certain embodiments, the term "treatment" covers any administration or application of a therapeutic for disease in a mammal, including a human, and includes inhibiting or slowing the disease or progression of the disease; partially or fully relieving the disease, for example, by causing regression, or restoring or repairing a lost, missing, or defective function; stimulating an inefficient process; or causing the disease plateau to have reduced severity. The term "treatment" also includes reducing the severity of any phenotypic characteristic and/or reducing the incidence, degree, or likelihood of that characteristic. Those in need of treatment include those already with the disorder as well as those prone to have the disorder or those in whom the disorder is to be prevented.

The term "effective amount" or "therapeutically effective amount" refers to an amount of a drug effective to treat a disease or disorder in a subject. In certain embodiments, an effective amount refers to an amount effective, at dosages and for periods of time necessary, to achieve the desired therapeutic or prophylactic result. A therapeutically effective amount of an FGFR2 inhibitor and/or a PD-1/PD-L1 inhibitor of the invention may vary according to factors such as the disease state, age, sex, and weight of the individual, and the ability of the antibody or antibodies to elicit a desired response in the individual. A therapeutically effective amount encompasses an amount in which any toxic or detrimental effects of the antibody or antibodies are outweighed by the therapeutically beneficial effects. In some embodiments, the expression "effective amount" refers to an amount of the antibody that is effective for treating the cancer.

Administration "in combination with" one or more further therapeutic agents includes simultaneous (concurrent) and consecutive (sequential) administration in any order.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. If the therapeutic agent is to be administered subcutaneously, the carrier ideally is not irritable to the skin and does not cause injection site reaction.

Additional definitions are provided in the sections that follow.

Exemplary FGFR2 Inhibitors

FGFR2 inhibitors of the methods and compositions herein may be FGFR2 antibodies, FGFR2 ECDs, or FGFR2 ECD fusion molecules.

Exemplary FGFR2 Antibodies

In any of the compositions or methods described herein involving an FGFR2 antibody, the FGFR2 antibody may be a humanized antibody, chimeric antibody, or human antibody. In any of the compositions or methods described herein, the FGFR2 antibody may be selected from a Fab, an Fv, an scFv, a Fab', and a (Fab')2. In any of the compositions or methods described herein, the FGFR2 antibody may be selected from an IgA, an IgG, and an IgD. In any of the compositions or methods described herein, the FGFR2 antibody may be an IgG. In any of the methods described herein, the antibody may be an IgG1 or IgG3.

Exemplary FGFR2 antibodies include antibodies that bind FGFR2-IIIb. In some embodiments, the FGFR2-IIIb antibodies bind FGFR2-IIIc with lower affinity than they bind to FGFR2-IIIb. In some embodiments, the FGFR2-IIIb antibodies do not detectably bind to FGFR2-IIIc.

The instant invention provides neutralizing mAbs that bind FGFR2IIIb but bind less well or not detectably to FGFRIIIc, or alternatively bind to FGFR2IIIc but less well or not detectably to FGFRIIIb, or in a third alternative bind to both FGFR2IIIb and FGFR2IIIc, and the use of any of these types of antibodies in a pharmaceutical composition, especially for the treatment of cancer or other diseases. The invention also provides mAbs, either neutralizing or non-neutralizing, that bind FGFR2 in one or more of its forms and inhibit, preferably completely, growth of a tumor xenograft that expresses FGFR2, e.g., a SNU-16 or OCUM-2M xenograft. Such a mAb may inhibit tumor growth by, e.g., transmitting a negative growth signal or a pro-apoptotic signal through FGFR2. MAbs of the invention are preferably specific for FGFR2 or bind it preferentially, that is they do not bind, or only bind to a much lesser extent (e.g., at least 10-fold less), proteins that are related to FGFR2 such as the other FGF receptors FGFR1, FGFR3 and FGFR4 as well as other membrane receptor tyrosine kinases. On the other hand, in some instances, mAbs that bind one or more of the other FGF receptors in addition to FGFR2 are preferred. MAbs of the invention typically have a binding affinity (association constant $K_a$) for FGFR2 of at least $10^7$ $M^{-1}$ but preferably $10^8$ $M^{-1}$ or higher, and most preferably $10^9 M^{-1}$ or higher or even $10^{10}$ $M^{-1}$ or higher. MAbs showing differential or preferential binding to one form of FGFR or FGFR2 over another, preferably show a preference of at least five, ten or hundred fold between the forms, e.g., as measured by $K_a$. Lack of binding between an antibody and antigen (i.e., the antibody does not bind the antigen) means any signal from an attempted binding reaction between the two is indistinguishable from a negative control, e.g., in which antibody or antigen is absent or replaced by an inactive agent.

An exemplary FGFR2-IIIb antibody for use in the embodiments herein is the HuGAL-FR21 antibody described in U.S. Pat. No. 8,101,723 B2, issued Jan. 24, 2012, which is specifically incorporated herein by reference. FIGS. 13 and 14 of U.S. Pat. No. 8,101,723 B2 show the amino acid sequences of the variable regions and full-length mature antibody chains of HuGAL-FR21, and are incorporated by reference herein. The heavy chain variable region sequences of antibody HuGAL-FR21, are underlined in FIG. 13 of U.S. Pat. No. 8,101,723 B2, and are specifically incorporated by reference herein. In some embodiments, the antibody is afucosylated. In some embodiments, the antibody is an IgG1 or IgG3 antibody that lacks fucose at Asn297. Additional antibodies that may be used in the embodiments herein include those described in US Patent Publication No. 2015-0050273-A1, which describes certain afucosylated FGFR2-IIIb antibodies, and which is incorporated by reference herein.

In some embodiments, the FGFR2-IIIb antibody comprises at least one, two, three, four, five, or six hypervariable regions (HVRs; e.g., CDRs) selected from (a) HVR-H1 comprising the amino acid sequence of SEQ ID NO: 6; (b) HVR-H2 comprising the amino acid sequence of SEQ ID NO: 7; (c) HVR-H3 comprising the amino acid sequence of SEQ ID NO: 8; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 11. In some embodiments, the antibody is afucosylated. In some embodiments, the antibody is an IgG1 or IgG3 antibody that lacks fucose at Asn297.

In some embodiments, the FGFR2-IIIb antibody comprises a heavy chain variable region and a light chain variable region. In some embodiments, the FGFR2-IIIb antibody comprises at least one heavy chain comprising a heavy chain variable region and at least a portion of a heavy chain constant region, and at least one light chain comprising a light chain variable region and at least a portion of a light chain constant region. In some embodiments, the FGFR2-IIIb antibody comprises two heavy chains, wherein each heavy chain comprises a heavy chain variable region and at least a portion of a heavy chain constant region, and two light chains, wherein each light chain comprises a light chain variable region and at least a portion of a light chain constant region. In some embodiments, the FGFR2-IIIb antibody comprises a heavy chain variable region comprising the amino acid sequence of SEQ ID NO: 4 and a light chain variable region comprising the amino acid sequence of SEQ ID NO: 5. In some embodiments, the FGFR2-IIIb antibody comprises a heavy chain comprising the amino acid sequence of SEQ ID NO: 2 and a light chain comprising the amino acid sequence of SEQ ID NO: 3. In some embodiments, the antibody is afucosylated. In some embodiments, the antibody is an IgG1 or IgG3 antibody that lacks fucose at Asn297.

In some embodiments, the FGFR2-IIIb antibody comprises six HVRs comprising (a) HVR-H1 comprising the amino acid sequence of SEQ ID NO: 6; (b) HVR-H2 comprising the amino acid sequence of SEQ ID NO: 7; (c) HVR-H3 comprising the amino acid sequence of SEQ ID NO: 8; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 11. In some embodiments, the FGFR2-IIIb antibody comprises the six HVRs as described above and binds to FGFR2-IIIb. In some embodiments, the FGFR-IIIb antibody does not bind to FGFR2-IIIc. In some embodiments, the antibody is afucosylated. In some embodiments, the antibody is an IgG1 or IgG3 antibody that lacks fucose at Asn297.

In one aspect, the FGFR2-IIIb antibody competes with an FGFR2-IIIb antibody comprising six HVRs comprising (a) HVR-H1 comprising the amino acid sequence of SEQ ID NO: 6; (b) HVR-H2 comprising the amino acid sequence of SEQ ID NO: 7; (c) HVR-H3 comprising the amino acid sequence of SEQ ID NO: 8; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 11. In some embodiments, the antibody is afucosylated. In some embodiments, the antibody is an IgG1 or IgG3 antibody that lacks fucose at Asn297.

In some embodiments, the FGFR2-IIIb antibody comprises at least one, at least two, or all three VH HVR sequences selected from (a) HVR-H1 comprising the amino acid sequence of SEQ ID NO: 6; (b) HVR-H2 comprising the amino acid sequence of SEQ ID NO: 7; and (c) HVR-H3 comprising the amino acid sequence of SEQ ID NO: 8. In some embodiments, the antibody is afucosylated. In some embodiments, the antibody is an IgG1 or IgG3 antibody that lacks fucose at Asn297.

In some embodiments, the FGFR2-IIIb antibody comprising at least one, at least two, or all three VL HVR sequences selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11. In some embodiments, the antibody is afucosylated. In some embodiments, the antibody is an IgG1 or IgG3 antibody that lacks fucose at Asn297.

In some embodiments, the FGFR2-IIIb antibody comprises (a) a VH domain comprising at least one, at least two, or all three VH HVR sequences selected from (i) HVR-H1 comprising the amino acid sequence of SEQ ID NO: 6, (ii) HVR-H2 comprising the amino acid sequence of SEQ ID NO: 7, and (iii) HVR-H3 comprising an amino acid sequence selected from SEQ ID NO: 8; and (b) a VL domain comprising at least one, at least two, or all three VL HVR sequences selected from (i) HVR-L1 comprising the amino acid sequence of SEQ ID NO: 9, (ii) HVR-L2 comprising the amino acid sequence of SEQ ID NO: 10, and (c) HVR-L3 comprising the amino acid sequence of SEQ ID NO: 11. In some embodiments, the antibody is afucosylated. In some embodiments, the antibody is an IgG1 or IgG3 antibody that lacks fucose at Asn297.

In some embodiments, the FGFR2-IIIb antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 4. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an FGFR2-IIIb antibody comprising that sequence retains the ability to bind to FGFR2-IIIb. In certain embodiments, such FGFR2-IIIb antibody retains the ability to selectively bind to FGFR2-IIIb without detectably binding to FGFR2-IIIc. In certain embodiments, a total of 1 to 10 amino acids have been substituted, inserted and/or deleted in SEQ ID NO: 4. In certain embodiments, substitutions, insertions, or deletions occur in regions outside the HVRs (i.e., in the FRs). Optionally, the FGFR2-IIIb antibody comprises the VH sequence in SEQ ID NO: 5, including post-translational modifications of that sequence. In a particular embodiment, the VH comprises one, two or three HVRs selected from: (a) HVR-H1 comprising the amino acid sequence of SEQ ID NO: 6; (b) HVR-H2 comprising the amino acid sequence of SEQ ID NO: 7; and (c) HVR-H3 comprising the amino acid sequence of SEQ ID NO: 8. In some embodiments, the antibody is afucosylated. In some embodiments, the antibody is an IgG1 or IgG3 antibody that lacks fucose at Asn297.

In some embodiments, the FGFR2-IIIb antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 5. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an FGFR2-IIIb antibody comprising that sequence retains the ability to bind to FGFR2-IIIb. In certain embodiments, the FGFR2-IIIb antibody retains the ability to selectively bind to FGFR2-IIIb without binding to FGFR2-IIIc. In certain embodiments, a total of 1 to 10 amino acids have been substituted, inserted and/or deleted in SEQ ID NO: 5. In certain embodiments, the substitutions, insertions, or deletions occur in regions outside the HVRs (i.e., in the FRs). Optionally, the FGFR2-IIIb antibody comprises the VL sequence in SEQ ID NO: 4, including post-translational modifications of that sequence. In a particular embodiment, the VL comprises one, two or three HVRs selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11. In some embodiments, the antibody is afucosylated. In some embodiments, the antibody is an IgG1 or IgG3 antibody that lacks fucose at Asn297.

In some embodiments, the FGFR2-IIIb antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 4 and a light chain variable domain (VL) having at least 90%, 91%, 92%, 93%, 94%, 95%, 96%, 97%, 98%, 99%, or 100% sequence identity to the amino acid sequence of SEQ ID NO: 5. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, and a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an FGFR2-IIIb antibody comprising that sequence retains the ability to bind to FGFR2-IIIb. In certain embodiments, such an FGFR2-IIIb antibody retains the ability to selectively bind to FGFR2-IIIb without binding to FGFR2-IIIc. In certain embodiments, a total of 1 to 10 amino acids have been substituted, inserted and/or deleted in SEQ ID NO: 4. In certain embodiments, a total of 1 to 10 amino acids have been substituted, inserted and/or deleted in SEQ ID NO: 5. In certain embodiments, substitutions, insertions, or deletions occur in regions outside the HVRs (i.e., in the FRs). Optionally, the FGFR2-IIIb antibody comprises the VH sequence in SEQ ID NO: 4 and the VL sequence of SEQ ID NO: 5, including post-translational modifications of one or both sequence. In a particular embodiment, the VH comprises one, two or three HVRs selected from: (a) HVR-H1 comprising the amino acid sequence of SEQ ID NO: 6; (b) HVR-H2 comprising the amino acid sequence of SEQ ID NO: 7; and (c) HVR-H3 comprising the amino acid sequence of SEQ ID NO: 8; and the VL comprises one, two or three HVRs selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11. In some embodiments, the antibody is afucosylated. In some embodiments, the antibody is an IgG1 or IgG3 antibody that lacks fucose at Asn297.

In some embodiments, the FGFR2-IIIb antibody a VH as in any of the embodiments provided above, and a VL as in any of the embodiments provided above. In one embodiment, the antibody comprises the VH and VL sequences in SEQ ID NO: 4 and SEQ ID NO: 5, respectively, including post-translational modifications of those sequences. In some embodiments, the antibody is afucosylated. In some embodiments, the antibody is an IgG1 or IgG3 antibody that lacks fucose at Asn297.

In some embodiments, the FGFR2-IIIb antibody comprises a heavy chain sequence having at least 90%, 91%, 92%, 93%, 94%, 95%, 96%, 97%, 98%, 99%, or 100% sequence identity to the amino acid sequence of SEQ ID NO: 2. In certain embodiments, a heavy chain sequence having at least 90%, 91%, 92%, 93%, 94%, 95%, 96%, 97%, 98%, or 99% identity contains substitutions (e.g., conservative substitutions), insertions, or deletions relative to the reference sequence, but an FGFR2-IIIb antibody comprising that sequence retains the ability to bind to FGFR2-IIIb. In certain embodiments, such an FGFR2-IIIb antibody retains the ability to selectively bind to FGFR2-IIIb without detectably binding to FGFR2-IIIc. In certain embodiments, a total of 1 to 10 amino acids have been substituted, inserted and/or deleted in SEQ ID NO: 2. In certain embodiments, substitutions, insertions, or deletions occur in regions outside the HVRs (i.e., in the FRs). Optionally, the FGFR2-IIIb antibody heavy chain comprises the VH sequence in SEQ ID NO: 2, including post-translational modifications of that sequence. In a particular embodiment, the heavy chain comprises one, two or three HVRs selected from: (a) HVR-H1 comprising the amino acid sequence of SEQ ID NO: 6; (b) HVR-H2 comprising the amino acid sequence of SEQ ID NO: 7; and (c) HVR-H3 comprising the amino acid sequence of SEQ ID NO: 8. In some embodiments, the antibody is afucosylated. In some embodiments, the antibody is an IgG1 or IgG3 antibody that lacks fucose at Asn297.

In some embodiments the FGFR2-IIIb antibody comprises a light chain having at least 90%, 91%, 92%, 93%, 94%, 95%, 96%, 97%, 98%, 99%, or 100% sequence identity to the amino acid sequence of SEQ ID NO: 3. In certain embodiments, a light chain sequence having at least 90%, 91%, 92%, 93%, 94%, 95%, 96%, 97%, 98%, or 99% identity contains substitutions (e.g., conservative substitutions), insertions, or deletions relative to the reference sequence, but an FGFR2-IIIb antibody comprising that sequence retains the ability to bind to FGFR2-IIIb. In certain embodiments, such an FGFR2-IIIb antibody retains the ability to selectively bind to FGFR2-IIIb without detectably binding to FGFR2-IIIc. In certain embodiments, a total of 1 to 10 amino acids have been substituted, inserted and/or deleted in SEQ ID NO: 3. In certain embodiments, the substitutions, insertions, or deletions occur in regions outside the HVRs (i.e., in the FRs). Optionally, the FGFR2-IIIb antibody light chain comprises the VL sequence in SEQ ID NO: 3, including post-translational modifications of that sequence. In a particular embodiment, the light chain comprises one, two or three HVRs selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11. In some embodiments, the antibody is afucosylated. In some embodiments, the antibody is an IgG1 or IgG3 antibody that lacks fucose at Asn297.

In some embodiments, the FGFR2-IIIb antibody comprises a heavy chain sequence having at least 90%, 91%, 92%, 93%, 94%, 95%, 96%, 97%, 98%, 99%, or 100% sequence identity to the amino acid sequence of SEQ ID NO: 2 and a light chain sequence having at least 90%, 91%, 92%, 93%, 94%, 95%, 96%, 97%, 98%, 99%, or 100% sequence identity to the amino acid sequence of SEQ ID NO: 3. In certain embodiments, a heavy chain sequence having at least 90%, 91%, 92%, 93%, 94%, 95%, 96%, 97%, 98%, or 99% identity contains substitutions (e.g., conservative substitutions), insertions, or deletions relative to the reference sequence, but an FGFR2-IIIb antibody comprising that sequence retains the ability to bind to FGFR2-IIIb. In certain embodiments, such an FGFR2-IIIb antibody retains the ability to selectively bind to FGFR2-IIIb without detectably binding to FGFR2-IIIc. In certain embodiments, a light chain sequence having at least 90%, 91%, 92%, 93%, 94%, 95%, 96%, 97%, 98%, or 99% identity contains substitutions (e.g., conservative substitutions), insertions, or deletions relative to the reference sequence, but an FGFR2-IIIb antibody comprising that sequence retains the ability to bind to FGFR2-IIIb. In certain embodiments, such an FGFR2-IIIb antibody retains the ability to selectively bind to FGFR2-IIIb without detectably binding to FGFR2-IIIc. In certain embodiments, a total of 1 to 10 amino acids have been substituted, inserted and/or deleted in SEQ ID NO: 2. In certain embodiments, a total of 1 to 10 amino acids have been substituted, inserted and/or deleted in SEQ ID NO: 3. In certain embodiments, substitutions, insertions, or deletions occur in regions outside the HVRs (i.e., in the FRs). Optionally, the FGFR2-IIIb antibody heavy chain comprises the VH sequence in SEQ ID NO: 2, including post-translational modifications of that sequence and the FGFR2-IIIb antibody light chain comprises the VL sequence in SEQ ID NO: 3, including post-translational modifications of that sequence. In a particular embodiment, the heavy chain comprises one, two or three HVRs selected from: (a) HVR-H1 comprising the amino acid sequence of SEQ ID NO: 6; (b) HVR-H2 comprising the amino acid sequence of SEQ ID NO: 7; and (c) HVR-H3 comprising the amino acid sequence of SEQ ID NO: 8; and the light chain comprises one, two or three HVRs selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11. In some embodiments, the antibody is afucosylated. In some embodiments, the antibody is an IgG1 or IgG3 antibody that lacks fucose at Asn297.

Additional exemplary FGFR2 antibodies are the GAL-FR22 and GAL-FR23 antibodies described in U.S. Pat. No. 8,101,723 B2, incorporated by reference herein. The light and heavy chain variable regions of GAL-FR22, for example, are provided as SEQ ID NOs: 7 and 8 in U.S. Pat. No. 8,101,723 B2, while the Kabat CDRs and the light and heavy chain variable regions are also provided in FIG. 16 of that patent, which are incorporated by reference herein. The GAL-FR21, GAL-FR22 and GAL-FR23 producing hybridomas are deposited at the American Type Culture Collection, PO Box 1549, Manassas Va., USA, 20108, as ATCC Numbers 9586, 9587, and 9408, on November 6, November 6, and Aug. 12, 2008, respectively. Thus, in some embodiments, the FGFR2 antibody is an antibody comprising the amino acid sequence of an antibody obtained from one of those three hybridoma strains.

The heavy and light chain variable regions of GAL-FR22 are also presented herein as SEQ ID NOs: 39 and 43, while the Kabat CDRs are presented herein as SEQ ID NOs: 40-42 and 44-46 herein. Thus, in some embodiments the FGFR2-IIIb antibody heavy chain variable region comprises: (i) CDR1 comprising the amino acid sequence of SEQ ID NO: 40; (ii) CDR2 comprising the amino acid sequence of SEQ ID NO: 41; and (iii) CDR3 comprising the amino acid sequence of SEQ ID NO: 42; and the light chain variable region comprises: (iv) CDR1 comprising the amino acid sequence of SEQ ID NO: 44; (v) CDR2 comprising the amino acid sequence of SEQ ID NO: 45; and (vi) CDR3 comprising the amino acid sequence of SEQ ID NO: 46.

In some embodiments, the FGFR2 antibody comprises an FGFR2-IIIb antibody in which the heavy chain variable domain that is at least 95%, such as at least 97%, at least 98%, or at least 99% identical to the amino acid sequence of SEQ ID NO:39, or that comprises the amino acid sequence of SEQ ID NO: 39. In some embodiments, the FGFR2 antibody comprises an FGFR2-IIIb antibody in which the light chain variable domain is at least 95%, such as at least 97%, at least 98%, or at least 99% identical to the amino acid sequence of SEQ ID NO:43, or that comprises the amino acid sequence of SEQ ID NO: 43. In some embodiments, the heavy chain variable domain is at least 95%, such as at least 97%, at least 98%, or at least 99% identical to the amino acid sequence of SEQ ID NO:39, or that comprises the amino acid sequence of SEQ ID NO: 39 and the light chain variable domain is at least 95%, such as at least 97%, at least 98%, or at least 99% identical to the amino acid sequence of SEQ ID NO:43, or that comprises the amino acid sequence of SEQ ID NO: 43. In some embodiments, the antibody is an IgG1 or IgG3 antibody that lacks fucose at Asn297.

Afucosylated FGFR2 Antibodies

In some embodiments, FGFR2 antibodies, for example the FGFR2-IIIb antibodies as described above, have a carbohydrate structure that lacks fucose attached (directly or indirectly) to an Fc region (i.e., afucosylated antibodies), i.e., the antibodies are afucosylated. In some embodiments, the afucosylated antibody is an IgG1 or IgG3 antibody that lacks fucose at Asn297.

Herein, antibodies are considered to be afucosylated when a plurality of such antibodies comprises at least 95% afucosylated antibodies. The amount of fucose may be determined by calculating the average amount of fucose within the sugar chain at Asn297 relative to the sum of all glycostructures attached to Asn 297 (e.g., complex, hybrid and high mannose structures). Nonlimiting exemplary methods of detecting fucose in an antibody include MALDI-TOF mass spectrometry (see, e.g., WO 2008/077546), HPLC measurement of released fluorescently labeled oligosaccharides (see, e.g., Schneider et al., "N-Glycan analysis of monoclonal antibodies and other glycoproteins using UHPLC with fluorescence detection," Agilent Technologies, Inc. (2012); Lines, *J. Pharm. Biomed. Analysis,* 14: 601-608 (1996); Takahasi, *J. Chrom.,* 720: 217-225 (1996)), capillary electrophoresis measurement of released fluorescently labeled oligosaccharides (see, e.g., Ma et al., *Anal. Chem.,* 71: 5185-5192 (1999)), and HPLC with pulsed amperometric detection to measure monosaccharide composition (see, e.g., Hardy, et al., *Analytical Biochem.,* 170: 54-62 (1988)).

Asn297 refers to the asparagine residue located at about position 297 in the Fc region (EU numbering of Fc region residues); however, in a given antibody sequence, Asn297 may also be located about ±3 amino acids upstream or downstream of position 297, i.e., between positions 294 and 300, due to minor sequence variations in antibodies. In an FGFR2-IIIb antibody described herein, Asn297 is found in the sequence QYNST, and is in bold and underlined in the Table of Sequences shown below, SEQ ID NO: 2.

Fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "afucosylated" or "fucose-deficient" antibodies include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing afucosylated antibodies include Lec13 CHO cells deficient in protein fucosylation (Ripka et al. *Arch. Biochem. Biophys.* 249:533-545 (1986); US Patent Application No. US 2003/0157108 A1, Presta, L; and WO 2004/056312 A1, Adams et al., especially at Example 11), and knockout cell lines, such as cell lines lacking a functional alpha-1,6-fucosyltransferase gene, FUT8, e.g., knockout CHO cells (see, e.g., Yamane-Ohnuki et al *Biotech. Bioeng.* 87: 614 (2004); Kanda, Y. et al., *Biotechnol. Bioeng.,* 94(4):680-688 (2006); and WO2003/085107).

FGFR2 antibodies herein may also have bisected oligosaccharides, e.g., in which a biantennary oligosaccharide attached to the Fc region of the antibody is bisected by GlcNAc. Such antibodies may have reduced fucosylation and/or improved ADCC function. Examples of such antibodies are described, e.g., in WO 2003/011878 (Jean-Mairet et al.); U.S. Pat. No. 6,602,684 (Umana et al.); and US 2005/0123546 (Umana et al). In some embodiments, FGFR2 antibodies have at least one galactose residue in the oligosaccharide attached to the Fc region. Such antibodies may have improved CDC function. Such antibodies are described, e.g., in WO 1997/30087 (Patel et al); WO 1998/58964 (Raju, S.); and WO 1999/22764 (Raju, S.).

In some embodiments of the invention, an afucosylated FGFR2 antibody mediates ADCC in the presence of human effector cells more effectively than an antibody with the same amino acid sequence that comprises fucose. Generally, ADCC activity may be determined using the in vitro ADCC assay disclosed in U.S. Patent Publication No. 2015-

0050273 A1, but other assays or methods for determining ADCC activity, e.g. in an animal model etc., are contemplated.

In some embodiments, the FGFR2 antibody comprises the heavy and light chain sequences of SEQ ID NOs: 2 and 3. In some embodiments, the antibody comprising the heavy and light chain sequences of SEQ ID NOs: 2 and 3 is afucosylated. FGFR2 ECDs and FGFR2 ECD Fusion Molecules In some embodiments, the FGFR2 inhibitor is an FGFR2 ECD such as an FGFR2 ECD fusion molecule. FGFR2 ECD fusion molecules may comprise fusion partners such as polymers, polypeptides, lipophilic moieties, and succinyl groups. Exemplary polypeptide fusion partners include serum albumin and an antibody Fc domain. Further exemplary polymer fusion partners include, but are not limited to, polyethylene glycol, including polyethylene glycols having branched and/or linear chains Certain exemplary fusion partners include, but are not limited to, an immunoglobulin Fc domain, albumin, and polyethylene glycol. The amino acid sequences of certain exemplary Fc domains are shown in SEQ ID NOs: 24 to 26.

Exemplary FGFR2 ECDs and FGFR2 ECD fusion molecules include those described in PCT publication WO 2007/014123. FGFR2 ECDs and FGFR2 ECD fusion molecules may comprise a native ECD amino acid sequence, including that of FGFR2-IIIb or FGFR2-IIIc BCD. Alternatively, FGFR2 ECDs and FGFR2 ECD fusion molecules may comprise an FGFR2 ECD with a C-terminal deletion of one or more and up to 22 amino acid residues counting from the C-terminus, wherein the FGFR2 ECD retains at least one of its FGF ligand binding activities. In some embodiments, the FGFR2 ECD has up to 22 amino acids at the C-terminus deleted. In some embodiments, the deletion does not extend to or include the valine residue at amino acid residue 357 of the native full length FGFR2-IIIb or amino acid residue 359 of the native full length FGFR2-IIIc.

For instance, in some embodiments, the FGFR2 ECD or FGFR2 ECD fusion molecule comprises the amino acid sequence of SEQ ID NO: 14, but wherein amino acid residues have been deleted from the amino-terminus and/or carboxy-terminus, and wherein the resulting molecule is capable of binding to FGF2. In some embodiments, the FGFR2 ECD or FGFR2 ECD fusion molecule comprises the amino acid sequence of SEQ ID NO: 15, which corresponds to the amino acid sequence of SEQ ID NO: 14, but with the last three carboxy-terminal amino acid residues, YLE, deleted. Further examples of such variants include those having the C-terminal 4 amino acid residues deleted (SEQ ID NO: 16), having the C-terminal 5 amino acid residues deleted (SEQ ID NO: 17), those having the C-terminal 8 amino acid residues deleted (SEQ ID NO: 18), those having the C-terminal 9 amino acid residues deleted (SEQ ID NO: 19), having the C-terminal 10 amino acid residues deleted (SEQ ID NO: 20), those having the C-terminal 14 amino acid residues deleted (SEQ ID NO: 21), those having the C-terminal 15 amino acid residues deleted (SEQ ID NO: 22), those having the C-terminal 16 amino acid residues deleted (SEQ ID NO: 23), those having the C-terminal 17 amino acid residues deleted (SEQ ID NO: 24), all as compared to the native FGFR2-IIIb or FGFR2-IIIc sequence. Any of the above FGFR2 ECD fragments may be coupled to any of the fusion partners described above to form an FGFR2 ECD fusion molecule.

In certain embodiments, at least one amino acid within the FGFR2 ECD sequence may be mutated to prevent glycosylation at that site in the polypeptide. Non-limiting exemplary FGFR2 ECD amino acids that may be glycosylated include N62, N102, N207, N220, N244, N276, N297, and N310 in SEQ ID NO: 28.

Additional exemplary FGFR2 ECD and FGFR2 ECD fusion molecules include those described in PCT Publication No. WO2010/017198. Included therein are FGFR2 ECDs and FGFR2 ECD fusion molecules with mutations in the "acid box" region of the FGFR2 ECD. Such an FGFR2 ECD acidic region mutein may be used either as an FGFR2 ECD or as an FGFR2 ECD fusion molecule. In certain embodiments, the FGFR2 ECD or FGFR2 ECD fusion molecule comprises the FGFR1 short acid box in place of the FGFR2 short acid box. For example, FGFR2 ECD residues 111 to 118 (SEQ ID NO: 28) may be replaced with FGFR1 ECD residues 105 to 112 (SEQ ID NO: 29). In some embodiments, the FGFR2 ECD or FGFR2 ECD fusion molecule comprises the amino acid sequence of SEQ ID NO: 30. In some embodiments, the FGFR2 ECD or FGFR2 ECD fusion molecule comprises the amino acid sequence of any of SEQ ID NOs: 31-34. Any of the "acid box" mutant FGFR2 ECD sequences such as SEQ ID NO:30 may also be combined with any of the above C-terminal deletion FGFR2 ECD sequences described above (SEQ ID NOs: 15-24), and optionally, joined to one or more fusion molecules (e.g., SEQ ID NOs: 32-34).

In certain embodiments, an FGFR2 ECD or FGFR2 ECD fusion molecule lacks a signal peptide. In certain embodiments, an FGFR2 ECD includes at least one signal peptide, which may be selected from a native FGFR2 signal peptide and/or a heterologous signal peptide, such as that from FGFR1, FGFR3, or FGFR4.

In the case of an FGFR2 ECD fusion molecule, the fusion partner may be linked to either the amino-terminus or the carboxy-terminus of the polypeptide. In certain embodiments, the polypeptide and the fusion partner are covalently linked. If the fusion partner is also a polypeptide ("the fusion partner polypeptide"), the polypeptide and the fusion partner polypeptide may be part of a continuous amino acid sequence. In such cases, the polypeptide and the fusion partner polypeptide may be translated as a single polypeptide from a coding sequence that encodes both the polypeptide and the fusion partner polypeptide. In certain embodiments, an FGFR2 ECD fusion molecule contains a "GS" linker between the FGFR2 ECD or the FGFR2 ECD acidic region mutein and the fusion partner. In certain embodiments, the polypeptide and the fusion partner are covalently linked through other means, such as, for example, a chemical linkage other than a peptide bond. In certain embodiments, the polypeptide and the fusion partner are noncovalently linked. In certain such embodiments, they may be linked, for example, using binding pairs. Exemplary binding pairs include, but are not limited to, biotin and avidin or streptavidin, an antibody and its antigen, etc.

Exemplary PD-1/PD-L1 Inhibitors

Exemplary PD-1/PD-L1 inhibitors include antibodies that inhibit PD-1, such as anti-PD-1 antibodies and anti-PD-L1 antibodies. Such antibodies may be humanized antibodies, chimeric antibodies, mouse antibodies, human antibodies, and antibodies comprising the heavy chain and/or light chain CDRs discussed herein. PD-1/PD-L1 inhibitors also include fusion molecules that block binding of PD-1 to PD-L1, such as AMP-224, and inhibitory PD-1 polypeptides such as AUR-012 that may compete with PD-1 for binding to PD-L1.

Exemplary PD-1/PD-L1 Antibodies

PD-1 is a key immune checkpoint receptor expressed by activated T and B cells and mediates immunosuppression.

PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1) and Programmed Death Ligand-2 (PD-L2). These ligands are expressed on antigen-presenting cells as well as many human cancers and have been shown to down regulate T cell activation and cytokine secretion upon binding to PD-1. Inhibition of the PD-1/PD-L1 interaction mediates potent antitumor activity in preclinical models.

Human monoclonal antibodies (HuMAbs) that bind specifically to PD-1 with high affinity have been disclosed in U.S. Pat. No. 8,008,449. Other anti-PD-1 mAbs have been described in, for example, U.S. Pat. Nos. 6,808,710, 7,488, 802, 8,168,757 and 8,354,509, and PCT Publication No. WO 2012/145493. Each of the anti-PD-1 HuMAbs disclosed in U.S. Pat. No. 8,008,449: (a) binds to human PD-1 with a $K_D$ of $1\times10^{-7}$M or less, as determined by surface plasmon resonance using a Biacore biosensor system; (b) does not substantially bind to human CD28, CTLA-4 or ICOS; (c) increases T-cell proliferation in a Mixed Lymphocyte Reaction (MLR) assay; (d) increases interferon-γ production in an MLR assay; (e) increases IL-2 secretion in an MLR assay; (f) binds to human PD-1 and cynomolgus monkey PD-1; (g) inhibits the binding of PD-L1 and/or PD-L2 to PD-1; (h) stimulates antigen-specific memory responses; (i) stimulates Antibody responses; and/or (j) inhibits tumor cell growth in vivo. Anti-PD-1 antibodies usable in the present invention include antibodies that bind specifically to human PD-1 and exhibit at least one, at least two, at least three, at least four or at least five of the preceding characteristics (a) through (j).

In one embodiment, the anti-PD-1 antibody is nivolumab. Nivolumab (also known as "Opdivo®"; formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 *Cancer Immunol Res.* 2(9): 846-56).

In another embodiment, the anti-PD-1 antibody is pembrolizumab. Pembrolizumab (also known as "Keytruda®", lambrolizumab, and MK-3475) is a humanized monoclonal IgG4 antibody directed against human cell surface receptor PD-1 (programmed death-1 or programmed cell death-1). Pembrolizumab is described, for example, in U.S. Pat. No. 8,900,587; see also the site with the address: "www" dot "cancer" dot "gov" slash "drugdictionary?cdrid=695789" (last accessed: Dec. 14, 2014). Pembrolizumab has been approved by the FDA for the treatment of relapsed or refractory melanoma.

In other embodiments, the anti-PD-1 antibody is MEDI0608 (formerly AMP-514), which is a monoclonal antibody against the PD-1 receptor. MEDI0608 is described, for example, in U.S. Pat. No. 8,609,089,B2 or at the Internet site: "www" dot "cancer" dot "gov" slash "drugdictionary?cdrid=756047" (last accessed Dec. 14, 2014).

In some embodiments, the anti-PD-1 antibody is Pidilizumab (CT-011), which is a humanized monoclonal antibody. Pidilizumab is described in U.S. Pat. No. 8,686,119 B2 or WO 2013/014668 A1.

Anti-PD-1 antibodies usable in the disclosed methods also include isolated antibodies that bind specifically to human PD-1 and cross-compete for binding to human PD-1 with nivolumab (see, e.g., U.S. Pat. No. 8,008,449; WO 2013/173223). The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar to those of nivolumab by virtue of their binding to the same epitope region of PD-1. Cross-competing antibodies can be readily identified based on their ability to cross-compete with nivolumab in standard PD-1 binding assays such as Biacore analysis, ELISA assays or flow cytometry (see, e.g., WO 2013/173223).

In certain embodiments, the antibodies that cross-compete for binding to human PD-1 with, or bind to the same epitope region of human PD-1 as, nivolumab are monoclonal antibodies. For administration to human subjects, these cross-competing antibodies can be chimeric antibodies, or can be humanized or human antibodies.

Anti-PD-1 antibodies usable in the methods of the disclosed invention also include antigen-binding portions of the above antibodies. Examples include (i) a Fab fragment, a monovalent fragment consisting of the $V_L$, $V_H$, $C_L$ and $C_{H1}$ domains; (ii) a F(ab')2 fragment, a bivalent fragment comprising two Fab fragments linked by a disulfide bridge at the hinge region; (iii) a Fd fragment consisting of the $V_H$ and $C_{H1}$ domains; and (iv) a Fv fragment consisting of the $V_L$ and $V_H$ domains of a single arm of an antibody.

A nonlimiting exemplary fusion molecule that is a PD-1/PD-L1 inhibitor is AMP-224 (Amplimmune, GlaxoSmithKline). A nonlimiting exemplary polypeptide that is a PD-1/PD-L1 inhibitor is AUR-012.

Exemplary Antibody Constant Regions

In some embodiments, an FGFR2 or an anti-PD-1 or anti-PD-L1 antibody described herein comprises one or more human constant regions. In some embodiments, the human heavy chain constant region is of an isotype selected from IgA, IgG, and IgD. In some embodiments, the human light chain constant region is of an isotype selected from κ and λ.

In some embodiments, an antibody described herein comprises a human IgG constant region. In some embodiments, when effector function is desirable, an antibody comprising a human IgG1 heavy chain constant region or a human IgG3 heavy chain constant region is selected. In some embodiments, an antibody described herein comprises a human IgG1 constant region. In some embodiments, an antibody described herein comprises a human IgG1 constant region, wherein N297 is not fucosylated. In some embodiments, an antibody described herein comprises a human IgG1 constant region and a human κ light chain.

Throughout the present specification and claims unless explicitly stated or known to one skilled in the art, the numbering of the residues in an immunoglobulin heavy chain is that of the EU index as in Kabat et al, *Sequences of Proteins of Immunological Interest,* 5th Ed. Public Health Service, National Institutes of Health, Bethesda, Md. (1991), expressly incorporated herein by reference. The "EU index as in Kabat" refers to the residue numbering of the human IgG1 EU antibody.

In certain embodiments, an antibody of the invention comprises a variant Fc region has at least one amino acid substitution compared to the Fc region of a wild-type IgG or a wild-type antibody. In certain embodiments, the variant Fc region has two or more amino acid substitutions in the Fc region of the wild-type antibody. In certain embodiments, the variant Fc region has three or more amino acid substitutions in the Fc region of the wild-type antibody. In certain embodiments, the variant Fc region has at least one, two or three or more Fc region amino acid substitutions described herein. In certain embodiments, the variant Fc region herein will possess at least about 80% homology with a native sequence Fc region and/or with an Fc region of a parent antibody. In certain embodiments, the variant Fc region herein will possess at least about 90% homology with a native sequence Fc region and/or with an Fc region of a parent antibody. In certain embodiments, the variant Fc region herein will possess at least about 95% homology with a native sequence Fc region and/or with an Fc region of a parent antibody.

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibodies with certain improved properties.

Antibodies may also have amino-terminal leader extensions. For example, one or more amino acid residues of the amino-terminal leader sequence are present at the amino-terminus of any one or more heavy or light chains of an antibody. An exemplary amino-terminal leader extension comprises or consists of three amino acid residues, VHS, present on one or both light chains of an antibody.

The in vivo or serum half-life of human FcRn high affinity binding polypeptides can be assayed, e.g., in transgenic mice, in humans, or in non-human primates to which the polypeptides with a variant Fc region are administered. See also, e.g., Petkova et al. *International Immunology* 18(12): 1759-1769 (2006).

Exemplary Chimeric Antibodies

In certain embodiments, an FGFR2 or anti-PD-1 or anti-PD-L1 antibody provided herein is a chimeric antibody. Certain chimeric antibodies are described, e.g., in U.S. Pat. No. 4,816,567; and Morrison et al, (1984) *Proc. Natl. Acad. Sci. USA,* 81: 6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

Nonlimiting exemplary chimeric antibodies include chimeric antibodies against either FGFR2 or PD-1/PD-L1 comprising heavy chain HVR1, HVR2, and HVR3, and/or light chain HVR1, HVR2, and HVR3 sequences described herein.

In some embodiments, a chimeric antibody described herein comprises one or more human constant regions. In some embodiments, the human heavy chain constant region is of an isotype selected from IgA, IgG, and IgD. In some embodiments, the human light chain constant region is of an isotype selected from κ and λ. In some embodiments, a chimeric antibody described herein comprises a human IgG constant region. In some embodiments, a chimeric antibody described herein comprises a human IgG4 heavy chain constant region. In some embodiments, a chimeric antibody described herein comprises a human IgG4 constant region and a human κ light chain.

As noted above, whether or not effector function is desirable may depend on the particular method of treatment intended for an antibody. Thus, in some embodiments, when effector function is desirable, a chimeric antibody comprising a human IgG1 heavy chain constant region or a human IgG3 heavy chain constant region is selected. In some embodiments, when effector function is not desirable, a chimeric antibody comprising a human IgG4 or IgG2 heavy chain constant region is selected. In some embodiments, a chimeric antibody described herein comprises a human IgG1 constant region wherein N297 is not fucosylated. In some embodiments, a chimeric antibody described herein comprises a human IgG1 constant region and a human κ light chain.

Exemplary Humanized Antibodies

In some embodiments, humanized antibodies that bind FGFR2 or PD-1/PD-L1 are used. Humanized antibodies are useful as therapeutic molecules because humanized antibodies reduce or eliminate the human immune response to non-human antibodies (such as the human anti-mouse antibody (HAMA) response), which can result in an immune response to an antibody therapeutic, and decreased effectiveness of the therapeutic.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs or CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, (2008) *Front. Biosci.* 13: 1619-1633, and are further described, e.g., in Riechmann et al, (1988) *Nature* 332:323-329; Queen et al, (1989) *Proc. Natl Acad. Sci. USA* 86: 10029-10033; U.S. Pat. Nos. 5,821,337, 7,527,791, 6,982,321, and 7,087,409; Kashmiri et al, (2005) *Methods* 36:25-34 (describing SDR (a-CDR) grafting); Padlan, (1991) *Mol. Immunol.* 28:489-498 (describing "resurfacing"); Dall'Acqua et al, (2005) *Methods* 36:43-60 (describing "FR shuffling"); and Osbourn et al, (2005) *Methods* 36:61-68 and Klimka et al, (2000) *Br. J. Cancer,* 83:252-260 (describing the "guided selection" approach to FR shuffling).

Human framework regions that may be used for humanization include but are not limited to: framework regions selected using the "best-fit" method (see, e.g., Sims et al. (1993) *J. Immunol.* 151: 2296); framework regions derived from the consensus sequence of human antibodies of a particular subgroup of light or heavy chain variable regions (see, e.g., Carter et al. (1992) *Proc. Natl. Acad. Sci. USA,* 89:4285; and Presta et al. (1993) *J. Immunol,* 151:2623); human mature (somatically mutated) framework regions or human germline framework regions (see, e.g., Almagro and Fransson, (2008) *Front. Biosci.* 13:1619-1633); and framework regions derived from screening FR libraries (see, e.g., Baca et al, (1997) *J. Biol. Chem.* 272: 10678-10684 and Rosok et al, (1996) *J. Biol. Chem.* 271: 22611-22618).

In some embodiments, humanized antibodies comprise one or more human constant regions. In some embodiments, the human heavy chain constant region is of an isotype selected from IgA, IgG, and IgD. In some embodiments, the human light chain constant region is of an isotype selected from κ and λ.

In some embodiments, a humanized antibody described herein comprises a human IgG constant region. In some embodiments, when effector function is desirable, the antibody comprises a human IgG1 heavy chain constant region or a human IgG3 heavy chain constant region. In some embodiments, a humanized antibody described herein comprises a human IgG1 constant region. In some embodiments, a humanized antibody described herein comprises a human IgG1 constant region wherein N297 is not fucosylated. In some embodiments, a humanized antibody described herein comprises a human IgG1 constant region and a human κ light chain.

Human Antibodies

Human FGFR2 or PD-1/PD-L1 antibodies can be made by any suitable method. Nonlimiting exemplary methods include making human antibodies in transgenic mice that comprise human immunoglobulin loci. See, e.g., Jakobovits et al., *Proc. Natl. Acad. Sci. USA* 90: 2551-55 (1993); Jakobovits et al., *Nature* 362: 255-8 (1993); Lonberg et al., *Nature* 368: 856-9 (1994); and U.S. Pat. Nos. 5,545,807; 6,713,610; 6,673,986; 6,162,963; 5,545,807; 6,300,129; 6,255,458; 5,877,397; 5,874,299; and 5,545,806.

Nonlimiting exemplary methods also include making human antibodies using phage display libraries. See, e.g., Hoogenboom et al., *J. Mol. Biol.* 227: 381-8 (1992); Marks et al., *J. Mol. Biol.* 222: 581-97 (1991); and PCT Publication No. WO 99/10494.

In some embodiments, a human antibody comprises one or more human constant regions. In some embodiments, the human heavy chain constant region is of an isotype selected from IgA, IgG, and IgD. In some embodiments, the human light chain constant region is of an isotype selected from κ and λ. In some embodiments, a human antibody described herein comprises a human IgG constant region. In some embodiments, a human antibody described herein comprises a human IgG4 heavy chain constant region. In some such embodiments, a human antibody described herein comprises an S241P mutation in the human IgG4 constant region. In some embodiments, a human antibody described herein comprises a human IgG4 constant region and a human κ light chain In some embodiments, when effector function is desirable, a human antibody comprising a human IgG1 heavy chain constant region or a human IgG3 heavy chain constant region is selected. In some embodiments, when effector function is not desirable, a human antibody comprising a human IgG4 or IgG2 heavy chain constant region is selected. In some embodiments, a humanized antibody described herein comprises a human IgG1 constant region wherein N297 is not fucosylated. In some embodiments, a humanized antibody described herein comprises a human IgG1 constant region and a human κ light chain Exemplary Antibody Conjugates In some embodiments, an FGFR2 or PD-1/PD-L1 antibody is conjugated to a label and/or a cytotoxic agent. As used herein, a label is a moiety that facilitates detection of the antibody and/or facilitates detection of a molecule to which the antibody binds. Nonlimiting exemplary labels include, but are not limited to, radioisotopes, fluorescent groups, enzymatic groups, chemiluminescent groups, biotin, epitope tags, metal-binding tags, etc. One skilled in the art can select a suitable label according to the intended application.

As used herein, a cytotoxic agent is a moiety that reduces the proliferative capacity of one or more cells. A cell has reduced proliferative capacity when the cell becomes less able to proliferate, for example, because the cell undergoes apoptosis or otherwise dies, the cell fails to proceed through the cell cycle and/or fails to divide, the cell differentiates, etc. Nonlimiting exemplary cytotoxic agents include, but are not limited to, radioisotopes, toxins, and chemotherapeutic agents. One skilled in the art can select a suitable cytotoxic according to the intended application.

In some embodiments, a label and/or a cytotoxic agent is conjugated to an antibody using chemical methods in vitro. Nonlimiting exemplary chemical methods of conjugation are known in the art, and include services, methods and/or reagents commercially available from, e.g., Thermo Scientific Life Science Research Produces (formerly Pierce; Rockford, Ill.), Prozyme (Hayward, Calif.), SACRI Antibody Services (Calgary, Canada), AbD Serotec (Raleigh, N.C.), etc. In some embodiments, when a label and/or cytotoxic agent is a polypeptide, the label and/or cytotoxic agent can be expressed from the same expression vector with at least one antibody chain to produce a polypeptide comprising the label and/or cytotoxic agent fused to an antibody chain. One skilled in the art can select a suitable method for conjugating a label and/or cytotoxic agent to an antibody according to the intended application.

Nucleic Acid Molecules Encoding Antibodies

Nucleic acid molecules comprising polynucleotides that encode one or more chains of an antibody are provided. In some embodiments, a nucleic acid molecule comprises a polynucleotide that encodes a heavy chain or a light chain of an antibody. In some embodiments, a nucleic acid molecule comprises both a polynucleotide that encodes a heavy chain and a polynucleotide that encodes a light chain, of an antibody. In some embodiments, a first nucleic acid molecule comprises a first polynucleotide that encodes a heavy chain and a second nucleic acid molecule comprises a second polynucleotide that encodes a light chain.

In some such embodiments, the heavy chain and the light chain are expressed from one nucleic acid molecule, or from two separate nucleic acid molecules, as two separate polypeptides. In some embodiments, such as when an antibody is an scFv, a single polynucleotide encodes a single polypeptide comprising both a heavy chain and a light chain linked together.

In some embodiments, a polynucleotide encoding a heavy chain or light chain of an antibody comprises a nucleotide sequence that encodes a leader sequence, which, when translated, is located at the N terminus of the heavy chain or light chain. As discussed above, the leader sequence may be the native heavy or light chain leader sequence, or may be another heterologous leader sequence.

Nucleic acid molecules may be constructed using recombinant DNA techniques conventional in the art. In some embodiments, a nucleic acid molecule is an expression vector that is suitable for expression in a selected host cell.

Antibody Expression and Production

Vectors

Vectors comprising polynucleotides that encode antibody heavy chains and/or light chains are provided. Vectors comprising polynucleotides that encode antibody heavy chains and/or light chains are also provided. Such vectors include, but are not limited to, DNA vectors, phage vectors, viral vectors, retroviral vectors, etc. In some embodiments, a vector comprises a first polynucleotide sequence encoding a heavy chain and a second polynucleotide sequence encoding a light chain. In some embodiments, the heavy chain and light chain are expressed from the vector as two separate polypeptides. In some embodiments, the heavy chain and light chain are expressed as part of a single polypeptide, such as, for example, when the antibody is an scFv.

In some embodiments, a first vector comprises a polynucleotide that encodes a heavy chain and a second vector comprises a polynucleotide that encodes a light chain. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells. In some embodiments, a mass ratio of between 1:1 and 1:5 for the vector encoding the heavy chain and the vector encoding the light chain is used. In some embodiments, a mass ratio of 1:2 for the vector encoding the heavy chain and the vector encoding the light chain is used.

In some embodiments, a vector is selected that is optimized for expression of polypeptides in CHO or CHO-derived cells, or in NSO cells. Exemplary such vectors are described, e.g., in Running Deer et al., *Biotechnol. Prog.* 20:880-889 (2004).

In some embodiments, a vector is chosen for in vivo expression of antibody heavy chains and/or antibody light chains in animals, including humans. In some such embodiments, expression of the polypeptide is under the control of a promoter that functions in a tissue-specific manner. For example, liver-specific promoters are described, e.g., in PCT Publication No. WO 2006/076288.

Host Cells

In various embodiments, antibody heavy chains and/or light chains may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S and DG44 cells; PER.C6® cells (Crucell); and NSO cells. In some embodiments, antibody heavy chains and/or light chains may be expressed in yeast. See, e.g., U.S. Publication No. US 2006/0270045 A1. In some embodiments, a particular eukaryotic host cell is selected based on its ability to make desired post-translational modifications to the antibody heavy chains and/or light chains. For example, in some embodiments, CHO cells produce polypeptides that have a higher level of sialylation than the same polypeptide produced in 293 cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, e.g., in Sambrook et al., *Molecular Cloning, A Laboratory Manual*, 3$^{rd}$ ed. Cold Spring Harbor Laboratory Press (2001). Nucleic acids may be transiently or stably transfected in the desired host cells, according to any suitable method.

In some embodiments, one or more polypeptides may be produced in vivo in an animal that has been engineered or transfected with one or more nucleic acid molecules encoding the polypeptides, according to any suitable method.

Purification of Antibodies

Antibodies may be purified by any suitable method. Such methods include, but are not limited to, the use of affinity matrices or hydrophobic interaction chromatography. Suitable affinity ligands include the antigen and ligands that bind antibody constant regions. For example, a Protein A, Protein G, Protein A/G, or an antibody affinity column may be used to bind the constant region and to purify an antibody. Hydrophobic interactive chromatography, for example, a butyl or phenyl column, may also suitable for purifying some polypeptides. Many methods of purifying polypeptides are known in the art.

Cell-Free Production of Antibodies

In some embodiments, an antibody is produced in a cell-free system. Nonlimiting exemplary cell-free systems are described, e.g., in Sitaraman et al., *Methods Mol. Biol.* 498: 229-44 (2009); Spirin, *Trends Biotechnol.* 22: 538-45 (2004); Endo et al., *Biotechnol. Adv.* 21: 695-713 (2003).

Therapeutic Compositions and Methods

Methods of Treating Cancer

In some embodiments, methods for treating cancer are provided, comprising administering an effective amount of an FGFR2 inhibitor described herein. Some such embodiments include methods of increasing the number of one or more of PD-L1 positive cells, NK cells, CD3+ T cells, CD4+ T cells, and CD8+ T cells in tumor tissue of a cancer subject, comprising administering an FGFR2 inhibitor, wherein the inhibitor is an FGFR2 antibody with enhanced ADCC activity. In some such embodiments, no immune stimulating agent is administered with the FGFR2 antibody.

In some other embodiments, methods for treating cancer are provided, comprising administering an effective amount of an FGFR2 inhibitor and an effective amount of at least one immune stimulating agent. In an exemplary embodiment, the at least one immune stimulating agent comprises a PD-1/PD-L1 inhibitor. In some embodiments, the FGFR2 inhibitor and the at least one immune stimulating agent, such as a PD-1/PD-L1 inhibitor, are administered concurrently. In some embodiments, the FGFR2 inhibitor and the at least one immune stimulating agent, such as a PD-1/PD-L1 inhibitor, are administered sequentially. In some embodiments, at least one, at least two, at least three doses, at least five doses, or at least ten doses of an FGFR2 inhibitor is administered prior to administration of at least one immune stimulating agent, such as a PD-1/PD-L1 inhibitor. In some embodiments, at least one, at least two, at least three doses, at least five doses, or at least ten doses of at least one immune stimulating agent, such as a PD-1/PD-L1 inhibitor, is administered prior to administration of an FGFR2 inhibitor. In some embodiments, the last dose of at least one immune stimulating agent, such as a PD-1/PD-L1 inhibitor, is administered at least one, two, three, five, days or ten, or one, two, three, five, twelve, or twenty four weeks prior to the first dose of FGFR2 inhibitor. In some other embodiment, the last dose of FGFR2 inhibitor is administered at least one, two, three, five, days or ten, or one, two, three, five, twelve, or twenty four weeks prior to the first dose of at least one immune stimulating agent, such as a PD-1/PD-L1 inhibitor. In some embodiments, a subject has received, or is receiving, PD-1/PD-L1 inhibitor therapy, and an FGFR2 inhibitor is added to the therapeutic regimen.

In some embodiments, the cancer is selected from gastric cancer, breast cancer, squamous cell cancer, small-cell lung cancer, pituitary cancer, esophageal cancer (including gastroesophageal junction adenocarcinoma), astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, renal cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer. In some embodiments, lung cancer is non-small cell lung cancer or lung squamous cell carcinoma. In some embodiments, leukemia is acute myeloid leukemia or chronic lymphocytic leukemia. In some embodiments, breast cancer is breast invasive carcinoma. In some embodiments, ovarian cancer is ovarian serous cystadenocarcinoma. In some embodiments, kidney cancer is kidney renal clear cell carcinoma. In some embodiments, colon cancer is colon adenocarcinoma. In some embodiments, bladder cancer is bladder urothelial carcinoma. In some embodiments, the cancer is selected from bladder cancer, cervical cancer (such as squamous cell cervical cancer), head and neck squamous cell carcinoma, rectal adenocarcinoma, non-small cell lung cancer, endometrial cancer, prostate adenocarcinoma, colon cancer, ovarian cancer (such as serous epithelial ovarian cancer), and melanoma. In some embodiments, the cancer is gastric (which includes gastroesophageal cancer) or bladder cancer (such as transitional cell carcinoma, also known as urothelial cancer).

In some embodiments, a cancer comprises an FGFR2 gene amplification, whereas in some embodiments the cancer does not comprise an FGFR2 amplification. In some embodiments, fluorescence in situ hybridization (FISH) is used to assess gene amplification, such as with probes to the FGFR2 gene locus and the chromosome 10 centromere. In some embodiments, where an amplification occurs, the FGFR2 amplification comprises an FGFR2:CEN10 (chromosome 10 centromere) ratio of >3. In some embodiments, FGFR2 amplification comprises an FGFR2:CEN10 ratio of ≥2. In other embodiments, however, the FGFR2 level comprises an FGFR2:CEN10 ratio of between 1 and 2, indicating that FGFR2 is not amplified.

In some embodiments, where the cancer comprises an FGFR2 gene amplification, the cancer overexpresses FGFR2-IIIb. In some embodiments, a cancer comprising FGFR2 amplification overexpresses FGFR2-IIIb to a greater extent than FGFR2-IIIc. In some embodiments, the cancer does not comprise a gene amplification, yet FGFR2-IIIb is overexpressed. In some embodiments, a cancer comprising FGFR2 amplification expresses FGFR2-IIIb at a normalized level that is more than 2-fold, 3-fold, 5-fold, or 10-fold greater than the normalized level of FGFR2-IIIc expression. In some embodiments, the expression levels are normalized to GUSB. In some embodiments, a cancer overexpresses FGFR2-IIIb but does not comprise FGFR2 gene amplification. In some embodiments, a gastric or bladder cancer comprises an FGFR2 gene amplification. In some embodiments, a gastric or bladder cancer comprises an FGFR2 gene amplification that overexpresses FGFR2-IIIb.

In some embodiments, a gastric or bladder cancer comprising FGFR2 amplification overexpresses FGFR2-IIIb to a greater extent than FGFR2-IIIc. In some embodiments, the gastric or bladder cancer does not comprise a gene amplification, yet FGFR2-IIIb is overexpressed. In some embodiments, a gastric or bladder cancer comprising FGFR2 amplification expresses FGFR2-IIIb at a normalized level that is more than 2-fold, 3-fold, 5-fold, or 10-fold greater than the normalized level of FGFR2-IIIc expression. In some embodiments, the expression levels are normalized to GUSB. In some embodiments, a gastric or bladder cancer overexpresses FGFR2-IIIb but does not comprise FGFR2 gene amplification. In some embodiments, overexpression is mRNA overexpression. In some embodiments, overexpression is protein overexpression. In some embodiments, a point mutation or translocation may cause an overexpression of FGFR2. Expression levels of FGFR2 species may be determined, for example, using IHC.

In some embodiments, the FGFR2 overexpression is determined by immunohistochemistry (IHC). For example, the overexpression may be determined by an IHC signal of 1+, 2+, or 3+ in at least 10% of tumor cells, such as in at least 20%, 30%, 40%, or 50% of tumor cells. For example, in some such embodiments, the cancer is gastric cancer and patients to be treated may have, for instance, an IHC signal for FGFR2b of 3+ in at least 10% of tumor cells (e.g. in cell membranes). In some embodiments, a gastric cancer patient may have 2+ or 3+ signal in at least 10% of tumor cells. In some embodiments, a gastric cancer patient may have at least 1+ signal in at least 10% of tumor cells.

In some embodiments, the FGFR2 overexpression may be reported as an "H score." For example, in some such embodiments, the tumor is a bladder cancer tumor. To determine an H score, first membrane staining intensity may be determined for cells in a fixed field, such as via IHC to obtain scores of 0, 1+, 2+, or 3+ and the H score can be calculated using the formula as follows: 1×(% of cells visualized with IHC intensity of 1+)+2×(% of cells visualized with IHC intensity of 2+)+3×(% of cells visualized with IHC intensity of 3+). Theoretically, an H score may range from 0 to 300 and equals 300 if all of the cells in the visual field have IHC staining of 3+. In some embodiments, the patient to be treated has a starting H score for FGFR2, such as FGFR2b (e.g. FGFR2IIIb), of >20, such as >30, >40, >50, or >100, or a range of 20-300, 20-100, 20-50, 20-40, or 20-30. In some embodiments, the patient has an H score of >10 or is within a range of 10-20 or 15-20. In other embodiments, the patient has an H score of 0-10, which may indicate a lack of FGFR2 overexpression. In some such embodiments, the patient is a bladder cancer patient.

In some embodiments, the cancer has already been determined to overexpress FGFR2IIIb and/or to carry an FGFR2 gene amplification. In other embodiments, the methods herein first assess either or both of the FGFR2IIIb expression and FGFR2 gene amplification status before treatment is given. And in addition, this disclosure provides methods of determining responsiveness to any of the FGFR2 inhibitors, treatments, and uses described above comprising assessing FGFR2IIIb expression and/or FGFR2 gene amplification in a cancer patient.

In some embodiments in which the patient suffers from gastric or bladder cancer, the method may comprise determining if the patient's cancer falls into one of the following categories, which may indicate responsiveness to the treatment or FGFR2 inhibitor composition: a) in the case of a gastric cancer subject, an IHC signal of 3+ in at least 10% of tumor cells; b) in the case of a gastric cancer subject, an IHC signal of 3+ in at least 10% of tumor cells as well as amplification of the FGFR2 gene; c) in the case of a gastric cancer subject, an IHC signal of 3+ in at least 10% of tumor cells without amplification of the FGFR2 gene; d) in the case of a gastric cancer subject, an IHC signal of 1+ or 2+ in at least 10% of tumor cells; e) in the case of a bladder cancer subject, an IHC signal of 1+ in at least 10% of tumor cells; f) in the case of a bladder cancer subject, an IHC signal of 2+ in at least 10% of tumor cells; g) in the case of a bladder cancer subject, an H score of greater than 20; h) in the case of a bladder cancer subject, an H score of 10-19; i) in the case of a bladder cancer subject, an H score of less than 10.

In some embodiments of the methods described herein, the subject is a PD-1/PD-L1 inhibitor "inadequate responder." A subject who is a PD-1/PD-L1 inhibitor inadequate responder, may have previously responded to a PD-1/PD-L1 inhibitor, but may have become less responsive to the PD-1/PD-L1 inhibitor, or the subject may have never responded to the PD-1/PD-L1 inhibitor. Inadequate response to a PD-1/PD-L1 inhibitor means that aspects of the condition that would be expected to improve following a standard dose of the PD-1/PD-L1 inhibitor do not improve, and/or improvement only occurs if greater than a standard dose is administered. In some embodiments, a PD-1/PD-L1 inhibitor inadequate responder has experienced, or is experiencing, an inadequate response to the PD-1/PD-L1 inhibitor after receiving a standard dose for at least two weeks, at least three weeks, at least four weeks, at least six weeks, or at least twelve weeks. A "standard" dose is determined by a medical professional, and may depend on the subject's age, weight, healthy history, severity of disease, the frequency of dosing, etc. In some embodiments, a PD-1/PD-L1 inhibitor inadequate responder has experienced, or is experiencing, an inadequate response to an anti-PD-1 antibody and/or an anti-PD-L1 antibody. In some embodiments, a PD-1/PD-L1 inhibitor inadequate responder has experienced, or is experiencing, an inadequate response to AMP-224. In some embodiments, a PD-1/PD-L1 inhibitor inadequate responder has experienced, or is experiencing, an inadequate response to a PD-1/PD-L1 inhibitor selected from nivolumab, pidilizumab, and pembrolizumab.

In any of the above method embodiments, the combination of the FGFR2 inhibitor and the at least one immune stimulating agent, such as a PD-1/PD-L1 inhibitor, may inhibit tumor growth in a mouse tumor model over a period of 1 week, 10 days, or 2 weeks, for example, by at least 10%, at least 20%, at least 30%, at least 40%, at least 50%, at least 60%, at least 70%, at least 80%, at least 90%, or at least 95%. In any of the above method embodiments, administration of the combination of the FGFR2 inhibitor and PD-1/PD-L1 inhibitor to the subject may reduce the volume of at least one tumor in the subject by at least 10° A, at least 20%, at least 30%, at least 40%, at least 50%, at least 60%, at least 70%, at least 80%, at least 90%, or at least 95%, for example, over a period of at least one month, two months, three months, six months, or one year.

FGFR2 Antibodies Increase Numbers of NK Cells, PD-L1 Expressing Cells, Macrophages, and CD3+, CD8+, and CD4+ T Cells and Also Increase the Ratio of Lymphoid to Myeloid Cells in Tumors In any of the above method embodiments, administration of the FGFR2 inhibitor may show an increase in NK cells, such as NKp46+ cells, an increase in PD-L1 expressing cells, an increase in CD3+, CD8+, and/or CD4+ T cells, an increase in macrophages, and/or an increase in the ratio of lymphoid to myeloid cells as compared to a control in tumors taken from a mouse tumor model, such as a xenograft or syngeneic tumor model, over a period of at least 1 day, 4 days, 1 week, 10 days, or 2 weeks, and for example, by at least 10%, at least 20%, at least 30%, at least 40%, at least 50%, at least 60%, at least 70%, at least 80%, at least 90%, or at least 95%. In some embodiments, the mouse tumor model is a 4T1 tumor model.

Data provided in the Examples herein show that treatment of mouse syngeneic tumor models with an afucosylated anti-FGFR2b antibody increases the number of NKp46+ cells in the murine tumor tissue while also inhibiting tumor growth. Similar treatment with an antibody with a mutation at N297 and lacking in ADCC activity (anti-FGFR2-N297Q) did not show an increase in NK cells and did not impact tumor growth. (See Examples 2a-b below.)

Data provided in the Examples herein also show that treatment of mouse syngeneic models with an afucosylated FGFR2 antibody increases the number of PD-L1 positive cells in tumor tissue. (See Example 2a.) This suggests that an FGFR2 inhibitor may combine well with a PD-1/PD-L1 inhibitor for cancer treatment and that the claimed combinations may have at least additive, and in some cases synergistic, effects in combination on tumor volume or tumor growth inhibition. Further data herein show that treatment of mouse syngeneic tumor models with an afucosylated FGFR2 antibody also increases the number of CD3+, CD8+, and CD4+ T cells in tumor tissue and increases the lymphoid to myeloid ratio. No such results were observed with an FGFR2 antibody containing an N297Q mutation designed to prevent effector function. (See Example 2b.) Additional data herein show that treatment of mouse syngeneic tumor models with an afucosylated FGFR2 antibody also increases the number of macrophages in tumor tissue. (See Example 2c.) These data suggest that inhibition of tumor growth observed with the afucosylated anti-FGFR2 antibody is facilitated in part by NK cell-mediated ADCC activity. In addition, the data suggest that this ADCC activity may increase PD-L1 expressing cells in the tumor, which may lead to the infiltration of T cells within the tumor. The increase in lymphoid to myeloid ratio further suggests that an afucosylated FGFR2 antibody may have potent anti-tumor activity as a single agent as well as when used in combination with a PD-1 inhibitor by altering the tumor microenvironment.

Accordingly, also included herein is a method of increasing the number of NK cells, PD-L1 positive cells, macrophages, CD3+, CD8+, and/or CD4+ T cells, and/or the lymphoid to myeloid cell ratio in a tumor tissue of a subject comprising administering to said subject an effective amount of an FGFR2 inhibitor, such as an FGFR2 antibody, such as an FGFR2 antibody with enhanced ADCC activity. In some embodiments where an FGFR2 antibody is administered, the antibody is afucosylated, such as afucosylated at position N297. In some embodiments, the increases may be observed after a period of at least 1 day, 4 days, 1 week, 10 days, or 2 weeks, and may be, for example, an increase of at least 10%, at least 20%, at least 30%, at least 40%, at least 50%, at least 60%, at least 70%, at least 80%, at least 90%, or at least 95% when compared to a control, such as tumor tissue prior to treatment or non-tumor tissue. The FGFR2 inhibitor may be administered, for example, under the dosage conditions described elsewhere herein.

Also included herein is a method of increasing the number of NK cells, PD-L1 positive cells, macrophages, CD3+, CD8+, and/or CD4+ T cells, and/or the lymphoid to myeloid cell ratio in a tumor tissue of a subject comprising administering to said subject an effective amount of an antibody with ADCC activity, such as with enhanced ADCC activity. In some embodiments, the antibody has enhanced ADCC activity due to afucosylation at position N297. In some embodiments, the increases may be observed after a period of at least 1 day, 4 days, 1 week, 10 days, or 2 weeks, and may be, for example, an increase of at least 10%, at least 20%, at least 30%, at least 40%, at least 50%, at least 60%, at least 70%, at least 80%, at least 90%, or at least 95% when compared to a control, such as tumor tissue prior to treatment or non-tumor tissue. In general, such an antibody may be administered in an amount in the range of about 10 µg/kg body weight to about 100 mg/kg body weight per dose. In some embodiments, the antibody may be administered in an amount in the range of about 50 µg/kg body weight to about 5 mg/kg body weight per dose. In some embodiments, the antibody may be administered in an amount in the range of about 100 µg/kg body weight to about 10 mg/kg body weight per dose. In some embodiments, the antibody may be administered in an amount in the range of about 100 µg/kg body weight to about 20 mg/kg body weight per dose. In some embodiments, the antibody may be administered in an amount in the range of about 0.5 mg/kg body weight to about 20 mg/kg body weight per dose. In some embodiments, the antibody may be administered at a dose of 0.1 to 10 mg/kg, such as at a dose of at least 0.1, 0.3, 0.5, 1, 2, 3, 4, 5, or 10 mg/kg, or within a dose range bounded by any two of the preceding numbers.

This application also includes methods of determining the number of NK cells, PD-L1 positive cells, macrophages, CD3+, CD8+, and/or CD4+ T cells, and/or the lymphoid to myeloid cell ratio in tumor tissue of a subject before and/or after administration of an antibody with ADCC activity or enhanced ADCC activity, for example, to determine whether the antibody is having such effects on at least one tumor of a subject. This application also includes methods of determining the number of NK cells, PD-L1 positive cells, CD3+, CD8+, and/or CD4+ T cells, and/or determining the lymphoid to myeloid cell ratio in tumor tissue of a subject before and/or after administration of an FGFR2 inhibitor, either alone or as part of the PD-1/PD-L1 inhibitor combination. Also included herein are methods of determining the number of NK cells, PD-L1 positive cells, CD3+, CD8+, and/or CD4+ T cells, and/or determining the lymphoid to myeloid cell ratio in tumor tissue of a subject receiving a combination of FGFR2 and PD-1/PD-L1 inhibitor treatment.

Determining the number of NK cells, PD-L1 positive cells, macrophages, CD3+, CD8+, and/or CD4+ T cells, and/or determining the lymphoid to myeloid cell ratio may be performed, for instance, via a biopsy of the tissue or some other way of obtaining a sample from the tumor for such texting. Such a biopsy or other sample may generally be taken, for instance, 1, 2, 3, 4, 7, 17, 30. 45, or 90 days following first administration of the antibody with ADCC activity or of the FGFR2 inhibitor. The number of NK cells, PD-L1 positive cells, macrophages, CD3+, CD8+, and/or CD4+ T cells, and/or the lymphoid to myeloid cell ratio may be determined, for example, relative to a control, such as a tumor sample prior to treatment or a sample from non-tumor tissue. In some embodiments, the number may be expressed as a percentage of a particular cell type such as CD45+ single cells. In some embodiments, the number of particular cell types may be determined by FACS analysis.

In some embodiments, if an increase in NK cells, PD-L1 positive cells, macrophages, CD3+, CD8+, and/or CD4+ T cells, and/or in the lymphoid to myeloid cell ratio is observed in such a test relative to the control, the subject may be further administered a PD-1/PD-L1 inhibitor. In some embodiments, if an increase is not observed or if a significant increase is not observed, the dosage of FGFR2 inhibitor or antibody with ADCC activity may be increased.

In some embodiments, such assessment of an increase in NK cells, PD-L1 positive cells, macrophoages, CD3+, CD8+, and/or CD4+ T cells, and/or in the lymphoid to myeloid cell ratio may be used to determine whether to give combination treatment with a PD-1/PD-L1 inhibitor or whether to continue treatment without adding a PD-1/PD-L1 inhibitor. For example, following FGFR2 inhibitor administration, a tumor sample from the subject may be evaluated for the number of NK cells, PD-L1 positive cells, macrophages, CD3+, CD8+, and/or CD4+ T cells, and/or the lymphoid to myeloid cell ratio in comparison to a control, and, if an increase in either or both of those types of cells is observed in the sample, a PD-1/PD-L1 inhibitor may be administered along with the FGFR2 inhibitor according to any of the method embodiments described herein.

Routes of Administration, Carriers, and Additional Pharmaceutical Compositions

In various embodiments, antibodies may be administered in vivo by various routes, including, but not limited to, oral, intra-arterial, parenteral, intranasal, intravenous, intramuscular, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. A nucleic acid molecule encoding an antibody may be coated onto gold microparticles and delivered intradermally by a particle bombardment device, or "gene gun," as described in the literature (see, e.g., Tang et al., *Nature* 356:152-154 (1992)). The appropriate formulation and route of administration may be selected according to the intended application.

In various embodiments, compositions comprising antibodies are provided in formulations with a wide variety of pharmaceutically acceptable carriers (see, e.g., Gennaro, *Remington: The Science and Practice of Pharmacy with Facts and Comparisons: Drugfacts Plus*, $20^{th}$ ed. (2003); Ansel et al., *Pharmaceutical Dosage Forms and Drug Delivery Systems*, $7^{th}$ ed., Lippencott Williams and Wilkins (2004); Kibbe et al., *Handbook of Pharmaceutical Excipients*, $3^{rd}$ ed., Pharmaceutical Press (2000)). Various pharmaceutically acceptable carriers, which include vehicles, adjuvants, and diluents, are available. Moreover, various pharmaceutically acceptable auxiliary substances, such as pH adjusting and buffering agents, tonicity adjusting agents, stabilizers, wetting agents and the like, are also available. Non-limiting exemplary carriers include saline, buffered saline, dextrose, water, glycerol, ethanol, and combinations thereof.

In various embodiments, compositions comprising antibodies may be formulated for injection, including subcutaneous administration, by dissolving, suspending, or emulsifying them in an aqueous or nonaqueous solvent, such as vegetable or other oils, synthetic aliphatic acid glycerides, esters of higher aliphatic acids, or propylene glycol; and if desired, with conventional additives such as solubilizers, isotonic agents, suspending agents, emulsifying agents, stabilizers and preservatives. In various embodiments, the compositions may be formulated for inhalation, for example, using pressurized acceptable propellants such as dichlorodifluoromethane, propane, nitrogen, and the like. The compositions may also be formulated, in various embodiments, into sustained release microcapsules, such as with biodegradable or non-biodegradable polymers. A non-limiting exemplary biodegradable formulation includes poly lactic acid-glycolic acid polymer. A non-limiting exemplary non-biodegradable formulation includes a polyglycerin fatty acid ester. Certain methods of making such formulations are described, for example, in EP 1 125 584 A1.

Pharmaceutical packs and kits comprising one or more containers, each containing one or more doses of an antibody or combination of antibodies are also provided. In some embodiments, a unit dosage is provided wherein the unit dosage contains a predetermined amount of a composition comprising an antibody or combination of antibodies, with or without one or more additional agents. In some embodiments, such a unit dosage is supplied in single-use prefilled syringe for injection. In various embodiments, the composition contained in the unit dosage may comprise saline, sucrose, or the like; a buffer, such as phosphate, or the like; and/or be formulated within a stable and effective pH range. Alternatively, in some embodiments, the composition may be provided as a lyophilized powder that may be reconstituted upon addition of an appropriate liquid, for example, sterile water. In some embodiments, the composition comprises one or more substances that inhibit protein aggregation, including, but not limited to, sucrose and arginine. In some embodiments, a composition of the invention comprises heparin and/or a proteoglycan.

Pharmaceutical compositions are administered in an amount effective for treatment or prophylaxis of the specific indication. The therapeutically effective amount is typically dependent on the weight of the subject being treated, his or her physical or health condition, the extensiveness of the condition to be treated, or the age of the subject being treated. In general, antibodies may be administered in an amount in the range of about 10 µg/kg body weight to about 100 mg/kg body weight per dose. In some embodiments, antibodies may be administered in an amount in the range of about 50 µg/kg body weight to about 5 mg/kg body weight per dose. In some embodiments, antibodies may be administered in an amount in the range of about 100 µg/kg body weight to about 10 mg/kg body weight per dose. In some embodiments, antibodies may be administered in an amount in the range of about 100 µg/kg body weight to about 20 mg/kg body weight per dose. In some embodiments, antibodies may be administered in an amount in the range of about 0.5 mg/kg body weight to about 20 mg/kg body weight per dose.

In some embodiments, a PD-1/PD-L1 inhibitor, such as an antibody or fusion molecule or polypeptide, is administered at a dose of 0.1 to 100 mg/kg, such as at a dose of 0.1, 0.3, 0.5, 1, 2, 3, 4, 5, 10, 15, 20, 25, or 30 mg/kg, or within a dose range bounded by any two of the preceding numbers. In some embodiments, an FGFR2 inhibitor, such as an antibody or fusion molecule or ECD polypeptide, is administered at a dose of 0.1, 0.3, 0.5, 1, 2, 3, 4, 5, or 10 mg/kg, such as within a dose range bounded by any two of the preceding numbers.

The antibody compositions may be administered as needed to subjects. Determination of the frequency of administration may be made by persons skilled in the art, such as an attending physician based on considerations of the condition being treated, age of the subject being treated, severity of the condition being treated, general state of health of the subject being treated and the like. In some embodiments, an effective dose of an antibody is administered to a subject one or more times. In various embodiments, an effective dose of an antibody is administered to the subject once a month, less than once a month, such as, for example, every two months or every three months. In other embodiments, an effective dose of an antibody is administered more than once a month, such as, for example, every three weeks, every two weeks or every week. In some embodiments, an effective dose of an antibody is administered once per 1, 2, 3, 4, or 5 weeks. In some embodiments, an effective dose of an antibody is administered twice or three times per week. An effective dose of an antibody is administered to the subject at least once. In some embodiments, the effective dose of an antibody may be administered multiple times, including for periods of at least a month, at least six months, or at least a year.

Compositions comprising an FGFR2 inhibitor as described herein and a PD-1/PD-L1 inhibitor as described herein are also provided. In some embodiments, the FGFR2 inhibitor and the PD-1/PD-L1 inhibitor are comprised within separate containers or within separate compartments of a single container, for example, such that they are not mixed together. In some embodiments, the FGFR2 inhibitor and the PD-1/PD-L1 inhibitor may be present in the same container or compartment, and thus mixed together. In some embodiments, the compositions comprise instructions for use, such as instructions for use in cancer treatment.

Combinations with Other Immune Stimulating Agents

In some embodiments, the FGFR2 inhibitor is combined with at least one immune stimulating agent other than a PD-1/PD-L1 inhibitor. Alternatively, in some embodiments, the combination of the FGFR2 inhibitor and the PD-1/PD-L1 inhibitor may be further combined with an effective amount of at least one additional immune stimulating agent.

Immune stimulating agents may include, for example, a small molecule drug or a biologic. Examples of biologic immune stimulating agents include, but are not limited to, antibodies, antibody fragments, fragments of receptor or ligand polypeptides, for example that block receptor-ligand binding, vaccines and cytokines.

In some embodiments, the at least one immune stimulating agent comprises an agonist of an immune stimulatory molecule, including a co-stimulatory molecule, while in some embodiments, the at least one immune stimulating agent comprises an antagonist of an immune inhibitory molecule, including a co-inhibitory molecule. In some embodiments, the at least one immune stimulating agent comprises an agonist of an immune-stimulatory molecule, including a co-stimulatory molecule, found on immune cells, such as T cells. In some embodiments, the at least one immune stimulating agent comprises an antagonist of an immune inhibitory molecule, including a co-inhibitory molecule, found on immune cells, such as T cells. In some embodiments, the at least one immune stimulating agent comprises an agonist of an immune stimulatory molecule, including a co-stimulatory molecule, found on cells involved in innate immunity, such as NK cells. In some embodiments, the at least one immune stimulating agent comprises an antagonist of an immune inhibitory molecule, including a co-inhibitory molecule, found on cells involved in innate immunity, such as NK cells. In some embodiments, the combination enhances the antigen-specific T cell response in the treated subject and/or enhances the innate immunity response in the subject.

In some embodiments, a combination of FGFR2 inhibitor and at least one immune stimulating agent results in an improved anti-tumor response in an animal cancer model, such as a mouse xenograft and/or syngeneic tumor model, compared to administration of the FGFR2 inhibitor alone. In some embodiments, the combination the FGFR2 inhibitor with at least one immune stimulating agent results in an additive or synergistic response in an animal cancer model, such as a mouse xenograft and/or syngeneic tumor model, compared to administration of either drug alone.

In embodiments involving a combination of FGFR2 inhibitor, PD-1/PD-L1 inhibitor, and at least one additional immune stimulating agent, the combination results in an improved anti-tumor response in an animal cancer model, such as a mouse xenograft and/or syngeneic tumor model, compared to administration of the FGFR2 inhibitor alone. In some embodiments, the combination the FGFR2 inhibitor the additional therapeutics results in an additive or synergistic response in an animal cancer model, such as a mouse xenograft and/or syngeneic tumor model, compared to administration of the individual therapeutics alone.

In certain embodiments, an immune stimulating agent targets a stimulatory or inhibitory molecule that is a member of the immunoglobulin super family (IgSF). For example, an immune stimulating agent may be an agent that targets (or binds specifically to) another member of the B7 family of polypeptides. An immune stimulating agent may be an agent that targets a member of the TNF family of membrane bound ligands or a co-stimulatory or co-inhibitory receptor binding specifically to a member of the TNF family. Exemplary TNF and TNFR family members that may be targeted by immune stimulating agents include CD40 and CD40L, OX-40, OX-40L, GITR, GITRL, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY and NGFR.

In some embodiments, an immune stimulating agent may comprise (i) an antagonist of a protein that inhibits T cell activation (e g, immune checkpoint inhibitor) such as CTLA4, LAG-3, TIM3, Galectin 9, CEACAM-1, BTLA, CD69, Galectin-1, TIGIT, CD113, GPR56, VISTA, B7-H3, B7-H4, 2B4, CD48, GARP, PD1H, LAIR1, TIM-1, TIM-4, and ILT4 and/or may comprise (ii) an agonist of a protein that stimulates T cell activation such as B7-2, CD28, 4-1BB (CD137), 4-1BBL, ICOS, ICOS-L, OX40, OX40L, GITR, GITRL, CD70, CD27, CD40, CD40L, DR3 and CD28H.

In some embodiments, an immune stimulating agent may comprise an agent that inhibits or is an antagonist of a cytokine that inhibits T cell activation (e.g., IL-6, IL-10, TGF-β, VEGF, and other immunosuppressive cytokines), and it some embodiments an immune stimulating agent may comprise an agent that is an agonist of a cytokine, such as IL-2, IL-7, IL-12, IL-15, IL-21 and IFNα (e.g., the cytokine itself) that stimulates T cell activation. In some embodiments, immune stimulating agents may comprise an antagonist of a chemokine, such as CXCR2 (e.g., MK-7123), CXCR4 (e.g. AMD3100), CCR2, or CCR4 (mogamulizumab).

In some embodiments, immune stimulating agents may include antagonists of inhibitory receptors on NK cells or agonists of activating receptors on NK cells. In some embodiments, the at least one immune stimulating agent is an antagonist of KIR.

Immune stimulating agents may also include agents that inhibit TGF-β signaling, agents that enhance tumor antigen presentation, e.g., dendritic cell vaccines, GM-CSF secreting cellular vaccines, CpG oligonucleotides, and imiquimod, or therapies that enhance the immunogenicity of tumor cells (e.g., anthracyclines).

Immune stimulating agents may also include certain vaccines such as mesothelin-targeting vaccines or attenuated listeria cancer vaccines, such as CRS-207.

Immune stimulating agents may also comprise agents that deplete or block Treg cells, such as agents that specifically bind to CD25.

Immune stimulating agents may also comprise agents that inhibit a metabolic enzyme such as indoleamine dioxigenase (IDO), dioxigenase, arginase, or nitric oxide synthetase.

Immune stimulating agents may also comprise agents that inhibit the formation of adenosine or inhibit the adenosine A2A receptor.

Immune stimulating agents may also comprise agents that reverse/prevent T cell energy or exhaustion and agents that trigger an innate immune activation and/or inflammation at a tumor site.

In some embodiments, immune stimulating agents may comprise a CD40 agonist such as a CD40 agonist antibody. The FGFR2 inhibitor and the PD-1/PD-L1 inhibitor combination can also be further combined in a combinatorial approach that targets multiple elements of the immune pathway, such as one or more of the following: at least one agent that enhances tumor antigen presentation (e.g., dendritic cell vaccine, GM-CSF secreting cellular vaccines, CpG oligonucleotides, imiquimod); at least one agent that inhibits negative immune regulation e.g., by inhibiting CTLA4 pathway and/or depleting or blocking Treg or other immune suppressing cells; a therapy that stimulates positive immune regulation, e.g., with agonists that stimulate the CD-137, OX-40 and/or GITR pathway and/or stimulate T cell effector function; at least one agent that increases systemically the frequency of anti-tumor T cells; a therapy that depletes or inhibits Tregs, such as Tregs in the tumor, e.g., using an antagonist of CD25 (e.g., daclizumab) or by ex vivo anti-CD25 bead depletion; at least one agent that impacts the function of suppressor myeloid cells in the tumor; a therapy that enhances immunogenicity of tumor cells (e.g., anthracyclines); adoptive T cell or NK cell transfer including genetically modified cells, e.g., cells modified by chimeric antigen receptors (CAR-T therapy); at least one agent that inhibits a metabolic enzyme such as indoleamine dioxigenase (IDO), dioxigenase, arginase or nitric oxide synthetase; at least one agent that reverses/ prevents T cell energy or exhaustion; a therapy that triggers an innate immune activation and/or inflammation at a tumor site; administration of immune stimulatory cytokines or blocking of immuno repressive cytokines.

For example, the at least one immune stimulating agent may comprise one or more agonistic agents that ligate positive costimulatory receptors; one or more antagonists (blocking agents) that attenuate signaling through inhibitory receptors, such as antagonists that overcome distinct immune suppressive pathways within the tumor microenvironment; one or more agents that increase systemically the frequency of anti-tumor immune cells, such as T cells, deplete or inhibit Tregs (e.g., by inhibiting CD25); one or more agents that inhibit metabolic enzymes such as IDO; one or more agents that reverse/prevent T cell energy or exhaustion; and one or more agents that trigger innate immune activation and/or inflammation at tumor sites.

In one embodiment, the at least one immune stimulating agent comprises a CTLA4 antagonist, such as an antagonistic CTLA4 antibody. Suitable CTLA4 antibodies include, for example, YERVOY (ipilimumab) or tremelimumab.

In some embodiments, the at least one immune stimulating agent comprises a LAG-3 antagonist, such as an antagonistic LAG-3 antibody. Suitable LAG-3 antibodies include, for example, BMS-986016 (WO10/19570, WO14/08218), or IMP-731 or IMP-321 (WO08/132601, WO09/44273).

In some embodiments, the at least one immune stimulating agent comprises a CD137 (4-1BB) agonist, such as an agonistic CD137 antibody. Suitable CD137 antibodies include, for example, urelumab or PF-05082566 (WO12/32433).

In some embodiments, the at least one immune stimulating agent comprises a GITR agonist, such as an agonistic GITR antibody. Suitable GITR antibodies include, for example, TRX-518 (WO06/105021, WO09/009116), MK-4166 (WO11/028683) or a GITR antibody disclosed in WO2015/031667.

In some embodiments, the at least one immune stimulating agent comprises an OX40 agonist, such as an agonistic OX40 antibody. Suitable OX40 antibodies include, for example, MEDI-6383, MEDI-6469 or MOXR0916 (RG7888; WO06/029879).

In some embodiments, the at least one immune stimulating agent comprises a CD27 agonist, such as an agonistic CD27 antibody. Suitable CD27 antibodies include, for example, varlilumab (CDX-1127).

In some embodiments, the at least one immune stimulating agent comprises MGA271, which targets B7H3 (WO11/109400).

In some embodiments, the at least one immune stimulating agent comprises a MR antagonist, such as lirilumab.

In some embodiments, the at least one immune stimulating agent comprises an IDO antagonist. IDO antagonists include, for example, INCB-024360 (WO2006/122150, WO07/75598, WO08/36653, WO08/36642), indoximod, NLG-919 (WO09/73620, WO09/1156652, WO11/56652, WO12/142237) or F001287.

In some embodiments, the at least one immune stimulating agent comprises a Toll-like receptor agonist, e.g., a TLR2/4 agonist (e.g., *Bacillus* Calmette-Guerin); a TLR7 agonist (e.g., Hiltonol or Imiquimod); a TLR7/8 agonist (e.g., Resiquimod); or a TLR9 agonist (e.g., CpG7909).

In some embodiments, the at least one immune stimulating agent comprises a TGF-β inhibitor, e.g., GC1008, LY2157299, TEW7197 or IMC-TR1.

Further Combination Therapy

Inhibitors may be administered alone or with other modes of treatment. They may be provided before, substantially contemporaneous with, or after other modes of treatment, for example, surgery, chemotherapy, radiation therapy, or the administration of a biologic, such as another therapeutic antibody. In some embodiments, the cancer has recurred or progressed following a therapy selected from surgery, chemotherapy, and radiation therapy, or a combination thereof.

For treatment of cancer, the inhibitors may be administered in conjunction with one or more additional anti-cancer agents, such as the chemotherapeutic agent, growth inhibitory agent, anti-angiogenesis agent and/or anti-neoplastic composition. Nonlimiting examples of chemotherapeutic agent, growth inhibitory agent, anti-angiogenesis agent, anti-cancer agent and anti-neoplastic composition that can be used in combination with the antibodies of the present invention are provided in the following definitions.

A "chemotherapeutic agent" is a chemical compound useful in the treatment of cancer. Examples of chemotherapeutic agents include, but are not limited to, alkylating agents such as thiotepa and Cytoxan® cyclosphosphamide; alkyl sulfonates such as busulfan, improsulfan and piposulfan; aziridines such as benzodopa, carboquone, meturedopa, and uredopa; ethylenimines and me thylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, *Chem Intl. Ed. Engl.,* 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, Adriamycin® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., Taxol® paclitaxel (Bristol-Myers Squibb Oncology, Princeton, N.J.), Abraxane® Cremophor-free, albumin-engineered nanoparticle formulation of paclitaxel (American Pharmaceutical Partners, Schaumberg, Ill.), and Taxotere® doxetaxel (Rhône-Poulenc Rorer, Antony, France); chloranbucil; Gemzar® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; Navelbine® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluorometlhylornithine (DMFO); retinoids such as retinoic acid; capecitabine; combretastatin; leucovorin (LV); oxaliplatin, including the oxaliplatin treatment regimen (FOLFOX); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

Further nonlimiting exemplary chemotherapeutic agents include anti-hormonal agents that act to regulate or inhibit hormone action on cancers such as anti-estrogens and selective estrogen receptor modulators (SERMs), including, for example, tamoxifen (including Nolvadex® tamoxifen), raloxifene, droloxifene, 4-hydroxytamoxifen, trioxifene, keoxifene, LY117018, onapristone, and Fareston® toremifene; aromatase inhibitors that inhibit the enzyme aromatase, which regulates estrogen production in the adrenal glands, such as, for example, 4(5)-imidazoles, aminoglutethimide, Megase® megestrol acetate, Aromasin® exemestane, formestanie, fadrozole, Rivisor® vorozole, Femara® letrozole, and Arimidex® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., Angiozyme® ribozyme) and a HER2 expression inhibitor; vaccines such as gene therapy vaccines, for example, Allovectin® vaccine, Leuvectin® vaccine, and Vaxid® vaccine; Proleukin® rIL-2; Lurtotecan® topoisomerase 1 inhibitor; Abarelix® rmRH; and pharmaceutically acceptable salts, acids or derivatives of any of the above.

An "anti-angiogenesis agent" or "angiogenesis inhibitor" refers to a small molecular weight substance, a polynucleotide (including, e.g., an inhibitory RNA (RNAi or siRNA)), a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenesis agent includes those agents that bind and block the angiogenic activity of the angiogenic factor or its receptor. For example, an anti-angiogenesis agent is an antibody or other antagonist to an angiogenic agent, e.g., antibodies to VEGF-A (e.g., bevacizumab (Avastin®)) or to the VEGF-A receptor (e.g., KDR receptor or Flt-1 receptor), anti-PDGFR inhibitors such as Gleevec® (Imatinib Mesylate), small molecules that block VEGF receptor signaling (e.g., PTK787/ZK2284, SU6668, Sutent®/SU11248 (sunitinib malate), AMG706, or those described in, e.g., international patent application WO 2004/113304). Anti-angiogensis agents also include native angiogenesis inhibitors, e.g., angiostatin, endostatin, etc. See, e.g., Klagsbrun and D'Amore (1991) *Annu. Rev. Physiol.* 53:217-39; Streit and Detmar (2003) *Oncogene* 22:3172-3179 (e.g., Table 3 listing anti-angiogenic therapy in malignant melanoma); Ferrara & Alitalo (1999) *Nature Medicine* 5(12): 1359-1364; Tonini et al. (2003) *Oncogene* 22:6549-6556 (e.g., Table 2 listing known anti-angiogenic factors); and, Sato (2003) *Int. J. Clin. Oncol.* 8:200-206 (e.g., Table 1 listing anti-angiogenic agents used in clinical trials).

A "growth inhibitory agent" as used herein refers to a compound or composition that inhibits growth of a cell (such as a cell expressing VEGF) either in vitro or in vivo. Thus, the growth inhibitory agent may be one that significantly reduces the percentage of cells (such as a cell expressing VEGF) in S phase. Examples of growth inhibitory agents include, but are not limited to, agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., *The Molecular Basis of Cancer*, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (Taxotere®, Rhone-Poulenc Rorer), derived from the European yew, is a semisynthetic analogue of paclitaxel (Taxol®, Bristol-Myers Squibb). Paclitaxel and docetaxel promote the assembly of microtubules from tubulin dimers and stabilize microtubules by preventing depolymerization, which results in the inhibition of mitosis in cells.

The term "anti-neoplastic composition" refers to a composition useful in treating cancer comprising at least one active therapeutic agent. Examples of therapeutic agents include, but are not limited to, e.g., chemotherapeutic agents, growth inhibitory agents, cytotoxic agents, agents used in radiation therapy, anti-angiogenesis agents, other cancer immunotherapeutic agents aside from PD-1/PD-L1 inhibitors, apoptotic agents, anti-tubulin agents, and other-agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (Tarceva®), platelet derived growth factor inhibitors (e.g., Gleevec® (Imatinib Mesylate)), a COX-2 inhibitor (e.g., celecoxib), interferons, CTLA-4 inhibitors (e.g., anti-CTLA antibody ipilimumab (YERVOY®)), PD-L2 inhibitors (e.g., anti-PD-L2 antibodies), TIM3 inhibitors (e.g., anti-TIM3 antibodies), cytokines, antagonists (e.g., neutralizing antibodies) that bind to one or more of the following targets ErbB2, ErbB3, ErbB4, PDGFR-beta, BlyS, APRIL, BCMA, PD-L2, CTLA-4, TIM3, or VEGF receptor(s), TRAIL/Apo2, and other bioactive and organic chemical agents, etc. Combinations thereof are also included in the invention.

SPECIFIC EMBODIMENTS

Certain specific embodiments of this disclosure include the following:

1. A method of treating cancer in a subject comprising administering to the subject a fibroblast growth factor receptor 2 (FGFR2) inhibitor and at least one immune stimulating agent, such as at least one programmed cell death 1 (PD-1)/programmed cell death ligand 1 (PD-L1) inhibitor.

2. The method of embodiment 1, wherein the at least one immune stimulating agent is a PD-1/PD-L1 inhibitor and wherein the PD-1/PD-L1 inhibitor is an antibody.

3. The method of embodiment 2, wherein the PD-1/PD-L1 inhibitor is an anti-PD-1 antibody.

4. The method of embodiment 3, wherein the anti-PD-1 antibody comprises the heavy chain and light chain CDRs of an antibody selected from nivolumab, pidilizumab, and pembrolizumab.

5. The method of embodiment 4, wherein the anti-PD-1 antibody comprises the heavy chain and light chain variable regions of an antibody selected from nivolumab, pidilizumab, and pembrolizumab.

6. The method of embodiment 5, wherein the anti-PD-1 antibody is selected from nivolumab, pidilizumab, and pembrolizumab.

7. The method of embodiment 2, wherein the PD-1/PD-L1 inhibitor is an anti-PD-L1 antibody.

8. The method of embodiment 7, wherein the anti-PD-L1 antibody comprises the heavy chain and light chain CDRs of an antibody selected from BMS-936559, MPDL3280A, MEDI4736, and MSB0010718C.

9. The method of embodiment 8, wherein the anti-PD-L1 antibody comprises the heavy chain and light chain variable regions of an antibody selected from BMS-936559, MPDL3280A, MEDI4736, and MSB0010718C.

10. The method of embodiment 9, wherein the anti-PD-L1 antibody is selected from BMS-936559, MPDL3280A, MEDI4736, and MSB0010718C.

11. The method of embodiment 1, wherein the at least one immune stimulating agent is a PD-1/PD-L1 inhibitor and wherein the PD-1/PD-L1 inhibitor is a PD-1 fusion molecule.

12. The method of embodiment 11, wherein the fusion molecule is AMP-224.

13. The method of embodiment 1, wherein the at least one immune stimulating agent is a PD-1/PD-L1 inhibitor and wherein the PD-1/PD-L1 inhibitor is a PD-1 polypeptide such as AUR-012.

14. The method of any one of embodiments 1 to 13, wherein the FGFR2 inhibitor is an FGFR2 antibody.

15. The method of embodiment 14, wherein the FGFR2 antibody is an FGFR2-IIIb antibody.

16. The method of embodiment 15, wherein the FGFR2-IIIb antibody has one or more of the following properties:
　a. binds to FGFR2-IIIb with higher affinity than to FGFR2-IIIc or does not detectably bind to FGFR2-IIIc;
　b. inhibits binding of FGF2 to human FGFR2;
　c. inhibits binding of FGF7 to human FGFR2;
　d. inhibits growth of a human tumor in a mouse tumor model;
　e. induces an ADCC activity;
　f. possesses enhanced ADCC activity;
　g. is afucosylated; and
　h. is capable of increasing the number of one or more of PD-L1 positive cells, NK cells, CD3+ T cells, CD4+ T cells, CD8+ T cells, and macrophages in tumor tissue in a mouse tumor model compared to a control.

17. The method of embodiment 15 or embodiment 16, wherein the FGFR2 antibody comprises heavy chain and light chain variable regions, wherein the heavy chain variable region comprises:
　(i) HVR-H1 comprising the amino acid sequence of SEQ ID NO: 6;
　(ii) HVR-H2 comprising the amino acid sequence of SEQ ID NO: 7; and
　(iii) HVR-H3 comprising the amino acid sequence of SEQ ID NO: 8; and the light chain variable region comprises:
　(iv) HVR-L1 comprising the amino acid sequence of SEQ ID NO: 9;
　(v) HVR-L2 comprising the amino acid sequence of SEQ ID NO: 10; and
　(vi) HVR-L3 comprising the amino acid sequence of SEQ ID NO: 11.

18. The method of embodiment 17, wherein the heavy chain variable region of the FGFR2 antibody comprises an amino acid sequence at least 95% identical to the amino acid sequence of SEQ ID NO: 4.

19. The method of embodiment 17 or 18, wherein the light chain variable region of the FGFR2 antibody comprises an amino acid sequence at least 95% identical to the amino acid sequence of SEQ ID NO: 5.

20. The method of any one of embodiments 17 to 19, wherein the heavy chain variable region of the FGFR2 antibody comprises the amino acid sequence of SEQ ID NO: 4.

21. The method of any one of embodiments 17 to 20, wherein the light chain variable region of the FGFR2 antibody comprises the amino acid sequence of SEQ ID NO: 5.

22. The method of embodiment 17, wherein the heavy chain of the FGFR2 antibody comprises an amino acid sequence at least 95% identical to the amino acid sequence of SEQ ID NO: 2.

23. The method of embodiment 17 or 22, wherein the light chain of the FGFR2 antibody comprises an amino acid sequence at least 95% identical to the amino acid sequence of SEQ ID NO: 3.

24. The method of any one of embodiments 17, 22 or 23, wherein the heavy chain of the FGFR2 antibody comprises the amino acid sequence of SEQ ID NO: 2.

25. The method of any one of embodiments 17 or 22 to 24, wherein the light chain of the FGFR2 antibody comprises the amino acid sequence of SEQ ID NO: 3.

26. The method of any one of embodiments 15 to 25, wherein the FGFR2 antibody is chimeric, humanized, or human.

27. The method of any one of embodiments 15 to 26, wherein the FGFR2 antibody is selected from a Fab, an Fv, an scFv, a Fab', and a (Fab')$_2$.

28. The method of any one of embodiments 17 to 27, wherein the FGFR2 antibody has one or more of the following properties:
　a. lacks a fucose at position Asn297;
　b. comprises a κ light chain constant region;
　c. comprises an IgG1 heavy chain constant region;
　d. has enhanced ADCC activity in vitro compared to an antibody having the same amino acid sequence that is fucosylated at position Asn297;
　e. has enhanced affinity for Fc gamma RIIIA compared to an antibody having the same amino acid sequence that is fucosylated at position Asn297; and
　f. is capable of increasing the number of one or more of PD-L1 positive cells, NK cells, CD3+ T cells, CD4+ T cells, CD8+ T cells, and macrophages in tumor tissue in a mouse tumor model compared to a control.

29. The method of any one of embodiments 1 to 13, wherein the FGFR2 inhibitor is an FGFR2 extracellular domain (ECD) or FGFR2 ECD fusion molecule.

30. The method of embodiment 29, wherein the FGFR2 inhibitor is an FGFR2 ECD fusion molecule comprising an FGFR2 ECD and at least one fusion partner selected from an Fc domain, albumin, and polyethylene glycol.

31. The method of embodiment 30, wherein the FGFR2 ECD or FGFR2 ECD fusion molecule comprises the amino acid sequence of any one of SEQ ID NOs: 13-33 or 29-33.

32. The method of any one of embodiments 1 to 31, wherein the FGFR2 inhibitor and the immune stimulating agent are administered concurrently or sequentially.

33. The method of embodiment 32, wherein one or more doses of the immune stimulating agent are administered prior to administering an FGFR2 inhibitor.

34. The method of embodiment 33, wherein the subject received a complete course of immune stimulating agent therapy prior to administration of the FGFR2 inhibitor.

35. The method of embodiment 34, wherein the FGFR2 inhibitor is administered during a second course of immune stimulating agent therapy.

36. The method of any one of embodiments 33 to 35, wherein the subject received at least one, at least two, at least three, or at least four doses of the at least one immune stimulating agent prior to administration of FGFR2 inhibitor.

37. The method of any one of embodiments 33 to 36, wherein at least one dose of the at least one immune stimulating agent is administered concurrently with the FGFR2 inhibitor.

38. The method of embodiment 32, wherein one or more doses of the FGFR2 inhibitor are administered prior to administering an immune stimulating agent.

39. The method of embodiment 38, wherein the subject received at least two, at least three, at least three, or at least four doses of the FGFR2 inhibitor prior to administration of the at least one immune stimulating agent.

40. The method of embodiment 38 or embodiment 39, wherein at least one dose of the FGFR2 inhibitor is administered concurrently with an immune stimulating agent.

41. The method any one of embodiments 1 to 40, wherein the FGFR2 inhibitor is administered at a dose of at least 0.1, 0.3, 0.5, 1, 2, 3, 4, 5, 6, 10, 15, 20, 25, or 30 mg/kg, or at a range bounded by any two of those mg/kg doses such as 6-10 mg/kg, 10-15, mg/kg, or 6-15 mg/kg.

42. The method of any one of embodiments 32-41 wherein the at least one immune stimulating agent comprises a PD-1/PD-L1 inhibitor.

43. The method of embodiment 42, wherein the PD-1/PD-L1 inhibitor is administered at a dose of at least 0.1, 0.3, 0.5, 1, 2, 3, 4, 5, or 10 mg/kg.

44. The method of any one of embodiments 1 to 43, wherein the FGFR2 inhibitor and the immune stimulating agent are administered once per 1, 2, 3, 4, or 5 weeks.

45. The method of any one of embodiments 1 to 44, wherein the cancer is selected from breast cancer, gastric cancer, non-small cell lung cancer, melanoma, squamous cell carcinoma of the head and neck, ovarian cancer, pancreatic cancer, renal cell carcinoma, hepatocellular carcinoma, bladder cancer, cholangiocarcinoma, esophageal cancer, and endometrial cancer.

46. The method of any one of embodiments 1 to 45, wherein the cancer is recurrent or progressive after a therapy selected from surgery, chemotherapy, radiation therapy, or a combination thereof.

47. The method of any one of embodiments 1 to 46, wherein (a) the cancer has previously been determined to overexpress FGFR2IIIb, either in the presence or in the absence of FGFR2 gene amplification, or (b) the method comprises a further step of determining whether the cancer overexpresses FGFR2IIIb and optionally also comprises a further step of determining whether the FGFR2 gene is amplified in tumor cells.

48. The method of embodiment 47, wherein FGFR2IIIb overexpression is determined by immunohistochemistry (IHC).

49. The method of embodiment 48, wherein the overexpression is determined by an IHC signal of 1+, 2+, or 3+ in at least 10% of tumor cells, such as in at least 20%, 30%, 40%, or 50% of tumor cells.

50. The method of any one of embodiments 47-49, wherein the FGFR2 gene amplification is determined by obtaining the ratio of FGFR2 to chromosome 10 centromere (CEN10) using fluorescence in situ hybridization (FISH), wherein the FGFR2 gene is considered amplified if the FGFR2/CEN10 ratio determined by FISH is greater than or equal to 2.

51. The method of any one of embodiments 47 to 50, wherein the cancer is gastric cancer or bladder cancer.

52. The method of any one of embodiments 48-50, wherein:
a) the cancer is gastric cancer, the cancer has an IHC signal of 3+ in at least 10% of tumor cells;
b) the cancer is gastric cancer, the cancer has an IHC signal of 3+ in at least 10% of tumor cells, and wherein the FGFR2 gene is amplified;
c) the cancer is gastric cancer, the cancer has an IHC signal of 3+ in at least 10% of tumor cells, and wherein the FGFR2 gene is not amplified;
d) the cancer is gastric cancer, and the cancer has an IHC signal of 1+ or 2+ in at least 10% of tumor cells;
e) the cancer is bladder cancer, and the cancer has an IHC signal of 1+ in at least 10% of tumor cells;
f) the cancer is bladder cancer, and the cancer has an IHC signal of 2+ in at least 10% of tumor cells;
g) the cancer is bladder cancer, and the cancer has an H score of 20 or greater;
h) the cancer is bladder cancer, and the cancer has an H score of 10-19; or
i) the cancer is bladder cancer, and the cancer has an H score of <10.

53. The method of any one of embodiments 1 to 52, wherein the subject is a PD-1/PD-L1 inhibitor inadequate responder.

54. The method of any one of embodiments 1 to 53, wherein administration of the FGFR2 inhibitor and a PD-1/PD-L1 inhibitor in a mouse tumor model of the cancer results in either additive or synergistic inhibition of tumor growth.

55. The method of embodiment 54, wherein the cancer is breast cancer and the mouse tumor model comprises 4T1 cells.

56. The method of any one of embodiments 1-55, wherein administration of the FGFR2 inhibitor in a mouse tumor model increases the number of NK cells in tumor tissue compared to a control.

57. The method of any one of embodiments 1-56, wherein administration of the FGFR2 inhibitor in a mouse tumor model increases the number of PD-L1 positive cells in tumor tissue compared to a control.

58. The method of any one of embodiments 1-57, wherein administration of the FGFR2 inhibitor in a mouse tumor model increases the number of CD3+, CD8+, and/or CD4+ T cells in tumor tissue compared to a control.

59. The method of any one of embodiments 1-58, wherein administration of the FGFR2 inhibitor in a mouse tumor model increases the ratio of lymphoid cells to myeloid cells in tumor tissue compared to a control.

60. A composition comprising an FGFR2 inhibitor as described in any one of embodiments 14 to 31 and at least one immune stimulating agent as described in any one of embodiments 2 to 13, such as at least one PD-1/PD-L1 inhibitor.

61. The composition of embodiment 60, wherein the FGFR2 inhibitor and the at least one immune stimulating agent are comprised within separate containers or compartments.

62. The composition of embodiment 60 or 61, further comprising instructions for use in cancer treatment.

63. The composition of any one of embodiments 60 to 62 for use in cancer treatment.

64. The composition of embodiment 63, wherein the cancer is selected from breast cancer, gastric cancer, non-small cell lung cancer, melanoma, squamous cell carcinoma of the head and neck, ovarian cancer, pancreatic cancer, renal cell carcinoma, hepatocellular carcinoma, bladder cancer, cholangiocarcinoma, esophageal cancer, and endometrial cancer.

65. The composition of any one of embodiments 63 to 64, wherein the cancer overexpresses FGFR2IIIb either in the presence or in the absence of FGFR2 gene amplification.

66. The composition of embodiment 65, wherein FGFR2IIIb overexpression is determined by immunohistochemistry (IHC).

67. The composition of embodiment 66, wherein the overexpression is determined by an IHC signal of 1+, 2+, or 3+ in at least 10% of tumor cells, such as in at least 20%, 30%, 40%, or 50% of tumor cells.

68. The composition of any one of embodiments 63-67, wherein cancer has an FGFR2/CEN10 ratio determined by FISH of greater than or equal to 2.

69. The composition of any one of embodiments 63 to 68, wherein the cancer is gastric cancer or bladder cancer.

70. The composition of any one of embodiments 63 to 69, wherein:
a) the cancer is gastric cancer, and the cancer has an IHC signal of 3+ in at least 10% of tumor cells;
b) the cancer is gastric cancer, the cancer has an IHC signal of 3+ in at least 10% of tumor cells, and wherein the FGFR2 gene is amplified;
c) the cancer is gastric cancer, the cancer has an IHC signal of 3+ in at least 10% of tumor cells, and wherein the FGFR2 gene is not amplified;
d) the cancer is gastric cancer, and the cancer has an IHC signal of 1+ or 2+ in at least 10% of tumor cells;
e) the cancer is bladder cancer, and the cancer has an IHC signal of 1+ in at least 10% of tumor cells;
f) the cancer is bladder cancer, and the cancer has an IHC signal of 2+ in at least 10% of tumor cells;
g) the cancer is bladder cancer, and the cancer has an H score of 20 or greater;
h) the cancer is bladder cancer, and the cancer has an H score of 10-19; or
i) the cancer is bladder cancer, and the cancer has an H score of <10.

71. A method of increasing the number of NK cells and/or PD-L1 positive cells in a tumor tissue of a subject with cancer comprising administering to said subject an effective amount of an FGFR2 inhibitor.

72. The method of embodiment 71, wherein the FGFR2 inhibitor is an inhibitor according to any one of embodiments 14-31.

73. The method of embodiment 71 or 72, wherein said method inhibits tumor growth or reduces volume of at least one tumor in the subject.

74. The method of embodiment 73, wherein the cancer is selected from breast cancer, gastric cancer, non-small cell lung cancer, melanoma, squamous cell carcinoma of the head and neck, ovarian cancer, pancreatic cancer, renal cell carcinoma, hepatocellular carcinoma, bladder cancer, cholangiocarcinoma, esophageal cancer, and endometrial cancer.

75. The method of any one of embodiments 71 to 74, wherein (a) the cancer has previously been determined to overexpress FGFR2IIIb, either in the presence or in the absence of FGFR2 gene amplification, or (b) the method comprises a further step of determining whether the cancer overexpresses FGFR2IIIb and optionally also comprises a further step of determining whether the FGFR2 gene is amplified in tumor cells.

76. The method of embodiment 75, wherein FGFR2IIIb overexpression is determined by immunohistochemistry (IHC).

77. The method of embodiment 76, wherein the overexpression is determined by an IHC signal of 1+, 2+, or 3+ in at least 10% of tumor cells, such as in at least 20%, 30%, 40%, or 50% of tumor cells.

78. The method of any one of embodiments 75 to 77, wherein the FGFR2 gene amplification is determined by obtaining the ratio of FGFR2 to chromosome 10 centromere (CEN10) using fluorescence in situ hybridization (FISH), wherein the FGFR2 gene is considered amplified if the FGFR2/CEN10 ratio determined by FISH is greater than or equal to 2.

79. The method of any one of embodiments 75 to 78, wherein the cancer is gastric cancer or bladder cancer.

80. The method of any one of embodiments 75 to 79, wherein:
a) the cancer is gastric cancer, and the cancer has an IHC signal of 3+ in at least 10% of tumor cells;
b) the cancer is gastric cancer, the cancer has an IHC signal of 3+ in at least 10% of tumor cells, and wherein the FGFR2 gene is amplified;
c) the cancer is gastric cancer, the cancer has an IHC signal of 3+ in at least 10% of tumor cells, and wherein the FGFR2 gene is not amplified;
d) the cancer is gastric cancer, and the cancer has an IHC signal of 1+ or 2+ in at least 10% of tumor cells;
e) the cancer is bladder cancer, and the cancer has an IHC signal of 1+ in at least 10% of tumor cells;
f) the cancer is bladder cancer, and the cancer has an IHC signal of 2+ in at least 10% of tumor cells;
g) the cancer is bladder cancer, and the cancer has an H score of 20 or greater;
h) the cancer is bladder cancer, and the cancer has an H score of 10-19; or
i) the cancer is bladder cancer, and the cancer has an H score of <10.

81. The method of any one of embodiments 71 to 80, wherein the method further comprises, following administration of the FGFR2 antibody, obtaining at least one tumor sample from the subject and determining the number of NK cells and/or PD-L1 positive cells and/or CD8+ T cells in the sample, and, if the number of NK cells and/or PD-L1 positive cells and/or CD8+ T cells is increased relative to a sample prior to FGFR2 antibody administration, administering at least one immune stimulating agent, such as at least one PD-1/PD-L1 inhibitor to the subject.

82. A method of treating cancer in a subject comprising administering to the subject an FGFR2 inhibitor and, if the subject is determined to have an increased number of NK cells and/or PD-L1 positive cells and/or CD8+ T cells relative to a sample prior to FGFR2 antibody administration, administering at least one immune stimulating agent, such as at least one PD-1/PD-L1 inhibitor to the subject.

83. The method of embodiment 82, wherein the FGFR2 inhibitor is an inhibitor according to any one of embodiments 14-31.

84. The method of embodiment 82 or 83, wherein the at least one immune stimulating agent comprises at least one PD-1/PD-L1 inhibitor according to any one of embodiments 2-13.

85. The method of any one of embodiments 82 to 84, wherein the FGFR2 inhibitor and the at least one immune stimulating agent are administered according to the method of embodiment 38 or 39.

86. A method of increasing the number of one or more of PD-L1 positive cells, NK cells, CD3+ T cells, CD4+ T cells, CD8+ T cells, and macrophages in tumor tissue of a cancer subject, comprising administering an FGFR2 inhibitor, wherein the inhibitor is an FGFR2 antibody with enhanced ADCC activity.

87. The method of embodiment 86, wherein the antibody is an antibody according to any one of embodiments 15-28.

88. The method of embodiment 86 or 87, wherein administration of the FGFR2 antibody in a mouse tumor model increases the number of one or more of PD-L1 positive cells, NK cells, CD3+ T cells, CD8+ T cells, CD4+ T cells, and macrophages in tumor tissue compared to a control, and/or increases the ratio of lymphoid to myeloid cells in the tumor tissue.

89. The method of any one of embodiments 86 to 88, wherein the subject suffers from breast cancer, gastric cancer, non-small cell lung cancer, melanoma, squamous cell carcinoma of the head and neck, ovarian cancer, pancreatic cancer, renal cell carcinoma, hepatocellular carcinoma, bladder cancer, cholangiocarcinoma, esophageal cancer, or endometrial cancer.

90. The method of any one of embodiments 86 to 89, wherein (a) the cancer has previously been determined to overexpress FGFR2IIIb, either in the presence or in the absence of FGFR2 gene amplification, or (b) the method comprises a further step of determining whether the cancer overexpresses FGFR2IIIb and optionally also comprises a further step of determining whether the FGFR2 gene is amplified in tumor cells.

91. The method of embodiment 90, wherein FGFR2IIIb overexpression is determined by immunohistochemistry (IHC).

92. The method of embodiment 91, wherein the overexpression is determined by an IHC signal of 1+, 2+, or 3+ in at least 10% of tumor cells, such as in at least 20%, 30%, 40%, or 50% of tumor cells.

93. The method of any one of embodiments 90 to 92, wherein the FGFR2 gene amplification is determined by obtaining the ratio of FGFR2 to chromosome 10 centromere (CEN10) using fluorescence in situ hybridization (FISH), wherein the FGFR2 gene is considered amplified if the FGFR2/CEN10 ratio determined by FISH is greater than or equal to 2.

94. The method of any one of embodiments 89 to 93, wherein subject suffers from gastric cancer or bladder cancer.

95. The method of any one of embodiments 90 to 94, wherein:
a) the cancer is gastric cancer, and the cancer has an IHC signal of 3+ in at least 10% of tumor cells;
b) the cancer is gastric cancer, the cancer has an IHC signal of 3+ in at least 10% of tumor cells, and wherein the FGFR2 gene is amplified;
c) the cancer is gastric cancer, the cancer has an IHC signal of 3+ in at least 10% of tumor cells, and wherein the FGFR2 gene is not amplified;
d) the cancer is gastric cancer, and the cancer has an IHC signal of 1+ or 2+ in at least 10% of tumor cells;
e) the cancer is bladder cancer, and the cancer has an IHC signal of 1+ in at least 10% of tumor cells;
f) the cancer is bladder cancer, and the cancer has an IHC signal of 2+ in at least 10% of tumor cells;
g) the cancer is bladder cancer, and the cancer has an H score 20 or greater;
h) the cancer is bladder cancer, and the cancer has an H score of 10-19; or
i) the cancer is bladder cancer, and the cancer has an H score of <10.

96. The method of any one of embodiments 86 to 95, wherein the FGFR2 antibody is administered at a dose of at least 0.1, 0.3, 0.5, 1, 2, 3, 4, 5, 6, 10, 15, 20, 25, or 30 mg/kg, or at a range bounded by any two of those mg/kg doses such as 6-10 mg/kg, 10-15, mg/kg, or 6-15 mg/kg, every week, every two weeks, every three weeks, or once a month.

97. A method of determining whether a gastric or bladder cancer patient will be responsive to treatment with an FGFR2 inhibitor comprising determining whether the gastric or bladder cancer overexpresses FGFR2IIIb by IHC, wherein the overexpression is determined by an IHC signal of 1+, 2+, or 3+ in at least 10% of tumor cells of the cancer, such as in at least 20%, 30%, 40%, or 50% of tumor cells.

98. The method of embodiment 97, wherein the method further comprises determining whether the FGFR2 gene is amplified by obtaining the ratio of FGFR2 to chromosome 10 centromere (CEN10) using fluorescence in situ hybridization (FISH), wherein the FGFR2 gene is considered amplified if the FGFR2/CEN10 ratio determined by FISH is greater than or equal to 2.

99. The method of embodiment 97 or 98, wherein the patient is determined to be responsive to FGFR2IIIb antibody treatment if:
a) the cancer is gastric cancer, and the cancer has an IHC signal of 3+ in at least 10% of tumor cells;
b) the cancer is gastric cancer, the cancer has an IHC signal of 3+ in at least 10% of tumor cells, and wherein the FGFR2 gene is amplified;
c) the cancer is gastric cancer, the cancer has an IHC signal of 3+ in at least 10% of tumor cells, and wherein the FGFR2 gene is not amplified;
d) the cancer is gastric cancer, and the cancer has an IHC signal of 1+ or 2+ in at least 10% of tumor cells;
e) the cancer is bladder cancer, and the cancer has an IHC signal of 1+ in at least 10% of tumor cells;
f) the cancer is bladder cancer, and the cancer has an IHC signal of 2+ in at least 10% of tumor cells;
g) the cancer is bladder cancer, and the cancer has an H score of 20 or greater;
h) the cancer is bladder cancer, and the cancer has an H score of 10-19; or
i) the cancer is bladder cancer, and the cancer has an H score of <10.

100. The method of any one of embodiments 97-99, wherein the FGFR2 inhibitor is an inhibitor according to any one of embodiments 14-31.

101. The method of any one of embodiments 97-100, wherein the treatment comprises administering the FGFR2 inhibitor at a dose of at least 0.1, 0.3, 0.5, 1, 2, 3, 4, 5, 6, 10, 15, 20, 25, or 30 mg/kg, or at a range bounded by any two of those mg/kg doses such as 6-10 mg/kg, 10-15, mg/kg, or 6-15 mg/kg.

102. The method of any one of embodiments 97-101, wherein the treatment comprises performing a method according to embodiment 71, 82, or 86.

103. The method of any one of embodiments 97-101, wherein the treatment further comprises administering at least one immune stimulating agent to the subject.

104. The method of embodiment 103, wherein the at least one immune stimulating agent comprises the immune stimulating agent of any one of embodiments 2-13.

105. The method of embodiment 103, wherein the treatment comprises administering the FGFR2 inhibitor and the at least one immune stimulating agent according to any one of the methods of embodiments 32-44 or wherein the treatment comprises administering the composition of any one of embodiments 60-62.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: ADCC Activity is Required for Tumor Growth Inhibition in a 4T1 Mouse Breast Tumor Model Seventy female BALB/c mice of eight weeks old (IACUC category: AUP 2011 #01-03) were purchased from Charles River Laboratories (Wilmington, Mass., USA). The animals were given at least a 3-day acclimation upon arrival and were housed 5 animals per cage with free access to food and water. Once acclimated, they were weighed, and shaved prior to tumor cell implantation.

Breast tumor line 4T1 from mouse strain BALB/cfC3H was used as the tumor model and was obtained from ATCC (Manassas, Va., USA: Catalog No. CRL-2539). The cells were cultured at 37° C. in RPMI 1640 Medium (Mediatech, Inc., Manassas, Va., USA; Cat. No. 10-041-CV) with 10% fetal bovine serum, 2 mM L-glutamine and 1% Penn/Strep.

Each mouse was inoculated with $5 \times 10^4$ 4 T1 cells by orthotopic injection under the 4th mammary papilla (teat) from the head of the mouse. Mouse tumor volumes and body weights were then regularly monitored until tumor volumes measured 100 mm³+/−25 mm³. Once tumors reached 100 mm³+/−25 mm³, mice were sorted according to tumor size into four groups for dosing. The first group was dosed with 20 mg/kg Fc-G1 antibody (intraperitoneally (IP), bi-weekly (BIW)), the second group with 20 mg/kg of an afucosylated FGFR2 antibody (anti-FGFR2) with the heavy and light chain HVRs of SEQ ID NOs: 6-11 (IP, BIW), and the third group with 20 mg/kg of the FGFR2 antibody with an N297Q mutation (anti-FGFR2-N297Q) rendering this molecule unable to stimulate ADCC activity (IP, BIW).

Figure 1A:
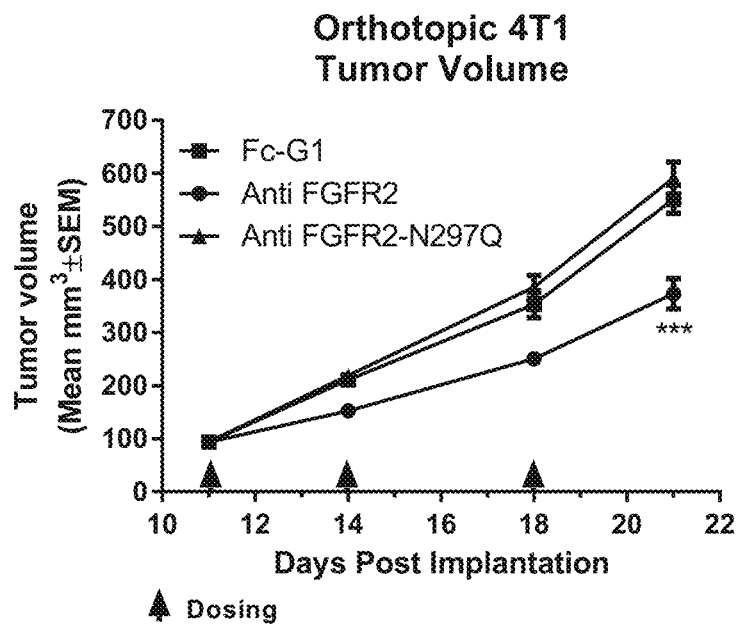
FIGS. 1a-1b show changes in volume of implanted mammary 4T1 tumor cells in BALB/c mice after treatment with an Ig-Fc control, an afucosylated anti-FGFR2b antibody (anti-FGFR2) comprising the heavy and light chain HVRs of SEQ ID NOs: 6-11, or an anti-FGFR2b antibody with the same amino acid sequence except for a substitution of Q for N at amino acid position 297 (anti-FGFR2-N297Q) in order to eliminate effector function. (See SEQ ID NO:12 in the sequence table below for a depiction of that mutation.) As shown in both FIG. 1a and FIG. 1b, only the anti-FGFR2 antibody showed 4T1 tumor growth inhibition. Statistical significance ($P<0.05=*$; $P<0.01=$; $P<0.001=*$; $P<0.001=****$) was determined by 1 way ANOVA followed by Tukey multiple comparisons test.
Figure 1B:
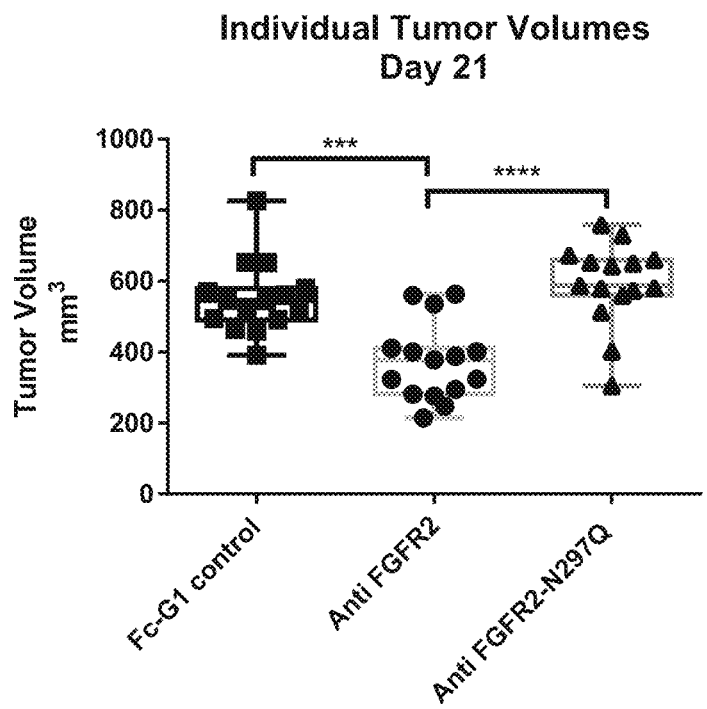

Overall, treatment with anti-FGFR2 results in a ~30% inhibition (P<0.001) of tumor growth compared to the FcG1 control, while treatment with anti-FGFR2-N297Q did not inhibit tumor growth compared to the control. (See FIGS. 1a-b.) These data support a role for ADCC as a mechanism of anti-FGFR2 tumor growth inhibition.

Example 2a: Exposure to an Anti-FGFR2 Antibody Results in an Increase in NK Cells and an Increase in PD-L1 Expressing Cells within Tumor Tissue For immunohistochemistry analysis, BALB/cfC3H mice were inoculated with $5 \times 10^4$ 4 T1 cells by orthotopic injection as described above. Once tumors reached 100 mm³+/−25 mm³ (day 0) mice were sorted according to tumor size into two dosing groups: vehicle or 10 mg/kg anti-FGFR2 (IP). Each group was subdivided into (a) mice that received one or two doses on day 0 or (b) mice that received one or two doses on day 3, and mice were euthanized 24 hours post dose on day 1 or 4, respectively, and processed for histology or FACS analysis.

For histology, on day 1 and day 4, 24 hours after the first and second treatment respectively, mice were euthanized with $CO_2$ and then perfused with phosphate-buffered saline (PBS), pH 7.4. Briefly, the mouse chest was opened rapidly, and a syringe with a 20-gauge needle was used to infuse 40 mL of PBS into the aorta via an incision in the left ventricle. Blood and PBS exited through an opening in the right atrium. The 4T1 orthotopic tumors were removed and immersed in 10% neutral buffered formalin at 4° C. After 2 hours the tissues were rinsed 3 times with PBS and then transferred in 30% sucrose in PBS overnight. The next day the tumors were frozen in OCT compound and stored at −80° C.

20-μm-think serial sections of each tumor were cut. Sections were dried on Superfrost Plus slides (VWR) for 1 to 2 hours. Specimens were permeabilized with PBS containing 0.3% Triton X-100 and incubated in 5% goat normal serum in PBS 0.3% Triton X-100 (blocking solution) for 1 hour at room temperature to block nonspecific antibody binding. After 1 hour the blocking solution was removed and the sections were incubated in the primary antibodies overnight. To detect NK cells, sections were incubated with rat anti-NKp46 (CD335; Biolegend, cat #137602) diluted 1:500 in blocking solution. To detect PD-L1, sections were incubated with rat anti-PD-L1 (eBioscience, cat #14-5982-82) diluted 1:500 in blocking solution. NK cells and PD-L1 staining were performed in serial sections, as both primary antibodies were generated in rat. Secondary antibody only negative control specimens were incubated in 5% normal serum rather than primary antibodies.

The next day, after rinsing with PBS containing 0.3% Triton X-100, specimens were incubated for 4 hours at room temperature with Alexa Fluor 594-labeled goat anti-rat (Jackson Immuno Research, cat #112-585-167) and Alexa Fluor 488-labeled goat anti-rabbit (Jackson Immuno Research, cat #111-545-144) secondary antibodies diluted 1:400 in PBS. After, specimens were rinsed with PBS containing 0.3% Triton X-100, then were fixed in 1% paraformaldehyde (PFA), rinsed again with PBS, and mounted in Vectashield with DAPI (Vector, H-1200). DAPI was used to label the cell nuclei.

Specimens were examined with a Zeiss Axiophot® 2 plus fluorescence microscope equipped with an AxioCam® HRc camera. Representative images for each experimental group showing the amount and distribution of the NKp46+ and PD-L1+ cells within the tumor were collected and are shown in FIGS. 2a-2d.

Figure 2A:
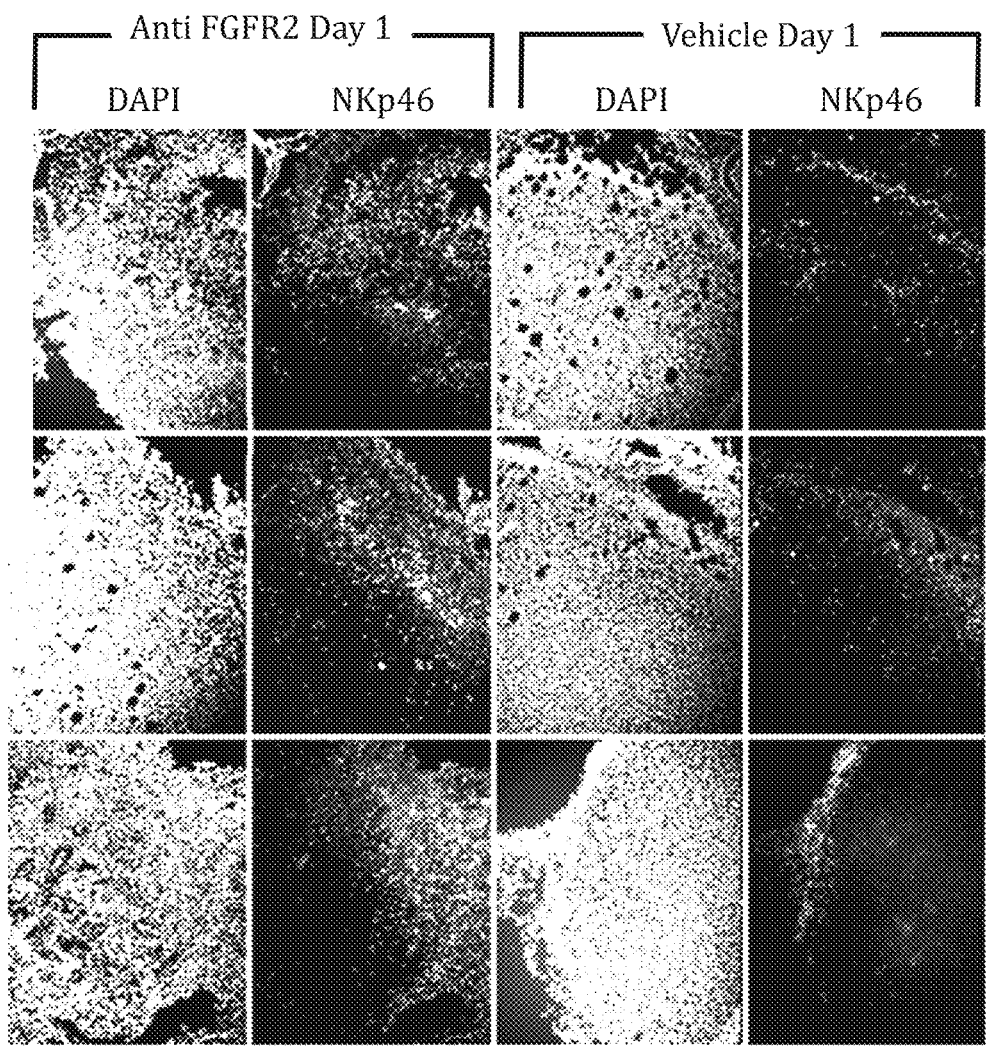
FIGS. 2a-2d show results from staining of 4T1 tumor cells for the presence of either NKp46 (FIGS. 2a-2b) or PD-L1 (FIGS. 2c-2d) compared with DAPI staining of cell nuclei either on day 1, one day after single dose treatment with vehicle control or anti-FGFR2 (FIGS. 2a and 2c), or on day four, one day after the second of two treatments given on day zero and day three with vehicle control or anti-FGFR2 (FIGS. 2b and 2d). Each image was taken from a different tumor and images were collected using a 10× objective. Treatment with anti-FGFR2 increased the number of NKp46+ cells in the 4T1 tumor compared to vehicle on both day 1 and day 4 (FIGS. 2a-2b) and increased the number of PD-L1+ cells compared to vehicle on both day 1 and day 4 (FIGS. 2c-2d).
Figure 2B:
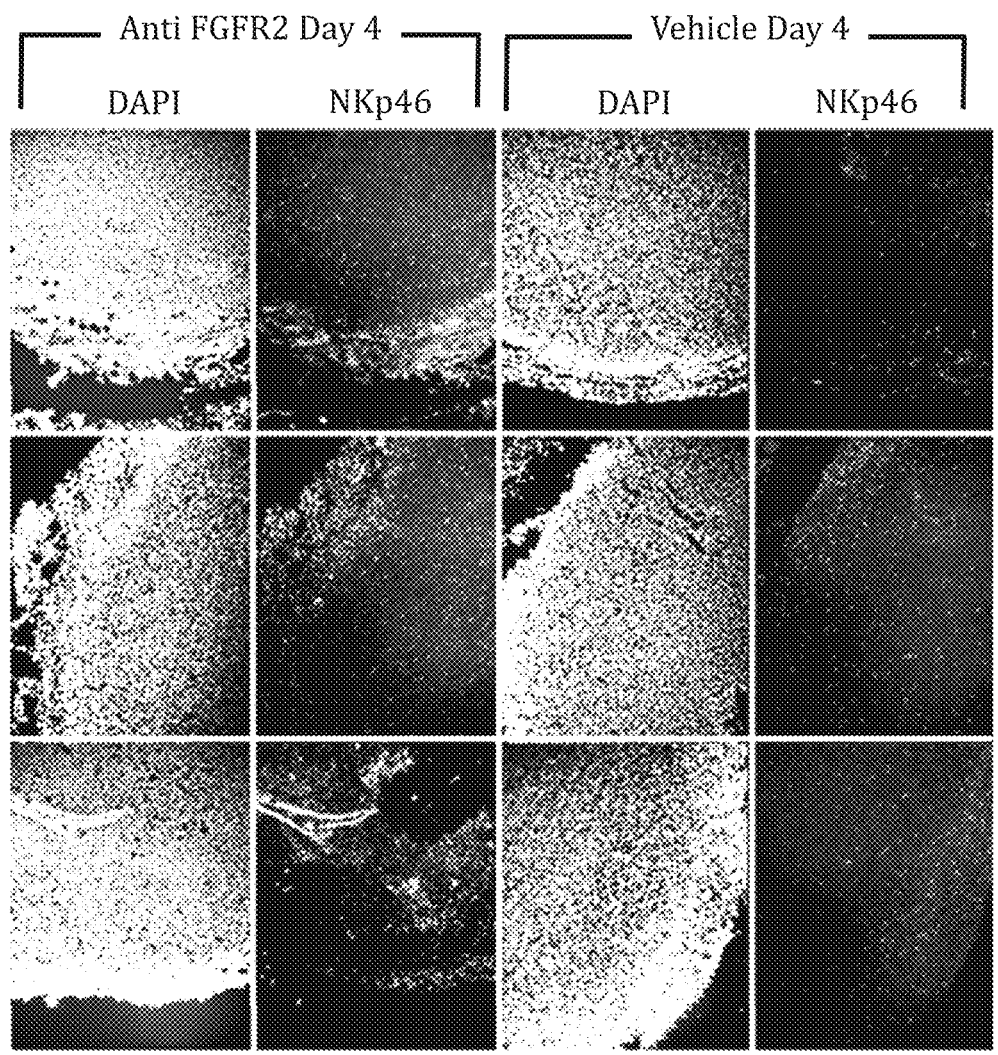

In 4T1 tumors from mice injected with vehicle, minimal scattered NKp46+ NK cells were detected and most of these cells were located at the tumor periphery. (FIG. 2a.) By comparison, after treatment with anti-FGFR2 at 10 mg/kg for 1 day the NKp46+ NK cells were more numerous. While most of these cells were found at the tumor edges, some had infiltrated the tumor center. (See FIG. 2a.) Similar results were observed on day 4 after a second dose of anti-FGFR2. (FIG. 2b.)

Figure 2C:
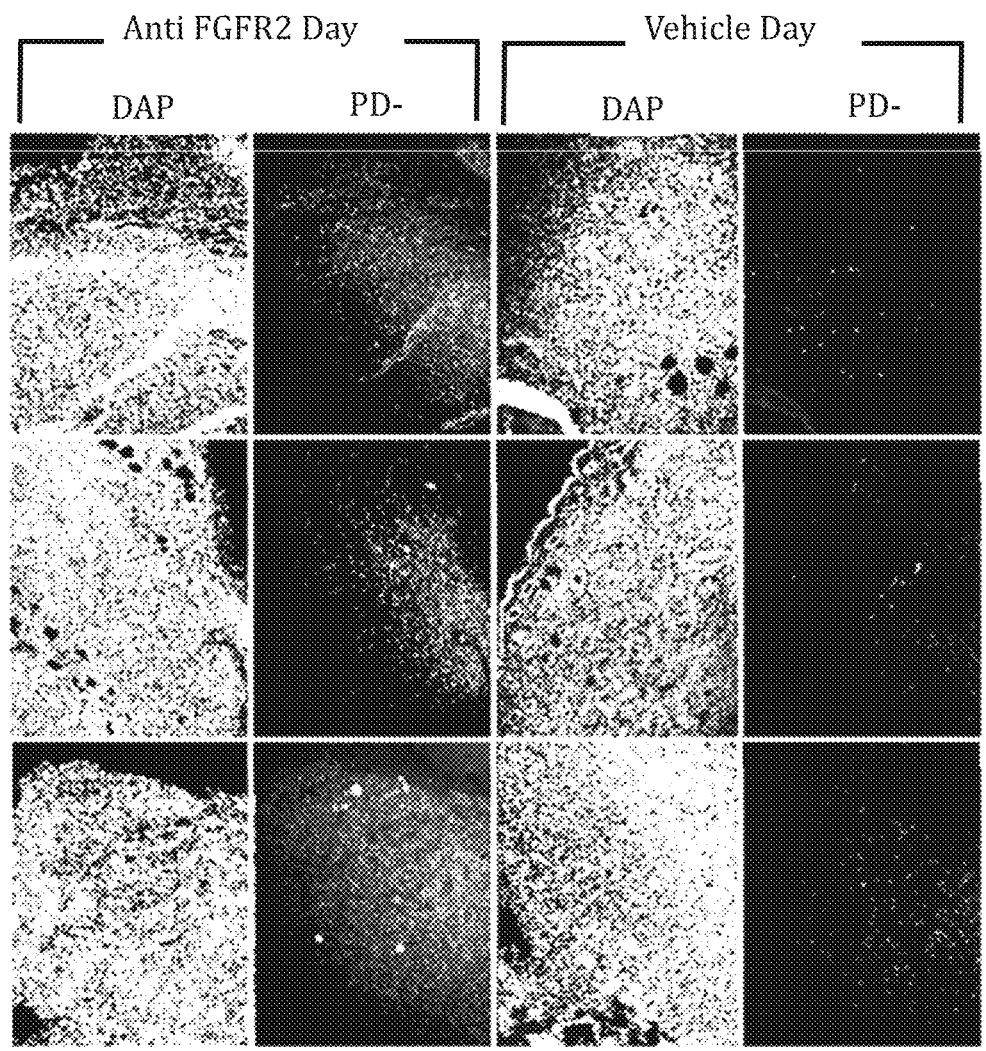
Figure 2D:
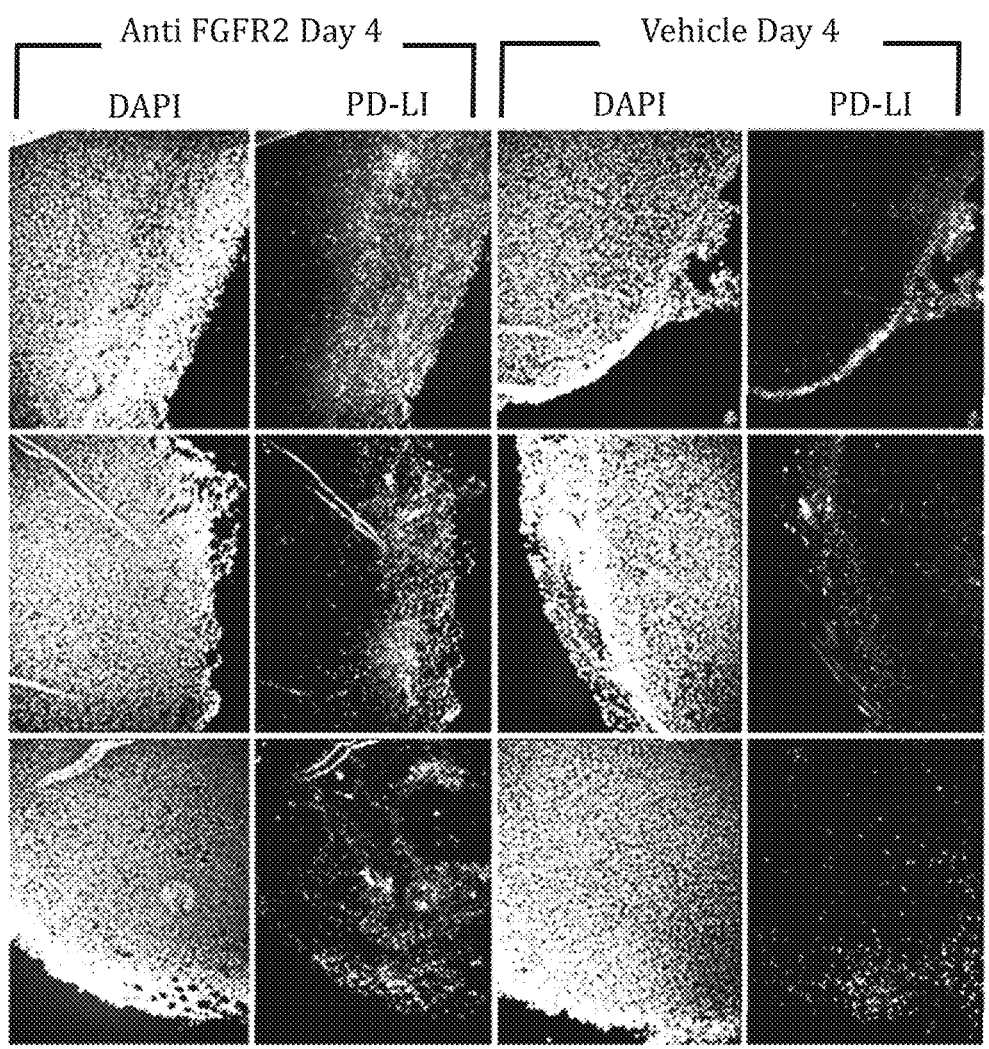

The PD-L1 staining revealed that in 4T1 tumors treated with vehicle for 1 day, PD-L1 immunoreactivity was found only in a few cells within the tumors. (FIG. 2c.) In contrast, 24 hours post 1 dose of anti-FGFR2, PD-L1 positive cells were more numerous within the tumor center. (FIG. 2c.) Similar results were observed at 4 days after the treatment started. (FIG. 2d.)

As an orthogonal assay to quantitate increases in NK cells, we performed FACS on 4T1 tumor bearing mice that received 2 doses of Saline or 10 mg/Kg anti-FGFR2 as described above. For FACS analysis, tumors were cut to 1-2 mm pieces and placed in DMEM with 10% FBS, 50 U/mL DNAse I and 250 U/mL Collagenase I (Worthington Biochemical Corporation, Lakewood, N.J.) in a shaking incubator for 30 min at 37° C. Cells were passed through a 70 µm nylon mesh strainer, and the single cell suspensions were stained according to standard protocols with antibodies purchased from BD Biosciences (San Jose, Calif.): CD45 (clone 30-F11) and CD11b (1D3); Affymtrix eBioscience (San Diego, Calif.): CD16/32 (FC receptor Block, 93), CD335 (NKp46, 29A1.4), CD8a (53.67), and CD3e (145-2C11); R&D Systems (Minneapolis, Minn.): EphA2 (233720); or ThermoFisher Scientific (Grand Island, N.Y.): Live/Dead Aqua. Cells were fixed and acquired the next day on a BD LSRII. The results were analyzed using FlowJo (V10, Ashland, Oreg.) with the following gating strategy: CD45+ EphA2−, singlets (FSC-H vs. FSC-A), Live cells (Live/Dead negative), and CD11b− to isolate live lymphocytes. The NK cells were gated as NKp46+ CD3−, and expressed as a percent of CD45+ Live Single cells.

Figure 3:
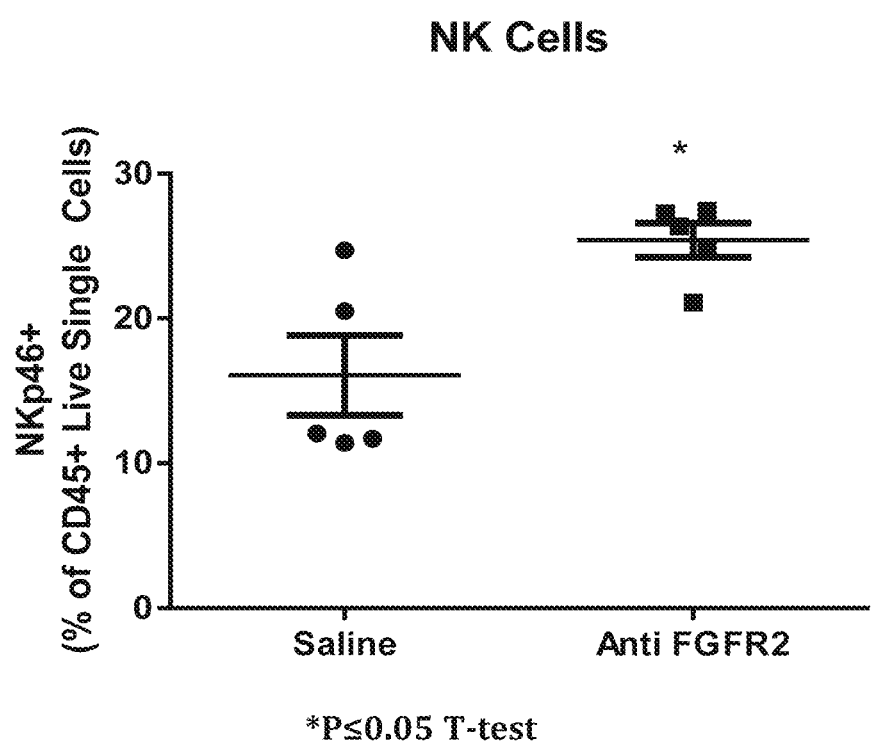
FIG. 3 shows an analysis of the effect of anti-FGFR2 exposure on the number of NKp46+ cells in the mouse 4T1 tumors on day 4. Treatment with anti-FGFR2 increased the NK cells in the tumors compared to vehicle control with a P of $<0.05$ by a t-test.

As shown in FIG. 3, tumors treated with anti-FGFR2 demonstrated an increased NK cells compared to tumors treated with Saline control.

Example 2b: Exposure to an Anti-FGFR2 Antibody and not Anti-FGFR2 N297Q Results in an Increase in NK Cells, T Cells and an Increase in PD-L1 Expressing Cells within Tumor Tissue BALB/cfC3H mice were inoculated with $5 \times 10^4$ 4 T1 cells by orthotopic injection as described above in Example 1. Once tumors reached 100 mm$^3$+/−25 mm$^3$ (day 0) mice were sorted according to tumor size into three dosing groups: vehicle (control group), 10 mg/kg afucosylated anti-FGFR2 antibody (IP) (anti-FGFR2 group), and 10 mg/kg anti-FGFR2 N297Q antibody (anti-FGFR2 N297Q group). The N297Q modification is a mutation in the Fc domain of the antibody that is intended to eliminate effector function of the antibody.

Each group was subdivided into (a) mice that received one or two doses on day 0 or (b) mice that received one or two doses on day 3, and mice were euthanized 24 hours post dose on day 1 or 4, respectively, and processed for histology or FACS analysis.

For histology, on day 1 and day 4, 24 hours after the first and second treatment respectively, mice were euthanized with $CO_2$ and then perfused with phosphate-buffered saline (PBS), pH 7.4. Briefly, the mouse chest was opened rapidly, and a syringe with a 20-gauge needle was used to infuse 40 mL of PBS into the aorta via an incision in the left ventricle. Blood and PBS exited through an opening in the right atrium. The 4T1 orthotopic tumors were removed and immersed in 10% neutral buffered formalin at 4° C. After 2 hours the tissues were rinsed 3 times with PBS and then transferred in 30% sucrose in PBS overnight. The next day the tumors were frozen in OCT compound and stored at −80 C.

20-µm-think serial sections of each tumor were cut. Sections were dried on Superfrost Plus slides (VWR) for 1 to 2 hours. Specimens were permeabilized with PBS containing 0.3% Triton X-100 and incubated in 5% goat normal serum in PBS 0.3% Triton X-100 (blocking solution) for 1 hour at room temperature to block nonspecific antibody binding. After 1 hour the blocking solution was removed and the sections were incubated in the primary antibodies overnight. To detect NK cells, sections were incubated with rat anti-NKp46 (CD335; Biolegend, cat #137602) diluted 1:500 in blocking solution. To detect PD-L1, sections were incubated with rat anti-PD-L1 (eBioscience, cat #14-5982-82) diluted 1:500 in blocking solution. To detect CD3+ T cells, sections were incubated with hamster anti-CD3 antibody (BD biosciences, cat #553058) at 1:500 in blocking solution. To detect CD4+ T cells, sections were incubated with rat anti-CD4 antibody (AbD Serotec, cat #MCA4635) at 1:500 in blocking solution. To detect CD8+ T cells, sections were incubated with rat anti-CD8 antibody (Abcam, cat #ab22378) at 1:500 in blocking solution. NK cells and PD-L1 staining were performed in serial sections, as both primary antibodies were generated in rat. CD3 and CD4 positive cells were stained together in the same section. CD3 and CD8 staining were also performed in the same sections. Secondary antibody only negative control specimens were incubated in 5% normal serum rather than primary antibodies.

The next day, after rinsing with PBS containing 0.3% Triton X-100, specimens were incubated for 4 hours at room temperature with Alexa Fluor 594-labeled goat anti-rat (Jackson Immuno Research, cat #112-585-167) and Alexa Fluor 488-labeled goat anti-hamster (Jackson Immuno Research, cat #127-545-160), secondary antibodies diluted 1:400 in PBS. Afterwards, specimens were rinsed with PBS containing 0.3% Triton X-100, then were fixed in 1% paraformaldehyde (PFA), rinsed again with PBS, and mounted in Vectashield with DAPI (Vector, H-1200). DAPI was used to label the cell nuclei.

Figure 5A:
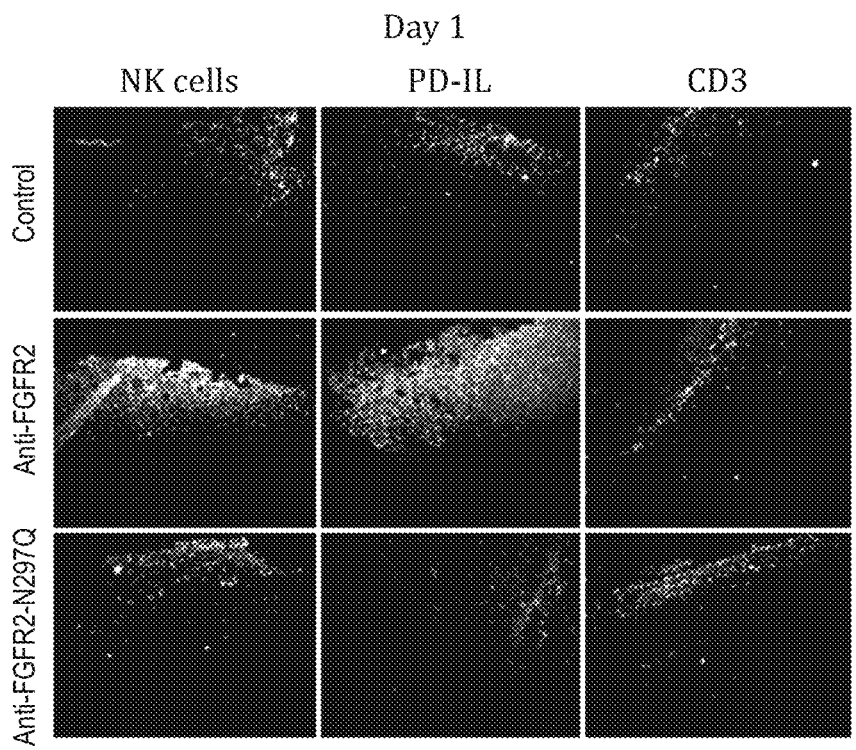
FIGS. 5a-5b show results from staining of 4T1 tumor cells for the presence of either NKp46 cells or PD-L1+ cells or CD3+ T cells either on day 1 (FIG. 5a), one day after single dose treatment with vehicle control or anti-FGFR2 or anti-FGFR2 N297Q, or on day 4, one day after the second of two treatments given on day zero and day three with vehicle control or anti-FGFR2 (FIG. 5b). Each image was taken from a different tumor and images were collected using a 10× objective. Treatment with anti-FGFR2 increased the number of NKp46+ cells in the 4T1 tumor compared to vehicle on both day 1 and day 4 and increased the number of PD-L1+ cells compared to vehicle on both day 1 and day 4, with a greater number of cells visible at day 4 than day 1. CD3+ T cells had also infiltrated the tumor by day 4 after treatment with anti-FGFR2.
Figure 5B:
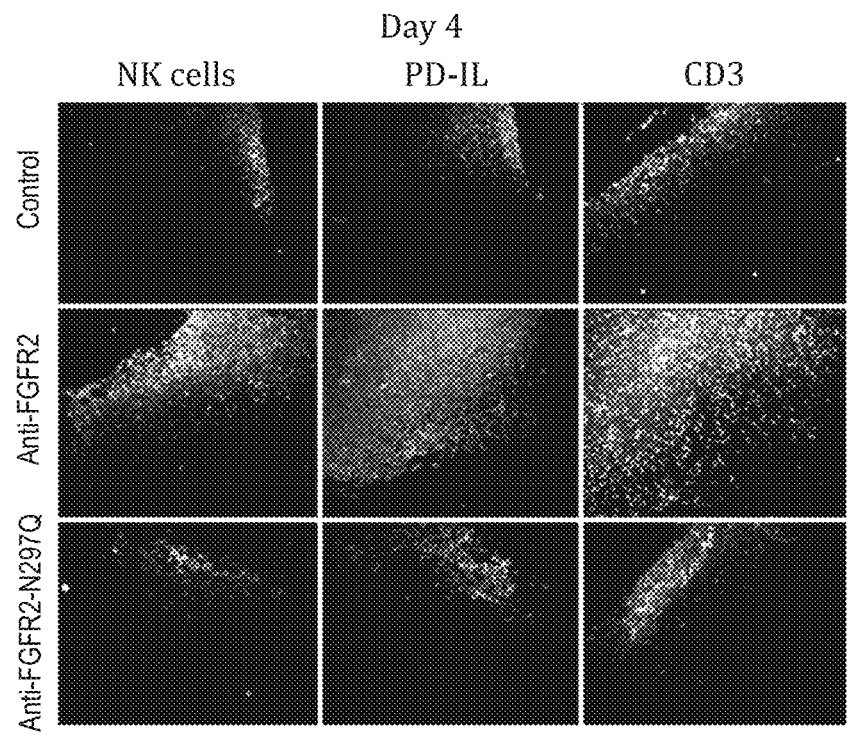

Specimens were examined with a Zeiss Axiophot® 2 plus fluorescence microscope equipped with an AxioCam® HRc camera. Representative images for each experimental group showing the amount and distribution of the NKp46+ and PD-L1+ cells within the tumor were collected and are shown in FIGS. 5a-5b.

In 4T1 tumors from mice injected with vehicle or anti-FGFR2 N297Q, minimal scattered NKp46+ NK cells were detected after 1 day of treatment and most of these cells were located at the tumor periphery. (FIG. 5a.) By comparison, after treatment with anti-FGFR2 at 10 mg/kg for 1 day, the NKp46+ NK cells were more numerous. While most of these cells were found at the tumor edges, some had infiltrated the tumor center. (See FIG. 5a.) Similar results were observed on day 4 after a second dose of anti-FGFR2. (FIG. 5b.)

The PD-L1 staining revealed that in 4T1 tumors treated with vehicle or anti-FGFR2 N297Q for 1 day, PD-L1 immunoreactivity was found only in a few cells within the tumors. (FIG. 5a.) In contrast, 24 hours post 1 dose of anti-FGFR2, PD-L1 positive cells were more numerous within the tumor center. Similar results were observed at 4 days after the treatment started. (FIG. 5b.)

Figure 6A:
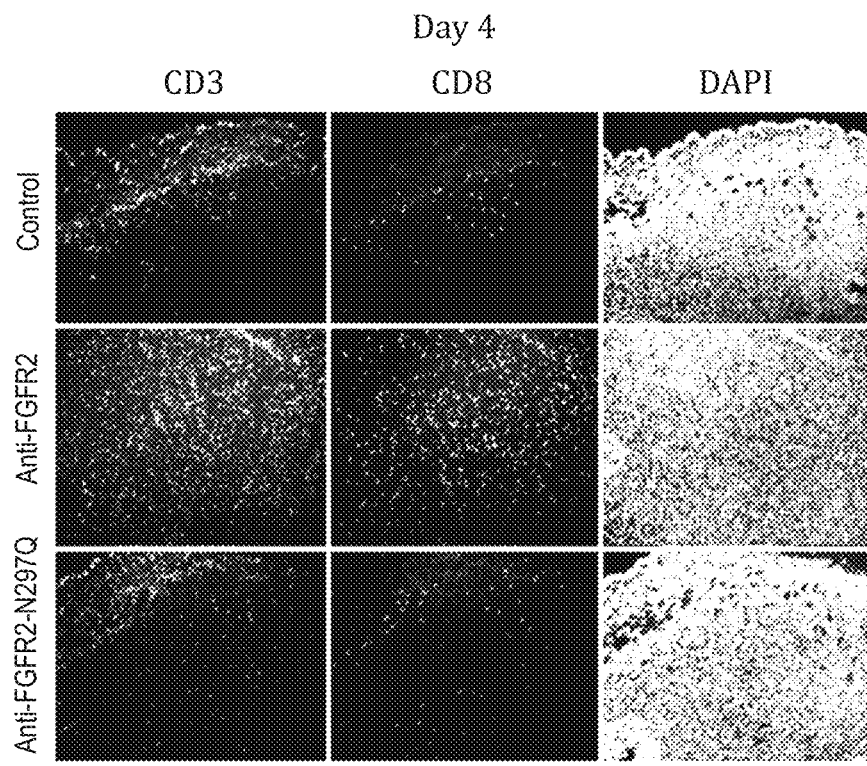
FIGS. 6a-6b show results from staining of 4T1 tumor cells for the presence of CD3+ and CD8+ T cells (FIG. 6a) or CD3+ and CD4+ T cells (FIG. 6b) on day 4 of the treatment protocol, adjacent to DAPI staining of cell nuclei.
Figure 6B:
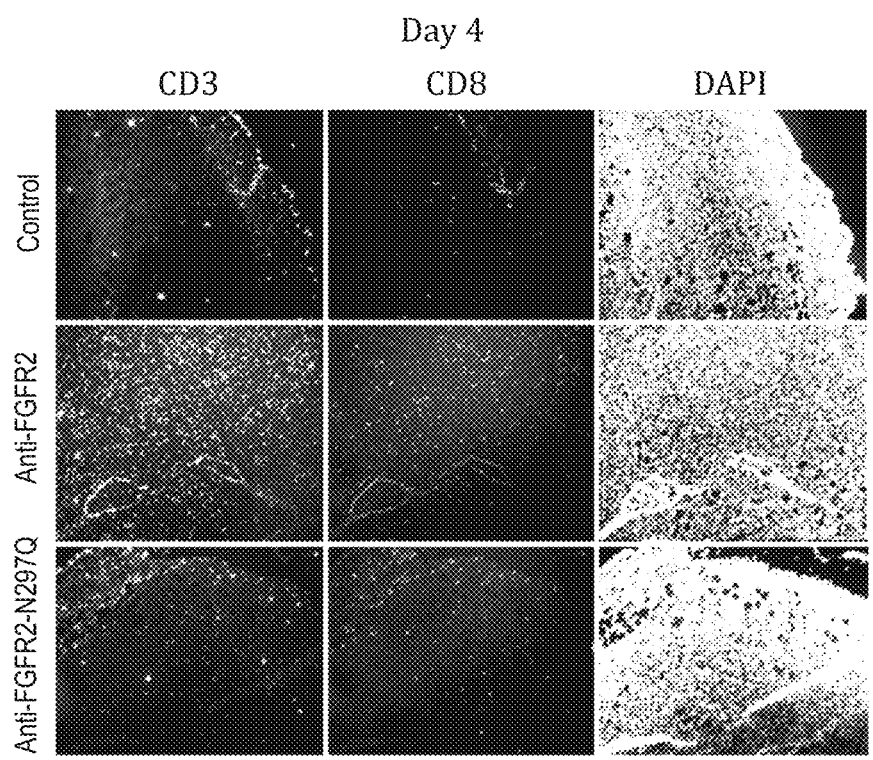

CD3, CD8 and CD4 staining revealed that, in tumors treated with vehicle or anti-FGFR2 N297Q for 1 day or 4 days, T Cell infiltration remained only at the periphery of the tumors. In contrast, on day 4, tumors treated with anti-FGFR2 resulted in an infiltration of CD3, CD8 and CD4 positive T Cells within the tumor center. (FIGS. 6a-6b.)

As an orthogonal assay to quantitate increases in NK cells, we performed FACS on 4T1 tumor bearing mice that received 2 doses of Saline or 10 mg/Kg anti-FGFR2 or anti-FGFR2 N297Q as described above. For FACS analysis, tumors were cut to 1-2 mm pieces and placed in DMEM with 10% FBS, 50 U/mL DNAse I and 250 U/mL Collagenase I (Worthington Biochemical Corporation, Lakewood, N.J.) in a shaking incubator for 30 min at 37° C. Cells were passed through a 70 μm nylon mesh strainer, and the single cell suspensions were stained according to standard protocols with antibodies purchased from BD Biosciences (San Jose, Calif.): CD45 (clone 30-F11) CD4, (GK1.5), and CD11b (1D3); Affymtrix eBioscience (San Diego, Calif.): CD16/32 (FC receptor Block, 93), CD335 (NKp46, 29A1.4), CD8a (53.67), and CD3e (145-2C11); R&D Systems (Minneapolis, Minn.): EphA2 (233720); or ThermoFisher Scientific (Grand Island, N.Y.): Live/Dead Aqua. Cells were fixed and acquired the next day on a BD LSRII. The results were analyzed using FlowJo (V10, Ashland, Oreg.) with the following gating strategy: CD45+ EphA2−, singlets (FSC-H vs. FSC-A), Live cells (Live/Dead negative), and CD11b− to isolate live lymphocytes. The NK cells were gated as NKp46+ CD3−. CD4 and CD8 T cells were gated on CD3+ cells, and each subset was expressed as a percent of CD45+ Live Single cells.

As shown in FIG. 10a, tumors treated with anti-FGFR2 demonstrated an increase in NK cells compared to tumors treated with Saline control or anti-FGFR2 N297Q. In addition, CD3, CD8 and CD4 T Cells were elevated 24 hours post the second dose (FIGS. 7-9) and there was a preferential increase in lymphoid to myeloid ratio with anti-FGFR2 treatment compared to vehicle or anti-FGFR2 N297Q (FIGS. 10b-c).

Example 2c: Exposure to an Anti-FGFR2 Antibody and not an Anti-FGFR2 N297Q Antibody Increases F480+ Macrophages within Tumor Tissue To detect macrophages in the 4T1 tumors, sections were incubated with rat anti-F480 antibody (Bio-Rad AbD Serotec Inc, cat #MCA497R) at 1:500 in blocking solution. NK cells, PD-L1 and F480 staining were performed in serial sections, as all these primary antibodies were generated in rat.

In 4T1 tumors from mice treated with control, abundant F480+ macrophages were detected throughout the tumors (FIG. 11, top panels). By comparison, after treatment with anti-FGFR2 at 10 mg/kg for 4 days the number of F480+ cells detected within the tumors was increased (FIG. 11, middle panels). This effect was not seen in 4T1-tumor bearing mice treated with anti-FGFR2 antibody at 10 mg/kg for 1 day or with anti-FGFR2-N297Q mutant antibody for 1 or 4 days (FIG. 11, lower panels).

Example 3: Combination of an FGFR2 Antibody and a PD-1 Antibody in a Breast 4T1 Syngeneic Tumor Model In this example, the anti-tumor effects of a combination of the afucosylated FGFR2 antibody (anti-FGFR2) and an anti-PD-1 antibody (Bio X Cell, West Lebanon, N.H., USA, clone RMP1-14) were evaluated in the 4T1 syngeneic murine model of breast cancer in immune-competent mice. The 4T1 model displays a modest overexpression of FGFR2-IIIb, but is not FGFR2-amplified.

Seventy female BALB/c mice of eight weeks old were purchased from Charles River Laboratories (Wilmington, Mass., USA). The animals were given at least a 3-day acclimation upon arrival and were housed 5 animals per cage with free access to food and water. Once acclimated, they were weighed, and shaved prior to tumor cell implantation.

Breast tumor line 4T1 from mouse strain BALB/cfC3H was used as the tumor model and was obtained from ATCC (Manassas, Va., USA: Catalog No. CRL-2539). The cells were cultured at 37° C. in RPMI 1640 Medium (Mediatech, Inc., Manassas, Va., USA; Cat. No. 10-041-CV) with 10% fetal bovine serum, 2 mM L-glutamine and 1% Penn/Strep.

Each mouse was inoculated with $5 \times 10^4$ 4 T1 cells by orthotopic injection under the 4th mammary papilla (teat) from the head of the mouse. Mouse tumor volumes and body weights were then regularly monitored until tumor volumes measured 150 $mm^3$ +/−25 $mm^3$. Once tumors reached 150 $mm^3$ +/−25 $mm^3$, mice were sorted according to tumor size into four groups for dosing. The first group was dosed with 10 mg/kg Ig-FC control (intraperitoneally (IP), bi-weekly (BIW)), the second group with 5 mg/kg of the anti-PD-1 antibody (IP, days 0, 3, and 7), the third group with 10 mg/kg of the FGFR2 antibody (IP, BIW), and the fourth group with a combination of the anti-PD-1 and FGFR2 antibodies at 5 and 10 mg/kg, respectively.

Figure 4A:
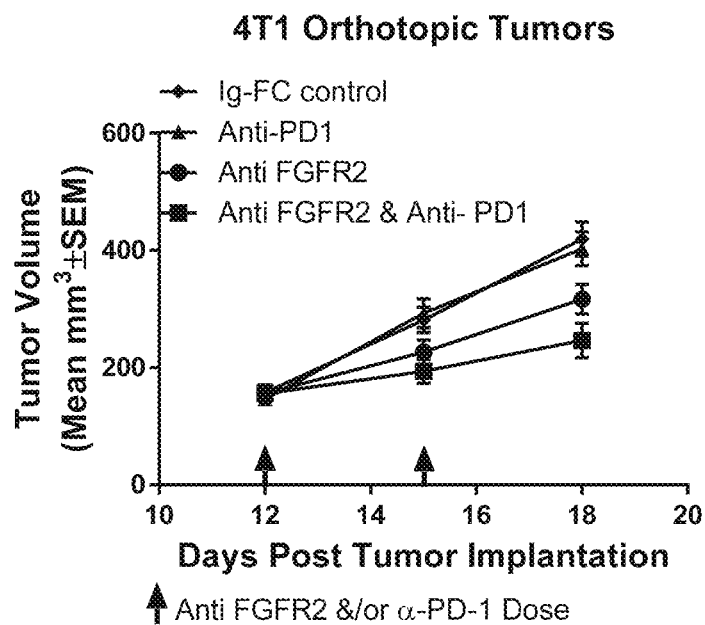
FIGS. 4a-4b show changes in implanted mammary 4T1 tumor volume in female BALB/c mice after treatment with an Ig-Fc control, an anti-PD-1 antibody, an afucosylated anti-FGFR2b antibody designated anti-FGFR2 and after a combination of treatment with the anti-PD-1 antibody and the afucosylated anti-FGFR2b antibody. In each graph, tumor volume is shown in mean $mm^3$+/−SEM.
Figure 4B:
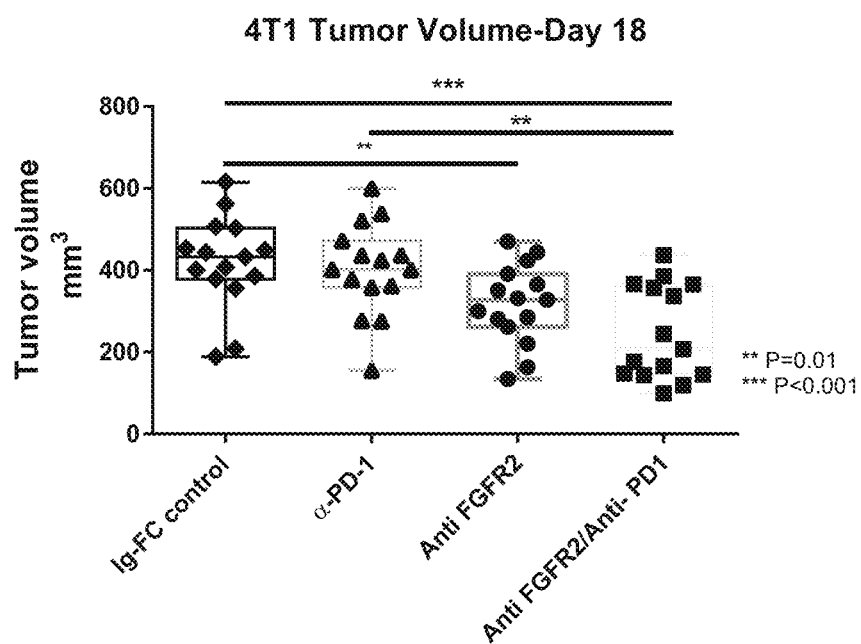

Tumor volumes were measured at 12 days post implantation (dosing day 0), 15 days post implantation, and 18 days post implantation. FIGS. 4a and b show that by day 18 the FGFR2 antibody significantly reduced 4T1 tumor volume in the mice (P<0.001 or P=0.01, respectively, by t-test), compared to the Ig-FC Control group. The combination of the FGFR2 antibody with the anti-PD-1 antibody further reduced tumor volume by day 18 in comparison to the FGFR2 antibody given alone (P=0.08, respectively). (See FIGS. 4a-b.) And the combination of the FGFR2 antibody with the anti-PD-1 antibody further reduced tumor volume by day 18 in comparison to the anti-PD-1 antibody given alone (P<0.01).

Overall, treatment with the FGFR2 antibody resulted in ~25% inhibition of tumor growth compared to the IgFC, while treatment with the anti-PD-1 antibody resulted in a 0% inhibition of tumor growth compared to the control. Treatment with both anti-FGFR2 and anti-PD-1 antibodies inhibited tumor growth by ~40%, demonstrating that the combination therapy has at least an additive benefit.

The table below shows an analysis of fractional tumor volumes (FTV) relative to the Fc-G1 control.

| Day [b] | FTV anti-FGFR2 | FTV anti-PD-1 | Expected [c] | Observed [d] | Expected/Observed [e] |
|---|---|---|---|---|---|
| 15 | 0.80 | 1.04 | 0.84 | 0.69 | 1.22 |
| 18 | 0.96 | 0.96 | 0.73 | 0.59 | 1.23 | a: FTV = fractional tumor volume = mean TV treated/mean TV control
[b] Day after tumor cell implantation
[c] Expected = (mean FTV drug 1) × (mean FTV drug 2)
[d] Observed = mean FTV for combination of drug 1 plus drug 2
[e] Value reported = expected (c) ÷ observed (d); values > 1 indicate synergistic response while values = 1 indicate additive response and values < 1 indicate antagonistic response This experiment studied the effect of anti-FGFR2 antibodies on NK cell-depleted tumor tissue. Breast tumor line 4T1 from mouse strain BALB/cfC3H was used as the tumor model and was obtained from ATCC (Manassas, Va., USA: Catalog No. CRL-2539). The cells were cultured at 37° C. in RPMI 1640 Medium (Mediatech, Inc., Manassas, Va., USA; Cat. No. 10-041-CV) with 10% fetal bovine serum, 2 mM L-glutamine and 1% Penn/Strep.

Each mouse was inoculated with $5 \times 10^4$ 4 T1 cells by orthotopic injection under the $4^{th}$ mammary papilla (teat) from the head of the mouse. Mouse tumor volumes and body weights were then regularly monitored until tumor volumes measured 100 mm$^3$+/−25 mm$^3$. Once tumors reached 125 mm$^3$+/−25 mm$^3$, mice were sorted according to tumor size into four groups for dosing (day 0). Group 1 was dosed with 10 mg/kg human Fc-G1 control antibody (intraperitoneally (IP), on day 0 and 3). Group 2 was dosed with 50 mg/kg rabbit anti-asialo GM1 antibody (Wako Chemicals, Osaka, Japan) i.v. once on day 0, an antibody designed to deplete NK cells from BalbC mice. Group 3 was dosed with 10 mg/kg of anti-FGFR2 (IP on day 0 and day 3). Group 4 was dosed with 50 mg/kg rabbit anti-asialo GM1 antibody (day 0) combined with 10 mg/kg anti-FGFR2 (IP on day 0 and day 3).

For histology, on day 4, 24 hours after the second treatment, mice were euthanized with $CO_2$ and then perfused with phosphate-buffered saline (PBS), pH 7.4. Briefly, the mouse chest was opened rapidly, and a syringe with a 20-gauge needle was used to infuse 40 mL of PBS into the aorta via an incision in the left ventricle. Blood and PBS exited through an opening in the right atrium. The 4T1 orthotopic tumors were removed and immersed in 10% neutral buffered formalin at 4° C. After 2 hours the tissues were rinsed 3 times with PBS and then transferred in 30% sucrose in PBS overnight. The next day the tumors were frozen in OCT compound and stored at −80 C.

20-μm-think serial sections of each tumor were cut. Sections were dried on Superfrost Plus slides (VWR) for 1 to 2 hours. Specimens were permeabilized with PBS containing 0.3% Triton X-100 and incubated in 5% goat normal serum in PBS 0.3% Triton X-100 (blocking solution) for 1 hour at room temperature to block nonspecific antibody binding. After 1 hour the blocking solution was removed and the sections were incubated in the primary antibodies overnight. To detect NK cells, sections were incubated with rat anti-NKp46 (CD335; Biolegend, cat #137602) diluted 1:500 in blocking solution. To detect PD-L1, sections were incubated with rat anti-PD-L1 (eBioscience, cat #14-5982-82) diluted 1:500 in blocking solution. To detect CD3+ T cells, sections were incubated with hamster anti-CD3 antibody (BD biosciences, cat #553058) at 1:500 in blocking solution. NK cells, and PD-L1 staining were performed in serial sections, as all these primary antibodies were generated in rat. Secondary antibody only negative control specimens were incubated in 5% normal serum rather than primary antibodies.

The next day, after rinsing with PBS containing 0.3% Triton X-100, specimens were incubated for 4 hours at room temperature with Alexa Fluor 594-labeled goat anti-rat (Jackson Immuno Research, cat #112-585-167) and Alexa Fluor 488-labeled goat anti-hamster (Jackson Immuno Research, cat #127-545-160), secondary antibodies diluted 1:400 in PBS. After, specimens were rinsed with PBS containing 0.3% Triton X-100, then were fixed in 1% paraformaldehyde (PFA), rinsed again with PBS, and mounted in Vectashield with DAPI (Vector, H-1200). DAPI was used to label the cell nuclei.

Specimens were examined with a Zeiss Axiophot® 2 plus fluorescence microscope equipped with an AxioCam® HRc camera. Representative images for each experimental group showing the amount and distribution of the NKp46+, CD3+, and PD-L1+ cells within the tumor were collected and are shown in FIGS. 12-14.

In 4T1 tumors from mice injected with Fc-G1 control antibody, minimal scattered NKp46+ NK cells were detected within the tumor (FIG. 12, top panels). Administration of the rabbit anti-asialo GM1 antibody dosed at 50 mg/kg reduced the number of NKp46+ NK cells compared to control (FIG. 12, second panels). After treatment with anti-FGFR2 at 10 mg/kg for 4 days the NKp46+ NK cells were more numerous. (See FIG. 12, third panels.) But this increase was not observed when anti-FGFR2 was combined with rabbit anti-asialo GM1 antibody and anti-FGFR2. After combination treatment the number of infiltrating NKp46+ NK cells was comparable to the control (FIG. 12, fourth panels).

The CD3 staining revealed that in 4T1 tumors treated with control for 4 days, few sparse CD3+ T cells were found within the tumor and most of them were located at the tumor periphery (FIG. 13, top panels). Treatment with the rabbit anti-asialo GM1 antibody dosed at 50 mg/kg did not impact the number of CD3+ T cells compared to control (FIG. 13, second panels). After treatment with anti-FGFR2 at 10 mg/kg for 4 days the number of infiltrating CD3+ T cells was increased (FIG. 13, third panels). By comparison, when anti-FGFR2 was combined with the rabbit anti-asialo GM1 antibody the number of infiltrating CD3+ T cells was comparable to the control (FIG. 13, fourth panels).

The PD-L1 staining revealed that in 4T1 tumors treated with control for 4 days, PD-L1 immunoreactivity was found only in sparse cells within the tumors (FIG. 14, top panels). Treatment with the rabbit anti-asialo GM1 antibody did not impact PD-L1 immunoreactivity (FIG. 14, second panels). Treatment with anti-FGFR2 alone increased the number of PD-L1 positive cells (FIG. 14, third panels) but when anti-FGFR2 was given in combination with the rabbit anti-asialo GM1 antibody the PD-L1 staining was similar to the control (FIG. 14, fourth panels).

Example 4b: Inhibition of Tumor Growth from an Anti-FGFR2 Antibody is Attenuated in the Presence of an NK Cell Depletion Agent This experiment studied the effect of depleting NK cells on anti-FGFR2 efficacy in the 4T1 syngeneic tumor model. Breast tumor line 4T1 from mouse strain BALB/cfC3H was used as the tumor model and was obtained from ATCC (Manassas, Va., USA: Catalog No. CRL-2539). The cells were cultured at 37° C. in RPMI 1640 Medium (Mediatech, Inc., Manassas, Va., USA; Cat. No. 10-041-CV) with 10% fetal bovine serum, 2 mM L-glutamine and 1% Penn/Strep.

Each mouse was inoculated with $5 \times 10^4$ 4 T1 cells by orthotopic injection under the $4^{th}$ mammary papilla (teat) from the head of the mouse. Mouse tumor volumes and body weights were then regularly monitored until tumor volumes measured 100 mm$^3$+/−25 mm$^3$. Once tumors reached 100 mm$^3$+/−25 mm$^3$, mice were sorted according to tumor size into four groups for dosing (day 0). Group 1 was dosed with PBS as control (intraperitoneally (IP), on day 0 and 3). Group 2 was dosed with 50 mg/kg rabbit anti-asialo GM1 antibody (Wako Chemicals, Osaka, Japan) i.v. once on day 0, an antibody designed to deplete NK cells in BalbC mice. Group 3 was dosed with 10 mg/kg of anti-FGFR2 (IP on day 0 and day 3). Group 4 was dosed with 50 mg/kg rabbit anti-asialo GM1 antibody (day 0) combined with 10 mg/kg anti-FGFR2 (IP on day 0 and day 3) and tumor volume was monitored biweekly.

Overall, treatment with anti-FGFR2 results in a ~35% inhibition (P<0.01) of tumor growth compared to the PBS control group and the anti-asialo GM1 antibody group (P<0.05). Treatment with anti-asialo GM1 antibody had no effect on tumor burden compared to the PBS control group. The combination of anti-asialo GM1 antibody with anti-FGFR2 resulted in attenuation of tumor growth inhibition compared to the anti-FGFR2 group (P<0.05) suggesting that NK cells and ADCC activity are integral in promoting tumor growth inhibition in the 4T1 syngeneic tumor model. Combined with the histology data, anti-FGFR2 inhibits 4T1 tumor burden via modifying the tumor microenvironment through the innate and adaptive immune system.

Example 4c: Anti-FGFR2-Driven Tumor Growth Inhibition is Blunted in CB17 SCID Mice which Lack an Adaptive Immune System Female CB17 SCID mice of eight weeks old were purchased from Charles River Laboratories (Wilmington, Mass., USA). The animals were given at least a 3-day acclimation upon arrival and were housed 5 animals per cage with free access to food and water. Once acclimated, they were weighed, and shaved prior to tumor cell implantation.

Syngeneic breast tumor line 4T1 from mouse was used as the tumor model and was obtained from ATCC (Manassas, Va., USA: Catalog No. CRL-2539). The cells were cultured at 37° C. in RPMI 1640 Medium (Mediatech, Inc., Manassas, Va., USA; Cat. No. 10-041-CV) with 10% fetal bovine serum, 2 mM L-glutamine and 1% Penn/Strep is this penicillin and streptomycin Each mouse was inoculated with $5\times10^4$ 4 T1 cells by orthotropic injection under the $4^{th}$ mammary papilla (teat) from the head of the mouse. Mouse tumor volumes and body weights were then regularly monitored until tumor volumes measured 80 mm$^3$+/−25 mm$^3$. On day 12, once tumors reached 80 mm$^3$+/−25 mm$^3$ mice were sorted according to tumor size into two groups for dosing. The first group was dosed with Vehicle control, the second group with 20 mg/Kg of afucosylated anti-FGFR2 antibody (intraperitoneally (IP), on day 12 and 15).

In contrast to the ~30%, P<0.001 reduction in tumor volume in BalbC mice (Example 1), treatment with the anti-FGFR2 antibody results in a ~20% inhibition, P<0.05 of tumor growth compared to the vehicle control in CB17 SCID mice harboring an intact innate immune system (NK Cells and macrophages) but devoid of adaptive immune cell components (T Cells and B Cells).

These data suggest that the anti-FGFR2 antibody can stimulate innate immune cells to initiate immediate tumor cell killing, yet CB17 SCID mice demonstrate a blunted response to anti-FGFR2 antibody treatment likely because they cannot engage the adaptive immune system. This further demonstrates that the anti-FGFR2 antibody works in concert with the innate and adaptive immune system to drive changes in the tumor microenvironment that result in sustained tumor growth inhibition in immune competent mice.

Example 5: Open-Label, Phase I Study of Cancer Patients with Advanced Solid Tumors Treated with an Anti-FGFR2 Antibody In a dose-escalating study of an afucosylated FGFR2 antibody comprising the heavy and light chain HVRs of SEQ ID NOs: 6-11, about 30 patients with any locally advanced or metastatic solid tumor or lymphoma and for which standard therapies have been exhausted are treated every 2 weeks in 28-day cycles with the antibody. In Part 1A of the study, six cohorts of patients are administered six different dose levels in a dose-escalation study: 0.3 mg/kg, 1 mg/kg, 3 mg/kg, 6 mg/kg, 10 mg/kg, and 15 mg/kg. Patients are assessed for any occurrence of dose-limiting toxicities in a 28 day cycle. Further 28-day cycles may follow if clinically indicated.

In Part 1B, further safety and efficacy evaluations are conducted in up to 30 gastric cancer patients and/or in patients who are known to be FGFR2 gene-amplified or FGFR2b protein-overexpressed. Subjects in this part will initially receive one dose level below the current highest dose level of the six cohorts in Part 1A, i.e. 0.3, 1, 3, or 10 mg/kg, with escalation to 15 mg/kg in Part 1B possible if no maximum tolerated dose is identified in Part 1A.

Once a reference dose is identified in Parts 1A and 1B of the study, Part 2 will commence. Part 2 includes patients with histologically documented gastric or gastroesophageal cancer or other histologically or cytologically confirmed solid tumor types with (a) FGFR2b overexpression with FGFR2 amplification; (b) FGFR2b overexpression without FGFR2 amplification, or (c) FGFR2b non-overexpression, and with locally recurrent or metastatic disease that has progressed following standard treatment or is not appropriate for standard treatment, and also with measureable disease as defined by RECIST version 1.1. Patients are grouped into three cohorts. About 30 patients have gastric cancer with both FGFR2b overexpression (determined to be 3+ by IHC analysis) and FGFR2 gene amplification (ratio of FGFR2 vs. CEN10 of ≥2 as determined by FISH analysis). About 30 patients have gastric cancer with FGFR2b overexpression (IHC 3+) but in the absence of FGFR2b gene amplification (FISH ratio of approximately 1). About 10 patients do not have FGFR2b overexpression (IHC analysis of 0 to 2+).

The detailed objectives, protocol, and inclusion/exclusion criteria for the study are as follows:

The primary objectives are to evaluate the safety profile of escalating doses of the antibody in patients with advanced solid tumors, and to determine the maximum tolerated dose (MTD) and recommended dose (RD) (Part 1A); and to evaluate the safety profile of escalating doses of antibody in patients with advanced gastric or gastroesophageal cancer (Part 1B), collectively referred to as "gastric cancer" herein. Secondary objectives are: (a) to characterize the PK profile of single and multiple doses of intravenously administered antibody in gastric cancer patients and in other solid tumor patients; (b) to evaluate the safety and tolerability of longer term exposure to antibody administered; (c) to evaluate the objective response rate (ORR) in patients with FGFR2b-selected gastric cancer (Part 2 only); and (d) to evaluate duration of response in responding patients with FGFR2b-selected gastric (Part 2 only).

Some exploratory objectives are: to evaluate the stable disease rate and duration in patients with FGFR2b overexpressing gastric tumors, either in the presence or absence of FGFR2 amplification (Part 2 only); to assess progression-free survival (PFS) in patients with FGFR2b overexpressing gastric tumors, either in the presence or absence of FGFR2 amplification (Part 2 only); and (c) to explore the association between extent of FGFR2b overexpression and FGFR2 amplification in tumor tissue and clinical outcome.

This is a three-part, open-label, safety, tolerability, and PK study. Patients are enrolled into either Part 1 (A or B), or Part 2 of the study, but not both Part 1 and 2. After an initial screening period of up to 28 days (4 weeks), patients are treated with the antibody every 2 weeks in 28-day cycles. In Part 1A, each enrolled patient is observed for 28 days for safety assessments and occurrence of dose-limiting toxicities (DLT Observation Period). Additional treatments may be administered every 2 weeks in 28 day cycles thereafter as clinically indicated (Extended Treatment Period). In Part 1B, patients are treated every 2 weeks in 28-day cycles at the current Part 1A DLT-cleared dose levels. In Part 2, patients are treated with anti-FGFR2 antibody every 2 weeks in 28-day cycles at a recommended dose (RD) selected after assessment of data obtained in Parts 1A and 1B.

Part 1A is a dose-escalation study in patients with any locally advanced or metastatic solid tumor or lymphoma for which standard therapies have been exhausted. Approximately 6 dose cohorts are anticipated, with a minimum of 3 patients enrolled in each cohort. The anticipated dose levels are: 0.3 mg/kg, 1 mg/kg, 3 mg/kg, 6 mg/kg, 10 mg/kg, and 15 mg/kg. Review of safety and PK parameters may inform decisions to add cohorts with alternative dose levels or dose regimens (e.g. less frequent dosing) in order to reach an optimal target exposure. All dose escalation decisions are based on assessment of DLTs, overall safety, and tolerability and will be made after the last patient enrolled in each cohort has completed the first treatment cycle. Dose escalation decisions will be agreed upon by the Cohort Review Committee (CRC), consisting of the Sponsor and Investigators. The maximum tolerated dose (MTD) is defined as the maximum dose at which <33% of patients experience a DLT during Cycle 1 (Safety and PK Assessment Period). If a DLT is observed in 1 of 3 patients, then 3 additional patients will be enrolled at that same dose level. Dose escalation may continue until 2 of 3-6 patients treated at a dose level experience a DLT. The next lower dose is then considered the MTD. Alternatively, an intermediate dose between the last cleared dose level and the dose level resulting in >33% DLTs may be explored before concluding that the MTD has been reached. Once the MTD or RD has been reached, 3-10 additional gastric cancer patients may be added prior to commencing Part 2, to further explore the safety and PK at this dose level.

The following algorithm is used for Part 1A dose escalation decisions:

| Number of Patients with DLTs | Action |
| --- | --- |
| 0/3 | Open next cohort |
| 1/3 | Enroll 3 more patients in same cohort |
| ≥2/3 | Stop enrollment. Enter 3 more patients at dose level below, if only 3 were previously entered |
| 1/6 | Open next cohort |
| ≥2/6 | Stop enrollment. Enter 3 more patients at dose level below, if only 3 were previously entered. |

In the event no MTD is identified yet drug exposures exceed those deemed necessary based on nonclinical pharmacology data or the clinical PK profile, the Sponsor and Investigators may decide to discontinue dose escalation.

On completion of Cycle 1 (Safety and PK Assessment Period), Part 1A patients may participate in an optional Extended Treatment Period, which begins on Day 1 of Cycle 2. Anti-FGFR2 antibody is administered every 2 weeks in 4-week cycles until disease progression, unacceptable toxicity, patient or physician request to discontinue, death, or termination of the study.

The purpose of Part 1B is to further assess safety and evaluate PK of the anti-FGFR2 antibody in gastric cancer patients prior to commencing Part 2. Clearance of some antibodies (e.g., bevacizumab and trastuzumab) has been shown to be more rapid in gastric cancer patients than in patients with other solid tumors. Enrolled patients may be gastric cancer patients whose tumors will be tested retrospectively, or those who are known to be FGFR2 gene-amplified or FGFR2b protein-overexpressed. In a staggered fashion with Part 1A dose escalation, patients in Part 1B are enrolled one dose level below the current highest dose level cohort being studied in Part 1A. For example, if the current dose level in Part 1A being studied is 3 mg/kg, enrollment of Part 1B patients will be at the 1 mg/kg dose level; if the current dose level being studied in Part 1A is 6 mg/kg, enrollment of Part 1B patients will be at the 3 mg/kg dose level.

In Part 1B, approximately 3 patients may be enrolled at each dose level, with an election by the Sponsor and investigators to enroll up to 6 patients per dose cohort. Dose escalation may continue in Part 1B up to 15 mg/kg if no MTD in Part 1A is identified.

Enrollment in Part 2 begins when a recommended dose (RD) has been identified by the CRC, based on overall safety, tolerability, PK, and estimates of efficacious exposures extrapolated from nonclinical data. The RD may or may not be the same as the MTD identified in Part 1A. For example, if the MTD is not reached, or if exposure at the MTD is much higher than the level believed to be required for efficacy, or if data from Part 1B patients or subsequent cycles of treatment from both Parts 1 (A and B) provide additional insight on the safety profile, then the RD may be a different, though not higher, dose than the MTD. Once the RD has been established, patients with gastric cancer selected based on FGFR2b expression are enrolled in Part 2 of the study. Part 2 patients are enrolled and treated in order to further characterize safety and preliminary efficacy in a selected cancer patient population with the greatest potential for clinical benefit from antibody treatment. Treatment may continue until disease progression, unacceptable toxicity, patient or physician decision to discontinue, death, or termination of the study.

Patients enrolling into Part 1(A or B) or Part 2 must meet all of the following inclusion criteria:
1) Understand and sign an Institutional Review Board/Independent Ethics Committee-approved informed consent form prior to any study-specific evaluation;
2) Life expectancy of at least 3 months;
3) ECOG performance status of 0 to 1;
4) Age ≥18 years at the time the informed consent form is signed except for the patients in Taiwan, where the patient's age must be ≥20 at the time the informed consent form is signed;
5) In sexually-active patients (i.e., females of child bearing potential, who have not undergone menopause as defined by 12 consecutive months of amenorrhea or had a permanent sterilization procedure and males, who have not had a permanent sterilization procedure), willingness to use 2 effective methods of contraception, of which one must be a physical barrier method (condom, diaphragm, or cervical/vault cap) until 6 months after the last dose of anti-FGFR2 antibody. Other effective forms of contraception are permanent sterilization (hysterectomy and/or bilateral oophorectomy, or bilateral tubal ligation with surgery, or vasectomy) at least 6 months prior to Screening. Female patients of childbearing potential must be on stable oral contraceptive therapy or intrauterine or implant device for at least 90 days prior to the study, or abstain from sexual intercourse as a way of living.
6) Adequate hematological and biological function, confirmed by the following laboratory values:
   a) Bone Marrow Function
      i) ANC≥1.5×10$^9$/L
      ii) Platelets >100×10$^9$/L
      iii) Hemoglobin ≥9 g/dL
   b) Hepatic Function
      i) Aspartate aminotransferase (AST) and alanine aminotransferase (ALT)≤3× upper limit of normal (ULN); if liver metastases, then ≤5×ULN
      ii) Bilirubin ≤1.5×ULN
   c) Renal Function
      i) Serum creatinine ≤1.5×ULN
7) Tumor tissue available for determination of FGFR2b expression and FGFR2 amplification (optional for Part 1A patients).

Patients enrolling into Part 1A (Dose-Escalation) of the study must also meet the following inclusion criteria:
8) Histologically or cytologically confirmed solid tumor or lymphoma that is locally recurrent or metastatic and has progressed following standard treatment or is not appropriate for standard treatment;
9) Measurable or Non-measurable disease.

Patients enrolling into Part 1B of the study must also meet the following inclusion criteria:
10) Histologically documented gastric or gastroesophageal cancer;
11) Tumor tissue for prospective or retrospective determination of FGFR2b expression and FGFR2 amplification;
12) Locally recurrent or metastatic disease that has progressed following standard treatment or is not appropriate for standard treatment;
13) Measurable disease as defined by RECIST version 1.1.

Patients enrolling into Part 2 (Dose-Expansion) of the study must also meet the following inclusion criteria:
14) Histologically documented gastric or gastroesophageal cancer with
   a) FGFR2b overexpression with FGFR2 amplification, or
   b) FGFR2b overexpression without FGFR2 amplification, or
   c) FGFR2b non-overexpression;
15) Locally recurrent or metastatic disease that has progressed following standard treatment or is not appropriate for standard treatment;
16) Measurable disease as defined by RECIST version 1.1.

Patients enrolling into Part 1(A or B) or Part 2 will be excluded if any of the following criteria apply:
1) Untreated or symptomatic central nervous system (CNS) metastases. Patients with asymptomatic CNS metastases are eligible provided they have been clinically stable for at least 4 weeks and do not require intervention such as surgery, radiation or any corticosteroid therapy for management of symptoms related to CNS disease.
2) Impaired cardiac function or clinically significant cardiac disease, including either of the following:
   a) Unstable angina pectoris ≤6 months prior to first scheduled dose of antibody
   b) Acute myocardial infarction ≤6 months prior to first scheduled dose of antibody
3) QTc segment >470 msec
4) Known human immunodeficiency virus (HIV) or acquired immunodeficiency syndrome (AIDS)-related illness, or history of chronic hepatitis B or C.
5) Treatment with any anticancer therapy or participation in another therapeutic clinical study with investigational drugs ≤14 days (≤28 days for patients in Korea) prior to first dose of antibody.
6) Ongoing adverse effects from prior treatment >NCI CTCAE Grade 1.
   a) Retinal disease or a history of retinal disease or detachment or, in the ophthalmologist's opinion, increased risk for retinal detachment
   b) Current evidence or previous history of retinal vein occlusion (RVO), or central serous retinopathy.
   c) Glaucoma diagnosed within 1 month prior to Study Day 1.
   d) Ongoing medical therapy for glaucoma.
   e) Previous intra-ocular injection or laser treatment for macular degeneration.
   f) Corneal defects, corneal ulcerations, keratitis, keratoconus, history of corneal transplant, or other known abnormalities of the cornea that may, in the opinion of an ophthalmologist, pose a risk with anti-FGFR2 antibody treatment.
   g) NSCLC patients with exon 19 or 21 EGFR mutation or ALK amplification who have not received an EGFR or ALK TKI, respectively (Part 1A only).
   h) Gastric and breast cancer patients with HER2 overexpression who have not received anti-HER2 targeted therapy.
   i) Major surgical procedures are not allowed 28 days prior to anti-FGFR2 antibody administration. In all cases the patient must be sufficiently recovered and stable before treatment administration.
   j) Females who are pregnant or breastfeeding; women of childbearing potential must not be considering getting pregnant during the study.
   k) Presence of any serious or unstable concomitant systemic disorder incompatible with the clinical study (e.g., substance abuse, psychiatric disturbance, or uncontrolled intercurrent illness including active infection, arterial thrombosis, and symptomatic pulmonary embolism).
   l) Presence of any other condition that may increase the risk associated with study participation or may interfere with the interpretation of study results, and, in the opinion of the Investigator, would make the patient inappropriate for entry into the study.
7) Known allergy or hypersensitivity to components of the anti-FGFR2 antibody formulation including polysorbate.
8) History of prior malignancy except:
   a) Curatively treated non-melanoma skin cancer or
   b) Solid tumor treated curatively more than 5 years previously without evidence of recurrence or
   c) History of other malignancy that in the Investigator's opinion would not affect the determination of study treatment effect.
9) In Part 1B and 2 (Dose Expansion), prior treatment with any selective inhibitor (e.g., AZD4547, BGJ398, JNJ-42756493, BAY1179470) of the FGF-FGFR pathway.

No waivers of these inclusion or exclusion criteria will be granted.

Part 2 will involve the following study cohorts A, C, D, E, and F. Cohort A will involve about 30 patients with gastric cancer with strong FGFR2b overexpression defined as IHC 3+≥10% tumor membrane staining Cohort C will involve about 10-30 gastric cancer patients without FGFR2b overexpression, as defined by IHC=0. Cohorts D-F may also be included. Cohort D will involve about 30 patients with gastric cancer with moderate FGFR2b overexpression defined as IHC 2+≥10% and/or IHC 3+<10% tumor membrane staining Cohort E will involve about 30 patients with gastric cancer with low FGFR2b overexpression defined as IHC 1+ and/or IHC 2+<10% tumor membrane staining Cohort F will involve about 30 non-gastric solid tumor patients per each tumor type tested. For bladder cancer patients, there will be two subgroups. Subgroup 1 will have H scores for FGFR2b of 10-19 and subgroup 2 will have H scores for FGFR2b of 20 or greater.

Study medication: Anti-FGFR2 antibody is supplied in a sterile vial for dilution into an intravenous bag for administration by the study site. In Part 1A, patients receive 2 doses of anti-FGFR2 antibody, 2 weeks apart. If this is tolerated without disease progression by the end of the first cycle, patients are eligible to continue on study in the Extended Treatment Period and receive anti-FGFR2 antibody every 2 weeks until disease progression or other cause for study withdrawal.

Dose adjustments: Dose reductions may be permitted for patients on treatment beyond the DLT period in Part 1A or any patient in Parts 1B or 2 upon discussion with and approval by the Sponsor. Patients may miss up to 2 consecutive doses (up to 6 weeks between doses) for adverse or other events; omission of additional dosing longer than 6 weeks for adverse or other events will necessitate the patient's removal from the study unless allowed by the study Sponsor. Intra-patient dose escalation above the starting dose for each patient in Part 1 (A and B) and Part 2 will not be permitted. If a patient's dose is decreased for a reason that is no longer relevant, dose escalation to the originally assigned dose may occur after discussion and approval by the Sponsor.

Concomitant Medications: Supportive care (e.g., antiemetics; analgesics for pain control) may be used at the Investigator's discretion and in accordance with institutional procedures. Hematopoietic stimulating agents may be used if indicated. Concomitant anticancer therapies of any kind are not permitted except chronic maintenance therapies, such as luteinizing hormone releasing hormone (LHRH)-modulating agents for breast or prostate cancer, which may be continued if the patient has been on these agents and 1) continued use is unlikely to result in additional reduction in tumor measurements and 2) is considered standard therapy for the patient.

Withdrawal: A patient must be discontinued from protocol-prescribed therapy if any of the following apply:
 Consent withdrawal at the request of the patient or their legally authorized representative;
 Progression of patient's disease. Patients who are receiving clinical benefit despite isolated disease progression may continue on study after discussion with Medical Monitor;
 Any event that would pose an unacceptable safety risk to the patient;
 A concurrent illness that would affect assessments of the clinical status to a significant degree;
 A positive pregnancy test at any time during the study;
 At the specific request of the Sponsor or its authorized representative (e.g., if the study is terminated for reasons of patient safety.

Pharmacokinetic assessments: Patients enrolled in Parts 1A and 1B have blood sampling for measurement of serum anti-FGFR2 antibody concentration during Cycle 1 Days 1, 2, 4, and 8. In addition, blood samples are collected both before and at the end of the infusion at Cycle 1 Day 15 and Cycles 2-5 Day 1 and every other cycle Day 1 starting from Cycle 5 as well as at the end of treatment. For patients in Part 2, Cycle 1 blood samples are collected both before and at the end of the Day 1 infusion, and on Day 8. Blood samples are collected on Cycle 1 Day 15 and Cycles 2-5 Day 1 and every other cycle Day 1 starting from Cycle 5 both before and at the end of each infusion as well as the end of treatment to explore the PK in the selected gastric cancer patients with FGFR2b overexpressing tumors with or without FGFR2 amplification. Standard PK parameters are determined based on serum anti-FGFR2 antibody concentration-time data.

Immunogenicity: All patients in the study have blood samples collected prior to dosing on Day 1 of Cycles 1-5 and every over cycle from Cycle 5 for measurement of antibodies against the anti-FGFR2 antibody.

Efficacy assessments: Efficacy measures include tumor assessments consisting of clinical examination and appropriate imaging techniques, preferably computed tomography (CT) scans of the chest, abdomen, and pelvis with appropriate slice thickness per RECIST; other assessments (magnetic resonance imaging [MRI]), X-ray, positron emission tomography (PET), and ultrasound) may be performed, if required. Tumor assessments are performed at Screening, then every 6 weeks from the first dose, for 24 weeks, and then approximately every 12 weeks thereafter. Once an initial complete response (CR) or partial response (PR) is noted, confirmatory scans must be performed 4-6 weeks later.

Safety assessments: Safety measures include AEs, hematology, clinical chemistry, urinalysis, vital signs, body weight, concomitant medications/procedures, ECOG performance status, targeted physical exams, ECGs, ophthalmology/retinal examinations, and anti-FGFR2 antibody dose modifications.

The total enrollment planned for this study is approximately 100-130 patients: approximately 20-30 patients are enrolled into Part 1A. In Part 1B, up to 30 patients with gastric cancer are enrolled. For Part 2, exploratory activity is examined by enrollment of one or more of:
 Cohort A: Approximately 30 patients with gastric cancer with both FGFR2b overexpression (IHC 3+) and FGFR2 amplification (FISH≥2 ratio);
 Cohort B: Approximately 30 patients with gastric cancer with FGFR2b overexpression (IHC 3+) in the absence of FGFR2 amplification (FISH ratio=1), to help characterize the predictive importance of FGFR2 selection.
 Cohort C: About 10-30 gastric cancer patients without FGFR2b overexpression, as defined by IHC=0 to 2+.
 Cohort D: About 30 patients with gastric cancer with moderate FGFR2b overexpression defined as IHC 2+≥10% and/or IHC 3+<10% tumor membrane staining
 Cohort E: About 30 patients with gastric cancer with low FGFR2b overexpression defined as IHC 1+ and/or IHC 2+<10% tumor membrane staining
 Cohort F: About 30 non-gastric solid tumor patients per each tumor type tested. For bladder cancer patients, there will be two subgroups. Subgroup 1 will have H scores for FGFR2b of 10-19 and subgroup 2 will have H scores for FGFR2b of 20 or greater.

Example 6: Treatment of a Urinary Bladder Cancer Patient with an Anti-FGFR2 Antibody This example describes treatment of a 76 year old male enrolled in the above study (see Example 5) who had been diagnosed with bladder cancer in July 2014 after presenting to his primary physician with hematuria with the afucosylated FGFR2 antibody comprising the heavy and light chain HVRs of SEQ ID NOs: 6-11 of the study described in Example 5. The patient had a diagnostic cystoscopy and biopsy and, subsequently, underwent resection of the primary tumor. He was staged as T2, N2, M0—tumor penetrating into the muscle wall and 3 of 6 sampled lymph nodes were positive—making him a stage 4 subject. He received 4 cycles of gemcitabine and cisplatin (SOC) in the adjuvant setting. In March 2015, about 6 months after completion of the adjuvant chemotherapy, the patient had a routine surveillance PET and CT. The CT demonstrated multiple enlarged lymph nodes in the pelvis and retroperitoneum, while the PET confirmed that these were metabolically active and consistent with recurrent, metastatic urinary bladder cancer (UBC). The patient began receiving the anti-FGFR2 antibody at a dose of 3 mg/kg approximately every two weeks. The largest lymph node for size and overall adenopathy was then tracked. Upon initial screening and first anti-FGFR2 dose in April 2015, the largest lymph node was 18×12 mm. Six weeks later, the largest node measured 15×11 mm, and 12 weeks later, it was 9×7 mm in size, thus diminishing by about one-half. In August 2014 no appreciable adenopathy had been observed. Subsequent re-staging scans have confirmed no appreciable lymphadenopathy and a PET performed in November 2015 showed no abnormal metabolic activity. The patient currently continued on the anti-FGFR2 antibody therapy.

Example 7: Immunohistochemistry Analysis of Urinary Bladder Cancer Samples for FGFR2b Overexpression To assess the frequency of FGFR2b overexpression in the bladder cancer population, immunohistochemistry (IHC) was used. Immunohistochemistry (IHC) was performed on normal bladder and archival urothelial cancer (UC) samples using a murine αFGFR2b antibody comprising the murine variable regions of GAL-FR21 (see U.S. Pat. No. 8,101,723 B2). 422 formalin-fixed paraffin-embedded UC sections, both primary and metastatic, whole section or in tissue microarray format, were stained and detected using a chromogenic substrate. Membranous tumor cell staining intensity was scored on a scale of 0-3, in which a score of "0" is given if no reactivity is observed or if there is membranous reactivity only in <10% of tumor cells; a score of "1+" is given if there is faint or barely perceptible membranous reactivity in at least 10% of tumor cells or if the cells are reactive only in a part of their membranes; a score of "2+" is given if there is weak to moderate complete, basolateral or lateral membranous reactivity in at least 10% of tumor cells; and a score of "3+" is given if there is strong complete basolateral or lateral membranous reactivity in at least 10% of tumor cells. Tumors with 1+ membranous reactivity in ≥10% of tumor cells were considered positive in this experiment.

Normal bladder has weak staining of the transitional epithelium (<1+). However, IHC analysis of the 422 archival primary UC samples showed that FGFR2b is overexpressed in >10% of samples with expression intensity of at least 1+.

Furthermore, the anti-FGFR2-responsive bladder cancer patient's (see Example 6) primary tumor sample from a surgical resection had 15% 2+ IHC staining and 35% 1+ staining with the FPR2-D antibody. This is in contrast to prior data from gastric cancer patients, in which patient tumor samples with 3+ staining were selected and have seen objective responses. The response of this patient to the anti-FGFR2 antibody (see Example 6) and the positive IHC staining in UC samples collectively suggest that that bladder cancer is an additional indication that may be sensitive to anti-FGFR2 antibody treatment.

Example 8: Open-Label Phase I Study of an Anti-FGFR2 Antibody in Combination with Nivolumab in Patients with Advanced Solid Tumors A two-part, open-label, multicenter, dose escalation and dose expansion study will be conducted to evaluate the safety, tolerability, pharmacokinetics (PK), pharmacodynamics (PD), and preliminary efficacy of an afucosylated FGFR2 antibody comprising the heavy and light chain HVRs of SEQ ID NOs: 6-11 in combination with nivolumab in patients with advanced solid tumors. Each part of the study will consist of 3 periods: screening (up to 28 days), treatment, and follow-up (up to 100 days). Anti-FGFR2 antibody and nivolumab will be given on Day 1 of each 14-day treatment cycle. Anti-FGFR2 antibody will be administered as an IV infusion over 30 minutes followed by a 30-minute rest, and then nivolumab will be administered as an IV infusion over 30 minutes. If any Grade 3 or higher infusion reaction is observed during the infusion of either drug at the proposed infusion rate, the infusion rate will be extended to 60 minutes for all current and subsequent patients for the duration of this study. Following completion of the treatment and follow-up periods of the study, all patients will be followed for survival.

The study will include a Part 1 dose escalation and a Part 2 dose expansion. Part 1 consists of two planned dosing cohorts of anti-FGFR2 antibody in combination with nivolumab in patients with gastric or gastroesophageal junction cancer (referred to collectively as gastric cancer). Phenotypic characterization will not be required for study entry into the dose escalation part of this study, but will be performed retrospectively. This phenotypic characterization will include, but is not limited to, analysis for the expression of FGFR2b and PD-L1 by immunohistochemistry (IHC). Each patient enrolled in Part 1 will be observed for 28 days (or upon completion of two 14-day cycles) for safety assessments and occurrence of dose-limiting toxicities (DLT Observation Period). Upon the first occurrence of a delayed DLT in any patient enrolled in Part 1 (defined as any AE that occurs between 4 to 6 weeks after administration of study drug), all ongoing and subsequent DLT periods will be expanded to 42 days (or upon completion of three 14-day cycles) for all remaining and subsequent patients enrolled in Part 1. Additional treatments may be administered every 2 weeks in 14-day cycles thereafter as clinically indicated (Extended Treatment Period).

Part 2 consists of two expansion cohorts in patients with advanced gastric cancer. Enrollment into Part 2 of the study will require prospective IHC analysis of FGFR2b expression, using a validated assay. Patients whose tumors are positive for FGFR2b by IHC will be permitted to enroll, provided other eligibility criteria are met. The two cohorts in Part 2 of the study will be defined by level of IHC-positivity for FGFR2b in the patient's tumor. Cohort 2a will include patients whose tumors stain with intensity of 1+ or 2+ in at least 10% of the tumor cells. Cohort 2b will include patients whose tumors stain with intensity of 3+ in at least 10% of the tumor cells. Opening of each of these cohorts will be at the discretion of the sponsor. The Part 2 dose expansion portion of the study is open-label. Patients meeting all of the eligibility criteria will be treated every 2 weeks in 14-day cycles with anti-FGFR2 antibody in combination with 3 mg/kg of nivolumab at a recommended dose (RD) selected after assessment of data obtained in Part 1. Patients will be enrolled into either Part 1 or Part 2 of the study, but not both.

In Part 1, two dose cohorts are anticipated, with a minimum of 6 gastric cancer patients enrolled in each cohort. The planned dose levels are as follows; the first patient will be enrolled in Dose Level 1:

Dose level −1: 6 mg/kg anti-FGFR2 antibody+3 mg/kg nivolumab (q2w)

Dose level 1: 10 mg/kg anti-FGFR2 antibody+3 mg/kg nivolumab (q2w)

Dose level 2: 15 mg/kg anti-FGFR2 antibody+3 mg/kg nivolumab (q2w)

All dose escalation decisions will be based on assessment of DLTs, overall safety, and tolerability and will be made after the last subject enrolled in each cohort has completed the prescribed DLT Observation Period. Dose escalation decisions will be agreed upon by the Cohort Review Committee (CRC), consisting of the Sponsor and Investigators. Review of safety and PK parameters may inform decisions to add cohorts with alternative dose levels in order to reach an optimal target exposure. Dose Level −1 will only be interrogated if DLTs are observed at Dose Level 1 that require an examination of a lower dose of anti-FGFR2 antibody. The highest dose level with ≤1 DLT observed will be deemed the recommended phase 2 dose (RP2D). An additional 8 patients will be enrolled in Part 1 of the study following the identification of the RP2D. The enrollment for Part 1, therefore, will be approximately 20 patients.

On completion of the DLT Observation Period, Part 1 patients may participate in an optional Extended Treatment Period, which begins on Day 1 of Cycle 2. Anti-FGFR2 antibody will continue to be administered in combination with nivolumab at the same dose levels every 2 weeks in 4-week cycles until disease progression, unacceptable toxicity, patient or physician request to discontinue, death, or termination of the study.

To further characterize the safety and efficacy of anti-FGFR2 antibody in combination with nivolumab, Part 2 will enroll approximately 40 advanced gastric cancer patients, within two cohorts, 20 patients per cohort. These two cohorts will differ in the degree of IHC positivity of the tumor for FGFR2b. Patients whose tumors are scored as 1+ or 2+ in ≥10% of tumor cells by central review (low or moderate over-expression) will be placed in Cohort 2A; patients whose tumors are graded as 3+≥10% of tumor cells will be enrolled in Cohort 2B. Enrollment in Part 2 will begin when a recommended dose (RD) has been identified by the CRC, based on overall safety and tolerability. The RD may or may not be the same as the MTD identified in Part 1. Anti-FGFR2 antibody will be administered in combination with nivolumab at the RD every 2 weeks in 4-week cycles until disease progression, unacceptable toxicity, patient or physician request to discontinue, death, or termination of the study.

If, after enrollment and evaluation of the first 20 patients, sufficient activity is observed to merit further exploration, enrollment will be open for another 20 patients per cohort. Opening of each cohort and addition of 20 patients to either cohort will be done at the discretion of the sponsor.

Patients enrolled into Part 2 will have their tumor tissue (archival and/or recent) tested retrospectively for PD-L1 expression using a validated immunohistochemistry (IHC) assay. A biopsy at the primary tumor site or metastatic site will be obtained (as feasible) before treatment and on-treatment to examine immune infiltrates and expression of selected tumor markers. An optional biopsy may be obtained of tumors that have responded and/or progressed on or after treatment to understand mechanisms of resistance.

Dose reductions for anti-FGFR2 antibody may be permitted for patients on treatment beyond the DLT period in Part 1 or any patient in Part 2 per the guidelines outlined in the protocol.

Up to approximately 60 subjects from North America and Europe are planned to be enrolled in this study. This includes 20 patients in the Part 1 dose escalation and approximately 40 patients in the Part 2 dose expansion.

Inclusion Criteria

Patients enrolling into Part 1 or Part 2 must meet all of the following inclusion criteria:

1. Understand and sign an Institutional Review Board/Independent Ethics Committee-approved informed consent form prior to any study-specific evaluation
2. Life expectancy of at least 3 months
3. ECOG performance status of 0 to 1
4. Age≥18 years at the time the informed consent form is signed
5. In sexually-active patients (i.e., females of child bearing potential, who have not undergone menopause as defined by 12 consecutive months of amenorrhea or had a permanent sterilization procedure, and males, who have not had a permanent sterilization procedure), willingness to use 2 effective methods of contraception, of which one must be a physical barrier method (condom, diaphragm, or cervical/vault cap) until 6 months after the last dose of anti-FGFR2 antibody. Other effective forms of contraception are permanent sterilization (hysterectomy and/or bilateral oophorectomy, or bilateral tubal ligation with surgery, or vasectomy) at least 6 months prior to Screening. Female patients of childbearing potential must be on stable oral contraceptive therapy or intrauterine or implant device for at least 90 days prior to the study, or abstain from sexual intercourse as a way of living.
6. Adequate hematological and biological function, confirmed by the following laboratory values:
   a) Bone Marrow Function
      ANC≥1.5×10$^9$/L
      Platelets >100×10$^9$/L
      Hemoglobin ≥9 g/dL
   b) Hepatic Function
      Aspartate aminotransferase (AST) and alanine aminotransferase (ALT) ≤3× upper limit of normal (ULN); if liver metastases, then ≤5×ULN
      Bilirubin ≤1.5×ULN
   c) Renal Function
      Serum creatinine ≤1.5×ULN
7. Histologically or cytologically confirmed gastric or gastroesophageal cancer that is locally recurrent or metastatic and has progressed following standard treatment or is not appropriate for standard treatment.

Patients enrolling into Part 1 (Dose Escalation) of the study must also meet the following inclusion criteria:

7. Measurable or evaluable disease

Patients enrolling into Part 2 (Dose-Expansion) of the study must also meet the following inclusion criteria:

8. Measurable disease as defined by RECIST version 1.1
9. Tumor positive for FGFR2b expression as determined by a validated IHC assay
10. Tumor tissue (archival or recent) for retrospective determination of PD-L1 expression Exclusion Criteria Patients enrolling into Part 1 or Part 2 will be excluded if any of the following criteria apply:

1. Untreated or symptomatic central nervous system (CNS) metastases. Patients with asymptomatic CNS metastases are eligible provided they have been clinically stable for at least 4 weeks and do not require intervention such as surgery, radiation or any corticosteroid therapy for management of symptoms related to CNS disease.
2. Impaired cardiac function or clinically significant cardiac disease, including either of the following:
   Unstable angina pectoris 6 months prior to first scheduled dose of anti-FGFR2 antibody
   Acute myocardial infarction 6 months prior to first scheduled dose of anti-FGFR2 antibody
3. QTc segment >470 msec
4. Known history of testing positive for human immunodeficiency virus (HIV) 1 or 2 or known acquired immunodeficiency syndrome (AIDS)
5. Positive test for hepatitis B virus surface antigen (HBsAg) or detectable hepatitis C virus ribonucleic acid (HCV RNA) indicating acute or chronic infection
6. Positive test for latent tuberculosis (TB) at screening (Quantiferon test) or evidence of active TB
7. Symptomatic interstitial lung disease or inflammatory pneumonitis
8. Active, known, or suspected autoimmune disease. Patients with type I diabetes mellitus, hypothyroidism requiring only hormone replacement, skin disorders (such as vitiligo, psoriasis, or alopecia) not requiring systemic treatment, or conditions not expected to recur in the absence of an external trigger are permitted to enroll.
9. Any uncontrolled inflammatory GI disease including Crohn's Disease and ulcerative colitis
10. History of anti-drug antibodies, severe allergic, anaphylactic, or other infusion-related reaction to a previous biologic agent
11. Immunosuppressive doses of systemic medications, such as steroids or absorbed topical steroids (doses >10 mg/day prednisone or equivalent daily) must be discontinued at least 2 weeks before study drug administration except in the case of tumor-related AE treatment. Patients with a condition requiring chronic systemic treatment with either corticosteroids (inhaled or topical steroids and adrenal replacement steroid doses >10 mg/day prednisone equivalent) or other immunosuppressive medications within 2 weeks of treatment are permitted in the absence of active autoimmune disease (except for patients with glioma).
12. Non-oncology vaccine therapies for prevention of infectious diseases (e.g., HPV vaccine) within 4 weeks of study drug administration. The inactivated seasonal influenza vaccine can be given to patients before treatment and while on therapy without restriction. Influenza vaccines containing live virus or other clinically indicated vaccinations for infectious diseases (i.e., pneumovax, varicella, etc.) may be permitted, but must be discussed with the Sponsor's Medical Monitor and may require a study drug washout period prior to and after administration of vaccine.
13. Treatment with any anti-cancer therapy or participation in another therapeutic clinical study with investigational drugs ≤14 days prior to first dose of study drug administration.
14. Ongoing acute adverse effects from prior treatment >NCI CTCAE Grade 1.
15. Gastric cancer patients with HER2 over-expression who have not received anti-HER2 targeted therapy.
16. Major surgical procedures are not allowed ≤28 days prior to FPA144 administration. In all cases the patient must be sufficiently recovered and stable before treatment administration.
17. Females who are pregnant or breastfeeding; women of childbearing potential must not be considering getting pregnant during the study.
18. Presence of any serious or unstable concomitant systemic disorder incompatible with the clinical study (e.g., substance abuse, psychiatric disturbance, or uncontrolled intercurrent illness including active infection, arterial thrombosis, and symptomatic pulmonary embolism).
19. Presence of any other condition that may increase the risk associated with study participation or may interfere with the interpretation of study results, and, in the opinion of the Investigator, would make the patient inappropriate for entry into the study.
20. Known allergy or hypersensitivity to components of the anti-FGFR2 antibody or nivolumab formulations including polysorbate.
21. Prior treatment with any selective inhibitor (e.g., AZD4547, BGJ398, JNJ-42756493, BAY1179470) of the FGF-FGFR pathway
22. History of prior malignancy except:
    a) Curatively treated non-melanoma skin cancer or
    b) Solid tumor treated curatively more than 5 years previously without evidence of recurrence or
    c) History of other malignancy that in the Investigator's opinion would not affect the determination of study treatment effect.

For pharmacokinetic analysis, blood samples will be collected from all patients. Standard PK parameters will be determined based on anti-FGFR2 antibody concentration-time data. Blood samples will also be collected to assay for anti-drug antibodies (ADA) to anti-FGFR2 antibody and nivolumab.

Efficacy measures will include tumor assessments comprising clinical examination and appropriate imaging techniques, preferably computed tomography (CT) scans of the chest, abdomen, and pelvis with appropriate slice thickness per RECIST 1.1; other assessments (magnetic resonance imaging (MRI), X-ray, positron emission tomography (PET), and ultrasound) may be performed, if required. Tumor assessments will be performed at Screening, then every 6 weeks from the first dose, for 24 weeks, and then approximately every 12 weeks thereafter. Once an initial complete response (CR) or partial response (PR) is noted, confirmatory scans must be performed 4-6 weeks later.

Tumor biopsies, mandatory as feasible, will be performed before treatment and either at 15 days or 29 days on-treatment for all patients in Part 2. Feasibility at each time-point will be assessed by the Investigator and should include a consideration of patient safety. Patients may also have an optional on-treatment biopsy upon documented tumor response and/or optional post-treatment biopsy upon documented tumor progression after discussion with the Sponsor.

A sample size of up to approximately 60 subjects is based on the study design for dose escalation in Part 1 and 20 patients per arm in the treatment arms in Part 2. Each individual arm in Part 2 of this study will proceed with a Simon two-stage design. The presumed observed response rate of nivolumab as monotherapy in advanced gastric cancer, unselected for PD-L1 expression is 12%; the ORR for anti-FGFR2 antibody may be different depending on the expression level of FGFR2b observed in the tumor. For Cohort 2A, the presumed ORR for anti-FGFR2 antibody is 0%. For Cohort 2B, the ORR for anti-FGFR2 antibody monotherapy is 30%. As such, Cohort 2A will not enroll the 20 patient expansion if <2 responses are observed out of the first 20 patients. For Cohort 2B, the 20 patient expansion will not be opened if <6 patients achieve an objective response from among the first 20 patients enrolled.

TABLE OF SEQUENCES

The table below provides a listing of certain sequences referenced herein

| SEQ. ID. NO. | Description | Sequence |
|---|---|---|
| 1 | Mature human FGFR2-IIIb | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS GDDEDDTDGA EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSPHRPILQA GLPANASTVV GGDVEFVCKV YSDAQPHIQW IKHVEKNGSK YGPDGLPYLK VLKHSGINSS NAEVLALFNV TEADAGEYIC KVSNYIGQAN QSAWLTVLPK QQAPGREKEI TASPDYLEIA IYCIGVFLIA CMVVTVILCR MKNTTKKPDF SSQPAVHKLT KRIPLRRQVT VSAESSSSMN SNTPLVRITT RLSSTADTPM LAGVSEYELP EDPKWEFPRD KLTLGKPLGE GCFGQVVMAE AVGIDKDKPK EAVTVAVKML KDDATEKDLS DLVSEMEMMK MIGKHKNIIN LLGACTQDGP LYVIVEYASK GNLREYLRAR RPPGMEYSYD INRVPEEQMT FKDLVSCTYQ LARGMEYLAS QKCIHRDLAA RNVLVTENNV MKIADFGLAR DINNIDYYKK TTNGRLPVKW MAPEALFDRV YTHQSDVWSF GVLMWEIFTL GGSPYPGIPV EELFKLLKEG HRMDKPANCT NELYMMMRDC WHAVPSQRPT FKQLVEDLDR ILTLTTNEEY LDLSQPLEQY SPSYPDTRSS CSSGDDSVFS PDPMPYEPCL PQYPHINGSV KT |
| 2 | αFGFR2b heavy chain; Asn297 is in bold and underlined | QVQLVQSGAE VKKPGSSVKV SCKASGYIFT TYNVHWVRQA PGQGLEWIGS IYPDNGDTSY NQNFKGRATI TADKSTSTAY MELSSLRSED TAVYYCARGD FAYWGQGTLV TVSSASTKGP SVFPLAPSSK STSGGTAALG CLVKDYFPEP VTVSWNSGAL TSGVHTFPAV LQSSGLYSLS SVVTVPSSSL GTQTYICNVN HKPSNTKVDK RVEPKSCDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SREEMTKNQV SLTCLVKGFY PSDIAVEWES NGQPENNYKT TPPVLDSDGS FFLYSKLTVD KSRWQQGNVF SCSVMHEALH NHYTQKSLSL SPGK |
| 3 | αFGFR2b light chain | DIQMTQSPSS LSASVGDRVT ITCKASQGVS NDVAWYQQKP GKAPKLLIYS ASYRYTGVPS RFSGSGSGTD FTFTISSLQP EDIATYYCQQ HSTTPYTFGQ GTKLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 4 | αFGFR2b heavy chain variable region | QVQLVQSGAE VKKPGSSVKV SCKASGYIFT TYNVHWVRQA PGQGLEWIGS IYPDNGDTSY NQNFKGRATI TADKSTSTAY MELSSLRSED TAVYYCARGD FAYWGQGTLV TVSS |
| 5 | αFGFR2b light chain variable region | DIQMTQSPSS LSASVGDRVT ITCKASQGVS NDVAWYQQKP GKAPKLLIYS ASYRYTGVPS RFSGSGSGTD FTFTISSLQP EDIATYYCQQ HSTTPYTFGQ GTKLEIK |
| 6 | αFGFR2b heavy chain (HC) HVR1 | TYNVH |
| 7 | αFGFR2b HC HVR2 | SIYPDNGDTS YNQNFKG |
| 8 | αFGFR2b HC HVR3 | GDFAY |

TABLE OF SEQUENCES-continued

The table below provides a listing of certain sequences referenced herein

| SEQ. ID. NO. | Description | Sequence |
|---|---|---|
| 9 | αFGFR2b light chain (LC) HVR1 | KASQGVSNDV A |
| 10 | αFGFR2b LC HVR2 | SASYRYT |
| 11 | αFGFR2b LC HVR3 | QQHSTTPYT |
| 12 | αFGFR2b N297Q heavy chain; the N297Q point mutation is bold and underlined | QVQLVQSGAE VKKPGSSVKV SCKASGYIFT TYNVHWVRQA PGQGLEWIGS IYPDNGDTSY NQNFKGRATI TADKSTSTAY MELSSLRSED TAVYYCARGD FAYWGQGTLV TVSSASTKGP SVFPLAPSSK STSGGTAALG CLVKDYFPEP VTVSWNSGAL TSGVHTFPAV LQSSGLYSLS SVVTVPSSSL GTQTYICNVN HKPSNTKVDK RVEPKSCDKT HTCPPCPAPE LLGGPSVFLF PPKPKDTLMI SRTPEVTCVV VDVSHEDPEV KFNWYVDGVE VHNAKTKPRE EQYQSTYRVV SVLTVLHQDW LNGKEYKCKV SNKALPAPIE KTISKAKGQP REPQVYTLPP SREEMTKNQV SLTCLVKGFY PSDIAVEWES NGQPENNYKT TPPVLDSDGS FFLYSKLTVD KSRWQQGNVF SCSVMHEALH NHYTQKSLSL SPGK |
| 13 | Mature human FGFR2-IIIc | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS GDDEDDTDGA EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSPHRPILQA GLPANASTVV GGDVEFVCKV YSDAQPHIQW IKHVEKNGSK YGPDGLPYLK VLKAAGVNTT DKEIEVLYIR NVTFEDAGEY TCLAGNSIGI SFHSAWLTVL PAPGREKEIT ASPDYLEIAI YCIGVFLIAC MVVTVILCRM KNTTKKPDFS SQPAVHKLTK RIPLRRQVTV SAESSSSMNS NTPLVRITTR LSSTADTPML AGVSEYELPE DPKWEFPRDK LTLGKPLGEG CFGQVVMAEA VGIDKDKPKE AVTVAVKMLK DDATEKDLSD LVSEMEMMKM IGKHKNIINL LGACTQDGPL YVIVEYASKG NLREYLRARR PPGMEYSYDI NRVPEEQMTF KDLVSCTYQL ARGMEYLASQ KCIHRDLAAR NVLVTENNVM KIADFGLARD INNIDYYKKT TNGRLPVKWM APEALFDRVY THQSDVWSFG VLMWEIFTLG GSPYPGIPVE ELFKLLKEGH RMDKPANCTN ELYMMMRDCW HAVPSQRPTF KQLVEDLDRI LTLTTNEEYL DLSQPLEQYS PSYPDTRSSC SSGDDSVFSP DPMPYEPCLP QYPHINGSVK T |
| 14 | FGFR2 ECD | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS GDDEDDTDGA EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSPHRPILQA GLPANASTVV GGDVEFVCKV YSDAQPHIQW IKHVEKNGSK YGPDGLPYLK VLKAAGVNTT DKEIEVLYIR NVTFEDAGEY TCLAGNSIGI SFHSAWLTVL PAPGREKEIT ASPDYLE |
| 15 | FGFR2 ECD Δ3 | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS GDDEDDTDGA EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI |

TABLE OF SEQUENCES-continued

The table below provides a listing of certain sequences referenced herein

| SEQ. ID. NO. | Description | Sequence |
|---|---|---|
| | | NHTYHLDVVE RSPHRPILQA GLPANASTVV GGDVEFVCKV YSDAQPHIQW IKHVEKNGSK YGPDGLPYLK VLKAAGVNTT DKEIEVLYIR NVTFEDAGEY TCLAGNSIGI SFHSAWLTVL PAPGREKEIT ASPD |
| 16 | FGFR2 ECD Δ4 | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS GDDEDDTDGA EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSPHRPILQA GLPANASTVV GGDVEFVCKV YSDAQPHIQW IKHVEKNGSK YGPDGLPYLK VLKAAGVNTT DKEIEVLYIR NVTFEDAGEY TCLAGNSIGI SFHSAWLTVL PAPGREKEIT ASP |
| 17 | FGFR2 ECD Δ5 | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS GDDEDDTDGA EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSPHRPILQA GLPANASTVV GGDVEFVCKV YSDAQPHIQW IKHVEKNGSK YGPDGLPYLK VLKAAGVNTT DKEIEVLYIR NVTFEDAGEY TCLAGNSIGI SFHSAWLTVL PAPGREKEIT AS |
| 18 | FGFR2 ECD Δ8 | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS GDDEDDTDGA EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSPHRPILQA GLPANASTVV GGDVEFVCKV YSDAQPHIQW IKHVEKNGSK YGPDGLPYLK VLKAAGVNTT DKEIEVLYIR NVTFEDAGEY TCLAGNSIGI SFHSAWLTVL PAPGREKEI |
| 19 | FGFR2 ECD Δ9 | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS GDDEDDTDGA EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSPHRPILQA GLPANASTVV GGDVEFVCKV YSDAQPHIQW IKHVEKNGSK YGPDGLPYLK VLKAAGVNTT DKEIEVLYIR NVTFEDAGEY TCLAGNSIGI SFHSAWLTVL PAPGREKE |
| 20 | FGFR2 ECD Δ10 | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS GDDEDDTDGA EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSPHRPILQA GLPANASTVV GGDVEFVCKV YSDAQPHIQW IKHVEKNGSK YGPDGLPYLK VLKAAGVNTT DKEIEVLYIR NVTFEDAGEY TCLAGNSIGI SFHSAWLTVL PAPGREK |
| 21 | FGFR2 ECD Δ14 | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS GDDEDDTDGA EDFVSENSNN KRAPYWTNTE KMEKRLHAVP AANTVKFRCP AGGNPMPTMR WLKNGKEFKQ EHRIGGYKVR |

TABLE OF SEQUENCES-continued

The table below provides a listing of certain sequences referenced herein

| SEQ. ID. NO. | Description | Sequence |
|---|---|---|
| | | NQHWSLIMES VVPSDKGNYT CVVENEYGSI NHTYHLDVVE RSPHRPILQA GLPANASTVV GGDVEFVCKV YSDAQPHIQW IKHVEKNGSK YGPDGLPYLK VLKAAGVNTT DKEIEVLYIR NVTFEDAGEY TCLAGNSIGI SFHSAWLTVL PAP |
| 22 | FGFR2 ECD Δ15 | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS GDDEDDTDGA EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSPHRPILQA GLPANASTVV GGDVEFVCKV YSDAQPHIQW IKHVEKNGSK YGPDGLPYLK VLKAAGVNTT DKEIEVLYIR NVTFEDAGEY TCLAGNSIGI SFHSAWLTVL PA |
| 23 | FGFR2 ECD Δ16 | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS GDDEDDTDGA EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSPHRPILQA GLPANASTVV GGDVEFVCKV YSDAQPHIQW IKHVEKNGSK YGPDGLPYLK VLKAAGVNTT DKEIEVLYIR NVTFEDAGEY TCLAGNSIGI SFHSAWLTVL P |
| 24 | FGFR2 ECD Δ17 | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS GDDEDDTDGA EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSPHRPILQA GLPANASTVV GGDVEFVCKV YSDAQPHIQW IKHVEKNGSK YGPDGLPYLK VLKAAGVNTT DKEIEVLYIR NVTFEDAGEY TCLAGNSIGI SFHSAWLTVL |
| 25 | Fc C237S | EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 26 | Fc | ERKCCVECPP CPAPPVAGPS VFLFPPKPKD TLMISRTPEV TCVVVDVSHE DPEVQFNWYV DGVEVHNAKT KPREEQFNST FRVVSVLTVV HQDWLNGKEY KCKVSNKGLP APIEKTISKT KGQPREPQVY TLPPSREEMT KNQVSLTCLV KGFYPSDIAV EWESNGQPEN NYKTTPPMLD SDGSFFLYSK LTVDKSRWQQ GNVFSCSVMH EALHNHYTQK SLSLSPGK |
| 27 | Fc | ESKYGPPCPS CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 28 | FGFR2(111-118) | DDEDDTDG |
| 29 | FGFR1(105-112) | EDDDDDDD |

TABLE OF SEQUENCES-continued

The table below provides a listing of certain sequences referenced herein

| SEQ. ID. NO. | Description | Sequence |
|---|---|---|
| 30 | FGFR2 ECD with R2(111-118) replaced by R1(105-112) | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS G EDDDDDDD A EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSPHRPILQA GLPANASTVV GGDVEFVCKV YSDAQPHIQW IKHVEKNGSK YGPDGLPYLK VLKAAGVNTT DKEIEVLYIR NVTFEDAGEY TCLAGNSIGI SFHSAWLTVL PAPGREKEIT ASPDYLE |
| 31 | FGFR2 ECD with R2(111-118) replaced by R1(105-112) + Fc | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETVVYF MVNVTDAISS G EDDDDDDD A EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSPHRPILQA GLPANASTVV GGDVEFVCKV YSDAQPHIQW IKHVEKNGSK YGPDGLPYLK VLKAAGVNTT DKEIEVLYIR NVTFEDAGEY TCLAGNSIGI SFHSAWLTVL PAPGREKEIT ASPDYLE EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 32 | FGFR2 ECD Δ3 + GS linker + Fc (also called FGFR2ECD(delta3)-GS linker-Fc and FGFR2-Fc) | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS GDDEDDTDGA EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSPHRPILQA GLPANASTVV GGDVEFVCKV YSDAQPHIQW IKHVEKNGSK YGPDGLPYLK VLKAAGVNTT DKEIEVLYIR NVTFEDAGEY TCLAGNSIGI SFHSAWLTVL PAPGREKEIT ASPD GS EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 33 | FGFR2 ECD Δ3 with R2(111-118) replaced by R1(105-112) | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS G EDDDDDDD A EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSPHRPILQA GLPANASTVV GGDVEFVCKV YSDAQPHIQW IKHVEKNGSK YGPDGLPYLK VLKAAGVNTT DKEIEVLYIR NVTFEDAGEY TCLAGNSIGI SFHSAWLTVL PAPGREKEIT ASPD |
| 34 | FGFR2 ECD Δ3 with R2(111-118) replaced by R1(105-112) + GS linker + Fc (also called FGFR2ECD | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS G EDDDDDDD A EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI |

TABLE OF SEQUENCES-continued

The table below provides a listing of certain sequences referenced herein

| SEQ. ID. NO. | Description | Sequence |
|---|---|---|
| | (FGFR2(111-118): FGFR1 (105-112): delta3)-GS linker-Fc and R2(111-118): R1(105-112)) | NHTYHLDVVE RSPHRPILQA GLPANASTVV GGDVEFVCKV YSDAQPHIQW IKHVEKNGSK YGPDGLPYLK VLKAAGVNTT DKEIEVLYIR NVTFEDAGEY TCLAGNSIGI SFHSAWLTVL PAPGREKEIT ASPD GS EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 35 | human PD-1 precursor (with signal sequence) UniProtKB/Swiss-Prot: Q15116.3, 01-OCT.-2014 | MQIPQAPWPV VWAVLQLGWR PGWFLDSPDR PWNPPTFSPA LLVVTEGDNA TFTCSFSNTS ESFVLNWYRM SPSNQTDKLA AFPEDRSQPG QDCRFRVTQL PNGRDFHMSV VRARRNDSGT YLCGAISLAP KAQIKESLRA ELRVTERRAE VPTAHPSPSP RPAGQFQTLV VGVVGGLLGS LVLLVWVLAV ICSRAARGTI GARRTGQPLK EDPSAVPVFS VDYGELDFQW REKTPEPPVP CVPEQTEYAT IVFPSGMGTS SPARRGSADG PRSAQPLRPE DGHCSWPL |
| 36 | human PD-1 (mature, without signal sequence) | PGWFLDSPDR PWNPPTFSPA LLVVTEGDNA TFTCSFSNTS ESFVLNWYRM SPSNQTDKLA AFPEDRSQPG QDCRFRVTQL PNGRDFHMSV VRARRNDSGT YLCGAISLAP KAQIKESLRA ELRVTERRAE VPTAHPSPSP RPAGQFQTLV VGVVGGLLGS LVLLVWVLAV ICSRAARGTI GARRTGQPLK EDPSAVPVFS VDYGELDFQW REKTPEPPVP CVPEQTEYAT IVFPSGMGTS SPARRGSADG PRSAQPLRPE DGHCSWPL |
| 37 | human PD-L1 precursor (with signal sequence) UniProtKB/Swiss-Prot: Q9NZQ7.1, 01-OCT.-2014 | MRIFAVFIFM TYWHLLNAFT VTVPKDLYVV EYGSNMTIEC KFPVEKQLDL AALIVYWEME DKNIIQFVHG EEDLKVQHSS YRQRARLLKD QLSLGNAALQ ITDVKLQDAG VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEIFYCT FRRLDPEENH TAELVIPELP LAHPPNERTH LVILGAILLC LGVALTFIFR LRKGRMMDVK KCGIQDTNSK KQSDTHLEET |
| 38 | human PD-L1 (mature, without signal sequence) | FT VTVPKDLYVV EYGSNMTIEC KFPVEKQLDL AALIVYWEME DKNIIQFVHG EEDLKVQHSS YRQRARLLKD QLSLGNAALQ ITDVKLQDAG VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEIFYCT FRRLDPEENH TAELVIPELP LAHPPNERTH LVILGAILLC LGVALTFIFR LRKGRMMDVK KCGIQDTNSK KQSDTHLEET |
| 39 | Anti-FGFR2 Gal-FR22 heavy chain variable region | QVQLKQSGPG LVQPSQSLSI TCTVSGFSLT SFGVHWVRQS PGKGLEWLGV IWSGGSTDYN ADFRSRLSIS KDNSKSQIFF KMNSLQPDDT IAYCANFYYG YDDYVMDYWG QGTSVTVSS |
| 40 | Anti-FGFR2 Gal-FR22 heavy chain CDR1 | SFGVH |
| 41 | Anti-FGFR2 Gal-FR22 heavy chain CDR2 | VIWSGGSTDYNADFRS |
| 42 | Anti-FGFR2 Gal-FR22 heavy chain CDR3 | FYYGYDDYVMDY |
| 43 | Anti-FGFR2 Gal-FR22 light chain variable region | DIQMTQSPSS LSASLGGRVT ITCKASQDIK NYIAWYQHKP GKSPRLLIHY TSTLQPGVPS RFSGSGSGRD YSFSISNLEP EDIATYYCLQ YDDDLYMFGG GTKLDIK |

TABLE OF SEQUENCES-continued

The table below provides a listing of certain sequences referenced herein

| SEQ. ID. NO. | Description | Sequence |
|---|---|---|
| 44 | Anti-FGFR2 Gal-FR22 light chain CDR1 | KASQDIKNYIA |
| 45 | Anti-FGFR2 Gal-FR22 light chain CDR2 | YTSTLQP |
| 46 | Anti-FGFR2 Gal-FR22 light chain CDR3 | LQYDDLYM |

What is claimed is:

1. A method of treating bladder cancer in a subject comprising administering to the subject a fibroblast growth factor receptor 2 (FGFR2) inhibitor and at least one programmed cell death 1 (PD-1)/programmed cell death ligand 1 (PD-L1) inhibitor, wherein the FGFR2 inhibitor is an anti-FGFR2-IIIb antibody that binds to FGFR2-IIIb and does not detectably bind to FGFR4; and wherein the anti-FGFR2-IIIb antibody comprises heavy and light chain variable domains, wherein the heavy chain variable domain comprises:
   (i) HVR-H1 comprising the amino acid sequence of SEQ ID NO: 6;
   (ii) HVR-H2 comprising the amino acid sequence of SEQ ID NO: 7; and
   (iii) HVR-H3 comprising the amino acid sequence of SEQ ID NO: 8;
and the light chain variable domain comprises:
   (iv) HVR-L1 comprising the amino acid sequence of SEQ ID NO: 9;
   (v) HVR-L2 comprising the amino acid sequence of SEQ ID NO: 10; and
   (vi) HVR-L3 comprising the amino acid sequence of SEQ ID NO: 11.

2. The method of claim 1, wherein the bladder cancer (a) has an H score of 20 or greater; or (b) has an H score of 10-19.

3. The method of claim 1, wherein the anti-FGFR2-IIIb antibody is afucosylated.

4. The method of claim 1, wherein the anti-FGFR2-IIIb antibody lacks a fucose at position Asn297 numbered according to the EU index as in Kabat.

5. The method of claim 1, wherein the heavy chain variable domain comprises the amino acid sequence of SEQ ID NO: 4 and the light chain variable domain comprises the amino acid sequence of SEQ ID NO: 5.

6. The method of claim 5, wherein the anti-FGFR2-IIIb antibody comprises a heavy chain amino acid sequence of SEQ ID NO: 2 and a light chain amino acid sequence of SEQ ID NO: 3, and wherein the anti-FGFR2-IIIb antibody lacks a fucose at position Asn297 numbered according to the EU index as in Kabat.

7. The method of claim 1, wherein the PD-L1/PD-1 inhibitor is an anti-PD-1 antibody.

8. The method of claim 7, wherein the anti-PD-1 antibody is nivolumab, pidilizumab, or pembrolizumab.

9. The method of claim 7, wherein the anti-PD-1 antibody is nivolumab.

10. The method of claim 7, wherein the anti-PD-1 antibody is pembrolizumab.

* * * * *